US008785625B2

(12) United States Patent
Suzuki et al.

(10) Patent No.: US 8,785,625 B2
(45) Date of Patent: *Jul. 22, 2014

(54) COMPOUND HAVING HETEROCYCLIC RING

(75) Inventors: Hideyuki Suzuki, Tokyo (JP); Shoji Hizatate, Tokyo (JP); Iwao Utsunomiya, Kanagawa (JP); Koichi Shudo, Tokyo (JP)

(73) Assignees: Research Foundation Itsuu Laboratory, Tokyo (JP); Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,848

(22) Filed: Feb. 14, 2012

(65) Prior Publication Data
US 2012/0208997 A1 Aug. 16, 2012

Related U.S. Application Data

(62) Division of application No. 12/225,819, filed as application No. PCT/JP2007/057060 on Mar. 30, 2007, now Pat. No. 8,148,362.

(30) Foreign Application Priority Data

Mar. 31, 2006 (JP) ................................. 2006-100889

(51) Int. Cl.
C07D 255/02 (2006.01)
C07D 273/06 (2006.01)

(52) U.S. Cl.
CPC ............ C07D 273/06 (2013.01); C07D 255/02 (2013.01)
USPC ......................................... 540/545; 540/554

(58) Field of Classification Search
None
See application file for complete search history.

(56) References Cited

U.S. PATENT DOCUMENTS

| 4,195,105 | A | 3/1980 | Mares et al. |
| 4,801,706 | A | 1/1989 | Winkley et al. |
| 5,523,403 | A | 6/1996 | Barbachyn |
| 5,529,998 | A | 6/1996 | Häbich et al. |
| 5,574,055 | A | 11/1996 | Borgulya et al. |
| 6,218,413 | B1 | 4/2001 | Hester, Jr. et al. |
| 6,239,152 | B1 | 5/2001 | Gordeev et al. |
| 6,255,304 | B1 | 7/2001 | Hester, Jr. et al. |
| 6,342,513 | B1 | 1/2002 | Hester, Jr. et al. |
| 6,362,189 | B1 | 3/2002 | Hester, Jr. et al. |
| 6,537,986 | B2 | 3/2003 | Hester, Jr. et al. |
| 6,734,307 | B2 | 5/2004 | Mehta et al. |
| 6,956,040 | B2 | 10/2005 | Mehta et al. |
| 7,056,942 | B2 | 6/2006 | Hildesheim et al. |
| 8,148,362 | B2 * | 4/2012 | Suzuki et al. ............ 514/211.08 |
| 2003/0153610 | A1 | 8/2003 | Straub et al. |
| 2005/0004174 | A1 | 1/2005 | Gordeev et al. |
| 2006/0258724 | A1 | 11/2006 | Straub et al. |
| 2008/0090815 | A1 | 4/2008 | Straub et al. |

FOREIGN PATENT DOCUMENTS

| EP | 1 130 016 | 9/2001 |
| GB | 1 543 081 | 3/1979 |
| JP | 11-322729 | 11/1999 |
| WO | 89/08111 | 9/1989 |
| WO | 95/07271 | 3/1995 |
| WO | 95/34540 | 12/1995 |
| WO | 97/09328 | 3/1997 |
| WO | 97/10223 | 3/1997 |
| WO | 98/01446 | 1/1998 |
| WO | 99/12914 | 3/1999 |
| WO | 99/24428 | 5/1999 |
| WO | 99/37630 | 7/1999 |
| WO | 99/64417 | 12/1999 |
| WO | 00/29396 | 5/2000 |
| WO | 00/32599 | 6/2000 |
| WO | 01/09107 | 2/2001 |
| WO | 02/06278 | 1/2002 |
| WO | 03/002560 | 1/2003 |
| WO | 03/007870 | 1/2003 |
| WO | 03/008389 | 1/2003 |
| WO | 03/011859 | 2/2003 |
| WO | 03/032962 | 4/2003 |
| WO | 03/066631 | 8/2003 |

(Continued)

OTHER PUBLICATIONS

Spong-Rodriguez. Advanced Drug Delivery Reviews, 2004, 56, 241-74.*
"IUPAC gold book", http://goldbook.iupac.org/A00123.html, accessed Nov. 27, 2007.*
International Search Report issued May 1, 2007 in International (PCT) Application No. PCT/JP2007/057060.
Jerzy Szotor et al., "Synthesis of Hexahydrotriazepine-1,2,5 Derivatives", Dissertationes Pharmaceuticae et Pharmacologicae, 24 (4), pp. 385-390, 1972.
Mona A. Mahran, "Hydrazinolysis of Some Substituted Ethyl Glycinate: New Findings", Alex. J. Pharm. Sci., vol. 10, No. 3, pp. 179-181, 1996.

(Continued)

Primary Examiner — Noble Jarrell
(74) Attorney, Agent, or Firm — Wenderoth, Lind & Ponack, L.L.P.

(57) ABSTRACT

The invention provides a novel oxazolidinone derivative represented by the formula (I):

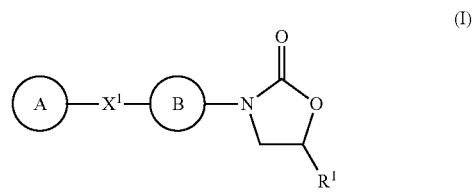

wherein
Ring A, $X^1$, Ring B and $R^1$ are as described in the description, and an antibacterial agent containing the same.

3 Claims, No Drawings

(56) References Cited

FOREIGN PATENT DOCUMENTS

| WO | 03/072553 | 9/2003 |
|---|---|---|
| WO | 2004/002967 | 1/2004 |
| WO | 2004/014392 | 2/2004 |
| WO | 2004/026848 | 4/2004 |
| WO | 2004/083206 | 9/2004 |
| WO | 2004/096221 | 11/2004 |
| WO | 2004/101552 | 11/2004 |
| WO | 2005/019213 | 3/2005 |
| WO | 2005/058888 | 6/2005 |
| WO | 2006/043490 | 4/2006 |
| WO | 2007/000644 | 1/2007 |
| WO | 2007/114326 | 10/2007 |

OTHER PUBLICATIONS

Mona A. Mahran et al., "Synthesis of Some Novel Perhydrotriazepine-3,6-diones of Potential Antifungal Activity", Alex. J. Pharm. Sci., vol. 10, No. 2, pp. 133-135, 1996.
English translation of PCT Written Opinion dated Oct. 21, 2008 in the International (PCT) Application PCT/JP2007/057060.
Supplementary European Search Report dated Jul. 9, 2009 in European Application No. 07 74 0496.
Supplementary European Search report issued Nov. 4, 2013 in corresponding European Application No. 13178030.6.

\* cited by examiner

COMPOUND HAVING HETEROCYCLIC RING

This application is a Divisional application of U.S. application Ser. No. 12/225,819, filed Dec. 30, 2008, now issued as U.S. Pat. No. 8,148,362, which was a national stage application of International Application No. PCT/JP2007/057060, filed Mar. 30, 2007.

FIELD OF INVENTION

The invention relates to a novel compound having a heterocyclic ring, preferably triazepane derivatives and oxadiazepane derivatives having 7-membered heterocycle. The invention also relates to oxazolidinone derivatives having such 7-membered heterocycle, a pharmaceutical composition (e.g., antimicrobial) comprising the same, and synthetic intermediates thereof.

BACKGROUND ART

Various oxazolidinone derivatives having antimicrobial activity were known in the art, as disclosed, for example, in U.S. Pat. No. 6,255,304 (Patent Document 1), U.S. Pat. No. 6,218,413 (Patent Document 2), U.S. Pat. No. 6,362,189 (Patent Document 3), U.S. Pat. No. 6,342,513 (Patent Document 4), U.S. Pat. No. 6,537,986 (Patent Document 5), WO2000/032599 (Patent Document 6), WO99/24428 (Patent Document 7), WO97/10223 (Patent Document 8), WO97/09328 (Patent Document 9), U.S. Pat. No. 5,523,403 (Patent Document 10), WO95/07271 (Patent Document 11), WO2004/014392 (Patent Document 12), U.S. Pat. No. 6,956,040 (Patent Document 13), U.S. Pat. No. 6,734,307 (Patent Document 14), WO2002/006278 (Patent Document 15), WO2003/008389 (Patent Document 16), WO2003/007870 (Patent Document 17), WO2005/058888 (Patent Document 18), WO2004/096221 (Patent Document 19), EP Patent No. Publication EP697412A (Patent Document 20), WO2000/027830 (Patent Document 21), Japanese Patent Publication 11-322729 (Patent Document 22), Japanese Patent Publication 9-221476 (Patent Document 23), WO95/34540 (Patent Document 24), WO002560 (Patent Document 25), WO99/64417 (Patent Document 26), EP Patent No. 657440B (Patent Document 27), WO2005/019213 (Patent Document 28), Japanese Patent Publication 2005-524660 (Patent Document 29), U.S. Pat. No. 6,239,152 (Patent Document 30), US Application Publication 2005/4174A1 (Patent Document 31), Japanese Patent Publication 2003-513885 (Patent Document 32), WO99/37630 (Patent Document 33), Japanese Patent Publication 2003-519141 (Patent Document 34), Japanese Patent Publication 2000-204084 (Patent Document 35), Japanese Patent Publication 11-322729 (Patent Document 36), Japanese Patent Publication 11-158164 (Patent Document 37), WO2004/101552 (Patent Document 38), WO2004/026848 (Patent Document 39), WO2003/11859 (Patent Document 40), WO2004/002967 (Patent Document 41).

Particularly, (S)—N—[[3-[3-fluoro-4-(4-morpholinyl)phenyl]-2-oxo-5-oxazolidinyl]methyl]acetamide ("linezolid"), as disclosed in WO95/07271 (Patent Document 11), has a potent antimicrobial activity against methicillin-resistant Staphylococcus aureus (MRSA) and vancomycin-resistant Enterococci (VRE) and it has been approved and marketed as a VRE anti-infectious drug.

Triazacycloheptane derivative was also known (Patent Document 42, Patent Document 43, Patent Document 44, Non-patent Document 1) but its antimicrobial activity was not disclosed.

Additionally, various quinolone or newquinolone antimicrobial agents were known as an antimicrobial drug. However, such a compound attached via its side chain with a triazacycloheptane derivative has not been reported.

[Patent Document 1] U.S. Pat. No. 6,255,304
[Patent Document 2] U.S. Pat. No. 6,218,413
[Patent Document 3] U.S. Pat. No. 6,362,189
[Patent Document 4] U.S. Pat. No. 6,342,513
[Patent Document 5] U.S. Pat. No. 6,537,986
[Patent Document 6] WO2000/032599
[Patent Document 7] WO99/24428
[Patent Document 8] WO97/10223
[Patent Document 9] WO97/09328
[Patent Document 10] U.S. Pat. No. 5,523,403
[Patent Document 11] WO95/07271
[Patent Document 12] WO2004/014392
[Patent Document 13] U.S. Pat. No. 6,956,040
[Patent Document 14] U.S. Pat. No. 6,734,307
[Patent Document 15] WO2002/006278
[Patent Document 16] WO2003/008389
[Patent Document 17] WO2003/007870
[Patent Document 18] WO2005/058888
[Patent Document 19] WO2004/096221
[Patent Document 20] EP Patent No. Publication EP697412A
[Patent Document 21] WO2000/027830
[Patent Document 22] Japanese Patent Publication 11-322729
[Patent Document 23] Japanese Patent Publication 9-221476
[Patent Document 24] WO95/34540
[Patent Document 25] WO002560
[Patent Document 26] WO99/64417
[Patent Document 27] EP Patent No. 657440B
[Patent Document 28] WO2005/019213
[Patent Document 29] Japanese Patent Publication 2005-524660
[Patent Document 30] U.S. Pat. No. 6,239,152
[Patent Document 31] US Application Publication 2005/4174A1
[Patent Document 32] Japanese Patent. Publication 2003-513885
[Patent Document 33] WO99/37630
[Patent Document 34] Japanese Patent Publication 2003-519141
[Patent Document 35] Japanese Patent Publication 2000-204084
[Patent Document 36] Japanese Patent Publication 11-322729
[Patent Document 37] Japanese Patent Publication 11-158164
[Patent Document 38] WO2004/101552
[Patent Document 39] WO2004/026848
[Patent Document 40] WO2003/11859
[Patent Document 41] WO2004/002967
[Patent Document 42] UK Patent No. 1543081
[Patent Document 43] EP Patent No. 358749
[Patent Document 44] U.S. Pat. No. 4,801,706
[Non-patent Document 1] Dissertationes Pharmaceuticae et Pharmacologicae (1972), 24 (4), 385-390

DISCLOSURE OF THE INVENTION

Problems to be Resolved by the Invention

There is still need for developments in antimicrobial agent that has strong antimicrobial activity against wide range of microorganisms. Additionally, there is need for a novel antimicrobial agent which is effective against resistant strains to currently used antimicrobials. The invention provides a novel oxazolidinone derivative and pharmaceutically acceptable salts thereof useful as an antimicrobial agent, and an antimicrobial drug comprising the same as an active ingredient. More preferably, the invention provides a compound having good solubility and pharmacokinetics, etc. Still more preferably, the invention provides a compound with reduced side effect, compared with conventional antimicrobial agents.

The invention also provides a novel quinolone antimicrobial agent. The invention further provides a novel compound useful as a medicament. Also, the invention provides synthetic intermediates of such compound.

Means of Solving the Problems

The inventors have discovered novel oxazolidinone derivatives having antimicrobial activity. Also, the inventor has discovered novel compounds having a heterocycle such as triazacycloheptane derivative, oxadiazepane derivative and the like, which have antimicrobial activity, and intermediates thereof. The invention has been accomplished on the basis of the above discoveries.

(1) A compound of the formula:

[Chemical Formula 1]

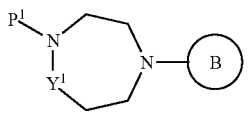

or a pharmaceutically acceptable salt or solvate thereof
wherein
$Y^1$ is $NP^2$ or O;
$P^1$ and $P^2$ are independently hydrogen, a substituent selected from Substituent Group S1 or an amino protecting group, or $P^1$ and $P^2$ may be taken together with N atom to which they are attached to form optionally substituted heterocycle;
Substituent Group S1 consists of optionally substituted lower alkyl, optionally substituted cycloalkyl, optionally substituted formyl, optionally substituted lower alkylcarbonyl, optionally substituted cycloalkylcarbonyl, optionally substituted lower alkyloxycarbonyl, optionally substituted arylcarbonyl, optionally substituted heterocyclecarbonyl, optionally substituted carbamoyl, lower alkylthio, cycloalkylthio, arylthio, optionally substituted lower alkylsulfonyl, optionally substituted phenylsulfonyl, optionally substituted aromatic heterocycle(lower)alkyl, optionally substituted aryl, and optionally substituted heterocyclic group;
Ring B is optionally substituted and optionally condensed benzene ring or optionally substituted heterocycle; with the proviso that the compound is not the following compounds:

[Chemical Formula 2]

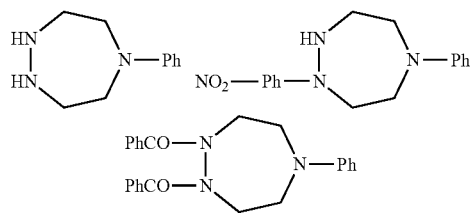

wherein Ph is phenyl.

(2) The compound according to (1) or a pharmaceutically acceptable salt or solvate thereof, wherein the substituent of Ring B optionally substituted is one or more substituent selected from the group consisting of halo, nitro, amino, amino protected with an amino protecting group, optionally substituted amide, formyl, carboxyl, carboxamide, optionally substituted alkyl, lower alkoxy, hydroxyimino, optionally substituted oxazolidinone, optionally substituted isoxazole, and optionally substituted heterocyclic group (preferably 5- or 6-membered).

(3) The compound according to (1) represented by the formula:

[Chemical Formula 3]

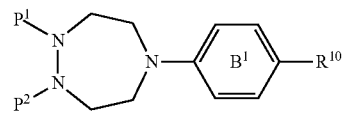

or a pharmaceutically acceptable salt or solvate thereof
wherein
$P^1$ and $P^2$ are hydrogen, a substituent selected from Substituent Group S1 or an amino protecting group, or $P^1$ and $P^2$ may be taken together with N atom to which they are attached to form optionally substituted heterocycle;
Ring $B^1$ is a benzene ring optionally substituted with one or more halogen atom;
$R^{10}$—$NO_2$ or —$NHP^3$;
$P^3$ is hydrogen or an amino protecting group.

(4) The compound according to (1) represented by the formula:

[Chemical Formula 4]

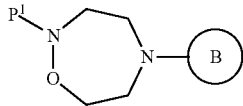

or a pharmaceutically acceptable salt or solvate thereof,
wherein
$P^1$ is hydrogen, a substituent selected from Substituent Group S1 or an amino protecting group;
Substituent Group S1 consists of optionally substituted lower alkyl, optionally substituted cycloalkyl, optionally substituted formyl, optionally substituted lower alkylcarbonyl, optionally substituted cycloalkylcarbonyl, optionally substituted lower alkyloxycarbonyl, optionally substituted arylcarbonyl, optionally substituted heterocyclecarbonyl, optionally substituted carbamoyl, lower alkylthio, cycloalkylthio, arylthio, optionally substituted lower alkylsulfonyl, optionally substituted phenylsulfonyl, optionally substituted aromatic heterocycle(lower)alkyl, optionally substituted aryl, and optionally substituted heterocyclic group;
Ring B is optionally substituted and optionally condensed benzene ring or optionally substituted heterocycle.

(5) The compound according to any one of (1), (2) or (4) wherein Ring B is a substituted quinoline ring.

(6) The compound according to (5) wherein Ring B is a residue of a quinolone antimicrobial compound or a newquinolone antimicrobial compound and connected at 7-position.

(7) A compound of the formula:

[Chemical Formula 5]

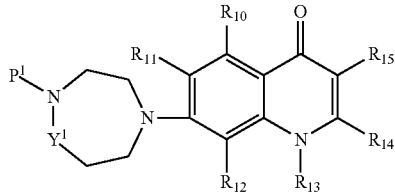
(I-3)

or a pharmaceutically acceptable salt or solvate thereof
wherein
$Y^1$ is $NP^2$ or O;
$P^1$ and $P^2$ are independently hydrogen, a substituent selected from Substituent Group S1 or an amino protecting group, or $P^1$ and $P^2$ may be taken together with N atom to which they are attached to form optionally substituted heterocycle;
$R^{10}$, $R^{11}$, $R^{12}$, $R^{13}$, $R^{14}$ and $R^{15}$ are independently hydrogen, lower alkyl, cycloalkyl, cycloalkyl lower alkyl, halo, lower alkoxy, carboxy, lower alkoxycarbonyl, amino, lower alkylamino, optionally substituted aryl, or optionally substituted heterocyclic group, or $R^{12}$ and $R^{13}$ are taken together with their neighboring atom(s) to form optionally substituted heterocycle.

(8) The compound according to (7) or a pharmaceutically acceptable salt or solvate thereof, wherein $R^{10}$ is hydrogen, $R^{11}$ is halo, $R^{12}$ is lower alkoxy, $R^{13}$ is cycloalkyl, $R^{14}$ is hydrogen, $R^{15}$ is carboxy or lower alkoxycarbonyl.

(9) A compound of the formula:

[Chemical Formula 6]

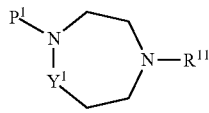

or a pharmaceutically acceptable salt or solvate thereof, wherein
$Y^1$ is $NP^2$ or O;
$P^1$ and $P^2$ are independently hydrogen, acyl group or an amino protecting group;
$R^{11}$ is hydrogen, acyl group or an amino protecting group, provided that —CO(CH$_2$)$_3$—CO$_2$H, -Ph and —CH$_2$Ph (Ph: phenyl) are excluded.

(10) The compound according to (9) represented by the formula:

[Chemical Formula 7]

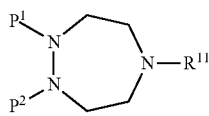

or a pharmaceutically acceptable salt or solvate thereof, wherein
$P^1$ and $P^2$ are independently hydrogen, acyl group or an amino protecting group;
$R^{11}$ is hydrogen, acyl group or an amino protecting group, provided that —CO(CH$_2$)$_3$—CO$_2$H, -Ph and —CH$_2$Ph (Ph: phenyl) are excluded.

(11) The compound according to (9) wherein $P^1$ and $P^2$ are independently an amino protecting group and $R^{11}$ is hydrogen.

(12) A compound of the formula:

[Chemical Formula 8]

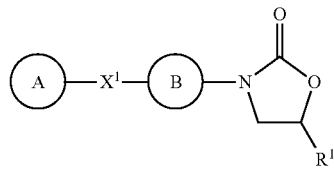
(I)

or a pharmaceutically acceptable salt or solvate thereof,
wherein
Ring A is
(A-1) at least 7-membered monocyclic hetero ring containing at least three N atoms;
(A-2) at least 6-membered monocyclic hetero ring containing at least two N atoms and at least one O atom; or
(A-3) at least 7-membered monocyclic hetero ring containing at least two N atoms and at least one S atom, wherein said monocyclic hetero ring is optionally substituted, and said monocyclic hetero ring is optionally condensed with another ring,
$X^1$ is a single bond, or a hetero atom-containing group selected from the group consisting of —O—, —S—, —NR$^2$—, —CO—, —CS—, —CONR$^3$—, —NR$^4$CO—, —SO$_2$NR$^5$—, and —NR$^6$SO$_2$—, wherein R$^2$, R$^3$, R$^4$, R$^5$ and R$^6$ are independently hydrogen or lower alkyl, or lower alkylene or lower alkenylene each optionally interrupted by said hetero atom-containing group;
Ring B is optionally substituted carbocycle or optionally substituted heterocycle;
$R^1$ is hydrogen, or an organic residue which is able to bind to the 5-position of oxazolidinone ring in oxazolidinone antimicrobial agent.

(13) The compound according to (12) or a pharmaceutically acceptable salt or solvate thereof wherein Ring A is (A-1) at least 7-membered monocyclic hetero ring containing at least three N atoms.

(14) The compound according to (12) or a pharmaceutically acceptable salt or solvate thereof wherein Ring A is (A-2) at least 6-membered monocyclic hetero ring containing at least two N atoms and at least one O atom.

(15) The compound according to (12) or a pharmaceutically acceptable salt or solvate thereof wherein Ring A is (A-3) at least 7-membered monocyclic hetero ring containing at least two N atoms and at least one S atom.

(16) The compound according to (12) represented by the formula:

[Chemical Formula 9]

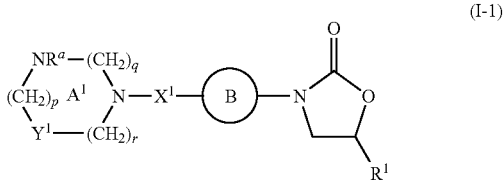
(I-1)

or a pharmaceutically acceptable salt or solvate thereof,
wherein
$Y^1$ is $NR^b$, O or S;
$R^b$ and $R^a$ are independently hydrogen or a substituent selected from Substituent Group S1, said Substituent Group S1 consists of optionally substituted lower alkyl, optionally substituted cycloalkyl, optionally substituted formyl, optionally substituted lower alkylcarbonyl, optionally substituted cycloalkylcarbonyl, optionally substituted lower alkyloxycarbonyl, optionally substituted arylcarbonyl, optionally substituted heterocyclecarbonyl, optionally substituted carbamoyl, lower alkylthiocarbonyl, cycloalkylthiocarbonyl, arylthiocarbonyl, optionally substituted lower alkylsulfonyl, optionally substituted phenylsulfonyl, optionally substituted aromatic heterocyclic group sulfonyl, optionally substituted aminosulfonyl, optionally substituted aryl, and optionally substituted heterocyclic group, or $R^a$ and $R^b$ are taken together with N atom to which they are attached to form optionally substituted heterocycle;

Ring $A^1$ may be substituted with a substituent other than $R^a$ and $R^b$;

p, q and r are independently an integer from 0 to 3, provided that $p+q+r \geq 4$ when $Y^1$ is $NR^b$ or S, $p+q+r \geq 3$ when $Y^1$ is O;

$X^1$ is a single bond, or a hetero atom-containing group selected from the group consisting of —O—, —S—, —$NR^2$—, —CO—, —CS—, —$CONR^3$—, —$NR^4CO$—, —$SO_2NR^5$—, and —$NR^6SO_2$— (wherein $R^2$, $R^3$, $R^4$, $R^5$ and $R^6$ are independently hydrogen or lower alkyl), or lower alkylene or lower alkenylene each optionally interrupted by said hetero atom-containing group;

Ring B is optionally substituted carbocycle or optionally substituted heterocycle;

$R^1$ is hydrogen, or an organic residue which is able to bind to the 5-position of oxazolidinone ring in oxazolidinone antimicrobial agent.

(17) The compound according to (16) or a pharmaceutically acceptable salt or solvate thereof wherein $Y^1$ is $NR^b$, $R^b$ is hydrogen or a substituent selected from Substituent Group S1 as defined above.

(18) The compound according to (16) or a pharmaceutically acceptable salt or solvate thereof wherein $R^a$ is hydrogen, $Y^1$ is $NR^b$, $R^b$ is hydrogen or a substituent selected from Substituent Group S1 as defined above.

(19) The compound according to (16) or a pharmaceutically acceptable salt or solvate thereof wherein $R^a$ is hydrogen or lower alkyl; $Y^1$ is $NR^b$, $R^b$ is hydrogen, optionally substituted lower alkyl, optionally substituted formyl, optionally substituted lower alkylcarbonyl, or optionally substituted carbamoyl.

(20) The compound according to (16) or a pharmaceutically acceptable salt or solvate thereof wherein p is 0; $Y^1$ is $NR^b$; $R^a$ and $R^b$ are taken together with their neighboring N atom to form optionally substituted heterocycle.

(21) The compound according to (16) or a pharmaceutically acceptable salt or solvate thereof wherein $Y^1$ is O.

(22) The compound according to (16) or a pharmaceutically acceptable salt or solvate thereof wherein $R^a$ is hydrogen, optionally substituted lower alkyl, optionally substituted formyl, optionally substituted lower alkylcarbonyl, or optionally substituted carbamoyl; $Y^1$ is O.

(23) The compound according to (16) or a pharmaceutically acceptable salt or solvate thereof wherein $Y^1$ is S.

(24) The compound according to (16) or a pharmaceutically acceptable salt or solvate thereof wherein $R^a$ is hydrogen or acyl; $Y^1$ is S.

(25) The compound according to (16) or a pharmaceutically acceptable salt or solvate thereof wherein p is 0; q+r=4.

(26) The compound according to (16) or a pharmaceutically acceptable salt or solvate thereof wherein p is 0; q=r=2.

(27) The compound according to (12) or (16) or a pharmaceutically acceptable salt or solvate thereof wherein $X^1$ is a single bond.

(28) The compound according to (12) or (16) or a pharmaceutically acceptable salt or solvate thereof wherein Ring B is optionally substituted benzene ring or optionally substituted 5- to 7-membered aromatic heterocycle.

(29) The compound according to (12) or (16) or a pharmaceutically acceptable salt or solvate thereof wherein Ring B is optionally substituted benzene ring.

(30) The compound according to (12) or (16) or a pharmaceutically acceptable salt or solvate thereof wherein Ring B is a benzene ring substituted with one or two halogen.

(31) The compound according to (12) or (16) or a pharmaceutically acceptable salt or solvate thereof wherein $R^1$ is optionally substituted aminomethylene or optionally substituted hydroxymethylene.

(32) The compound according to (12) or (16) or a pharmaceutically acceptable salt or solvate thereof wherein $R^1$ is substituted aminomethylene.

(33) The compound according to (12) or (16) or a pharmaceutically acceptable salt or solvate thereof wherein $R^1$ is —$CH_2NHCOR^7$ (wherein $R^7$ is optionally substituted lower alkyl, optionally substituted lower alkyloxy, cycloalkyl, optionally substituted heterocycle, lower alkylamino or optionally substituted phenyl), or —$CH_2NHCSR^8$ (wherein $R^8$ is optionally substituted lower alkyl, optionally substituted lower alkyloxy, cycloalkyl, optionally substituted heterocycle, lower alkylamino or optionally substituted phenyl).

(34) The compound according to (16) or a pharmaceutically acceptable salt or solvate thereof wherein $Y^1$ is $NR^b$; $R^b$ is hydrogen or a substituent selected from Substituent Group S1 as defined above; p is 0; q+r=4; $X^1$ is a single bond; Ring B is optionally substituted benzene ring or optionally substituted 5- to 7-membered aromatic heterocycle; $R^1$ is —$CH_2NHCOR^7$ wherein $R^7$ is optionally substituted lower alkyl or —$CH_2NHCSR^8$ wherein $R^8$ is optionally substituted lower alkyloxy; Ring $A^1$ may be substituted further with a substituent other than $R^a$ and $R^b$.

(35) The compound according to (16) or a pharmaceutically acceptable salt or solvate thereof wherein $R^a$ is hydrogen or lower alkyl; $Y^1$ is $NR^b$, $R^b$ is hydrogen or optionally substituted lower alkyl, optionally substituted formyl, optionally substituted lower alkylcarbonyl or optionally substituted carbamoyl; p is 0; q=r=2; $X^1$ is a single bond; Ring B is optionally substituted benzene ring; $R^1$ is —$CH_2NHCOR^7$ wherein $R^7$ is optionally substituted lower alkyl or —$CH_2NHCSR^8$ wherein $R^8$ is optionally substituted lower alkyloxy; Ring $A^1$ may be substituted further with a substituent other than $R^a$ and $R^b$.

(36) The compound according to (16) or a pharmaceutically acceptable salt or solvate thereof wherein $R^a$ is hydrogen or lower alkyl; $Y^1$ is $NR^b$, $R^b$ is optionally substituted lower alkyl, optionally substituted lower alkylcarbonyl or optionally substituted carbamoyl; p is 0; q=r=2; $X^1$ is a single bond; Ring B is optionally substituted benzene ring with one or two halogen; $R^1$ is —$CH_2NHCOR^7$ wherein $R^7$ is optionally substituted lower alkyl or —$CH_2NHCSR^8$ wherein $R^8$ is optionally substituted lower alkyloxy.

(37) The compound according to (36) or a pharmaceutically acceptable salt or solvate thereof wherein $R^b$ is —$COCH_2OH$, or —CONH— (optionally substituted heterocyclic group).

(38) The compound according to (16) or a pharmaceutically acceptable salt or solvate thereof wherein p is 0; q=r=2; $Y^1$ is $NR^b$, $R^a$ and $R^b$ are taken together with their neighboring N atom to form optionally substituted heterocycle; $X^1$ is a single bond; Ring B is optionally substituted benzene ring; $R^1$ is —$CH_2NHCOR^7$ wherein $R^7$ is optionally substituted lower alkyl, optionally substituted lower alkyloxy, cycloalkyl, optionally substituted heterocycle, lower alkylamino or optionally substituted phenyl or —CH$_2$NHCSR$^8$ wherein R$^8$ is optionally substituted lower alkyl, optionally substituted lower alkyloxy, cycloalkyl, optionally substituted heterocycle, lower alkylamino or optionally substituted phenyl; Ring A$^1$ may be substituted further with a substituent other than R$^a$ and R$^b$.

(39) The compound according to (16) or a pharmaceutically acceptable salt or solvate thereof wherein p is 0; q=r=2; Y$^1$ is NR$^b$, R$^a$ and R$^b$ are taken together with their neighboring N atom to form 5- or 6-membered optionally substituted heterocycle with oxo, and the other position on said heterocycle is optionally substituted or condensed; X$^1$ is a single bond; Ring B is optionally substituted benzene ring with one or two halogen; R$^1$ is —CH$_2$NHCOR$^7$ wherein R$^7$ is optionally substituted lower alkyl or —CH$_2$NHCSR$^8$ wherein R$^8$ is optionally substituted lower alkyloxy.

(40) The compound according to (39) or a pharmaceutically acceptable salt or solvate thereof wherein Ring A$^1$ is represented by the formula:

[Chemical Formula 10]

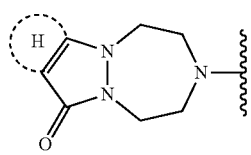

(A-1)

wherein Ring H is optionally substituted monocyclic heterocycle.

(41) The compound according to (16) or a pharmaceutically acceptable salt or solvate thereof wherein Y$^1$ is O; p is 0; q+r=4; X$^1$ is a single bond; Ring B is optionally substituted benzene ring or optionally substituted 5- to 7-membered aromatic heterocycle; R$^1$ is —CH$_2$NHCOR$^7$ wherein R$^7$ is optionally substituted lower alkyl, optionally substituted lower alkyloxy, cycloalkyl, optionally substituted heterocycle, lower alkylamino or optionally substituted phenyl or —CH$_2$NHCSR$^8$ wherein R$^8$ is optionally substituted lower alkyl, optionally substituted lower alkyloxy, cycloalkyl, optionally substituted heterocycle, lower alkylamino or optionally substituted phenyl; Ring A$^1$ may be substituted further with a substituent other than R$^a$ and R$^b$.

(42) The compound according to (16) or a pharmaceutically acceptable salt or solvate thereof wherein Y$^1$ is O; R$^a$ is hydrogen, optionally substituted lower alkyl, optionally substituted formyl, optionally substituted lower alkylcarbonyl, optionally substituted carbamoyl; p is 0; q=r=2; X$^1$ is a single bond; Ring B is optionally substituted benzene ring with one or two halogen; R$^1$ is —CH$_2$NHCOR$^7$ wherein R$^7$ is optionally substituted lower alkyl or —CH$_2$NHCSR$^8$ wherein R$^8$ is optionally substituted lower alkyloxy.

(43) The compound according to (42) or a pharmaceutically acceptable salt or solvate thereof wherein R$^a$ is —COCH$_2$OH, —CONH-(optionally substituted heterocyclic group), or CONHC(=NH)N(CH$_3$)$_2$.

(44) A pharmaceutical composition comprising the compound according to any one of (1) to (43) or a pharmaceutically acceptable salt or solvate thereof.

(45) An antimicrobial agent comprising the compound according to any one of (1) to (43) or a pharmaceutically acceptable salt or solvate thereof.

As presented by the formula (I), the oxazolidinone derivative is structurally characterized in that Ring A, which is at least 6-membered or 7-membered, preferably 7-membered heterocycle, binds to the N atom at position 3 of oxazolidinone ring via one carbocycle or heterocycle and an optional spacer.

In another preferred embodiment, the compound of the invention is characterized in that it has triazacycloheptane skeleton.

In further embodiment, the compound of the invention is characterized in that it has oxadiazepane skeleton wherein one N atom in the triazacycloheptane skeleton is replaced with O atom.

Effect of the Invention

The oxazolidinone derivative, triazacycloheptane derivative or oxadiazepane derivative of the invention is useful as a pharmaceutical active ingredient (e.g., antimicrobial) or a synthetic intermediate thereof. Also, the oxazolidinone derivative of the invention has a potent antimicrobial activity against gram-positive bacteria and gram-negative bacteria. Especially, the compound exhibits antimicrobial activity with wide spectrum against drug-resistant gram-positive bacteria, including methicillin-resistant *Staphylococcus aureus* (MRSA), vancomycin resistant *enterococcus* (VRE), penicillin resistant pneumococcus (PRSP). More preferably, the compound of the invention is effective against linezolid resistant (LZD-R) organisms. The compound of the invention more preferably shows good solubility or absorbability, which allows administration by injection. Still more preferably, the compound of the invention reduces the side-effects concerned in conventional antimicrobial agents (e.g., linezolid), such as bone marrow suppression, monoamine oxidase (MAO) inhibiting activity, neurotoxicity. Decreased MAO inhibition is preferred because side-effects such as metabolism suppression of dopamine, serotonin, etc., blood pressure elevation, agitation, etc. are concerned by such inhibition. Additionally, preferred compound of the invention also shows good profiles in pharmacokinetics such as CYP inhibition, PK profile, plasma stability.

Also, the compound of the invention, wherein triazacycloheptane skeleton or oxadiazepane skeleton is connected to quinolone skeleton, shows a potent antimicrobial activity against various bacteria. Especially, the compound shows antimicrobial activity equal to or more (e.g., more than 4 times) than commercial newquinolone antimicrobial drug (e.g., ciprofloxacin, gatifloxacin, moxifloxacin) against various bacteria including VRE (vancomycin resistant *enterococcus*), MRSA (methicillin-resistant *Staphylococcus aureus*).

Thus, by having triazacycloheptane skeleton, oxadiazepane skeleton or similar structure thereof as a partial structure, the compound of the invention remarkably improves its pharmaceutical activity, pharmacokinetics and/or side-effects and very useful as a pharmaceutical compound.

Also, a synthetic intermediate of the invention having triazacycloheptane skeleton, oxadiazepane skeleton is useful for the production of various pharmaceutical compounds including antimicrobial agent.

BEST MODE FOR CARRYING OUT THE INVENTION

The terms as used herein are described bellow. Each term, alone or in combination with another term, has the following meaning unless otherwise specifically indicated.

The substituent for the term "optionally substituted" in Substituent Group S1 is selected from amino, optionally substituted lower alkylamino, optionally substituted lower alkylcarbonylamino, halo, halogenated lower alkyl, halogenated lower alkoxy, lower alkyl, optionally substituted lower alkoxy, carboxy, oxo, hydroxy, lower alkoxycarbonyl, lower alkylcarbonyloxy, lower alkylcarbonylamino, optionally substituted phenylcarbonylamino, optionally substituted aryl, optionally substituted aryloxy, optionally substituted arylcarbonyl, optionally substituted aralkyl, optionally substituted aralkyloxy, optionally substituted heterocyclic group, optionally substituted heterocyclic lower alkyl, optionally substituted heterocyclocarbonyl, carbamoyl, lower alkyl carbamoyl, nitro, cycloalkyl and the like.

Examples of the substituent for optionally substituted aryl, optionally substituted aryloxy, optionally substituted arylcarbonyl, optionally substituted aralkyl, optionally substituted aralkyloxy, optionally substituted heterocyclic group, optionally substituted heterocyclic lower alkyl, and optionally substituted heterocyclocarbonyl include amino, nitro, lower alkylamino, halo, halogenated lower alkyl, halogenated lower alkoxy, lower alkyl, lower alkoxy, carboxy, oxo, hydroxy, lower alkylcarbonyl, lower alkoxycarbonyl, morpholino, carbamoyl, lower alkyl carbamoyl and the like.

The term "lower alkyl" refers to C1-C6 straight or branched monovalent hydrocarbon radical. For example, methyl, ethyl, n-propyl, isopropyl, n-butyl, isobutyl, sec-butyl, tert-butyl, n-pentyl, isopentyl, neo-pentyl, n-hexyl, isohexyl and the like.

The term "lower alkylene" refers to straight or branched C1-C6 alkylene and includes methylene, ethylene, trimethylene, propylene, tetramethylene, ethyl ethylene, pentamethylene, hexamethylene and the like.

The term "lower alkenylene" refers to straight or branched chain group of 2 to 6 carbon atoms having one or more double bond in the "lower alkylene" as defined above and includes, for example, vinylene, propenylene, butenylene and the like.

The term "carbocycle" refers to aryl, cycloalkyl or cycloalkenyl and includes cyclobutane, cyclopentane, cyclohexane, cycloheptane, benzene, naphthalene and the like. 5- to 7-membered ring is preferable, and 6-membered ring is especially preferable.

The term "heterocycle" and "heterocyclic group", as used herein, refers to a ring wherein a carbon atom in the above "carbocycle" is replaced with at least one hetero atom independently selected from N atom, oxygen atom or sulphur atom. For example, heteroaryl, heteroring, etc. are exemplified for this term.

The term "monocyclic heterocycle" refers to aromatic cyclic group or non-aromatic cyclic group containing at least one hetero atom selected from N atom, oxygen atom or sulphur atom in its ring.

The term "heteroaryl" refers to monocyclic aromatic heterocyclic group or condensed aromatic heterocyclic group. The monocyclic aromatic heterocyclic group refers to a group induced from a 5- to 8-membered aromatic ring that contains optionally one to four O, S, P and/or N atom in Ring And has a binding position at any substitutable position. The condensed aromatic heterocyclic group refers to a group wherein a 5- to 8-membered aromatic ring, which contains optionally one to four O, S, P and/or N atom in the ring, is condensed with one to four 5- to 8-membered aromatic carbocycle(s) or other 5- to 8-membered aromatic heteroring(s) and has a binding position at any substitutable position. Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazolyl-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl (e.g., 2-benzoxazolyl, 4-benzoxazolyl, 5-benzoxazolyl, 6-benzoxazolyl, 7-benzoxazolyl, 8-benzoxazolyl), quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazynyl (e.g., 1-phenazinyl, 2-phenazinyl) or phenothiazinyl (e.g., 1-phenothiazinyl, 2-phenothiazinyl, 3-phenothiazinyl, 4-phenothiazinyl), etc.

The term "heteroring" refers to a non-aromatic heterocyclic group which has at least one N, O and/or S atom in Ring And has a binding position at any substitutable position. The term "non-aromatic heterocyclic group" refers to a group containing one or more O, S or N atom, induced from a 5- to 7-membered non-aromatic ring or a condensed ring thereof wherein two or more such rings are condensed. Examples of "heterocycle" include 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl, etc. The term "non-aromatic heterocyclic group" may be saturated or unsaturated as far as it is non-aromatic.

The term "cycloalkyl" includes cycloalkyl of three to eight carbon atoms. Examples of "cycloalkyl" include cyclopropyl, cyclobutyl, cyclopentyl, cyclohexylyl, cycloheptyl and cyclooctyl.

The term "aryl" refers to monocyclic or condensed aromatic hydrocarbon. Examples of "aryl" include phenyl, 1-naphthyl, 2-naphthyl, anthryl and the like.

The term "an organic residue which is able to bind to the 5-position of oxazolidinone ring in oxazolidinone antimicrobial agent" for $R^1$ refers to any organic residue that can bind to the 5-position of the oxazolidinone ring of the oxazolidinone antimicrobial compound, which is known as disclosed in the patents listed above in the section "Background Art", capable of synthesis by those skilled in the art, or may be disclosed in the future. Examples of such organic residue include optionally substituted alkyl, optionally substituted cycloalkyl, optionally substituted alkenyl, optionally substituted cycloalkenyl, optionally substituted aryl, optionally substituted heteroaryl, —CN, optionally substituted carbamoyl, optionally substituted lower alkoxycarbonyl, optionally substituted amino and the like. Examples of the substituent for "optionally substituted" include optionally substituted amino, optionally substituted hydroxy, lower alkyl, lower alkenyl, lower alkynyl, lower alkoxy, lower alkylcarbonyl, lower alkylsulfonyloxy, halo, carboxy, halogenated lower alkyl, halogenated lower alkoxy, lower alkylcarbonyl, lower alkoxycarbonyl, carbamoyl, lower alkyl carbamoyl. Examples of the substituent for optionally substituted amino include —COR$^7$ or —CSR$^8$, lower alkylsulfonyl, lower alkylaminosulfonyl, lower alkyl, lower alkylcarbonylamino, as described bellow.

Preferably, R$^1$ is optionally substituted alkyl (substituents: optionally substituted amino, optionally substituted hydroxy, azido, halo, —NCS, etc.), more preferably, optionally substituted aminomethylene or optionally substituted hydroxymethylene, still more preferably, substituted aminomethylene, even more preferably —CH$_2$NHCOR$^7$ or —CH$_2$NHCSR$^8$. R$^7$ may be optionally substituted lower alkyl, optionally substituted lower alkoxy, cycloalkyl, optionally substituted heterocycle (preferably nitrogen-containing 5- to 7-membered ring), lower alkylamino, lower alkylsulfonyl or optionally substituted phenyl, preferably optionally substituted lower alkyl. Preferable substituent for said amino, lower alkyl, heterocycle or phenyl include halo, hydroxy, lower alkoxy, optionally substituted phenyl, optionally substituted phenyloxy, lower alkyl, carboxy, lower alkoxycarbonyl, lower alkylsulfonyl, preferably halo, hydroxy, lower alkoxy, more preferably halogen (e.g., F). Particular preferably, R$^7$ is lower alkyl optionally substituted with halogen (e.g., —CH$_3$, —CHF$_2$).

R$^8$ may be optionally substituted lower alkyl, optionally substituted lower alkyloxy, cycloalkyl, optionally substituted heterocycle (preferably nitrogen-containing 5- to 7-membered ring), lower alkylamino or optionally substituted phenyl, preferably, optionally substituted lower alkyloxy. Preferable substituent for said lower alkyloxy is halo, hydroxy, lower alkoxy, optionally substituted phenyl, optionally substituted phenyloxy, preferably halogen (e.g., F). More preferably, R$^8$ is lower alkyloxy (e.g., —OCH$_3$).

Examples of the substituent for optionally substituted hydroxymethylene include R$^7$.

Examples of "lower alkylcarbonyl" include acetyl, propionyl, butyryl, isobutyryl, valeryl, isovaleryl, pivaloyl, hexanoyl, octanoyl, methoxyethylcarbonyl, 2,2,2-trifluoroethylcarbonyl, ethoxycarbonylmethylcarbonyl and the like.

Examples of "cycloalkylcarbonyl" include cyclopropylcarbonyl, cyclohexylylcarbonyl and the like.

Examples of "lower alkyloxycarbonyl" include methyloxycarbonyl, ethyloxycarbonyl, n-propyloxycarbonyl, isopropyloxycarbonyl, n-butyloxycarbonyl, t-butyloxycarbonyl, n-pentyloxycarbonyl and the like.

Examples of "arylcarbonyl" include benzoyl, naphthylcarbonyl and the like.

In case where "optionally substituted carbocycle", "optionally substituted heterocycle", "optionally substituted lower alkyl", "optionally substituted lower alkylcarbonyl", "optionally substituted cycloalkylcarbonyl", "optionally substituted lower alkyloxy carbonyl", "optionally substituted arylcarbonyl", "optionally substituted heterocyclecarbonyl", "optionally substituted carbamoyl", etc. are substituted, it may be substituted at any position with same or different substituent selected from the following Substituent Group B. Substituent Group B includes, for example, hydroxy, carboxy, halogen (F, Cl, Br, I), haloalkyl (e.g., CF$_3$, CH$_2$CF$_3$, CH$_2$CCl$_3$, etc.), haloalkoxy (e.g., CF$_3$), alkyl (e.g., methyl, ethyl, isopropyl, tert-butyl, etc.), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy, etc.), alkenyloxy (e.g., vinyloxy, allyloxy, etc.), alkoxycarbonyl (e.g., methoxycarbonyl, ethoxycarbonyl, tert-butoxycarbonyl, etc.), carboxy, carboxamide, nitro, nitroso, optionally substituted amino (e.g., alkylamino (e.g., methylamino, ethylamino, dimethylamino, amino protected with amino protecting group, etc.), acylamino (e.g., acetylamino, benzoylamino, etc.), optionally substituted amide, aralkylamino (e.g., benzylamino, tritylamino), hydroxyamino, etc.), azido, aryl (e.g., phenyl, etc.), aralkyl (e.g., benzyl, etc.), cyano, isothiocyano, isocyanato, thiocyanato, isothiocyanato, mercapto, alkylthio (e.g., methylthio, etc.), alkylsulfonyl (e.g., methanesulfonyl, ethanesulfonyl), optionally substituted carbamoyl (e.g., alkylcarbamoyl such as methylcarbamoyl, ethylcarbamoyl, dimethylcarbamoyl, etc.), sulfamoyl, acyl (e.g., formyl, acetyl, etc.), formyl, formyloxy, haloformyl, oxalo, thioformyl, thiocarboxy, dithiocarboxy, thiocarbamoyl, sulfino, sulfo, sulfoamino, hydrazino, azido, ureido, amidino, guanidino, phthalimido, oxo, optionally substituted alkyl, lower alkoxy, optionally substituted oxazolidinone, and optionally substituted isoxazole or the substituents as disclosed in the following examples.

For "amino protecting groups", any amino protecting group well known in the art can be used, and preferably, it can be lower alkoxycarbonyl (e.g., t-butoxycarbonyl), optionally substituted aralkyloxy carbonyl (e.g., benzyl oxycarbonyl, p-nitrobenzyl oxycarbonyl), lower alkyl.

The first embodiment of the invention relates to a novel compound of the following formula, having 7-membered monocyclic hetero ring structure, preferably 1,2,5-triazacycloheptane (hereinafter referred to as "triazepane") or 1-oxa-2,5-diazacycloheptane (hereinafter referred to as "oxadiazepane"), i.e., triazepane derivative and oxadiazepane derivative:

[Chemical Formula 11]

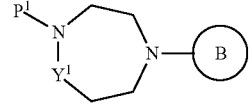

wherein
Y$^1$ is NP$^2$ or O, preferably N;
P$^1$ and P$^2$ are independently hydrogen, a substituent selected from Substituent Group S1 or an amino protecting group, or P$^1$ and P$^2$ are taken together with N atom to which they are attached to form optionally substituted heterocycle. P$^1$ and P$^2$ are preferably R$^a$ and R$^b$ as defined bellow for Compound (I).

Substituent Group S1 consists of optionally substituted lower alkyl, optionally substituted cycloalkyl, optionally substituted formyl, optionally substituted lower alkylcarbonyl, optionally substituted cycloalkylcarbonyl, optionally substituted lower alkyloxycarbonyl, optionally substituted arylcarbonyl, optionally substituted heterocyclecarbonyl, optionally substituted carbamoyl, lower alkylthio, cycloalkylthio, arylthio, optionally substituted lower alkylsulfonyl, optionally substituted phenylsulfonyl, optionally substituted aromatic heterocyclic group, optionally substituted aryl, and optionally substituted heterocyclic group.

Examples of each group are as described bellow for Compound (I).

Ring B is benzene ring optionally substituted or condensed, or optionally substituted heterocycle. The heterocycle means the heterocycle as defined above and may be monocyclic or condensed ring. When Ring B is benzene ring, it is represented preferably by the formula:

[Chemical Formula 12]

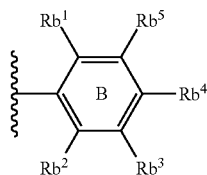

The substituents $Rb^1$ to $Rb^5$ are preferably selected from the group consisting of hydrogen, halo, nitro, amino, amino protected with an amino protecting group, optionally substituted amide, formyl, carboxyl, carboxamide, optionally substituted alkyl, lower alkoxy, optionally substituted oxazolidinone, optionally substituted isoxazole, lower alkyl, cycloalkyl, cycloalkyl lower alkyl, lower alkoxycarbonyl, lower alkylamino, optionally substituted aryl, and optionally substituted heterocyclic group.

In one preferred embodiment, any one or two of $Rb^1$, $Rb^2$, Rb and $Rb^5$ is halogen.

In one preferred embodiment, $Rb^4$ is nitro, amino, amino protected with an amino protecting group, or optionally substituted oxazolidinone.

In one preferred embodiment, $Rb^5$, $Rb^1$ and $Rb^2$ are $R^{10}$, $R^{11}$ and $R^{12}$ as defined bellow, respectively.

In one preferred embodiment, two substituents next to each other, such as $Rb^1$ and $Rb^5$, $Rb^5$ and $Rb^4$, $Rb^4$ and $Rb^3$ or $Rb^3$ and $Rb^2$, are taken together with neighboring carbon atoms to form optionally substituted monocyclic, preferably 4- to 7-membered, carbocycle or heterocycle. Said heterocycle has preferably one to three O, S, and/or N atom. More preferably, it has at least one N atom. Examples of the substituent for said carbocycle or heterocycle include substituents as described for $Rb^1$ to $Rb^5$, oxo, and substituents as described bellow for $R^{13}$, $R^{14}$ and $R^{15}$.

In one preferred embodiment, Ring B is the main backbone of the antimicrobial compound and includes, for example, quinoline ring, quinolone skeleton, β-lactams skeleton (e.g., cephem ring, cepham ring, carbapenem ring, carbapenam ring), glycopeptide skeleton (e.g., vancomycin, teicoplanin), macrolide skeleton (e.g., erythromycin, serotomycin, telithromycin), tetracycline skeleton, and benzene ring that binds to the oxazolidinone ring of oxazolidinone antimicrobial drugs (e.g., linezolid). By the connection of the 7-membered heterocycle structure to the main backbone of the compound, the antimicrobial compound of the invention can be improved in its antimicrobial activity and pharmacokinetics and reduced in its side-effect.

One preferred embodiment of the compound is represented by the following formula:

[Chemical Formula 13]

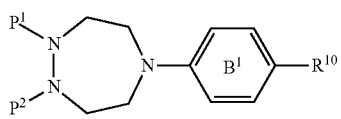

wherein
$P^1$ and $P^2$ are hydrogen, a substituent selected from Substituent Group S1 or an amino protecting group, or $P^1$ and $P^2$ are taken together with N atom to which they are attached to form optionally substituted heterocycle;
Ring $B^1$ is optionally substituted benzene ring with one or more halogen atom;
$R^{10}$ is $-NO_2$, $-NHP^3$, or other reactive functional group (e.g., $-OH$, $-COOR$ wherein R is hydrogen or a carboxy protecting group, $-SH$);
$P^3$ is hydrogen or an amino protecting group.

The above compound is useful as an intermediate for the production of oxazolidinone antimicrobial agent, particularly Compound (I) as described bellow.

When Ring B is a substituted quinoline ring, preferably a residue of quinolone antimicrobial compounds or newquinolone antimicrobial compounds, the compound is as represented bellow. Example of such quinolone or newquinolone antimicrobial compound include, for example, norfloxacin (NFLX), ofloxacin (OFLX), tosufloxacin (TFLX), fleroxacin (FLRX), ciprofloxacin (CPFX), sparfloxacin (SPFX), levofloxacin (LVFX), gatifloxacin (GFLX), pazufloxacin (PFLX). In this case, Ring B preferably binds at 7-position to the quinoline ring.

[Chemical Formula 14]

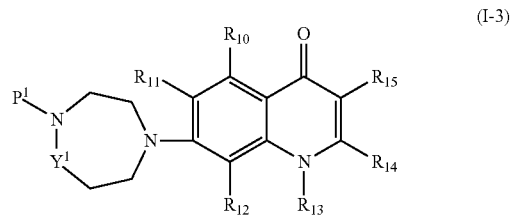

(I-3)

wherein
$Y^1$ is $NP^2$ or O, preferably $NP^2$;
$P^1$ and $P^2$ are independently hydrogen, a substituent selected from Substituent Group S1 or an amino protecting group, or $P^1$ and $P^2$ are taken together with N atom to which they are attached to form optionally substituted heterocycle.

More preferably, $P^2$ is hydrogen, $P^1$ is hydrogen, optionally substituted lower alkyl, optionally substituted lower alkylcarbonyl (Examples of substituent: hydroxy, lower alkoxy, acetyl, amino, lower alkylamino, halo, carboxy, carbamoyl, lower alkyl carbamoyl, heterocycle).
$R^{10}$ to $R^{15}$ are independently hydrogen, lower alkyl, cycloalkyl, cycloalkyl lower alkyl, halo, lower alkoxy, carboxy, lower alkoxycarbonyl, amino, lower alkylamino, optionally substituted aryl, or optionally substituted heterocyclic group; or $R^{12}$ and $R^{13}$ are taken together with adjacent atoms to form optionally substituted heterocycle preferably 5- or 6-membered (Example of substituent: lower alkyl, hydroxy, lower alkoxy, amino, lower alkylamino, cycloalkyl).

More preferably, $R^{10}$ is hydrogen, $R^{11}$ is halo, $R^{12}$ is lower alkoxy, $R^{13}$ is cycloalkyl, $R^{14}$ is hydrogen, $R^{15}$ is carboxy or lower alkoxycarbonyl.

The present invention also relates to a compound of the formula:

[Chemical Formula 15]

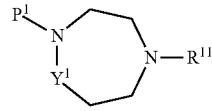

wherein
$Y^1$ is $NP^2$ or O;
$P^1$ and $P^2$ are independently hydrogen, acyl group or an amino protecting group;

$R^{11}$ is hydrogen, acyl group or an amino protecting group, provided that —CO(CH$_2$)$_3$—CO$_2$H, -Ph and —CH$_2$Ph (Ph: phenyl) are excluded.

Such compound is useful as an intermediate for the production of various compounds (e.g., antimicrobial agent, antivirus agent, antiobesity agent, CNS disease therapeutic agent, anti-inflammatory agent) that have 7-membered heterocycle moiety of the formula:

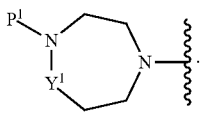

[Chemical Formula 16]

In another embodiment, the invention provides oxazolidinone derivatives of the formula:

[Chemical Formula 17]

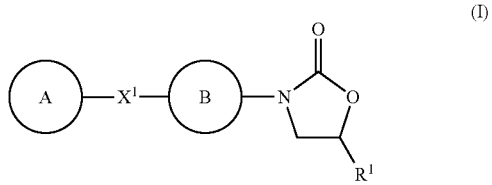

(I)

Embodiment 1

In one embodiment of the invention, Ring A of the formula I is at least 7-membered monocyclic heterocycle containing at least three nitrogen atoms, preferably a 7-membered monocyclic heterocycle containing three nitrogen atoms. The positions of these nitrogen atoms are not limited, and preferably, two N atoms are located in adjacent positions. Also, Ring A and $X^1$ may bind to each other at any position, and preferably, one N atom at Ring A connects to $X^1$. More preferably, following groups are exemplified.

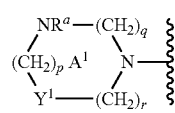

[Chemical Formula 18]

$Y^1$ is $NR^b$.

p, q and r are independently an integer from 0 to 3; p+q+r≥4 and preferably p+q+r=4. More preferably, p=0, q=r=2.

Ring $A^1$ may be substituted further with a substituent other than $R^a$ and $R^b$ (e.g., hydroxy, lower alkyl, lower alkoxy, halogen).

Still more preferably, Ring $A^1$ is represented by the formula:

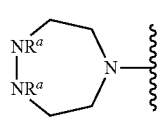

[Chemical Formula 19]

$R^b$ and $R^a$ are independently hydrogen or a substituent selected from Substituent Group S1, and preferably, one of which is hydrogen and the other is a substituent selected from Substituent Group S1, or both of which are substituent selected from Substituent Group S1.

Substituent Group S1 consists of optionally substituted lower alkyl, optionally substituted cycloalkyl, optionally substituted formyl, optionally substituted lower alkylcarbonyl, optionally substituted cycloalkylcarbonyl, optionally substituted lower alkyloxycarbonyl, optionally substituted arylcarbonyl, optionally substituted heterocyclecarbonyl, optionally substituted carbamoyl, lower alkylthiocarbonyl, cycloalkylthiocarbonyl, arylthiocarbonyl, optionally substituted lower alkylsulfonyl, optionally substituted phenylsulfonyl, optionally substituted aromatic heterocyclic group sulfonyl and optionally substituted aminosulfonyl.

Substituents for "optionally substituted" in Substituent Group S1 can be selected from amino, optionally substituted lower alkylamino, optionally substituted lower alkylcarbonylamino, halo, halogenated lower alkyl, lower alkyl, optionally substituted lower alkoxy (e.g., halogenated lower alkoxy), carboxy, oxo, hydroxy, lower alkoxycarbonyl, lower alkylcarbonyloxy, optionally substituted phenylcarbonylamino, optionally substituted aryl, optionally substituted aryloxy, optionally substituted arylcarbonyl, optionally substituted aralkyl, optionally substituted aralkyloxy, optionally substituted heterocyclic group, optionally substituted heterocyclic lower alkyl, optionally substituted heterocyclecarbonyl, carbamoyl, lower alkyl carbamoyl, nitro, cycloalkyl, etc.

Examples of the substituent for said optionally substituted aryl, optionally substituted aryloxy, optionally substituted arylcarbonyl, optionally substituted aralkyl, optionally substituted aralkyloxy, optionally substituted heterocyclic group, optionally substituted heterocyclic lower alkyl, optionally substituted heterocyclecarbonyl include amino, nitro, lower alkylamino, halo, halogenated lower alkyl, halogenated lower alkoxy, lower alkyl, lower alkoxy, carboxy, oxo, hydroxy, lower alkylcarbonyl, lower alkoxycarbonyl, morpholino and the like.

$R^a$ is preferably hydrogen or lower alkyl (e.g., methyl).

$R^b$ is preferably hydrogen, optionally substituted lower alkyl, optionally substituted formyl, optionally substituted lower alkylcarbonyl or optionally substituted carbamoyl, more preferably, optionally substituted lower alkyl, optionally substituted lower alkylcarbonyl, or optionally substituted carbamoyl.

Examples of the substituent for said optionally substituted lower alkyl include, preferably, hydroxy, lower alkoxy, carboxy, lower alkoxycarbonyl, lower alkylcarbonyloxy, amino, optionally substituted lower alkylamino, lower alkylcarbonylamino, cycloalkylcarbonylamino, hydroxyamino, lower alkoxyamino, halo, carbamoyl, lower alkyl carbamoyl, nitro, cycloalkyl, optionally substituted phenyl, optionally substituted phenyloxy, optionally substituted phenyl carbonyl, optionally substituted heterocyclic group (preferably 5- to 6-membered aromatic heterocyclic group), optionally substituted heterocylooxy, optionally substituted heterocyclocarbonyl and oxo. Examples of the substituent for said optionally substituted lower alkylamino include halo, hydroxy, lower alkoxy, amino, carboxy, optionally substituted heterocyclic group (preferably 5- to 6-membered aromatic heterocyclic group) and phenyl. Examples of the substituent for said optionally substituted phenyl or heterocyclic group include amino, halo, hydroxy, lower alkyl, lower alkoxy, carboxy, lower alkoxycarbonyl, lower alkylcarbonyloxy, nitro, and morpholino.

Examples of the substituent for said optionally substituted formyl include, preferably, optionally substituted amino, optionally substituted lower alkyloxy, optionally substituted lower alkyloxycarbonyl, carboxy, optionally substituted phenyl, optionally substituted phenyloxy, optionally substituted heterocyclic group (preferably 5- to 6-membered), optionally substituted heterocyclooxy (preferably 5- to 6-membered) and optionally substituted cycloalkyl. Examples of the substituent for said optionally substituted amino include hydroxy, lower alkoxy, lower alkoxycarbonyl, lower alkyl, optionally substituted heterocyclic group (substituents: lower alkyl, lower alkoxy, hydroxy, carboxy, amino, nitro, lower alkylamino, hydroxy lower alkyl; heterocyclic group is preferably 5- to 6-membered, more preferably aromatic heterocyclic group (e.g., triazole, tetrazole, pyridyl)), optionally substituted heterocyclic lower alkyl, mono- or di-lower alkylamino, $C(=NH)N(CH_3)_2$. Examples of the substituent for said optionally substituted lower alkyloxy include optionally substituted aryl (e.g., phenyl). Examples of the substituent for said optionally substituted phenyl or heterocyclic group include amino, halo, hydroxy, lower alkyl, lower alkoxy, carboxy, lower alkoxycarbonyl, lower alkylcarbonyloxy, nitro and morpholino. Examples of the substituent for said optionally substituted cycloalkyl include lower alkylcarbonyl, lower alkoxycarbonyl.

Examples of the substituent for said optionally substituted lower alkylcarbonyl include preferably hydroxy, optionally substituted lower alkoxy (substituents: halo, carboxy, hydroxy, optionally substituted phenyl or heterocyclic group (preferably 5- to 6-membered aromatic heterocyclic group)), cyano, amino, hydroxyamino, lower alkoxyamino, optionally substituted lower alkylamino (substituents: halo, carboxy, hydroxy, optionally substituted phenyl or heterocyclic group (preferably 5- to 6-membered aromatic heterocyclic group)), cycloalkylamino, lower alkylcarbonyloxy, lower alkoxycarbonyl, optionally substituted lower alkylcarbonylamino, optionally substituted phenylcarbonylamino, carboxy, halo, optionally substituted phenyl, optionally substituted phenyloxy, optionally substituted heterocyclic group (preferably 5- to 6-membered heterocyclic group), optionally substituted heterocyclooxy, carbamoyl, lower alkyl carbamoyl, lower alkylsulfonylamino and oxo, and preferably, hydroxy, amino, lower alkylcarbonylamino and optionally substituted phenylcarbonylamino. More preferably, examples of the substituent for said optionally substituted lower alkylcarbonyl include —$COCH_3$, —$COCH_2CH_3$, —$COCH_2OH$, —$COCH_2NH_2$, particular preferably —$COCH_2OH$. Examples of the substituent for said optionally substituted phenyl and optionally substituted heterocyclic group include amino, halo, hydroxy, lower alkyl, lower alkoxy, carboxy, lower alkoxycarbonyl, lower alkylcarbonyloxy, nitro, and morpholino.

Examples of the substituent for said "optionally substituted isoxazole", "optionally substituted heterocyclic group (preferably 5- or 6-membered)" include the groups as defined for $R^1$ in compound (I).

$R^a$ and $R^b$ can be taken together with N atom to which they are attached to form optionally substituted heterocycle, preferably 5- to 7-membered ring. Said heterocycle may be a condensed ring. Examples of substituents on such heterocycle include optionally substituted amino (e.g., lower alkylamino, acetylamino), halo, halogenated lower alkyl, halogenated lower alkoxy, lower alkyl, lower alkoxy, carboxy, oxo, hydroxy, optionally substituted, phenyl or heterocyclic group and the like. $R^a$ and $R^b$ are preferably taken together with N atom to which they are attached to form one or two 5- or 6-membered heterocycle D optionally substituted with oxo, wherein said heterocycle D is optionally substituted with the substituent R at another position. Said substituent R is selected from lower alkyl, lower alkenyl, lower alkynyl, lower alkoxy, cycloalkyl, optionally substituted, phenyl or heterocyclic group (preferably 5- to 6-membered aromatic heterocyclic group; examples of substituents: carboxy, amino, halo, lower alkoxy, halogenated lower alkyl), optionally substituted phenyl lower alkyl, optionally substituted heterocyclic lower alkyl, acyl, carboxy, lower alkoxycarbonyl, lower alkylsulfonyl, hydroxy, halo, amino, lower alkylamino, carbamoyl, lower alkyl carbamoyl, etc. Said heterocycle D is also optionally condensed with 5- to 6-membered carbocycle optionally substituted or heterocycle optionally substituted (e.g., Ring H as follows). Preferably, Examples of the substituent for said carbocycle or said heterocycle include carboxy, amino, optionally substituted acetylamino (substituents: carboxy, hydroxy, amino, morpholino), halogen. Preferably, in this case, Ring $A^1$ forms a condensed ring as follows:

[Chemical Formula 20]

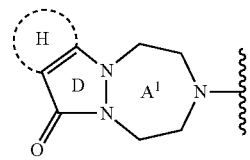
(A-1)

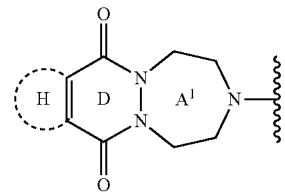
(A-2)

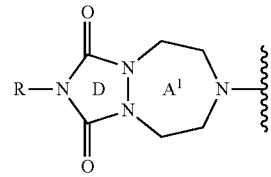
(A-3)

(A-4)

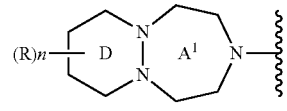
(A-5)

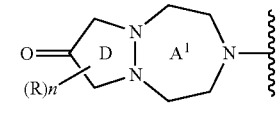
(A-6)

wherein Ring D is as defined above; Ring H is independently monocyclic heterocycle optionally substituted; R is a substituent as defined above; N is 1 or 2.

Preferably, Ring H is optionally substituted 5- to 6-membered ring, more preferably, aromatic hetero ring, still more preferably, a nitrogen-containing aromatic heterocycle (e.g., pyridine ring, pyrimidine ring, pyrazine ring). Examples of the substituent for said Ring H include lower alkyl, hydroxy, carboxy, lower alkoxy, amino, lower alkylamino, optionally substituted acetylamino (substituents: hydroxy, carboxy, amino, lower alkoxy), heterocyclic group carbonylamino (heterocycle is preferably 5- to 6-membered aliphatic ring).

Embodiment 2

In one embodiment of the invention, Ring A of the formula I is at least 6-membered monocyclic hetero ring that contains at least two nitrogen atoms and at least one oxygen atom, and preferably, 6-membered or 7-membered monocyclic hetero ring containing two nitrogen atoms and one oxygen atom. The positions of the nitrogen atom and oxygen atom are not limited, and preferably, one nitrogen atom and oxygen atom are located in adjacent positions. Also, Ring A may be connected to $X^1$ at any position, and preferably, one N atom at Ring A is connected to $X^1$. More preferably, following groups are exemplified.

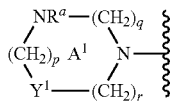

[Chemical Formula 21]

$Y^1$ is O, and the other variables are as defined above in Embodiment 1.

p, q and r are independently an integer from 0 to 3, p+q+r≥3, preferably p+q+r=3 or 4, more preferably 4. Still more preferably, p=0 and q=r=2.

Ring $A^1$ may be substituted further with a substituent other than $R^a$ (e.g., hydroxy, lower alkyl, lower alkoxy, halogen). Preferably, Ring $A^1$ is represented by the formula:

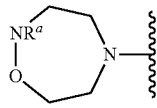

[Chemical Formula 22]

More preferably, $R^a$ is hydrogen, optionally substituted lower alkyl, optionally substituted cycloalkyl, optionally substituted formyl, optionally substituted lower alkylcarbonyl, optionally substituted cycloalkylcarbonyl, optionally substituted lower alkylthio, optionally substituted phenylthiourea, optionally substituted heterocyclic group thio (preferably 5- to 6-membered ring), optionally substituted lower alkylsulfonyl, optionally substituted phenylsulfonyl, —C(=NH)NH₂, optionally substituted aminothiocarbonyl, aminosulfonyl, or lower alkylaminosulfonyl, and preferably hydrogen or optionally substituted formyl.

Preferably, substituent for "optionally substituted" in $R^a$ is hydroxy, optionally substituted amino, carboxy, halo, optionally substituted lower alkoxy (substituents: hydroxy, carboxy, lower alkoxy, amino, halogen), cycloalkyl, lower alkylcarbonyl, lower alkoxycarbonyl, lower alkylcarbonylamino, optionally substituted or condensed heterocyclic group (preferably 5- to 6-membered cyclic group), optionally substituted or condensed heterocyclic group carbonyl, optionally substituted or condensed phenyl, optionally substituted or condensed phenylcarbonyl, optionally substituted or condensed phenyloxy. Examples of the substituent for said optionally substituted amino include optionally substituted lower alkyl (substituents: halo, carboxy, hydroxy, lower alkoxy, amino, imino, optionally substituted heterocyclic group (preferably 5- to 6-membered ring)), cycloalkyl, optionally substituted or condensed heterocyclic group (preferably 5- to 6-membered ring, condensed ring such as benzene ring), hydroxy, lower alkoxy, lower alkoxycarbonyl, lower alkylcarbonyl, optionally substituted phenyl carbonyl, and optionally substituted heterocyclecarbonyl. Examples of the substituent for said optionally substituted phenyl, optionally substituted heterocyclic group include hydroxy, lower alkoxy, lower alkoxycarbonyl, lower alkenyloxy, lower alkenyloxycarbonyl, amino, lower alkylamino, halo, carboxy, nitro, phenyl, heterocyclic group (preferably 5- to 6-membered ring), optionally substituted lower alkyl (substituents: hydroxy, amino, halo, carboxy).

Embodiment 3

In one embodiment of the invention, Ring A of the formula I is at least 7-membered monocyclic hetero ring containing at least two nitrogen atoms and at least one sulphur atom, preferably 7-membered monocyclic hetero ring containing two nitrogen atoms and one sulphur atom. The positions of these nitrogen atoms and sulphur atom are not limited, and preferably, one N atoms and S atom are located in adjacent positions. Also, Ring A may be connected to $X^1$ at any position, and preferably, one N atom at Ring A is connected to $X^1$. More preferably, following groups are exemplified.

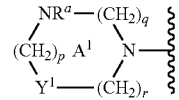

[Chemical Formula 23]

wherein $Y^1$ is S, and the other variables are as defined above in Embodiment 1.

p, q and r are independently an integer from 0 to 3, p+q+r≥4, preferably p+q+r=4. More preferably, p=0 and q=r=2.

Ring $A^1$ may be substituted further with a substituent other than $R^a$ (e.g., hydroxy, lower alkyl, lower alkoxy, halogen).

Preferably, Ring $A^1$ is represented by the following formula:

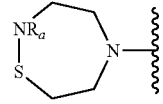

[Chemical Formula 24]

Examples of $R^a$ include groups as defined above in Embodiment 2, and more preferably, hydrogen, optionally substituted lower alkyl, or acyl (e.g., optionally substituted lower alkylcarbonyl; substituents is preferably hydroxy).

Further, the Ring A as defined above may be condensed with another ring.

In case where said Ring A is a condensed ring, it can be condensed with one to four 5- to 8-membered carbocycle (5- to 8-membered aromatic carbocycle) and/or other 5- to 8-membered heterocycle (optionally containing one to four O, S and/or N atom in the ring). For the ring to be condensed with. Ring A, 5- or 6-membered ring is preferred.

Examples of the substituent for said condensed ring include amino, lower alkylamino, halo, halogenated lower alkyl, halogenated lower alkoxy, lower alkyl, lower alkoxy, carboxy, oxo, hydroxy and the like.

More preferably, Compound (I) includes the following compounds.

[Chemical Formula 25]

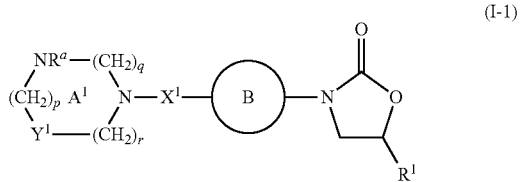

(I-1)

Ring $A^1$ is as defined above in Embodiments 1-3.

The followings describe about other variables in the structure.

$X^1$ is a single bond or any spacer moiety. Examples for such spacer include a hetero atom-containing group selected from the group consisting of —O—, —S—, —$NR^2$—, —CO—, —CS—, —$CONR^3$—, —$NR^4CO$—, —$SO_2NR^5$— and —$NR^6SO_2$— (wherein $R^2$ to $R^6$ are independently hydrogen or lower alkyl), or lower alkylene or lower alkenylene each optionally interrupted with said hetero atom-containing group. The position interrupted in said hetero atom-containing group is not limited, but it may be between carbon atoms that forms lower alkylene or lower alkenylene. Also, it may be interrupted between carbon atoms of lower alkylene or lower alkenylene and Ring $A^1$ or Ring B. The length of said hetero atom-containing group is not limited and preferably 1-3 atoms. More preferably, $X^1$ is a single bond. The lower alkylene is preferably C1-C3, the lower alkenylene is preferably C2-C3.

Ring B is optionally substituted carbocycle or optionally substituted heterocycle. Preferably, it can be optionally substituted carbocycle, more preferably 5- to 7-membered ring, particular preferably 6-membered ring, still more preferably optionally substituted benzene ring.

Examples of substituents for Ring B include amino, lower alkylamino, halo, halogenated lower alkyl, halogenated lower alkoxy, lower alkyl, lower alkoxy, carboxy, oxo, hydroxy and the like, and preferably halogen. Number of such substituent is preferably one to four, more preferably one to two.

In case where said Ring B is a heterocycle, it is preferably 5- to 7-membered ring, more preferably aromatic heterocycle (e.g., pyridine).

Preferably, Ring B is represented by the following formula:

[Chemical Formula 26]

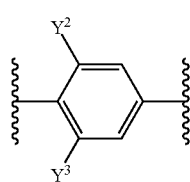

wherein $Y^2$ and $Y^3$ are independently hydrogen or halogen, preferably at least one of which is halo, more preferably both of which are halogen (e.g., F).

$R^1$ is as defined above, more preferably substituted aminomethylene, but various substituents other than these specific groups are promising in terms of the antimicrobial activity of the compound.

Preferred embodiments of Compound (I-1) are described bellow.

(1) $Y^1$ is $NR^b$; $R^b$ is hydrogen or a substituent selected from Substituent Group S1 as defined above; p is 0; q+r=4; $X^1$ is a single bond; Ring B is optionally substituted benzene ring or optionally substituted 5- to 7-membered aromatic heterocycle; $R^1$ is —$CH_2NHCOR^7$ ($R^7$ is optionally substituted lower alkyl) or —$CH_2NHCSR^8$ ($R^8$ is optionally substituted lower alkyloxy); Ring $A^1$ may be substituted with a substituent other than $R^a$ and $R^b$.

More preferably, (2) $R^a$ is hydrogen or lower alkyl; $Y^1$ is $NR^b$, $R^b$ is hydrogen or optionally substituted lower alkyl, optionally substituted formyl or optionally substituted lower alkylcarbonyl; p is 0; q=r=2; $X^1$ is a single bond; Ring B is optionally substituted benzene ring (substituent is preferably one or two halogen); $R^1$ is —$CH_2NHCOR^7$ (wherein $R^7$ is optionally substituted lower alkyl) or —$CH_2NHCSR^8$ (wherein $R^8$ is optionally substituted lower alkyloxy); Ring $A^1$ may be substituted with a substituent other than $R^a$ and $R^b$.

More preferably, examples of $R^b$ include hydrogen, optionally substituted lower alkyl (preferably, substituent is selected from hydroxy, lower alkoxy, carboxy, lower alkoxycarbonyl, amino, optionally substituted lower alkylamino, halo, carbamoyl, lower alkyl carbamoyl, nitro, cycloalkyl, optionally substituted phenyl or optionally substituted heterocyclic group, and more preferably, hydroxy, lower alkoxy, carboxy, and still more preferably, hydroxy), and optionally substituted formyl (preferably, substituent is optionally substituted amino, optionally substituted lower alkyloxy, carboxy, optionally substituted phenyl, or optionally substituted heterocyclic group (preferably 5- to 6-membered; such as oxadiazol, isoxazole, triazole, tetrazole)).

Still more preferably, (3) $R^b$ is —$COCH_2OH$, —CONH-(optionally substituted heterocyclic group, preferably 5- to 6-membered ring), or optionally substituted lower alkyloxy carbonyl.

In another preferred embodiment, (4) $R^a$ and $R^b$ are taken together with N atom to which they are attached to form optionally substituted or condensed heterocycle, preferably 5- to 7-membered ring; p is 0; q+r=4; $X^1$ is a single bond; Ring B is optionally substituted benzene ring or optionally substituted 5- to 7-membered aromatic heterocycle, preferably optionally substituted benzene ring (substituent: halogen); $R^1$ is —$CH_2NHCOR^7$ (wherein $R^7$ is optionally substituted lower alkyl), or —$CH_2NHCSR^8$ (wherein $R^8$ is optionally substituted lower alkyloxy); Ring $A^1$ may be substituted with a substituent other than $R^a$ and $R^b$.

More preferably, $R^a$ and $R^b$ are, as defined above, taken together with their neighboring N atoms to form 5- or 6-membered heterocycle D optionally substituted with one or two oxo, wherein said heterocycle D is optionally substituted at other position. In this case, Ring $A^1$ forms a heterocycle as represented above by the formulae (A-1) to (A-6), more preferably the formula (A-1). Ring H is, as defined above, preferably optionally substituted 5- to 6-membered ring, more preferably aromatic hetero ring, still more preferably nitrogen-containing aromatic hetero ring (e.g., pyridine ring, pyrimidine ring, pyrazine ring).

In still another preferred embodiment, (5) $Y^1$ is O; p is 0; q+r=4; $X^1$ is a single bond; Ring B is optionally substituted benzene ring or optionally substituted 5- to 7-membered aromatic heterocycle, more preferably optionally substituted benzene ring; $R^1$ is —$CH_2NHCOR^7$ wherein $R^7$ is optionally substituted lower alkyl or —$CH_2NHCSR^8$ wherein $R^8$ is optionally substituted lower alkyloxy; Ring $A^1$ may be substituted with a substituent other than $R^a$ and $R^b$.

(6) $Y^1$ is O; $R^a$ is hydrogen, optionally substituted lower alkyl, optionally substituted cycloalkyl, optionally substituted formyl, optionally substituted lower alkylcarbonyl; p is 0; q=r=2; $X^1$ is a single bond; Ring B is benzene ring optionally substituted with one or two halogen; $R^1$ is —CH$_2$NHCOR$^7$ wherein $R^7$ is optionally substituted lower alkyl or —CH$_2$NHCSR$^8$ wherein $R^8$ is optionally substituted lower alkyloxy.

Preferably, substituent for optionally substituted formyl is optionally substituted amino. Substituent for optionally substituted lower alkylcarbonyl is preferably hydroxy.

More preferably, $R^a$ is —COCH$_2$OH, —CONH-(optionally substituted heterocyclic group, preferably 5- to 6-membered ring), —CONHC(=NH)N(CH$_3$)$_2$, or optionally substituted lower alkyloxy carbonyl.

Compound (I) is particularly characterized in Ring A, which can contributes to improvement of antimicrobial activity, water solubility, pharmacokinetics, safety, etc.

The compound s of the invention can be prepared according to the procedure as shown in Scheme I and II. Reagents and conditions used in the reaction can be selected appropriately by those skilled in the art, for example, according to the description in Japanese Patent Publication NO. 7-508665.

Scheme I

[Chemical Formula 27]

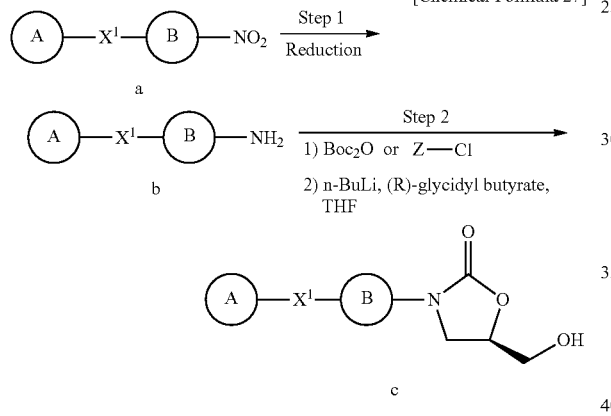

wherein Ring A, $X^1$ and Ring B are as defined above, Ph is phenyl group, MS is methanesulfonyl group, Z is benzyloxycarbonyl group.

In Step 1, the nitro group of Compound a is reduced to obtain Compound b according to an appropriate reduction method such as for example hydrogenation reduction with a catalyst such as platinum oxide, Raney nickel, palladium carbon or the like, or a reaction method using iron powder with hydrochloric acid, acetic acid or the like. Compound a is commercially available or can be prepared easily by those skilled in the art from reagent commercially available.

In Step 2, Compound b is urethanated in an appropriate organic solvent with di-tert-butyl dicarbonate or urethanated with benzyloxycarbonyl chloride in the presence of a base such as triethylamine, potassium carbonate, sodium carbonate, sodium hydrogen carbonate, etc., in water or an organic solvent such as acetone, methanol, tetrahydrofuran or a combined solvent thereof. Then, it is treated with a base such as n-butyllithium in an appropriate aprotic organic solvent, such as tetrahydrofuran, N,N-dimethylformamide,
at a temperature in a range from −78° C. to the reflux temperature of the solvent, and followed by reacted with glycidyl butyrate to obtain Compound C.

Additionally, Compound C obtained in the above Scheme I may be further converted to Compound g according to the following Scheme II.

Scheme II

[Chemical Formula 28]

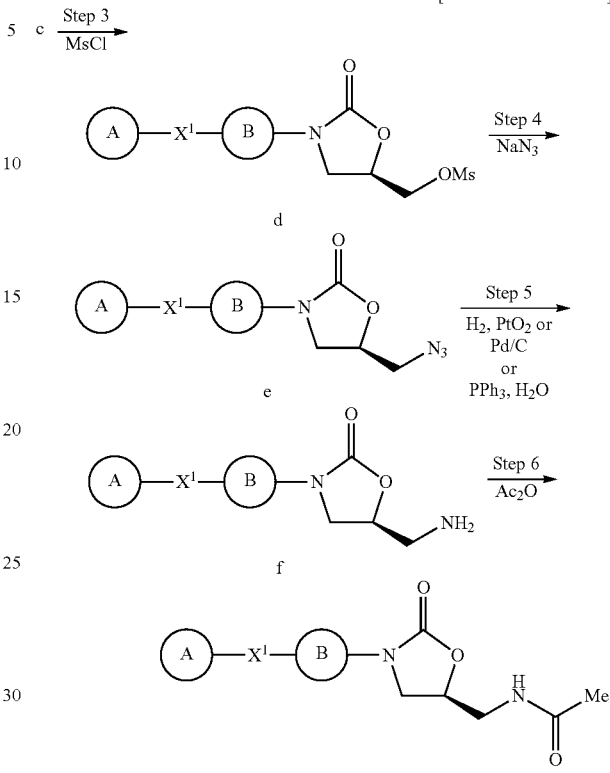

In Step 3, Compound c is reacted with methanesulfonyl chloride in the presence of a base such as triethylamine in an organic solvent, such as dichloromethane, tetrahydrofuran, etc., at a temperature in a range of under ice cooling to the reflux temperature of the solvent to obtain Compound d.

In Step 4, Compound d is reacted with sodium azide in an organic solvent, such as tetrahydrofuran, N,N-dimethylformamide, etc., at a temperature in a range of under ice cooling to the reflux temperature of the solvent to obtain Compound e.

In Step 5, the azido group of Compound e is reduced according to an appropriate reduction method, for example a hydrogenation reduction method using a catalyst such as platinum oxide, palladium carbon or the like, to obtain Compound f.

In Step 6, Compound f is acylated with an appropriate anhydrous acid such as acetic anhydride in a basic solvent such as pyridine to obtain Compound g.

Optionally, the compound as obtained above may further be modified with any substituent at 5-position of the oxazolidinone ring to obtain various oxazolidinone derivatives. Also, Ring A, Ring B, and $X^1$ moiety may further be modified. Such modification is within a level of those skilled in the art and is readily practiced by those skilled in the art.

In case where any intermediate has a group reactive during reaction (e.g., —OH, —NH$_2$, —COOH) in the above synthesis, such group can be protected appropriately before the reaction. For example, it may be protected with an appropriate protecting group, such as t-butoxycarbonyl group, benzyloxycarbonyl group, and then readily removed thereafter at an appropriate time, according to Greene, T. W., Wuts, P. G. M., "Protective Groups in Organic Synthesis", 2nd ed.; John Wiley & Sons: New York (1991).

The present invention also provides a pharmaceutical composition comprising a compound of the invention or a pharmaceutically acceptable salt thereof or a hydrate thereof as an active ingredient. Based on the antimicrobial activity of the compound, examples of such pharmaceutical composition include antimicrobial drugs. When the compound of the invention is used in a treatment, the compound, a salt thereof or solvate thereof is administered to an animal, including human, which is affected with infection in a therapeutically effective amount. Route for administration may be oral or parenteral. For this purpose, the compound of the invention or a salt thereof is combined with a pharmaceutically acceptable carrier, diluent or excipient and incorporated into a capsule or compressed to a tablet. Alternatively, the composition may be in a dosage form such as powder or granule. For parenteral administration, it is formulated into an aqueous solution or suspension suitable for subcutaneous injection, intravenous injection, intraperitoneal injection, intramuscular injection, etc. Also, the composition can be provided as suppositories, topical formulations, eye-drops and the like. Examples of pharmaceutically acceptable salts of the compound of the invention include salt or intra-molecular salts with inorganic bases, ammonia, organic bases, inorganic acids, organic acids, basic amino acids, halogen ions, etc. Examples of said inorganic base include alkali metals (Na, K, etc.), alkaline earth metals (Ca, Mg, etc.). Examples of the organic base include trimethylamine, triethylamine, choline, procaine, ethanolamine, etc. Examples of the inorganic acid include hydrochloric acid, hydrobromic acid, sulphuric acid, nitric acid, phosphoric acid and the like. Examples of organic acid include p-toluenesulphonic acid, methanesulphonic acid, formic acid, trifluoro acetate, maleic acid and the like. Examples of basic amino acid include lysine, arginine, ornithine, histidine and the like. The above salts may be a solvate.

Oral administration can be practiced in a solid or liquid dose form prepared according to a conventional method, such as tablet, powder, capsule, granule, suspension, solution, syrup, lozenge, sublingual tablet and other dosage forms. If necessary, unit dosage form for oral administration can be microcapsulated. Also, such formulation can be applied with a coating or embedded into polymer or wax, in order to prolong the duration of activity or provide sustained release.

Parenteral administration can be practiced in a liquid dosage form prepared according to a conventional method, such as an injectable solution and suspension. Among others, oral administration and intravenous administration by injection are preferred. For administration, of course, it should be practiced in a dosage form suitable for such administration.

Preferable dose for oral administration is generally about 10 mg to 4000 mg, preferably 100 mg to 2000 mg per day. For parenteral administration, preferable dose is about 10 mg to 4000 mg, preferably 50 mg to 2000 mg per day.

While the following Examples, Test Examples and Formulation Examples describe further the present invention, the invention should not be limited to these Examples, Test Examples and Formulation Examples. Accordingly, one skilled in the art could readily prepare any compound of the invention by selecting appropriately starting materials, reagents and conditions in a reaction, with referring to, and with any modification if necessary, to the above general description and the following Examples.

Abbreviations used in Preparations and Examples have the following meanings.

Ac=acetyl group, Et=ethyl group, Me=methyl group, Ph=phenyl group, Boc=t-butoxycarbonyl group, Cbz=benzyloxycarbonyl group, Bn=benzyl group.

Example 1

Preparation of Compounds 12 and 13

[Chemical Formula 29]

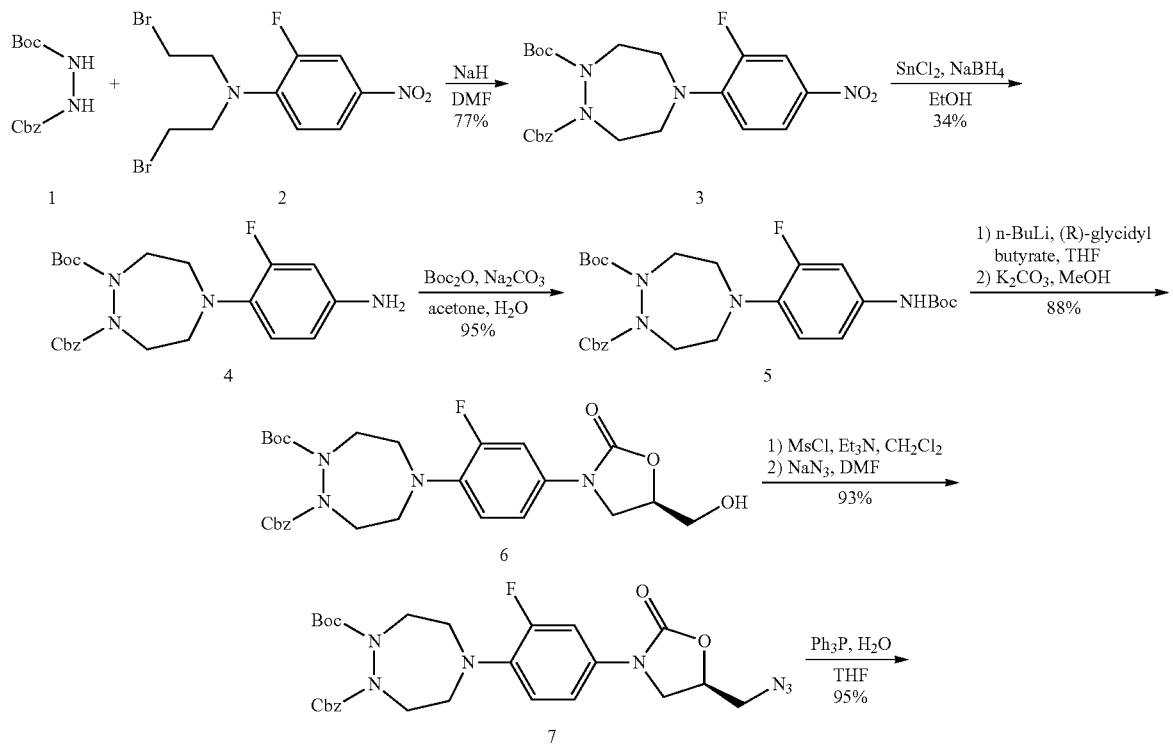

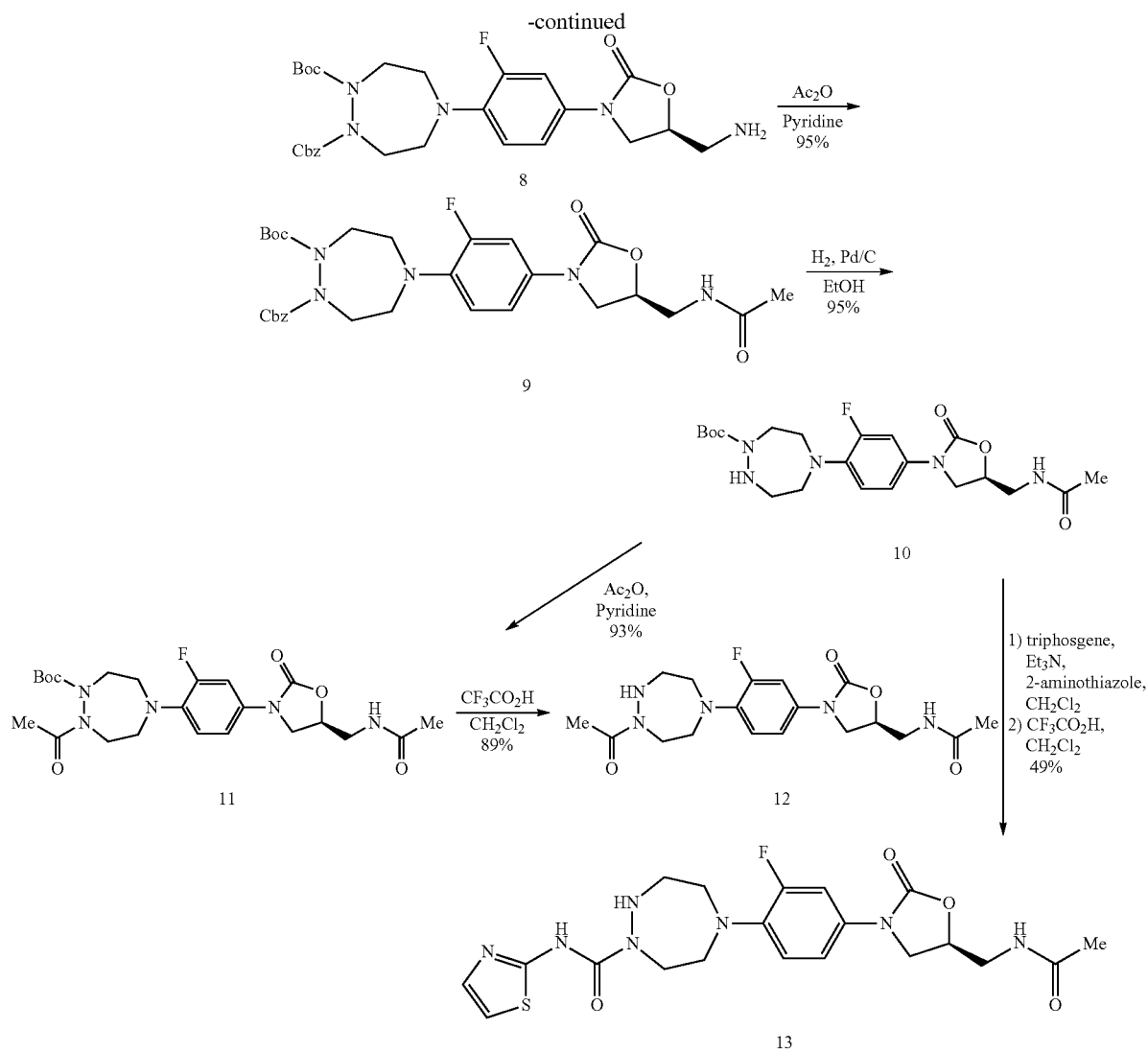

a. Compound 3

An eggplant-shape flask was charged with NaH (60% in mineral oil; 1.2714 g, 31.79 mmol) and washed three times with n-hexane (5 cm³×3). After residual n-hexane was removed under reduced pressure, dimethylformamide (50 cm³) was added. Compound 1 (3.6313 g, 13.64 mmol) was added at room temperature and then stirred for 30 minutes at this temperature. Compound 2 (5.6310 g, 15.22 mmol) was then added dropwise at room temperature and stirred for 20 minutes at this temperature. The mixture was poured into water (200 cm³), followed by added with ethyl acetate (100 cm³) for separation, and extracted twice with ethyl acetate, washed once with water and once with saturated aqueous sodium chloride, and dried over anhydrous sodium sulfate. After the drying reagent was filtered out, solvent was concentrated in vacuo. The residue was purified by silica gel column chromatography (BW-200, 120 g, eluant: from 20%→40% ethyl acetate/n-hexane) to afford Compound 3 (4.9678 g, 10.47 mmol). Yield: 77%.

$^1$H NMR (CDCl$_3$) δ=1.32-1.48 (9H, t-Bu), 3.21-4.32 (8H), 5.03-5.25 (2H, m, CH$_2$Ph), 6.74-6.85 (1H, m), 7.22-7.42 (5H, m), and 7.84-7.95 (2H, m).

b. Compound 4

Compound 3 (4.9678 g, 10.47 mmol) was dissolved in ethanol (200 cm³), SnCl$_2$.2H$_2$O (13.0278 g, 57.73 mmol) was added. The mixture was heated to 80-90° C. and stirred for two hours. At the same temperature, NaBH$_4$ (0.2778 g, 7.34 mmol) was dissolved in ethanol (10 cm³), and the solution was added slowly dropwise and stirred for additional one hour. After about two-thirds of ethanol was removed, saturated aqueous sodium hydrogen carbonate was added carefully until any effervescent is not occurred. The mixture was extracted four time with ethyl acetate, washed with saturated aqueous sodium chloride, and dried over anhydrous sodium sulfate. The drying reagent was filtered out, solvent was concentrated in vacuo. The residue was purified by silica gel column chromatography (BW-200.80 g, eluant: 10%→20%→50%→100% ethyl acetate/n-hexane) to afford Compound 4 (1.6021 g, 3.60 mol). Also, the compound, wherein the Boc-group has been removed, was obtained (M=344.38, 1.6304 g, 4.73 mmol, 45%). Yield: 34%.

$^1$H NMR (CDCl$_3$) δ=1.32-1.50 (9H, Boc), 3.00-3.58 (8H, m), 3.90-4.24 (2H, m), 5.05-5.30 (2H, m, CH$_2$Ph), 6.30-6.45 (2H, m), 6.72-6.82 (1H, m), and 7.28-7.37 (5H, m, CH$_2$Ph).

c. Compound 5

Compound 4 (1.6021 g, 3.60 mmol) was dissolved in methanol (20 cm$^3$), and sodium carbonate (0.5856 g, 5.53 mmol) and Boc$_2$O (1.1708 g, 5.36 mmol) was added. The mixture was stirred for 17 hours at room temperature. The mixture was separated with addition of Water (30 cm$^3$) and ethyl acetate (50 cm$^3$), followed by washed twice with ethyl acetate, and dried over anhydrous sodium sulfate. The drying reagent was filtered out, solvent was concentrated in vacuo. The residue was purified by silica gel column chromatography (BW-200, 50 g, eluant: 10%→20%→30% ethyl acetate/n-hexane) to afford Compound 5 (1.8683 g, 3.43 mmol). Yield: 95%.

$^1$H NMR (CDCl$_3$) δ=1.34-1.52 (18H, Boc), 3.10-3.52 (6H, m), 3.95-4.28 (2H, m), 5.05-5.29 (2H, m, CH$_2$Ph), 6.38 (1H, brs, NHBoc), 6.77-6.89 (2H, m), and 7.21-7.36 (6H, m).

d. Compound 6

Compound 5 (1.8683 g, 3.43 mmol) in dried tetrahydrofuran (20 cm$^3$) was subjected to aryl substitution and cooled to −78° C. To this solution, n-BuLi (1.54 M in n-hexane; 2.5 cm$^3$, 3.85 mmol) was added slowly dropwise, and then stirred at the temperature for 10 min. (R)-glycidylbutyrate (0.6084 g, 4.22 mmol) dissolved in dried tetrahydrofuran (3 cm$^3$) was added slowly dropwise, and the mixture was cooled to room temperature and stirred for 20 minutes. water (30 cm$^3$) was added, and the mixture was extracted five times with ethyl acetate and dried over anhydrous sodium sulfate. After filtration, solvent was removed to obtain the residue (2.2370 g). The residue was dissolved in methanol (20 cm$^3$), added with potassium carbonate (5.0776 g, 36.74 mmol) and stirred for 6 hours at room temperature. Water (30 cm$^3$) was added, and the mixture was extracted five times with ethyl acetate and dried over anhydrous sodium sulfate. The drying reagent was filtered out, and solvent was concentrated in vacuo. The residue was purified by silica gel column chromatography (BW-200.30 g, eluant: 50%→100% ethyl acetate/n-hexane→2% methanol/dichloromethane) to afford Compound 6 (1.5838 g, 3.01 mmol). Yield: 88%.

$^1$H NMR (CDCl$_3$) δ=1.34-1.47 (9H, Boc), 2.59 (1H, br, OH), 3.16-3.40 (6H, m), 3.70-3.82 (1H, m), 3.89-4.27 (5H, m), 4.68-4.78 (1H, m, CH$_2$CHCH$_2$OH), 5.06-5.30 (2H, m, CH$_2$Ph), 6.83-6.93 (1H, m), 7.02-7.13 (1H, m), and 7.27-7.46 (6H, m).

e. Compound 7

A solution of Compound 6 (1.5834 g, 3.01 mmol), triethylamine (0.65 cm$^3$, 4.62 mmol) and dried dichloromethane (30 cm$^3$), which has been cooled to 0° C. and diluted with dried dichloromethane (3 cm$^3$), was added dropwise with methanesulfonyl chloride (0.3 cm$^3$, 3.88 mmol) and stirred for 20 minutes at 0° C. Saturated aqueous NaHCO$_3$ (50 cm$^3$) was added, and the mixture was extracted three times with trichloromethane and dried over anhydrous sodium sulfate. After filtration, solvent was removed to obtain the residue (1.9525 g). The residue was dissolved in dimethylformamide (15 cm$^3$), which was added with sodium azide (0.5870 g, 9.03 mmol) and stirred for two hours at 80 to 90° C. Water (50 cm$^3$) was added, the mixture was extracted three times with ethyl acetate. The organic layer was washed sequentially with water and saturated aqueous sodium chloride, and dried over anhydrous sodium sulfate. After filtration, After filtration, solvent was removed to obtain the residue. Purification by silica gel column chromatography (BW-200.40 g, eluant: 25%→30%→50% ethyl acetate/n-hexane) afforded Compound 7 (1.5894 g, 2.79 mmol). Yield: 93%.

$^1$H NMR (CDCl$_3$) δ=1.34-1.47 (9H, Boc), 3.18-4.28 (12H, m), 4.73-4.83 (1H, m, CH$_2$CHCH$_2$N$_3$), 5.06-5.28 (2H, m, CH$_2$Ph), 6.85-6.93 (1H, m), 7.02-7.13 (1H, m), and 7.28-7.45 (6H, m).

f. Compound 8

Compound 7 (1.5894 g, 2.79 mmol) was dissolved in tetrahydrofuran (20 cm$^3$), followed by added with triphenylphosphine (1.1128 g, 4.240 mmol) and water (1 cm$^3$) at room temperature, and the mixture was stirred for 16 hours at room temperature and for two hours at about 60° C. After confirming the consumption of the starting material, Solvent was removed, and the residue was then purified by silica gel column chromatography (BW-200.30 g, eluant: ethyl acetate→5%→15% methanol/trichloromethane) to afford Compound 8 (1.4394 g, 2.65 mmol). Yield: 95%.

$^1$H NMR (CDCl$_2$) δ=1.34-1.48 (9H, Boc), 2.95 (1H, dd, J=5.8, 13.7 Hz), 3.11 (1H, dd, J=4.0, 13.7 Hz), 3.16-3.59 (6H, m), 3.76-3.84 (1H, m), 3.94-4.27 (3H, m), 4.62-4.72 (1H, m, CH$_2$CHCH$_2$N$_3$), 5.06-5.29 (2H, m, CH$_2$Ph), 6.84-6.92 (1H, m), 7.03-7.14 (1H, m), and 7.25-7.48 (6H, m).

g. Compound 9

Compound 8 (1.4394 g, 2.65 mmol) was dissolved in pyridine (20 cm$^3$), and followed by added with acetic anhydride (2.0 cm$^3$) and stirred for 1 hour at room temperature. Solvent was removed, and the residue was purified by silica gel column chromatography (BW-200.30 g, eluant: 0%→3%→5% methanol/trichloromethane) to afford Compound 9 (1.4769 g, 2.52 mmol). Yield: 95%.

h. Compound 10

Compound 9 (1.1139 g, 1.902 mmol) was dissolved in 5% ethanol (50 cm$^3$), followed by added with 10% Pd/C (0.2073 g) for H$_2$ Substitution carefully, and then the mixture was stirred at room temperature for 90 hours. After filtration through celite, Solvent was removed, and the residue was then purified by silica gel column chromatography (BW-200.30 g, eluant: 0%→2%→4% methanol/trichloromethane) to afford Compound 10 (0.8159 g, 1.807 mmol). Yield: 95%

$^1$H NMR (CDCl$_3$) δ=1.38 (9H, brs, Boc), 2.03 (3H, s, ac), 3.08-3.16 (2H, m), 3.40-3.48 (2H, m), 3.53-3.77 (8H, m), 4.00 (1H, t, J=9.0 Hz), 4.72-4.81 (1H, m), 6.45 (1H, brs, NHAc), 6.87 (1H, t, J=9.0 Hz), 6.99 (1H, dd, J=2.4, 9.0 Hz), and 7.36 (1H, dd, J=2.4, 15.1 Hz).

i. Compound 11

Compound 10 (0.2016 g, 0.477 mmol) was dissolved in pyridine (5 cm$^3$), followed by added with acetic anhydride (3 cm$^3$) and stirred for 18 hours room temperature. Solvent was removed, and the residue was then purified by silica gel column chromatography (BW-200.15 g, eluant: 50%→100% ethyl acetate/n-hexane→4% methanol/trichloromethane) to afford Compound 11 (0.2055 g, 0.416 mmol). Yield: 93%.

$^1$H NMR (CDCl$_3$) δ=1.48 (9H, s, Boc), 2.03 (3H, s, NHAc), 2.05 (3H, s, NNAc), 3.08-3.78 (10H, m), 4.01 (1H, dt, J=3.0, 9.1 Hz), 4.25-4.40 (1H, m), 4.72-4.82 (1H, m), 6.08 (1H, t, J=6.0 Hz, NHAc), 6.89 (1H, t, J=9.1 Hz), 7.05 (1H, br d, J=9 Hz), and 7.40 (1H, dd, J=2.5, 14.6 Hz).

j. Compound 12

Compound 11 (0.1462 g, 0.296 mmol) was dissolved in dichloromethane (5 cm$^3$), followed by added with trifluoroacetic acid (1 cm$^3$) and stirred at room temperature for two hours. Saturated aqueous potassium carbonate was added to adjust to neutral pH, and followed by extracted five times with trichloromethane. After dryness over anhydrous sodium sulfate, the drying reagent was filtered out and solvent was remove. The residue was purified by silica gel column chromatography (BW-200.15 g, eluant: 0%→5%→10% methanol/trichloromethane) to afford Compound 12 (0.1034 g, 0.263 mmol). Yield: 89%.

$^1$H NMR (CDCl$_3$) δ=1.97 (3H, s, NNAc), 2.03 (3H, s, NHAc), 3.06-3.14 (1H, m), 3.16-3.23 (1H, m), 3.34-3.44 (3H, m), 3.54-3.80 (6H, m), 3.88-3.94 (1H, m), 4.01 (1H, t, J=8.8 Hz), 4.72-4.81 (1H, m), 6.08-6.16 (1H, br), 6.84-6.93 (1H, m), 6.96-6.75 (1H, m), and 7.37-7.48 (1H, m).

k. Compound 13

2-aminothiazole (135.6 mg, 1.354 mmol) was dissolved in dichloromethane (10 cm³), followed by added with triphosgene (138.1 mg, 0.465 mmol) at 0° C. After dropwise addition of triethylamine (0.4 cm³, 2.846 mmol), Compound 10 (154.4 mg, 0.342 mmol) was added. The mixture was cooled to room temperature and stirred for 75 hours. 10% citric acid aqueous solution (20 cm³) was added and extracted twice with trichloromethane. After dryness over anhydrous sodium sulfate, the drying reagent was filtered out. Solvent was removed, and the residue was then dissolved in dichloromethane (10 cm³), followed by added with trifluoroacetic acid (1.0 cm³) and stirred at room temperature for 24 hours. The mixture was neutralized with saturated aqueous sodium carbonate and extracted five times with 10% methanol/trichloromethane. After dryness over anhydrous sodium sulfate, the drying reagent was filtered out. Solvent was removed, and the residue was then purified by silica gel column chromatography (BW-200.10 g, eluant: 1%→3%→5% methanol/trichloromethane) to afford Compound 13 (80.0 mg, 0.168 mmol). Yield: 49%.

¹H NMR (CDCl₃) δ=2.02 (3H, s, ac), 3.22-4.25 (12H, m), 4.70-4.81 (1H, m), 6.73 (1H, t, J=6.1 Hz, NHAc), 6.84-7.03 (3H, m), 7.33-7.43 (2H, m), and 9.84 (1H, s, N═C—NHC═O).

Example 2

Preparation of Compound 24

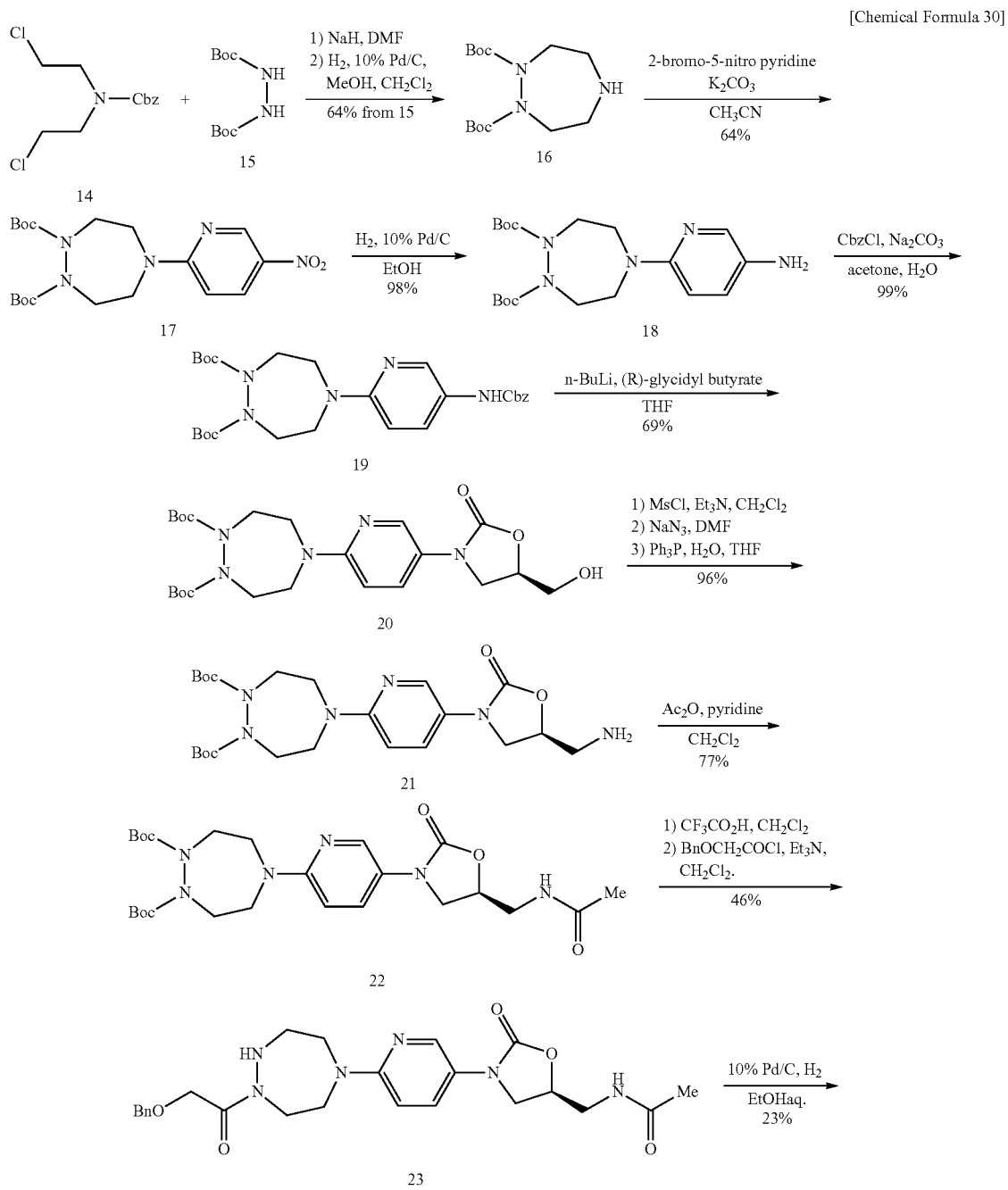

[Chemical Formula 30]

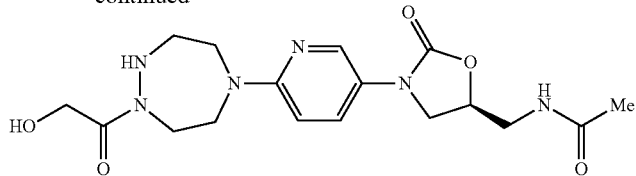

24 a. Compound 16

To a suspension of commercially available bis(chloroethyl)amine monohydrate (5.7974 g, 32.48 mmol) and sodium carbonate (3.6300 g, 34.25 mmol) in methanol (80 cm$^3$) and water (40 cm$^3$), benzyl chloroformate (6.0 cm$^3$, 33.77 mmol) was added slowly dropwise at 0° C., and the mixture was stirred for 3 hours at this temperature. Methanol was removed by half, water (50 cm$^3$) was added, followed by extracted for times with dichloromethane, washed with saturated aqueous sodium chloride. After dryness over sodium sulfate, filtration and concentration to obtain the residue containing Compound 14 as a main product (10.674 g). Another eggplant-shape flask was charged with NaH (60% in mineral oil; 2.0544 g, 51.36 mmol) and washed with n-hexane (5 cm$^3$×3). Residual n-hexane was removed under reduced pressure, dimethylformamide (80 cm$^3$) was added and aryl substituted. After cooling to 0° C., Compound 15 (4.1983 g, 18.07 mmol) was added and stirred for 10 min. at this temperature. The above residue containing Compound 14 (10.674 g) was dissolved in dimethylformamide (20 cm$^3$) and added dropwise to the mixture and stirred gently for 41 hours with cooling to room temperature. The mixture was poured into water (400 cm$^3$), and extracted three times with ethyl acetate and once with water, washed with saturated aqueous sodium chloride. Purification by silica gel column chromatography (BW-200, 150 g, eluant: 15%→20%→30% ethyl acetate/n-hexane) afforded 7.1642 g of desired residue containing 7-membered ring compound (5-Cbz derivative) as a main product. The residue was dissolved in methanol (120 cm$^3$) and dichloromethane (40 cm$^3$), followed by added with 10% Pd/C (0.7241 g) for H$_2$ substitution and stirred at room temperature for 23 hours. After celite filtration, filtrate was concentrated, and the residue was purified by silica gel column chromatography (BW-200, 100 g, eluant:ethyl acetate→methanol:triethylamine:dichloromethane=10:2:88) to afford Compound 16 (3.4838 g, 11.56 mmol). Yield: 64%

$^1$H NMR (CDCl$_3$) δ=1.43-1.51 (18H, Boc×2), 2.96-3.54 (6H, m), and 3.98-4.26 (2H, m), and 6.62 (1H, brs, NH).

b. Compound 17

Compound 16 (5.6532 g, 18.76 mmol) was dissolved in CH$_3$CN (40 cm$^3$), followed by added with potassium carbonate (2.8864 g, 20.88 mmol) and 2-chloro-5-nitro pyridine (3.5675 g, 22.50 mmol), and the mixture was heated under reflux for 19 hours. Water (50 cm$^3$) was added to the mixture, which was then extracted four times with ethyl acetate. After dryness over anhydrous sodium sulfate, the drying reagent was filtered out. Solvent was removed, and the residue was then purified by silica gel column chromatography (BW-200, 120 g, eluant: 10%→20%→30% ethyl acetate/n-hexane) to afford solid Compound 17 (5.0881 g, 12.02 mmol). Yield: 64%

$^1$H NMR (CDCl$_3$) δ=1.43 (18H, s, Boc×2), 3.12-3.45 (2H, m), 3.66-4.31 (6H, m), 6.53 (1H, d, J=9.6 Hz), 8.23 (1H, dd, J=2.8, 9.6 Hz), and 9.04 (1H, m).

c. Compound 18

Compound 17 (5.2346 g, 12.36 mmol) was dissolved in ethanol (100 cm$^3$), followed by added with 10% Pd/C (1.4253 g) to obtain a suspension. The suspension was subjected to hydrogen substitution and stirred at room temperature for 3.5 hours.

After filtration through celite, solvent was removed. The residue (0.8354 g) was purified by silica gel column chromatography (BW-200.80 g, eluant: 30%→50%→100% ethyl acetate/n-hexane) to afford Compound 18 (4.7463 g, 12.06 mmol). Yield: 98% d. Compound 19

Compound 18 (4.7463 g, 12.06 mmol) was dissolved in acetone (40 cm$^3$) and water (20 cm$^3$), followed by added with sodium carbonate (1.7605 g, 16.61 mmol) and benzyl chloroformate (2.60 cm$^3$, 14.63 mmol), and stirred at room temperature for 1 hour. Acetone was removed, and ethyl acetate (100 cm$^3$) was added to separate the phase. After dryness over anhydrous sodium sulfate, the drying reagent was filtered out. Solvent was removed, and the residue was then purified by silica gel column chromatography (BW-200.90 g, eluant: 10%→35% ethyl acetate/n-hexane) to afford Compound 19 (6.2841 g, 11.91 mmol).

e. Compound 20

Compound 19 (6.2841 g, 11.91 mmol) was dissolved in dried tetrahydrofuran (50 cm$^3$), followed by subjected to aryl substitution and cooled to −78° C. To this solution, n-BuLi (1.58 M in n-hexane; 8.0 cm$^3$, 12.64 mmol) was added slowly dropwise, followed by stirring at this temperature for 5 min. (R)-glycidyl butyrate (1.9001 g, 13.18 mmol) in dried tetrahydrofuran (2 cm$^3$) was added slowly dropwise, and cooled to room temperature and stirred for 21 hour. Water (50 cm$^3$) was added and the mixture was extracted four times with ethyl acetate, washed once with saturated aqueous sodium chloride. After dryness over anhydrous sodium sulfate, the drying reagent was filtered out. Solvent was removed, and the residue was then purified by silica gel column chromatography (BW-200.80 g, eluant: 50%→100% ethyl acetate/n-hexane) to afford Compound 20 (4.0759 g, 8.258 mmol). Yield: 69%.

$^1$H NMR (CDCl$_3$) δ=1.43 (18H, s, Boc×2), 2.75 (1H, brs, OH), 3.10-4.26 (12H, m), 4.69-4.79 (1H, m), 6.53 (1H, d, J=9.3 Hz), 7.82-7.92 (1H, m), and 8.07-8.12 (1H, m).

f. Compound 21

To the mixture of Compound 20 (4.0759 g, 8.26 mmol), triethylamine (1.8 cm$^3$, 12.81 mmol) and dried dichloromethane (80 cm$^3$) at. 0° C., methanesulfonyl chloride (0.8 cm$^3$, 10.34 mmol) was added dropwise and stirred at 0° C. for 20 min. Saturated aqueous sodium hydrogen carbonate (50 cm$^3$) was added to the mixture to separate the phase, and aqueous layer was extracted twice with trichloromethane. The organic layer was combined and dried over anhydrous sodium sulfate. After filtration, solvent was removed. The residue (4.8528 g) was dissolved in dimethylformamide (40 cm$^3$), followed by added with sodium azide (1.0125 g, 15.57 mmol) and stirred at 40 to 50° C. for 15 hours. Water (150 cm³) was added and extracted three times with ethyl acetate, washed once with saturated aqueous sodium chloride. After dryness over anhydrous sodium sulfate, the drying reagent was filtered out, and solvent was removed. The residue (4.4467 g) was dissolved in tetrahydrofuran (40 cm³), followed by added with triphenylphosphine (3.2983 g, 12.58 mmol) and water (2.0 cm³) at room temperature, and the mixture was stirred for two hours at 50° C. Solvent was removed, and the residue was purified by silica gel column chromatography (BW-200, 100 g, eluant:ethyl acetate→15% methanol/trichloromethane) to afford Compound 21 (3.8884 g, 7.89 mmol). Yield: 96%.

¹H NMR (CDCl₃) δ=1.43 (18H, s, Boc×2), 2.88-4.26 (12H, m), 4.63-4.75 (1H, m), 6.55 (1H, d, J=9.3 Hz), 7.86-7.96 (1H, m), and 8.06-8.12 (1H, m).

g. Compound 22

Compound 21 (1.0932 g, 2.219 mmol) in dichloromethane (10 cm³) was added with pyridine (1.0 cm³) and acetic anhydride (1.0 cm³), and the mixture was stirred at room temperature for 25 hours. Solvent was removed, and the residue was purified by silica gel column chromatography (BW-200.40 g, eluant: 50% ethyl acetate/n-hexane→3% methanol/ethyl acetate→3% methanol/trichloromethane) to afford Compound 22 (0.9087 g, 1.700 mmol). Yield: 77%.

¹H NMR (CDCl₃) δ=1.43 (18H, s, Boc×2), 2.03 (3H, s, ac), 3.10-4.26 (12H, m), 4.73-4.82 (1H, m), 6.02 (1H, t, J=6.2 Hz, NHAc), 6.55 (1H, d, J=9.3 Hz), 7.76-7.83 (1H, m), and 8.07-8.11 (1H, m).

h. Compound 23

Compound 22 (0.2444 g, 0.457 mmol) in dichloromethane (10 cm³) was added with trifluoroacetic acid (1.0 cm³), and the mixture was stirred at room temperature for 3 hours. Solvent was removed, and the residue was dissolved in dichloromethane (10 cm³), followed by added with BnOCH₂COCl (0.1293 g, 0.700 mmol) in triethylamine (0.5 cm³) and dichloromethane (2 cm³) and stirred at room temperature for 21 hours. Water (20 cm³) was added and extracted five times with 10% methanol/trichloromethane. After dryness over anhydrous sodium sulfate, the drying reagent was filtered out. Solvent was removed, and the residue was purified by silica gel column chromatography (BW-200.10 g, eluant: 3% methanol/trichloromethane) to afford Compound 23 (0.1010 g, 0.209 mmol). Yield: 46%.

i. Compound 24

Compound 23 (0.1010 g, 0.209 mmol) in ethanol (5 cm³) was added with 10% Pd/C (0.0981 g) to obtain a suspension. The suspension was subjected to hydrogen substitution, and stirred at room temperature for 64 hours. After filtration through celite, solvent was removed. The residue (0.8354 g) was purified by silica gel column chromatography (BW-200.80 g, eluant: 3%→10% methanol/trichloromethane) to afford Compound 24 (0.0190 g, 0.0484 mmol). Yield: 23%.

¹H NMR (CDCl₃) δ=2.03 (3H, s, ac), 3.00-4.04 (12H, m), 4.33 (2H, s, CH₂OH), 4.73-4.83 (1H, m), 6.37 (1H, t, J=6.0 Hz, NHAc), 6.51-6.57 (1H, m), 7.75-7.82 (1H, m), and 8.09-8.12 (1H, m).

Example 3

Preparation of Compounds 35 and 36

[Chemical Formula 31]

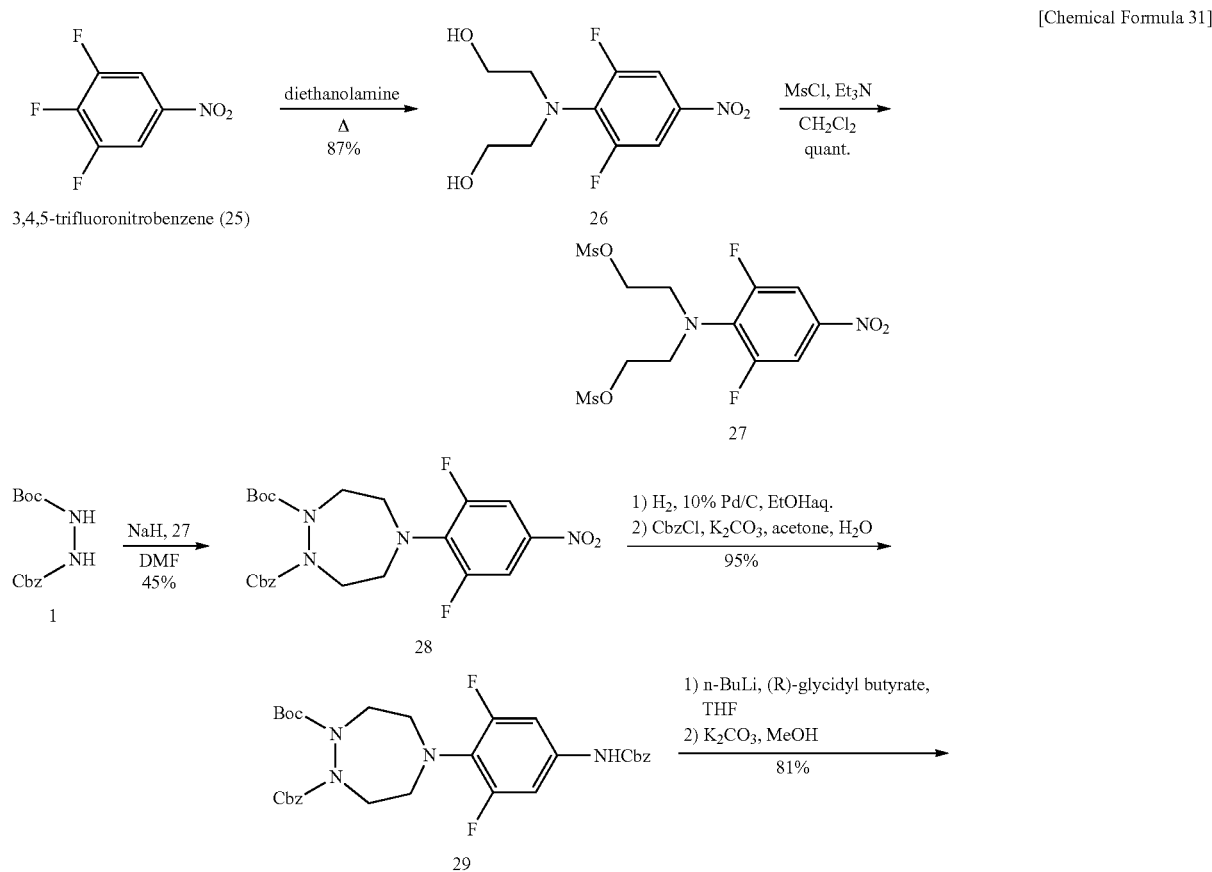

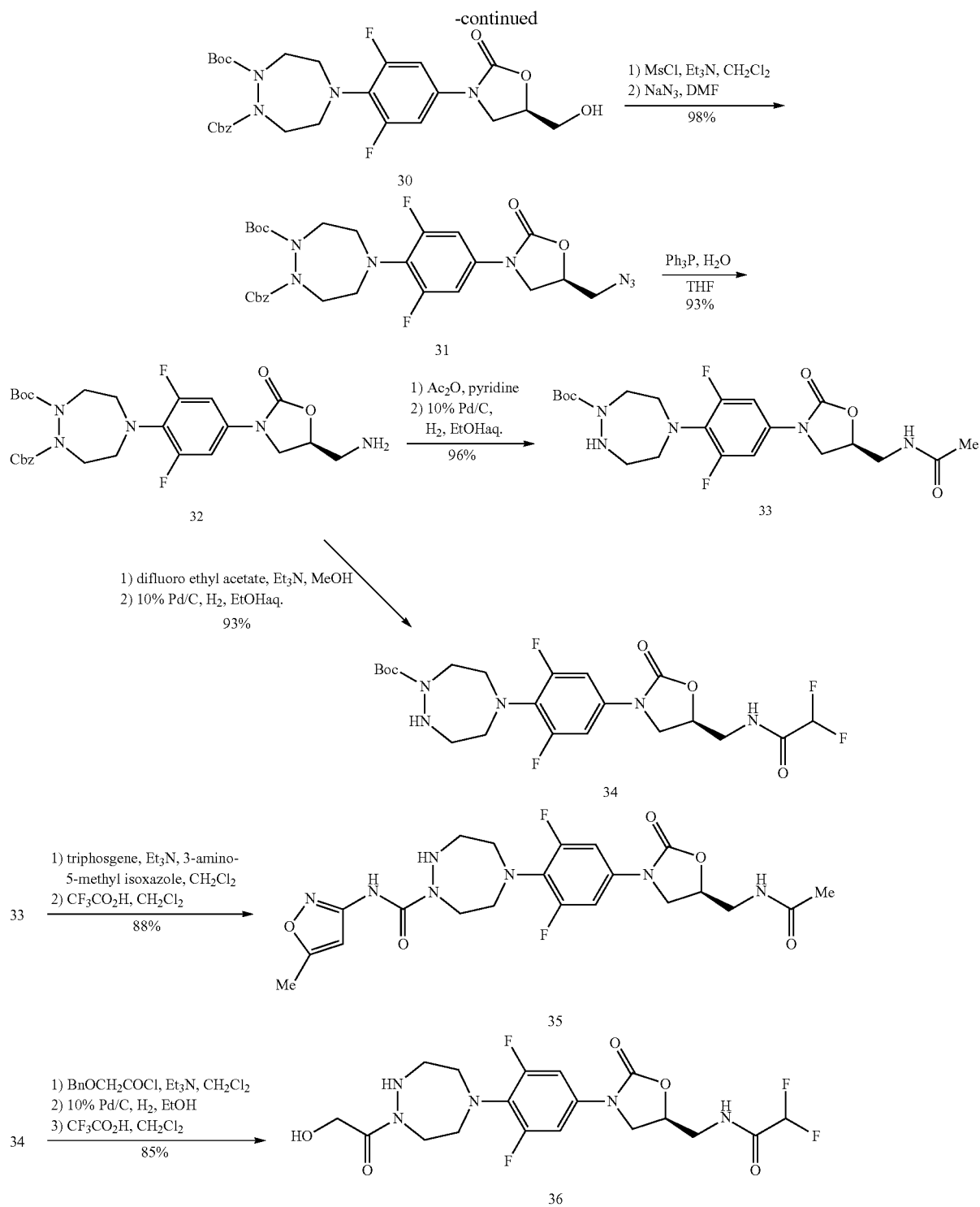

a. Compound 26

3,4,5-trifluoro nitro benzene (25) (3.6970 g, 23.32 mmol) in diethanolamine (19.40 g, 184.5 mmol) was stirred at 110-120° C. for two hours. Water (50 cm³) was added and extracted five times with ethyl acetate. After dryness over anhydrous sodium sulfate, the drying reagent was filtered out. Solvent was removed, and the residue was purified by silica gel column chromatography (BW-200, 150 g, eluant: 1%→2%→5%→10% methanol/trichloromethane) to afford Compound 26 (7.5182 g, 28.67 mmol). Yield: 87%.

¹H NMR (CDCl₃) δ=2.41 (2H, brs, OH×2), 3.47-3.58 (4H, m), 3.69-3.81 (4H, m), and 7.80 (2H, d, J=9.1 Hz).

b. Compound 27

To a solution of Compound 26 (7.5182 g, 28.67 mmol), triethylamine (10.0 cm³, 71.15 mmol) and dried dichloromethane (100 cm³) at 0° C., methanesulfonyl chloride (5.0 cm³, 64.60 mmol) was added dropwise and stirred at 0° C. for 1 hour. Saturated aqueous sodium hydrogen carbonate (100 cm³) was added to separate the phase. The aqueous layer was extracted three times with trichloromethane, and the organic layer was combined and dried over anhydrous sodium sulfate. After filtration, solvent was removed, and the residue (4.8528 g) was purified by silica gel column chromatography (BW-200, 150 g, eluant: 20%→50% ethyl acetate/n-hexane→1%→2% methanol/trichloromethane) to afford Compound 27 (11.9906 g, 28.66 mmol). Yield: 100%.

¹H NMR (CDCl₃) δ=3.00 (6H, s, Ms×2), 3.71-3.76 (4H, m), 4.29-4.34 (4H, m), and 7.83 (2H, d, J=9.1 Hz).

c. Compound 28

An eggplant-shape flask was charged with NaH (60% in mineral oil; 2.4320 g, 60.80 mmol) and washed with n-hexane (5 cm³×3). Residual n-hexane was removed under reduced pressure, and dimethylformamide (80 cm³) was added. Compound (7.5056 g, 28.19 mmol) was added at room temperature, and the mixture was stirred at this temperature for 30 minutes. Compound 27 (11.9906 g, 28.66 mmol) in dimethylformamide (30 cm³) was added dropwise at room temperature, and the mixture was stirred for 20 minutes at this temperature. The mixture was poured into water (400 cm³), followed by extracted four times with ethyl acetate, twice with water, and washed once with saturated aqueous sodium chloride. After dryness over anhydrous sodium sulfate, the drying reagent was filtered out, and solvent was concentrated in vacuo. The residue was purified by silica gel column chromatography (BW-200, 150 g, eluant: 10%→20%→50% ethyl acetate/n-hexane) to afford Compound 28 (6.3121 g, 12.82 mmol). Yield: 45%.

¹H NMR (CDCl₃) δ=1.36 (9H, s, Boc), 3.23-3.77 (6H, m), 3.96-4.25 (2H, m), 5.08-5.31 (2H, m, OCH₂Ph), 7.30-7.39 (5H, m), and 7.77 (2H, d, J=9.9 Hz).

d. Compound 29

Compound 28 (6.3121 g, 12.82 mmol) was dissolved in a combined solution of ethanol (100 cm³) and water (1 cm³). To the solution, 10% Pd/C (0.6837 g) was added to obtain a suspension. The suspension was subjected to hydrogen substitution and stirred at room temperature for 41 hour. After filtration through celite, solvent was removed. The residue (0.8354 g) was dissolved in acetone (60 cm³) and water (30 cm³), and the mixture was added with sodium carbonate (3.2019 g, 30.21 mmol) and benzyl chloroformate (5.0 cm³, 28.14 mmol). The mixture was stirred at room temperature for 1 hour. Acetone was removed, water (100 cm³) and ethyl acetate (100 cm³) were added to separate the phase. After dryness over anhydrous sodium sulfate, the drying reagent was filtered out, and solvent was removed. The residue was purified by silica gel column chromatography (BW-200, 120 g, eluant: 10%→15%→30% ethyl acetate/n-hexane) to afford Compound 29 (7.2419 g, 12.14 mmol). Yield: 95%.

e. Compound 30

Compound 29 (7.2419 g, 12.14 mmol) in dried tetrahydrofuran (60 cm³) was subjected to aryl substitution and cooled to −78° C. To this solution, n-BuLi (1.54 M in n-hexane; 8.8 cm³, 13.55 mmol) was added slowly dropwise, and followed by stirred for 5 min. at this temperature. (R)-glycidyl butyrate (1.9622 g, 13.61 mmol) in dried tetrahydrofuran (2 cm³) was then added slowly dropwise, and cooled to room temperature and stirred for 20 minutes. Water (50 cm³) was added to the mixture, which was extracted five times with ethyl acetate, and dried over anhydrous sodium sulfate. The drying reagent was filtered out, and solvent was removed. The residue (8.9592 g) was dissolved in methanol (50 cm³) and added with potassium carbonate (5.0460 g, 36.51 mmol). The mixture was stirred at room temperature for 1 hour. Methanol was removed, and water (50 cm³) was added and extracted five times with ethyl acetate. After dryness over anhydrous sodium sulfate, the drying reagent was filtered out, and solvent was removed. Purification by silica gel column chromatography (BW-200, 120 g, eluant: 50%→1% methanol/ethyl acetate) afforded Compound 30 (5.5651 g, 9.89 mmol). Yield: 81%.

¹H NMR (CDCl₃) δ=1.36 (9H, s, Boc), 2.81 (1H, t, J=6.3 Hz, CH₂OH), 3.03-4.16 (12H, m), 4.68-4.78 (1H, m), 5.07-5.32 (2H, m, OCH₂Ph), 7.12 (2H, br d, J=9 Hz), and 7.28-7.40 (5H, m).

f. Compound 31

To a solution of Compound 30 (5.5651 g, 9.89 mmol), triethylamine (2.0 cm³, 14.23 mmol) and dried dichloromethane (50 cm³) at 0° C., methanesulfonyl chloride (1.0 cm³, 12.92 mmol) was added dropwise and stirred at 0° C. for 15 minutes. Methanol (1 cm³) and saturated aqueous sodium hydrogen carbonate (30 cm³) were added to separate the phase. The aqueous layer was extracted twice with trichloromethane, and the organic layer was combined and dried over anhydrous sodium sulfate. After filtration, solvent was removed. The residue was dissolved in dimethylformamide (50 cm³), and sodium azide (1.0848 g, 16.69 mmol) was added and stirred at 40-50° C. for 16 hours. Water (100 cm³) was added to the mixture, which was extracted three times with ethyl acetate, washed once with saturated aqueous sodium chloride. After dryness over anhydrous sodium sulfate, the drying reagent was filtered out, and solvent was removed. The residue was purified by silica gel column chromatography (BW-200, 100 g, eluant: 20→30→50% ethyl acetate/n-hexane) to afford Compound 31 (5.7033 g, 9.71 mmol). Yield: 98%.

¹H NMR (CDCl₃) δ=1.37 (9H, s, Boc), 3.05-4.20 (12H, m), 4.74-4.84 (1H, m), 5.08-5.33 (2H, m, OCH₂Ph), 7.12 (2H, br d, J=9 Hz), and 7.30-7.40 (5H, m).

g. Compound 32

Compound 31 in tetrahydrofuran (50 cm³) was added with triphenylphosphine (3.9751 g, 15.16 mmol) and water (1.0 cm³) at room temperature and stirred at 50° C. for 16 hours. Solvent was removed, and the residue was purified by silica gel column chromatography (BW-200, 120 g, eluant: ethyl acetate→10% methanol/trichloromethane) to afford Compound 32 (5.0795 g, 9.05 mmol). Yield: 93%.

¹H NMR (CDCl₃) δ=1.37 (9H, s, Boc), 2.88-4.18 (12H, m), 4.63-4.73 (1H, m), 5.08-5.33 (2H, m, OCH₂Ph), 7.13 (2H, br d, J=9 Hz), and 7.30-7.40 (5H, m).

h. Compound 33

Compound 32 (0.9751 g, 1.736 mmol) in pyridine (5 cm³) was added with acetic anhydride (3.0 cm³) and stirred at room temperature for 1 hour. Solvent was removed, and the residue was dissolved in a combined liquid of ethanol (20 cm³) and water (2 cm³), and followed by added with 10% Pd/C (0.5584 g) to obtain a suspension. The suspension was subjected to hydrogen substitution and stirred at room temperature for 44 hours. After filtration through celite, solvent was removed. The residue was purified by silica gel column chromatography (BW-200.30 g, eluant: 1%→3% methanol/trichloromethane) to afford Compound 33 (0.7821 g, 1.666 mmol). Yield: 96%.

¹H NMR (CDCl₃) δ=1.49 (9H, s, Boc×2), 2.03 (3H, s, ac), 3.02-3.08 (2H, m), 3.23-3.30 (2H, m), 3.37-3.44 (2H, m), 3.57-3.75 (5H, m), 3.99 (1H, t, J=9.1 Hz), 4.73-4.82 (1H, m), 6.12 (1H, t, J=6.0 Hz, NHAc), and 7.08 (2H, d, J=10.7 Hz).

i. Compound 34

Compound 32 (0.9751 g, 1.736 mmol) in methanol (5 cm³) was added with triethylamine (1.0 cm³) and (1.0 cm³), and the mixture was stirred at room temperature for 1 hour. Solvent was removed, and the residue was dissolved in a combined liquid of ethanol (20 cm³) and water (4 cm³), and added with 10% Pd/C (0.4436 g) to obtain a suspension. The suspension was subjected to hydrogen substitution, and stirred at room temperature for 42 hours. After filtration through celite, solvent was removed. The residue was purified by silica gel column chromatography (BW-200.30 g, eluant: 2%→3% methanol/trichloromethane) to afford Compound 34 (0.7005 g, 1.386 mmol). Yield: 93%.

¹H NMR (CDCl₃) δ=1.49 (9H, s, Boc×2), 3.02-3.08 (2H, m), 3.23-3.30 (2H, m), 3.37-3.45 (2H, m), 3.57-3.73 (4H, m), 3.79-3.90 (1H, m), 4.05 (1H, t, J=9.1 Hz), 4.77-4.87 (1H, m), 5.94 (1H, t, J=54.0 Hz, CHF₂), and 6.99-7.12 (3H, m).

j. Compound 35

3-amino-5-methyl isoxazole (103.5 mg, 1.06 mmol) in dichloromethane (10 cm³) was added with triphosgene (104.5 mg, 0.352 mmol) at 0° C. and then with triethylamine (0.4 cm³, 2.85 mmol) dropwise, and the mixture was stirred at this temperature for 10 min. At this temperature, Compound (87.4 mg, 0.187 mmol) was added, and cooled to room temperature and stirred for 24 hours. 10% citric acid aqueous solution (20 cm³) was added to the mixture, which was extracted three times with trichloromethane. After dryness over anhydrous sodium sulfate, the drying reagent was filtered out. Solvent was removed, and the residue was dissolved in dichloromethane (5 cm³), followed by added with trifluoroacetic acid (0.5 cm³), and the mixture was stirred at room temperature for 16 hours. The mixture was neutralized with 10% sodium carbonate aqueous solution (20 cm³), and extracted four times with 10% methanol/trichloromethane. After dryness over anhydrous sodium sulfate, the drying reagent was filtered out, and solvent was removed. The residue was purified by silica gel column chromatography (BW-200, 8 g, eluant: 2%→5% methanol/trichloromethane) to afford Compound 35 (81.5 mg, 0.165 mmol). Yield: 88%.

¹H NMR (CDCl₃) δ=2.03 (3H, s, ac), 2.38 (3H, s, C=C-Me), 3.16-3.24 (2H, m), 3.29-3.42 (4H, m), 3.62-4.03 (6H, m), 4.77-4.88 (1H, m), 6.21-6.33 (1H, br, NHC=O), 6.65 (1H, s, Me-C=CH), 7.10 (2H, d, J=10.7 Hz), and 9.14 (1H, s, NH Ar).

k. Compound 36

Compound 34 (78.9 mg, 0.156 mmol) in dichloromethane (3 cm³) was added with triethylamine (0.05 cm³, 0.356 mmol) at room temperature, and BnOCH₂COCl (36.5 mg, 0.198 mmol) in dichloromethane (1 cm³) was added and stirred for 1 hour. A small amount of methanol was added, and then water (20 cm³) was added and extracted twice with trichloromethane. After dryness over anhydrous sodium sulfate, the drying reagent was filtered out, and solvent was removed. The residue was dissolved in ethanol (5 cm³), followed by added with 10% Pd/C (88.9 mg) and subjected to H₂ substitution and stirred at room temperature for 122 hours. After celite filtration, solvent was removed. The residue was dissolved in dichloromethane (5 cm³), followed by added with trifluoroacetic acid (0.5 cm³) and stirred at room temperature for 21 hours. The mixture was neutralized with 10% sodium carbonate aqueous solution (30 cm³), and extracted four times with 10% methanol/trichloromethane. After dryness over anhydrous sodium sulfate, the drying reagent was filtered out, and solvent was removed. The residue was purified by silica gel column chromatography (BW-200, 8 g, eluant: 1%→2%→5% methanol/trichloromethane) to afford Compound 36 (61.2 mg, 0.132 mmol). Yield: 85%.

¹H NMR (CDCl₃) δ=3.11-3.19 (2H, m), 3.26-3.42 (4H, m), 3.63-3.90 (5H, m), 4.06 (1H, t, J=9.1 Hz), 4.39 (2H, s, CH₂OH), 4.79-4.90 (1H, m), 5.95 (1H, t, J=54.1 Hz, CHF₂), 7.08 (2H, d, J=10.7 Hz), and 7.45 (1H, t, J=6.2 Hz, NHC=O).

The compounds of Examples 4-103, which structures and physical data are as follows, were prepared according to the procedures in Examples as described above.

Example 4

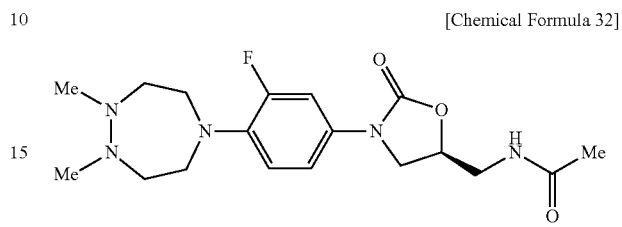

[Chemical Formula 32]

¹H NMR (CDCl₃) δ 2.03 (1H, s, Ac), 2.53 (6H, s, Me×2), 3.15-3.21 (4H, m), 3.36-3.43 (4H, m), 3.61-3.68 (2H, m), 3.75 (1H, dd, J=6.6, 9.1 Hz), 4.01 (1H, t, J=9.1 Hz), 4.73-4.82 (1H, m, CH₂CHCH₂NHAc), 6.74-6.82 (1H, br, NHAc), 6.80-6.87 (1H, m), 6.96-7.03 (1H, m), and 7.31-7.38 (1H, m).

Example 5


[Chemical Formula 33]

¹H NMR (CDCl₃) δ 1.09 (3H, t, J=7.1 Hz, NCH₂CH₃), 2.03 (3H, s, Ac), 2.53 (3H, s, NMe), 2.72 (2H, q, J=7.1 Hz), 3.12-3.27 (4H, m), 3.34-3.42 (4H, m), 3.55-3.76 (3H, m), 4.01 (1H, t, J=9.1 Hz), 4.71-4.81 (1H, m, CH₂CHCH₂NHAc), 6.25 (1H, t, J=6.2 Hz, NHAc), 6.82-6.90 (1H, m), 6.98-7.04 (1H, m), and 7.32-7.40 (1H, m).

Example 6

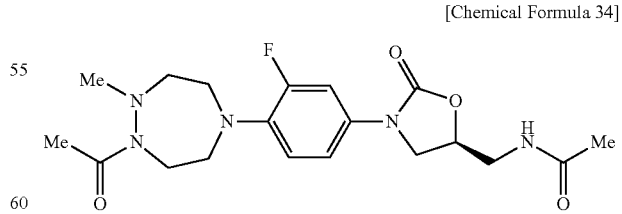

[Chemical Formula 34]

¹H NMR (CDCl₃) δ 2.03 (3H, s, NHAc), 2.19 (3H, s, NAc), 2.57 (3H, NMe), 2.84-2.99 (2H, m), 3.16-3.77 (8H, m), 4.01 (1H, t, J=9.1 Hz), 4.24-4.34 (1H, m), 4.69-4.82 (1H, m, CH₂CHCH₂NHAc), 6.28 (1H, br, NHAc), 6.85-6.93 (1H, m), 6.97-7.03 (1H, m), and 7.38-7.47 (1H, m).

Example 7

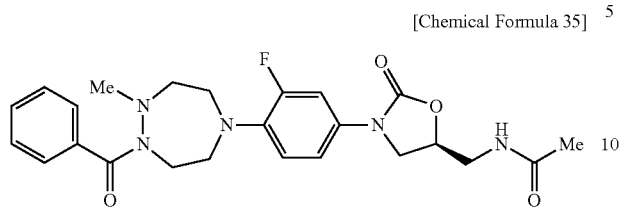

[Chemical Formula 35]

$^1$H NMR (CDCl$_3$) δ 2.02 (3H, s, Ac), 2.51 (3H, s, NMe), 2.92 (1H, dd, J=7.8, 12.5 Hz), 3.12 (1H, dd, J=8.2, 14.0 Hz), 3.28-3.53 (5H, m), 3.60 (1H, dt, J=6.1, 14.6 Hz), 3.68 (1H, dd, J=3.3, 6.1 Hz), 3.74 (1H, dd, J=6.9, 9.1 Hz), 4.02 (1H, t, J=9.1 Hz), 4.44-4.53 (1H, m), 4.72-4.82 (1H, m, CH$_2$CHCH$_2$NHAc), 6.19 (1H, t, J=6.1 Hz, NHAc), 6.90-6.98 (1H, m), 7.00-7.06 (1H, m), and 7.33-7.58 (1H, m).

Example 8

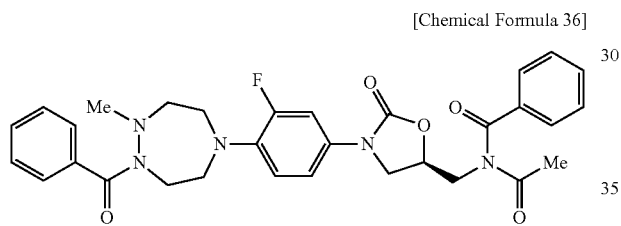

[Chemical Formula 36]

$^1$H NMR (CDCl$_3$) δ 2.17 (3H, s, Ac), 2.51 (3H, s, NMe), 2.87-2.97 (1H, m), 3.06-3.16 (1H, m), 3.28-3.52 (5H, m), 3.70 (1H, dd, J=6.1, 9.1 Hz), 4.03-4.24 (3H, m), 4.45-4.55 (1H, m), 4.89-4.99 (1H, m, CH$_2$CHCH$_2$NHAc), 6.89-7.08 (2H, m), and 7.33-7.71 (11H, m).

Example 9

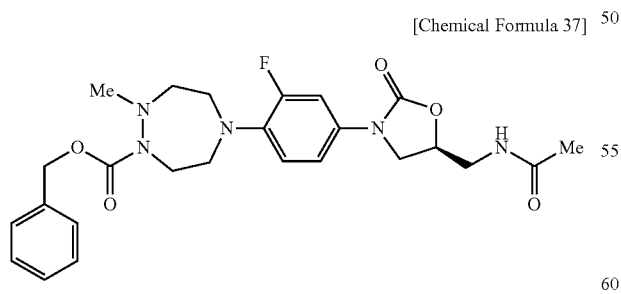

[Chemical Formula 37]

$^1$H NMR (CDCl$_3$) δ 2.02 (3H, s, Ac), 2.64 (1.5H, s, NMe), 2.77 (1.5H, s, NMe), 2.82-3.77 (11H, m), 3.94-4.05 (2H, m), 4.70-4.81 (1H, m, CH$_2$CHCH$_2$NHAc), 5.09-5.29 (2H, m, CH$_2$Ph), 6.14 (1H, t, J=6.0 Hz, NHAc), 6.81-6.92 (1H, m), 6.97-7.04 (1H, m), and 7.2@5-7.44 (6H, m).

Example 10

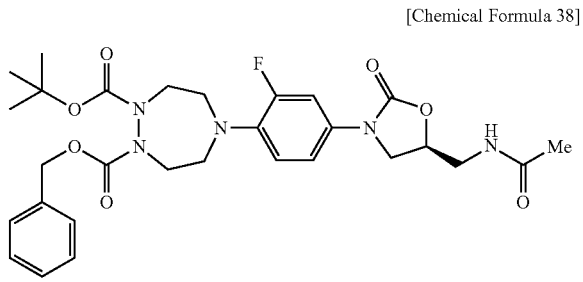 [SMILES: CC(=O)NC[C@H]1CN(c2ccc(N3CCN(C(=O)OCc4ccccc4)N(C(=O)OC(C)(C)C)CC3)c(F)c2)C(=O)O1]

[Chemical Formula 38]

$^1$H NMR (CDCl$_3$) δ 1.34 (9H, s, Boc), 2.02 (3H, s, Ac), 3.18-3.76 (9H, m), 3.95-4.27 (3H, m), 4.71-4.81 (1H, m), 5.06-5.28 (2H, m, CH$_2$Ph), 6.13 (1H, br t, J=6 Hz, NHAc), 6.87 (1H, t, J=9.1 Hz), 6.98-7.07 (1H, m), and 7.30-7.44 (6H, m).

Example 11

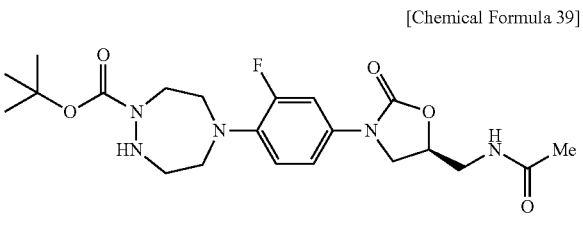 [SMILES: CC(=O)NC[C@H]1CN(c2ccc(N3CCNN(C(=O)OC(C)(C)C)CC3)c(F)c2)C(=O)O1]

[Chemical Formula 39]

$^1$H NMR (CDCl$_3$) δ 1.38 (9H, br s, Boc), 2.03 (3H, s, Ac), 3.08-3.16 (2H, m), 3.40-3.48 (2H, m), 3.53-3.77 (8H, 4.00 (1H, t, J=9.0 Hz), 4.72-4.81 (1H, m), 6.45 (1H, br s, NHAc), 6.87 (1H, t, J=9.0 Hz), 6.99 (1H, dd, J=2.4, 9.0 Hz), and 7.36 (1H, dd, J=2.4, 15.1 Hz).

Example 12

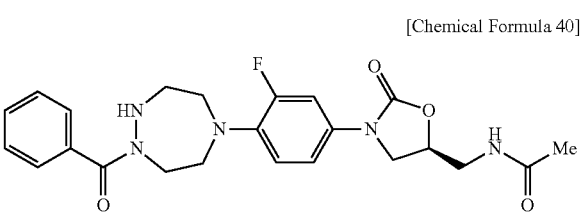 [SMILES: CC(=O)NC[C@H]1CN(c2ccc(N3CCNN(C(=O)c4ccccc4)CC3)c(F)c2)C(=O)O1]

[Chemical Formula 40]

$^1$H NMR (CDCl$_3$) δ 2.01 (3H, s, Ac), 3.20-3.79 (11H, m), 4.01 (1H, t, J=9.1 Hz), 4.77 (1H, br), 5.95 (1H, br, NNH), 6.39 (1H, br, NHAc), 6.84-6.95 (1H, m), 6.98-7.15 (2H, m), and 7.2@5-7.41 (5H, m).

Example 13

[Chemical Formula 41]

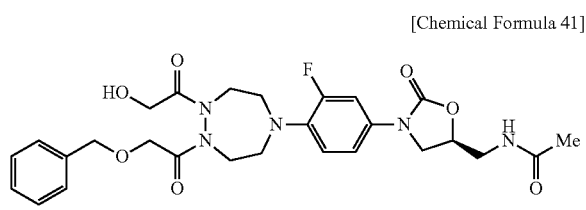 [SMILES: CC(=O)NC[C@H]1CN(c2ccc(N3CCN(C(=O)CO)N(C(=O)COCc4ccccc4)CC3)c(F)c2)C(=O)O1]

$^1$H NMR (CDCl$_3$) δ 2.02 (3H, s, NHAc), 3.10-3.77 (9H, m), 3.95-4.26 (5H, m), 4.39-4.69 (4H, m), 4.71-4.81 (1H, m), 6.10-6.25 (1H, br, NHAc), 6.97 (1H, t, J=9.1 Hz), 7.03 (1H, br d, J=9 Hz), 7.30-7.39 (5H, m, CH$_2$Ph), and 7.41 (1H, br d, J=15 Hz).

Example 14

[Chemical Formula 42]

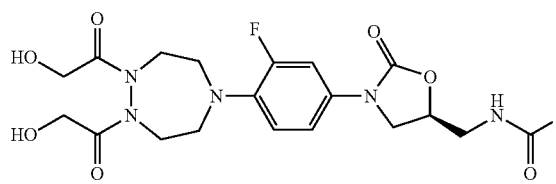

$^1$H NMR (CDCl$_3$) δ 2.02 (3H, s, Ac), 3.02 (2H, t, J=4.7 Hz), 3.14-3.78 (9H, m), 3.97-4.26 (5H, m), 4.49-4.63 (2H, m), 4.72-4.82 (1H, m), 6.06 (1H, t, J=6.0 Hz, NHAc), 6.90 (1H, t, J=9.1 Hz), 7.02-7.09 (1H, m), and 7.4@2-7.50 (1H, m).

Example 15

[Chemical Formula 43]

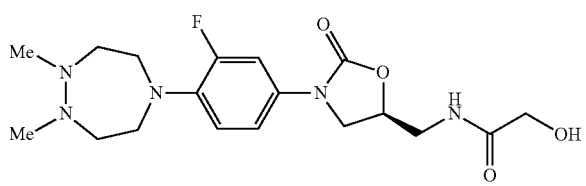

$^1$H NMR (CDCl$_3$) δ 2.52 (6H, s, Me×2), 3.12-3.20 (4H, m), 3.34-3.43 (4H, m), 3.59-3.78 (3H, m), 4.01 (1H, t, J=9.0 Hz), 4.11 (2H, s, CH$_2$OH), 4.73-4.83 (1H, m), 6.82 (1H, t, J=9.1 Hz), 7.01 (1H, dd, J=2.4, 9.1 Hz), 7.31 (1H, dd, J=2.4, 14.8 Hz), and 7.35 (1H, br s, NH).

Example 16

[Chemical Formula 44]

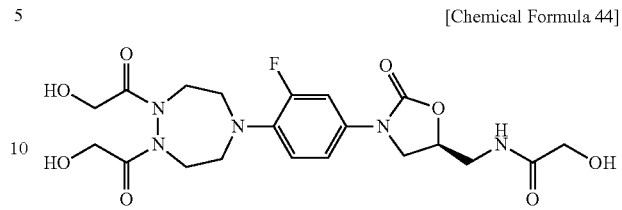

$^1$H NMR (CDCl$_3$) δ 3.10-3.62 (9H, m), 3.74-4.30 (10H, m), 4.68-4.79 (1H, m), 5.05 (1H, t, J=6.0 Hz), 5.60 (1H, t, J=6.0 Hz, NH), 7.04-7.16 (2H, m), 7.40-7.50 (1H, m), and 8.08 (1H, t, J=6.0 Hz).

Example 17

[Chemical Formula 45]

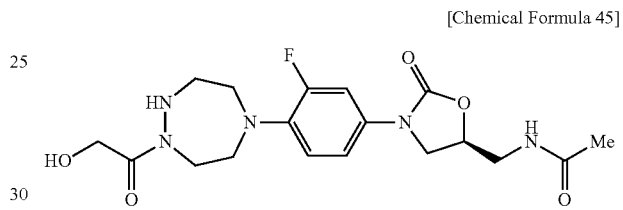

$^1$H NMR (CDCl$_3$) δ 2.02 (3H, s, Ac), 3.12-3.78 (9H, m), 3.91-4.05 (3H, m), 4.37 (2H, br s, CH$_2$OH), 4.72-4.81 (1H, m), 6.27 (1H, br s, NHAc), 6.89 (1H, t, J=9.1 Hz), 6.98-7.06 (1H, m), and 7.37-7.46 (1H, m).

Example 18

[Chemical Formula 46]

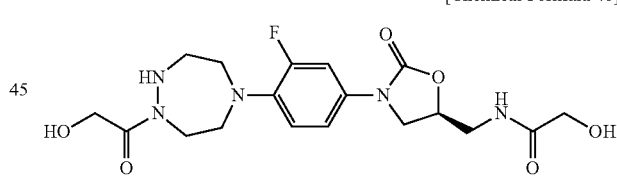

$^1$H NMR (CDCl$_3$) δ 2.94-3.52 (9H, m), 3.58-4.16 (8H, m), 4.37 (2H, br s), 4.74-4.84 (1H, m), 6.89 (1H, t, J=9.1 Hz), 6.99-7.16 (2H, m), and 7.3@6-7.45 (1H, m).

Example 19

[Chemical Formula 47]

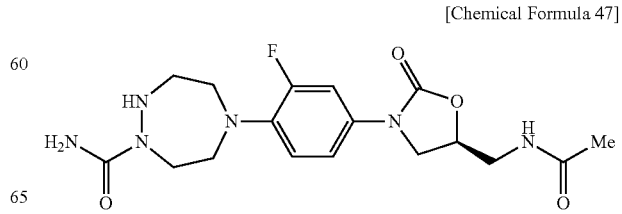

¹H NMR (CDCl₃) δ 2.02 (3H, s, Ac), 3.17-3.23 (2H, m), 3.35-3.42 (4H, m), 3.55-3.77 (3H, m), 3.81-3.89 (2H, m), 4.00 (1H, t, J=9.1 Hz), 4.71-4.81 (1H, m), 5.61 (1H, br s, NHH), 6.38 (1H, br, s, NHH), 6.89 (1H, t, J=9.1 Hz), 7.02 (1H, ddd, J=0.8, 2.5, 9.1 Hz), and 7.2@8-7.42 (2H, m).

Example 20

[Chemical Formula 48]

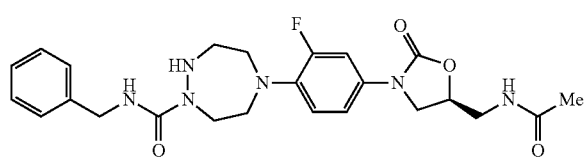

¹H NMR (CDCl₃) δ 2.02 (3H, s, Ac), 3.12-3.78 (11H, m), 3.81-4.01 (2H, m), 4.00 (1H, t, J=9.1 Hz), 4.42 (2H, AB), 4.71-4.81 (1H, m), 6.14 (1H, br), 6.76 (1H, br t, J=5.5 Hz), 6.86-6.93 (1H, m), 6.98-7.07 (1H, m), and 7.2@2-7.46 (6H, m).

Example 21

[Chemical Formula 49]

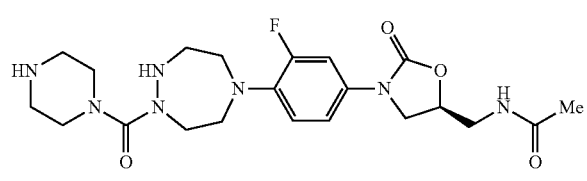

¹H NMR (DMSO-d₆+CDCl₃) δ 2.02 (3H, s, Ac), 2.94-4.12 (20H, m), 4.66-4.86 (1H, m), 6.85-7.08 (2H, m), 7.35-7.45 (1H, m), and 7.95-8.10 (1H, br, NHAc).

Example 22

[Chemical Formula 50]

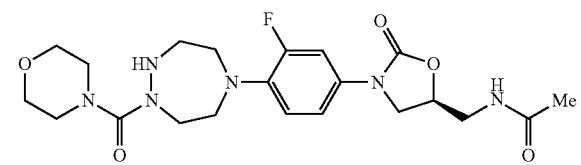

¹H NMR (CDCl₃) δ 2.02 (3H, s, Ac), 3.13-3.76 (19H, m), 4.00 (1H, t, J=8.9 Hz), 4.71-4.81 (1H, m, CH₂CHCH₂), 6.19 (1H, br s, NHAc), 6.90 (1H, t, J=9.1 Hz), 7.01 (1H, br d, J=9 Hz), and 7.39 (1H, dd, J=2.6, 14.8 Hz).

Example 23

[Chemical Formula 51]

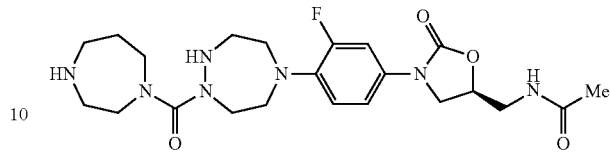

Example 24

[Chemical Formula 52]

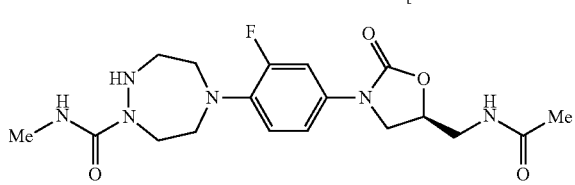

¹H NMR (CDCl₃) δ 2.02 (3H, s, NHAc), 2.80 (3H, d, J=4.8 Hz, MeNH—C=O), 3.10-4.04 (12H, m), 4.71-4.81 (1H, m, CH₂CHCH₂), 6.26-6.42 (2H, br, MeNH—C=O and NHAc), 6.88 (1H, t, J=9.1 Hz), 6.96-7.04 (1H, m), and 7.3@5-7.45 (1H, m).

Example 25

[Chemical Formula 53]

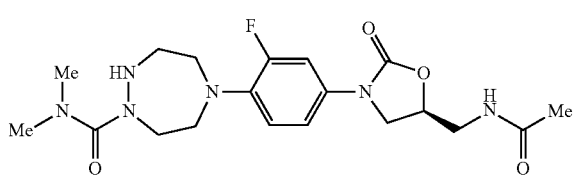

¹H NMR (CDCl₃) δ 2.02 (3H, s, Ac), 2.86 (6H, s, NMe₂), 3.12-4.06 (12H, m), 4.71-4.81 (1H, m, NCH₂CHCH₂), 6.25 (1H, br s, NHAc), 6.90 (1H, t, J=9.1 Hz), 7.01 (1H, br d, J=9 Hz), and 7.38 (1H, dd, J=2.5, 14.6 Hz).

Example 26

[Chemical Formula 54]

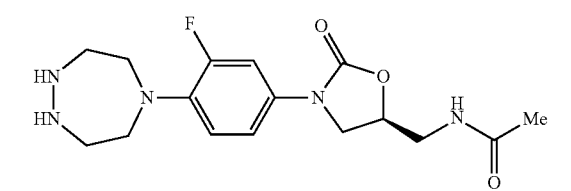

¹H NMR (CDCl₃) δ 2.02 (3H, s, Ac), 3.05-3.11 (4H, m), 3.43-3.50 (4H, m), 3.61-3.68 (2H, m), 3.75 (1H, dd, J=6.6, 9.1 Hz), 4.00 (1H, t, J=9.1 Hz), 4.72-4.82 (1H, m), 6.89 (1H, t, J=9.1 Hz), 6.89-6.99 (1H, br, NHAc), 7.01 (1H, dd, J=2.5, 9.1 Hz), and 7.34 (1H, dd, J=2.5, 15.1 Hz).

Example 27

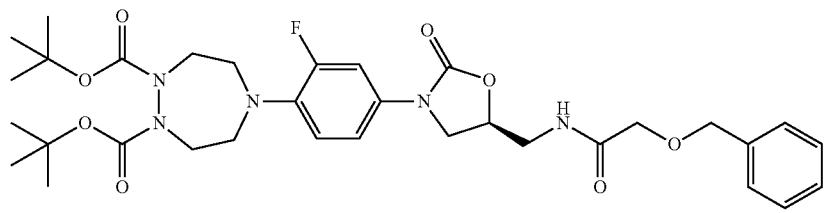

$^1$H NMR (CDCl$_3$) δ 1.46 (18H, s, Boc×2), 3.17-3.78 (9H, m), 3.92-4.23 (5H, m), 4.55 (2H, s, CH$_2$Ph), 4.69-4.80 (1H, m), 6.88 (1H, t, J=9.1 Hz), 6.98-7.14 (2H, m), and 7.2@6-7.42 (6H, m).

Example 28

[Chemical Formula 56]

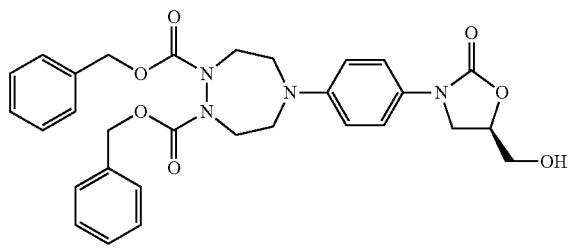

$^1$H NMR (CDCl$_3$) δ 2.40 (1H, br s, OH), 3.10-4.04 (10H, m), 4.15-4.36 (2H, m), 4.65-4.78 (1H, m), 4.95-5.20 (4H, m, CH$_2$Ph××2), 6.68 (1H, d, J=7.8 Hz), and 7.15-7.45 (2H, m).

Example 29

[Chemical Formula 57]

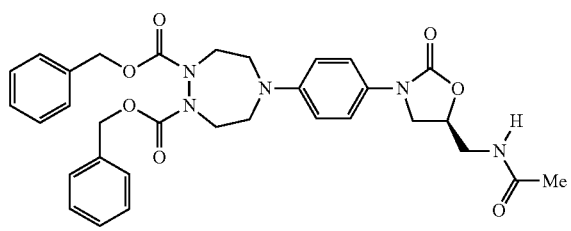

$^1$H NMR (CDCl$_3$) δ 1.99 (s, Ac, a$_1$), 2.00 (s, Ac, a$_2$), 3.22-4.34 (m, b$_1$), 4.66-4.77 (m, b$_2$), 4.96-5.18 (m, b$_3$), 6.63-6.71 (m, c$_1$), 7.17-7.34 (m, c$_2$). integral ratio; a$_1$+a$_2$:b$_1$:b$_2$:b$_3$:c$_1$:c$_2$+c$_3$=3:13:1:4:3:11.

Example 30

[Chemical Formula 58]

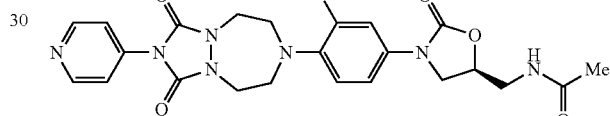

$^1$H NMR (CDCl$_3$) δ 2.03 (3H, s, Ac), 3.44-3.51 (4H, m), 3.57-3.80 (3H, m), 4.03 (1H, t, J=8.9 Hz), 4.13-4.18 (4H, m), 4.73-4.82 (1H, m, CH$_2$CHCH$_2$), 5.99 (1H, t, J=6.3 Hz, NHAc), 7.00 (1H, t, J=9.1 Hz), 7.11 (1H, br d, J=9 Hz), 7.49 (1H, dd, J=2.6, 14.0 Hz), 7.76-7.80 (2H, m), and 8.69-8.73 (2H, m).

Example 31

[Chemical Formula 59]

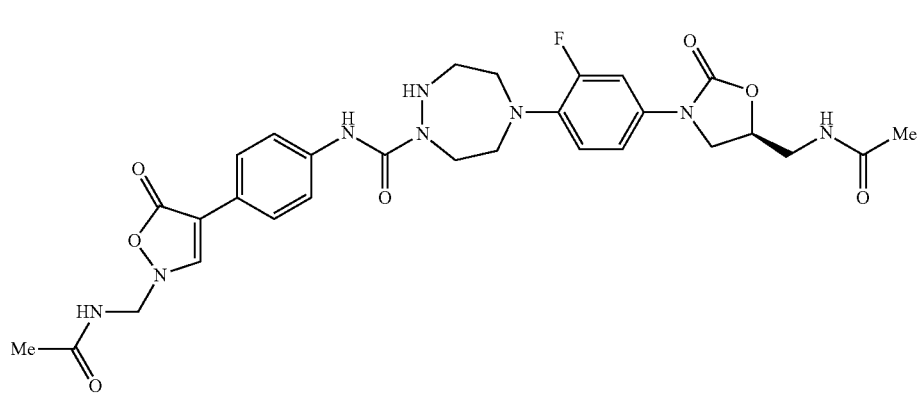

$^1$H NMR (DMSO-d$_6$) δ 1.83 (6H, s, Ac×2), 3.05-3.14 (2H, m), 3.28-3.48 (6H, m), 3.68 (1H, dd, J=6.3, 9.2 Hz), 3.73-3.82 (2H, m), 4.06 (1H, t, J=9.1 Hz), 4.64-4.74 (1H, m), 4.98 (2H, d, J=6.3 Hz, NCH$_2$N), 5.36 (1H, t, J=6.1 Hz), 7.00-7.15 (2H, m), 7.44 (1H, dd, J=2.5, 15.6 Hz), 7.57-7.66 (4H, m), 8.23 (1H, t, J=6.0 Hz), 8.79 (1H, s, N—CH=C), 8.88 (1H, t, J=6.0 Hz), and 9.07 (1H, s).

Example 32

[Chemical Formula 60]

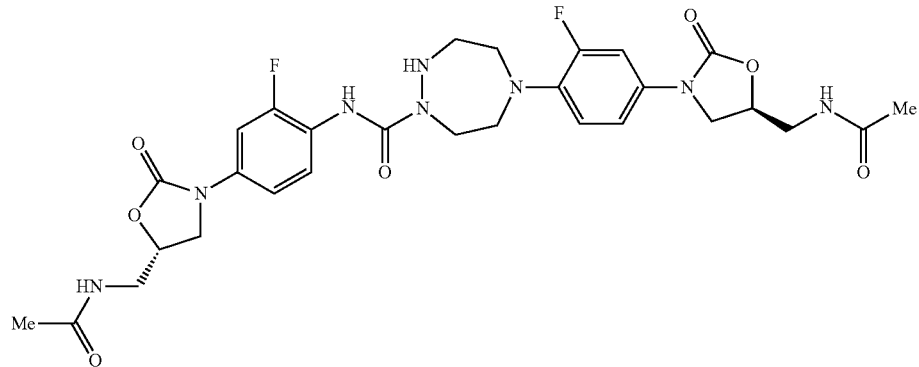

$^1$H NMR (DMSO-d$_6$) δ 1.83 (6H, s, Ac×2), 3.00-4.15 (16H, m), 4.64-4.76 (2H, m), 5.49 (1H, t, J=6.1 Hz), 7.00-7.24 (3H, m), 7.40-7.63 (2H, m), 7.98 (1H, t, J=9.1 Hz), 8.23 (2H, br s), and 8.84 (1H, s).

Example 33

[Chemical Formula 61]

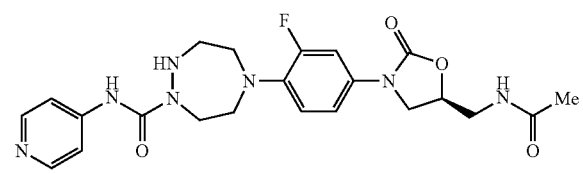

$^1$H NMR (CDCl$_3$) δ 2.00 (3H, s, Ac), 3.08-3.76 (9H, m), 3.92-4.21 (5H, m), 4.38-4.80 (7H, m), 6.52 (1H, br s, NHAc), 6.84 (1H, t, J=9.1 Hz), 6.97-7.05 (1H, m), and 7.25-7.43 (11H, m).

Example 34

[Chemical Formula 62]

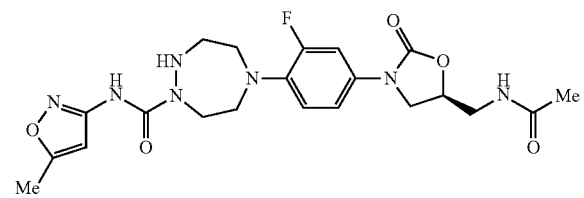

$^1$H NMR (CDCl$_3$) δ 2.02 (3H, s, Ac), 2.38 (3H, s, Aryl-Me), 3.22-4.04 (12H, m), 4.71-4.81 (1H, m), 6.20 (1H, br s, NHAc), 6.63 (1H, s, CH=CMe), 6.90 (1H, t, J=9.1 Hz), 7.03 (1H, br d, J=9 Hz), 7.41 (1H, dd, J=2.5, 14.6 Hz), and 9.10 (1H, s, Aryl-NHC=O).

Example 35

[Chemical Formula 63]

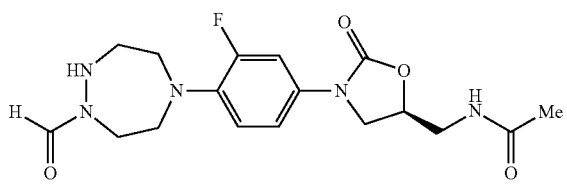

$^1$H NMR (CDCl$_3$) δ 2.03 (3H, s, NHAc), 3.10-3.16 (1H, m), 3.23-3.29 (1H, m), 3.34-3.39 (1H, m), 3.41-3.45 (2H, m), 3.55-3.86 (6H, m), 3.96-4.05 (1H, m), 4.71-4.82 (1H, m, CH$_2$CHCH$_2$), 6.32 (1H, br s, NHAc), 6.81-6.93 (1H, m), 6.97-7.06 (1H, m), 7.36-7.43 (1H, m), 7.89 (0.5H, s, CHO) and 8.33 (0.5H, s, CHO).

Example 36

[Chemical Formula 64]

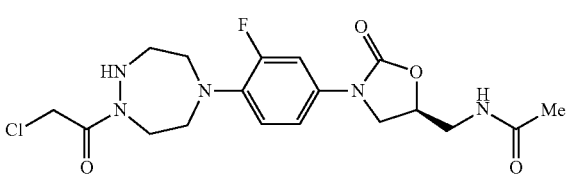

$^1$H NMR (CDCl$_3$) δ 2.03 (3H, s, Ac), 3.23-3.45 (6H, m), 3.56-3.78 (4H, m), 3.91-4.05 (2H, m), 4.44 (2H, s, CH$_2$Cl), 4.72-4.82 (1H, m, CH$_2$CHCH$_2$), 6.30 (1H, br s, NHAc), 6.85-6.93 (1H, m), 6.98-7.06 (1H, m), and 7.38-7.46 (1H, m).

Example 37

[Chemical Formula 65]

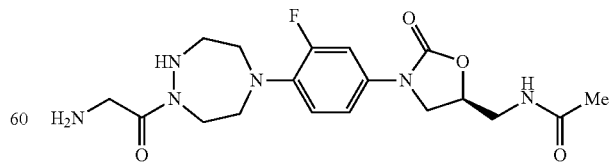

$^1$H NMR (CDCl$_3$) δ 2.02 (3H, s, Ac), 3.09-3.22 (2H, m), 3.32-3.44 (4H, m), 3.52-3.77 (6H, m), 3.89-3.94 (1H, m), 3.97-4.04 (1H, m), 4.72-4.81 (1H, m, CH$_2$CHCH$_2$), 6.34 (1H, br t, J=6 Hz, NHAc), 6.83-6.92 (1H, m), 6.98-7.06 (1H, m), and 7.40 (1H, dd, J=2.4, 14.6 Hz).

Example 38

[Chemical Formula 66]

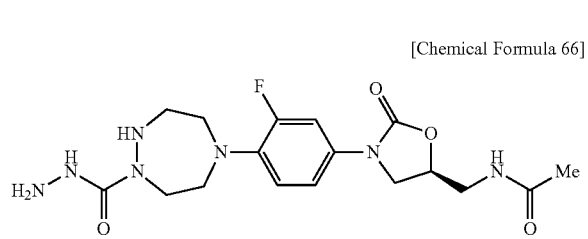

¹H NMR (DMSO-d₆) δ 1.83 (3H, s, Ac), 2.92-3.72 (11H, M), 4.06 (1H, t, J=9.1 Hz), 4.64-4.74 (1H, m, CH₂CHCH₂), 4.96 (1H, t, J=6.1 Hz), 6.99 (1H, t, J=9.1 Hz), 7.10 (1H, dd, J=2.5, 9.1 Hz), 7.41 (1H, dd, J=2.5, 15.7 Hz), and 8.24 (1H, t, J=6.1 Hz).

Example 39

[Chemical Formula 67]

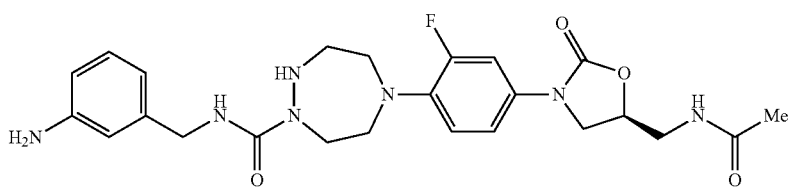

¹H NMR (CDCl₃) δ 2.03 (3H, s, Ac), 2.59 (6H, s, NMe₂), 3.11-3.19 (2H, m), 3.34-3.41 (4H, m), 3.52-3.78 (5H, m), 4.00 (1H, t, J=9.1 Hz), 4.72-4.82 (1H, m, CH₂CHCH₂), 6.46 (1H, t, J=6.0 Hz, NHAc), 6.89 (1H, t, J=9.1 Hz), 7.01 (1H, br d, J=9 Hz), 7.17 (1H, s, NHNMe₂), and 7.39 (1H, dd, J=2.5, 14.6 Hz).

Example 40

[Chemical Formula 68]

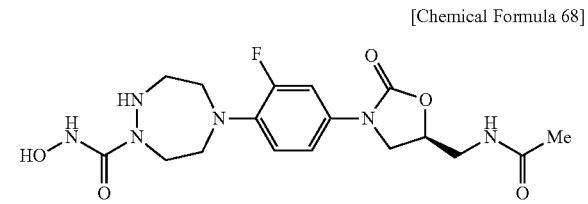

Example 41

[Chemical Formula 69]

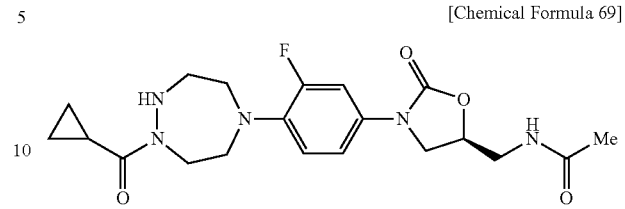

¹H NMR (CDCl₃) δ 0.68-0.96 (4H, m), 1.62-1.67 (1H, m), 2.03 (3H, s, Ac), 3.06-3.44 (5H, m), 3.55-3.95 (6H, m), 4.01 (1H, t, J=9.1 Hz), 4.72-4.81 (1H, m, CH₂CHCH₂), 6.18 (1H, br, NHAc), 6.89 (1H, br t, J=9 Hz), 7.01 (1H, br t, J=9 Hz), and 7.41 (1H, br t, J=15 Hz).

Example 42

[Chemical Formula 70]

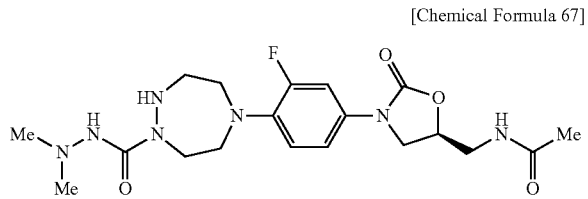 [SMILES: CC(=O)NC[C@H]1CN(c2ccc(N3CCNN(C(=O)NN(C)C)CC3)c(F)c2)C(=O)O1]

¹H NMR (CDCl₃) δ 1.99 (3H, s, Ac), 3.09-3.17 (2H, m), 3.33-3.42 (2H, m), 3.50-3.91 (8H, m), 3.96 (1H, t, J=8.9 Hz), 4.30 (2H, d, J=6.0 Hz, NHCH₂-Aryl), 4.68-4.77 (1H, m, CH₂CHCH₂), 6.53-6.67 (3H, m), 6.75 (1H, t, J=6.1 Hz), 6.83-6.91 (2H, m), 6.99 (1H, br d, J=9 Hz), 7.04-7.11 (1H, m), and 7.37 (1H, dd, J=2.8, 14.8 Hz).

Example 43

[Chemical Formula 71]

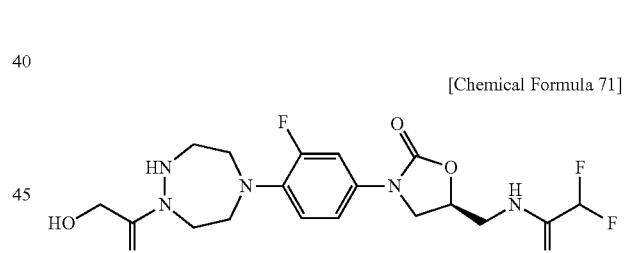

¹H NMR (CDCl₃) δ 3.17-3.25 (2H, m), 3.32-3.47 (4H, m), 3.57-4.00 (5H, m), 4.07 (1H, t, J=9.1 Hz), 4.37 (2H, s, CH₂OH), 4.76-4.86 (1H, m), 5.94 (1H, t, J=54.1 Hz, CHF₂), 6.86-7.07 (3H, m), and 7.36-7.44 (1H, m).

Example 44

[Chemical Formula 72]

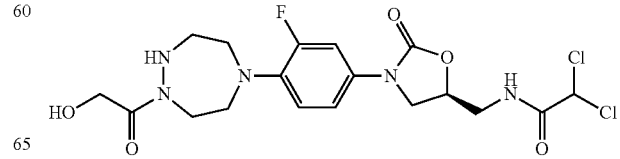

¹H NMR (DMSO-d₆) δ 2.97-3.76 (11H, m), 4.06 (1H, t, J=8.8 Hz), 4.19 (2H, s, CH₂OH), 4.62-4.75 (1H, m), 7.02 (1H, t, J=9.9 Hz), 7.11 (1H, dd, J=2.5, 9.9 Hz), 7.43 (1H, dd, J=2.5, 15.7 Hz), 8.24 (1H, t, J=5.8 Hz), and 8.32 (1H, s).
Example 45
[Chemical Formula 73]
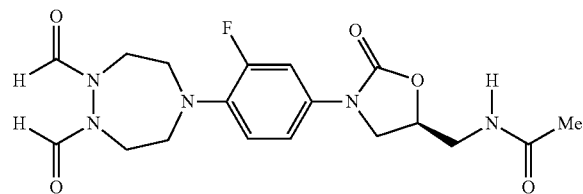
Example 46
[Chemical Formula 74]
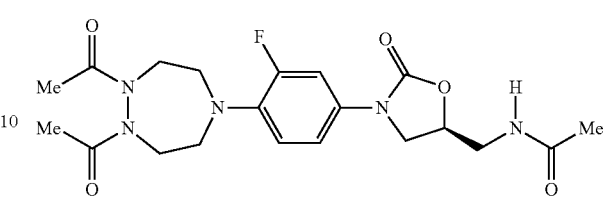
¹H NMR (CDCl₃) δ 2.02 (3H, s, Ac), 2.09 (6H, s, AcN-NAc), 3.14-3.26 (4H, m), 3.43-3.54 (2H, m), 3.56-3.78 (3H, m), 3.79-4.05 (1H, m), 4.48-4.60 (2H, m), 4.72-4.82 (1H, m), 6.25 (1H, t, J=6.0 Hz, NHAc), 6.89 (1H, t, J=9.1 Hz), 7.05 (1H, br d, J=9 Hz), and 7.41 (1H, dt, J=14.6, 2.5 Hz).
Example 48
[Chemical Formula 75]
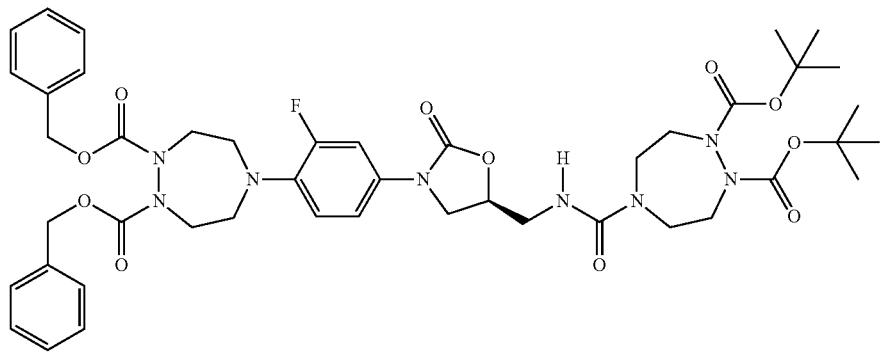
¹H NMR (CDCl₃) δ 1.40-1.52 (18H, Boc×2), 3.05-4.36 (20H, m), 4.68-4.78 (1H, m), 4.96-5.20 (5H, m), 6.67 (2H, br d, J=8.8 Hz), and 7.17-7.35 (12H, m).
Example 49
[Chemical Formula 76]
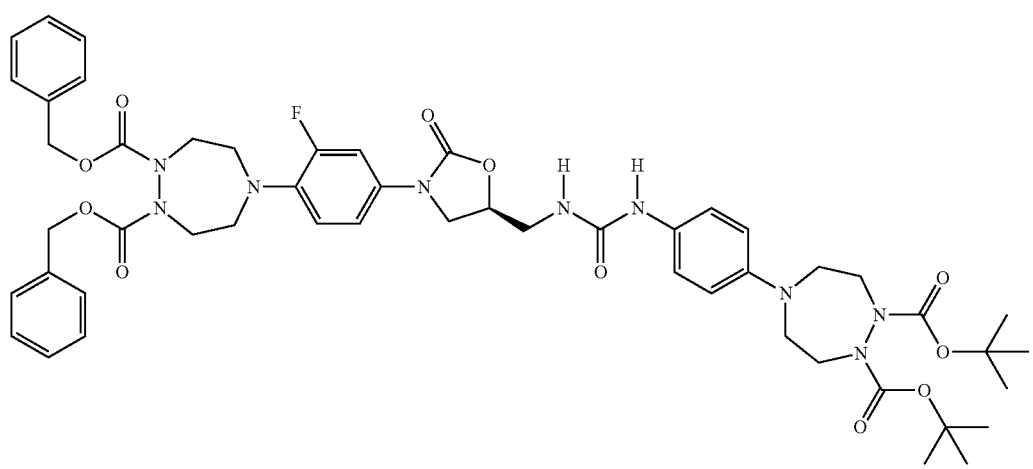

¹H NMR (CDCl₃) δ 1.36-1.43 (18H, Boc×2), 3.12-4.36 (16H, m), 4.69-4.79 (1H, m), 4.96-5.20 (4H, m), 5.34-5.52 (1H, m), 6.60-6.70 (5H, m), and 7.02-7.38 (14H, m).

Example 50

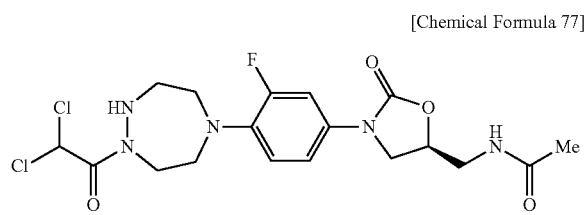 [SMILES: CC(=O)NC[C@H]1CN(c2ccc(N3CCNN(C(=O)C(Cl)Cl)CC3)c(F)c2)C(=O)O1]

Example 51

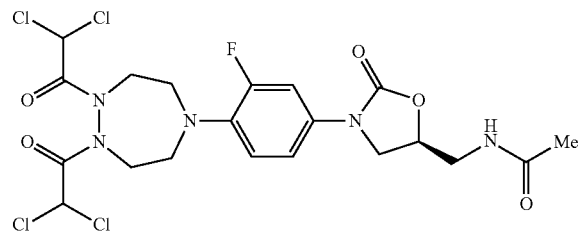

Example 52

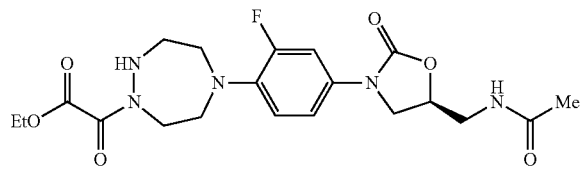

¹H NMR (CDCl₃) δ 1.31 (3H, t, J=7.2 Hz, OCH₂CH₃), 1.99 (3H, s, Ac), 3.15-3.25 (2H, m), 3.28-3.35 (2H, m), 3.38-3.45 (2H, m), 3.57-3.85 (5H, m), 3.98 (1H, t, J=8.8 Hz), 4.29 (2H, q, J=7.2 Hz, OCH₂CH₃), 4.69-4.79 (1H, m), 6.72 (1H, t, J=6.1 Hz, NHAc), 6.86 (1H, t, J=9.1 Hz), 6.94-7.03 (1H, m), and 7.37 (1H, dd, J=2.5, 14.6 Hz).

Example 53

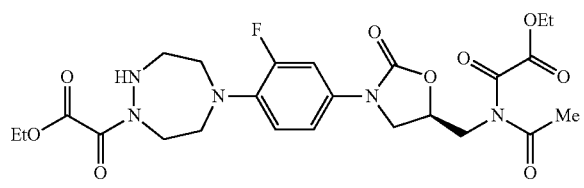

¹H NMR (CDCl₃) δ 1.34 (3H, t, J=7.1 Hz), 1.37 (3H, t, J=7.1 Hz), 2.47 (3H, s, Ac), 3.20-3.47 (6H, m), 3.70-4.20 (6H, m), 4.32 (2H, q, J=7.1 Hz), 4.37 (2H, q, J=7.1 Hz), 4.80-4.91 (1H, m), 6.91 (1H, t, J=9.1 Hz), 6.99-7.08 (1H, m), and 7.40 (1H, dd, J=2.5, 14.6 Hz).

Example 54

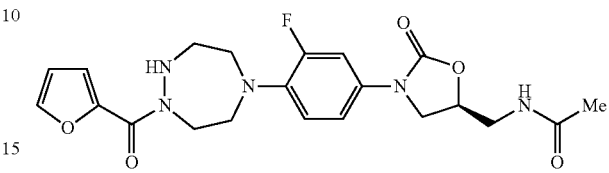

¹H NMR (CDCl₃) δ 2.02 (3H, s, Ac), 3.20-3.76 (10H, m), 3.95-4.15 (2H, m), 4.70-4.81 (1H, m), 6.30-6.40 (1H, br), 6.48 (1H, dd, J=1.7, 3.6 Hz), 6.86-7.03 (2H, m), 7.38 (1H, dd, J=2.6, 14.8 Hz), and 7.53 (1H, s).

Example 55

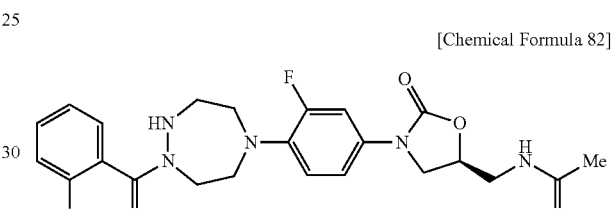

¹H NMR (CDCl₃) δ 2.01 (3H, s, Ac), 3.02-4.12 (12H, m), 4.72-4.82 (1H, m), 6.38 (1H, br s, NHAc), and 6.82-7.44 (7H, m).

Example 56

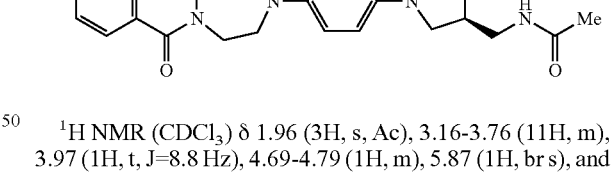

¹H NMR (CDCl₃) δ 1.96 (3H, s, Ac), 3.16-3.76 (11H, m), 3.97 (1H, t, J=8.8 Hz), 4.69-4.79 (1H, m), 5.87 (1H, br s), and 6.81-7.38 (7H, m).

Example 57

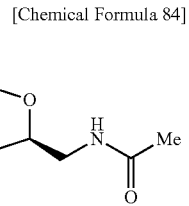

¹H NMR (CDCl₃) δ 2.03 (3H, s, Ac), 3.38-3.50 (4H, m), 3.65-3.69 (2H, m), 3.79 (1H, dd, J=6.5, 9.1 Hz), 4.03 (1H, t, J=9.1 Hz), 4.38-4.47 (4H, m), 4.75-4.85 (1H, m), 6.82 (1H, t, J=6.1 Hz, NHAc), 6.99 (1H, t, J=9.1 Hz), 7.05-7.11 (2H, m), 7.46 (1H, dd, J=2.5, 14.0 Hz), 8.16 (1H, dd, J=1.7, 8.0 Hz), and 8.53 (1H, dd, J=1.7, 5.0 Hz).

Example 58

[Chemical Formula 85]

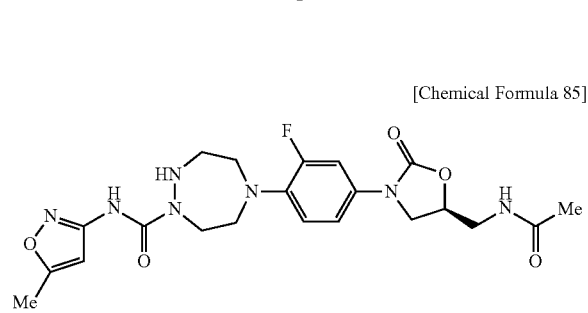

¹H NMR (CDCl₃) δ 2.03 (3H, s, Ac), 2.24 (3H, s, Aryl-Me), 3.24-4.05 (12H, m), 4.72-4.82 (1H, m), 6.03 (1H, s), 6.35 (1H, t, J=6.0 Hz, NHAc), 6.90 (1H, t, J=9.0 Hz), 7.00-7.06 (1H, m), 7.41 (1H, dd, J=2.5, 14.6 Hz), and 9.29 (1H, s, Aryl-NHC=O).

Example 59

[Chemical Formula 86]

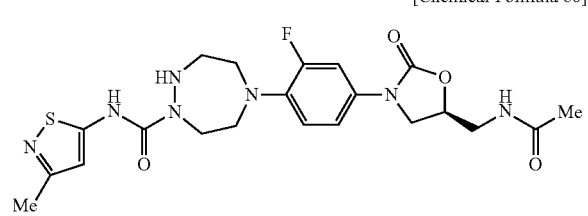

¹H NMR (CDCl₃) δ 2.02 (3H, s, Ac), 2.37 (3H, s, Aryl-Me), 3.23-4.03 (12H, m), 4.71-4.80 (1H, m), 6.42 (1H, t, J=6.0 Hz, NHAc), 6.48 (1H, s), 6.88 (1H, t, J=9.2 Hz), 7.00 (1H, br dd, J=3, 9 Hz), 7.40 (1H, dd, J=2.5, 14.6 Hz), and 9.33 (1H, s, Aryl-NHC=O).

Example 60

[Chemical Formula 87]

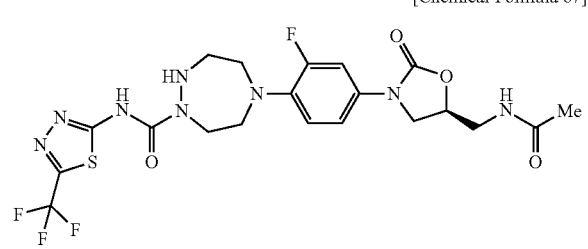

¹H NMR (CDCl₃) δ 2.02 (3H, s, Ac), 2.37 (3H, s, Aryl-Me), 3.24-4.04 (12H, m), 4.70-4.81 (1H, m), 6.40 (1H, t, J=6.0 Hz, NHAc), 6.48 (1H, s), 6.88 (1H, t, J=9.2 Hz), 7.00 (1H, br dd, J=3, 9 Hz), 7.40 (1H, dd, J=2.7, 14.4 Hz), and 9.33 (1H, s, Aryl-NHC=O).

Example 61

[Chemical Formula 88]

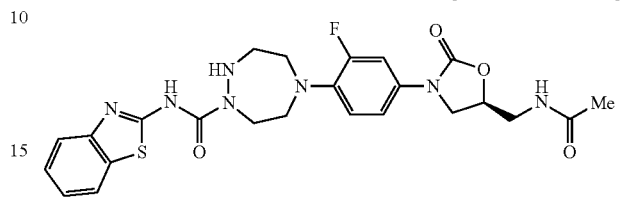

¹H NMR (CDCl₃) δ 2.02 (3H, s, Ac), 3.26-4.08 (12H, m), 4.71-4.81 (1H, m), 6.16 (1H, t, J=6.0 Hz), 6.87-7.81 (5H, m), 7.68-7.81 (2H, m), and 9.96 (1H, s, Aryl-NHC=O).

Example 62

[Chemical Formula 89]

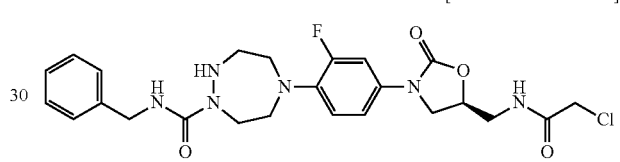

¹H NMR (CDCl₃) δ 3.11-3.18 (2H, m), 3.35-3.43 (4H, m), 3.53-3.78 (6H, m), 3.84-4.02 (2H, m), 4.41 (2H, AB), 4.68-4.78 (1H, m), 6.76 (1H, t, J=6.0 Hz, CHCH₂NHC=O), 6.84-7.05 (2H, m), 7.20-7.45 (6H, m), and 7.74 (1H, t, J=6.3 Hz, NHCH₂Ph).

Example 63

[Chemical Formula 90]

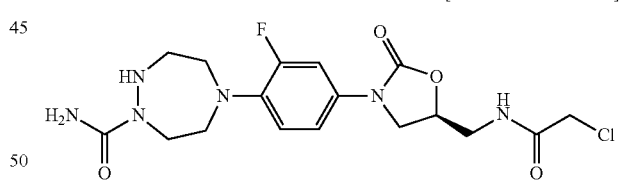

Example 64

[Chemical Formula 91]

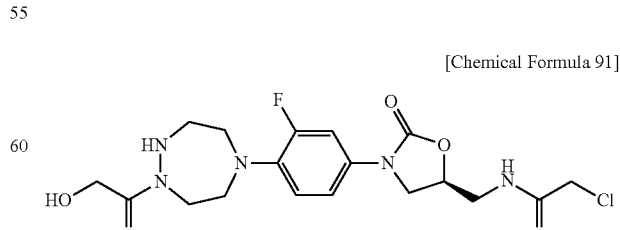

¹H NMR (DMSO-d₆) δ 2.95-4.11 (13H, m), 4.20 (2H, s), 4.63-4.74 (1H, m), 6.98-7.14 (2H, m), 7.44 (1H, br d, J=16 Hz), and 8.26 (1H, br t, J=6 Hz).

Example 65

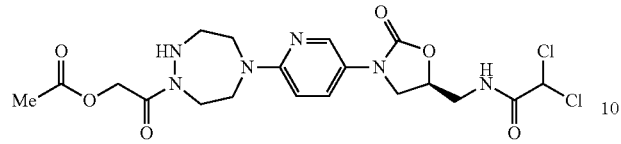

[Chemical Formula 92]

¹H NMR (CDCl₃) δ 2.16 (3H, s, Ac), 3.13-4.10 (12H, m), 4.78-4.88 (1H, m), 4.93 (2H, s, CH₂OAC), 6.04 (1H, s, CHCl₂), 6.50-6.57 (1H, m), 7.52 (1H, t, J=6.1 Hz, NHC=O), 7.73 (1H, dd, J=2.8, 9.1 Hz), and 8.09 (1H, d, J=2.8 Hz).

Example 66

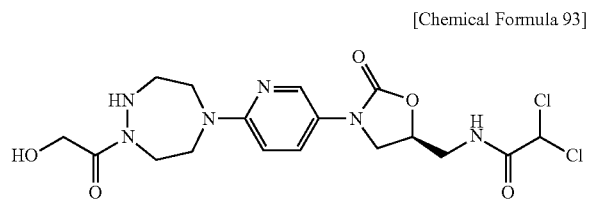 [SMILES: O=C(NC[C@H]1CN(c2ccc(N3CCNN(C(=O)CO)CC3)nc2)C(=O)O1)C(Cl)Cl]

[Chemical Formula 93]

¹H NMR (CDCl₃) δ 3.00-4.10 (12H, m), 4.34 (2H, AB, CH₂OH), 4.79-4.88 (1H, m), 5.98 (1H, s, CHCl₂), 6.52-6.58 (1H, m), 7.11 (1H, t, J=6.0 Hz, NHC=O), 7.77-7.82 (1H, m), and 8.08-8.11 (1H, m).

Example 67

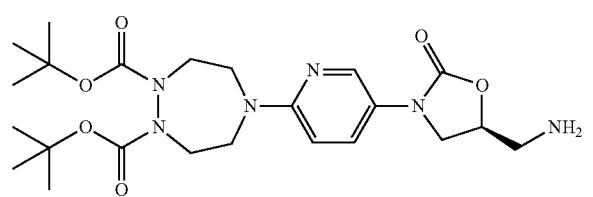

[Chemical Formula 94]

¹H NMR (CDCl₃) δ 1.43 (18H, s, Boc×2), 2.88-4.26 (12H, m), 4.63-4.75 (1H, m), 6.55 (1H, d, J=9.3 Hz), 7.86-7.96 (1H, m), and 8.06-8.12 (1H, m).

Example 68

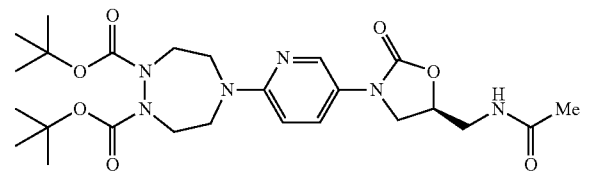

[Chemical Formula 95]

¹H NMR (CDCl₃) δ 1.43 (18H, s, Boc×2), 2.03 (3H, s, Ac), 3.10-4.26 (12H, m), 4.73-4.82 (1H, m), 6.02 (1H, t, J=6.2 Hz, NHAc), 6.55 (1H, d, J=9.3 Hz), 7.76-7.83 (1H, m), and 8.07-8.11 (1H, m).

Example 69

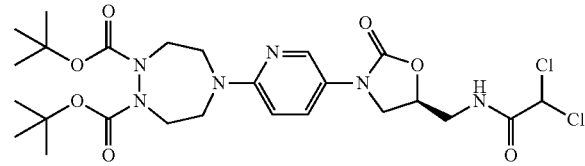

[Chemical Formula 96]

¹H NMR (CDCl₃) δ 1.43 (18H, s, Boc×2), 3.10-4.26 (12H, m), 4.79-4.89 (1H, m), 5.98 (1H, s, CHCl₂), 6.55 (1H, d, J=9.3 Hz), 7.28 (1H, br s, NHC=O), 7.72-7.81 (1H, m), and 8.06-8.11 (1H, m).

Example 70

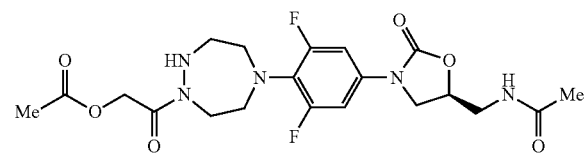

[Chemical Formula 97]

¹H NMR (CDCl₃) δ 2.03 (3H, s, NHAc), 2.10 (3H, s, OAC), 3.06-3.52 (6H, m), 3.63-3.78 (3H, m), 3.99 (1H, t, J=9.1 Hz), 4.19 (2H, AB, CH₂OAC), 4.40-4.50 (2H, m), 4.74-4.84 (1H, m), 6.34 (1H, br t, J=6 Hz, NHAc), and 7.11 (2H, d, J=10.7 Hz).

Example 71

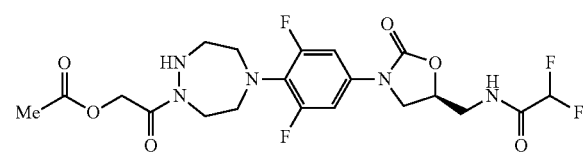

[Chemical Formula 98]

¹H NMR (CDCl₃) δ 2.10 (3H, s, OAC), 3.06-3.52 (6H, m), 3.62-3.74 (2H, m), 3.79-3.89 (1H, m), 4.06 (1H, t, J=9.1 Hz), 4.19 (2H, AB, CH₂OAC), 4.40-4.50 (2H, m), 4.78-4.89 (1H, m), 5.94 (1H, t, J=54.1 Hz, CHF₂), 6.97-7.10 (1H, br, NHC=O), and 7.10 (2H, d, J=10.7 Hz).

Example 72

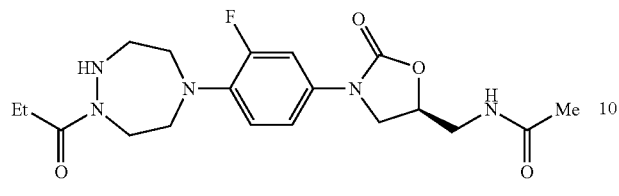

[Chemical Formula 99]

¹H NMR (CDCl₃) δ 1.02-1.15 (3H, m, CH₃CH₂C=O), 2.02 (3H, s, Ac), 2.20 (1H, q, J=7.6 Hz, CH₃CHHC=O), 2.58 (1H, q, J=7.6 Hz, CH₃CHHC=O), 3.05-3.13 (1H, m), 3.16-3.22 (1H, m), 3.30-3.45 (3H, m), 3.56-3.78 (5H, m), 3.86-4.05 (2H, m), 4.72-4.82 (1H, m), 6.64-6.76 (1H, br, NHAc), 6.87 (1H, t, J=9.1 Hz), 6.96-7.04 (1H, m), and 7.34-7.45 (1H, m).

Example 73

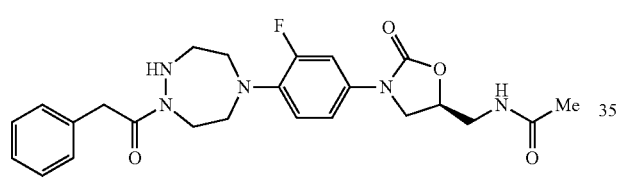

[Chemical Formula 100]

¹H NMR (CDCl₃) δ 2.01 (3H, s, Ac), 3.04-3.39 (6H, m), 3.54-4.05 (6H, m), 3.92 (2H, s, CH₂Ph), 4.70-4.81 (1H, m), 6.28 (1H, br t, J=6 Hz, NHAc), 6.78-7.05 (2H, m), and 7.13-7.42 (6H, m).

Example 74

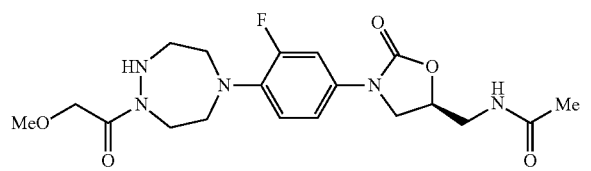

[Chemical Formula 101]

¹H NMR (CDCl₃) δ 2.02 (3H, s, Ac), 3.16-3.21 (2H, m), 3.32-3.41 (4H, m), 3.45 (3H, s, OMe), 3.60-4.02 (6H, m), 4.35 (2H, s, CH₂OMe), 4.71-4.82 (1H, m), 6.70 (1H, t, J=6.1 Hz, NHAc), 6.87 (1H, t, J=9.1 Hz), 7.01 (1H, dd, J=2.5, 9.1 Hz), and 7.39 (1H, dd, J=2.5, 14.6 Hz).

Example 75

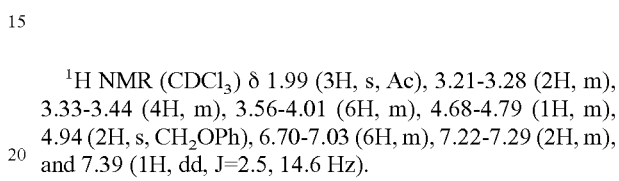

[Chemical Formula 102]

¹H NMR (CDCl₃) δ 1.99 (3H, s, Ac), 3.21-3.28 (2H, m), 3.33-3.44 (4H, m), 3.56-4.01 (6H, m), 4.68-4.79 (1H, m), 4.94 (2H, s, CH₂OPh), 6.70-7.03 (6H, m), 7.22-7.29 (2H, m), and 7.39 (1H, dd, J=2.5, 14.6 Hz).

Example 76

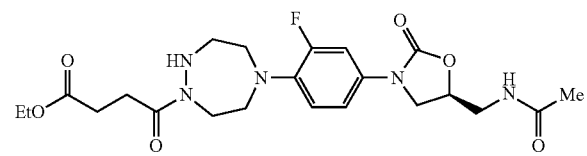

[Chemical Formula 103]

¹H NMR (CDCl₃) δ 1.25 (3H, t, J=7.5 Hz, CH₃CH₂O), 2.03 (3H, s, Ac), 2.45-2.93 (4H, m), 3.06-3.78 (10H, m), 3.86-3.92 (1H, m), 4.01 (1H, t, J=9.1 Hz), 4.13 (2H, q, J=7.5 Hz, CH₃CH₂O), 4.72-4.82 (1H, m), 6.56 (1H, br s, NHAc), 6.88 (1H, t, J=9.1 Hz), 6.97-7.05 (1H, m), and 7.34-7.45 (1H, m).

Example 77

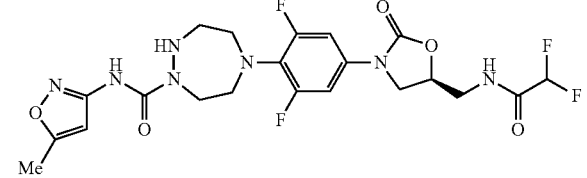

[Chemical Formula 104]

¹H NMR (CDCl₃) δ 2.38 (3H, s, Aryl-Me), 3.16-3.24 (2H, m), 3.29-3.42 (4H, m), 3.62-3.76 (2H, m), 3.78-3.91 (2H, m), 3.98 (1H, t, J=6.0 Hz), 4.06 (1H, t, J=9.1 Hz), 4.79-4.89 (1H, m), 5.94 (1H, t, J=54.1 Hz, CHF₂), 6.64 (1H, s, Me-C=CH), 7.09 (2H, d, J=10.7 Hz), and 9.15 (1H, s, Aryl-NHC=O).

Example 78

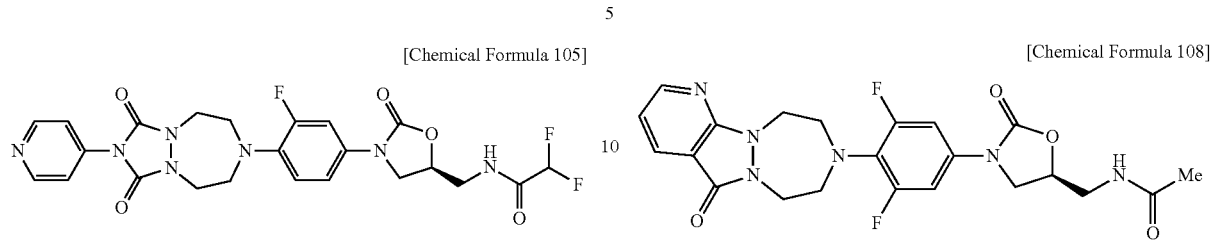

[Chemical Formula 105]

$^1$H NMR (CDCl$_3$) δ 3.44-3.50 (4H, m), 3.61-3.77 (2H, m), 3.87 (1H, ddd, J=3.3, 6.6, 14.6 Hz), 4.10 (1H, t, J=9.1 Hz), 4.13-4.19 (4H, m), 4.78-4.88 (1H, m), 5.94 (1H, t, J=54.1 Hz, CHF$_2$), 6.84 (1H, br t, J=6 Hz, NHC=O), 7.00 (1H, t, J=9.0 Hz), 7.10 (1H, dd, J=2.5, 9.0 Hz), 7.46 (1H, dd, J=2.5, 13.9 Hz), 7.78 (2H, d, J=4.7 Hz,), and 8.71 (2H, d, J=4.7 Hz).

Example 79

[Chemical Formula 106]

$^1$H NMR (CDCl$_3$) δ 3.41-3.50 (4H, m), 3.63-3.76 (2H, m), 3.84 (1H, ddd, J=3.3, 6.3, 14.6 Hz), 4.07 (1H, t, J=9.1 Hz), 4.10-4.16 (4H, m), 4.79-4.89 (1H, m), 5.94 (1H, t, J=54.1 Hz, CHF$_2$), 7.07-7.15 (1H, br, NHC=O), 7.14 (2H, d, J=10.7 Hz), 7.78 (2H, d, J=4.7 Hz), and 8.71 (2H, d, J=4.7 Hz).

Example 80

[Chemical Formula 107]

$^1$H NMR (CDCl$_3$) δ 3.39-3.51 (4H, m), 3.60-3.77 (2H, m), 3.86 (1H, ddd, J=3.2, 6.6, 14.2 Hz), 4.10 (1H, t, J=9.1 Hz), 4.39-4.48 (4H, m), 4.78-4.88 (1H, m), 5.94 (1H, t, J=54.1 Hz, CHF$_2$), 6.90-7.02 (1H, br, NHAc), 7.00 (1H, t, J=9.1 Hz), 7.06-7.11 (2H, m), 7.46 (1H, dd, J=2.5, 13.7 Hz), 8.18 (1H, dd, J=1.7, 7.7 Hz), and 8.55 (1H, dd, J=1.7, 4.7 Hz).

Example 81

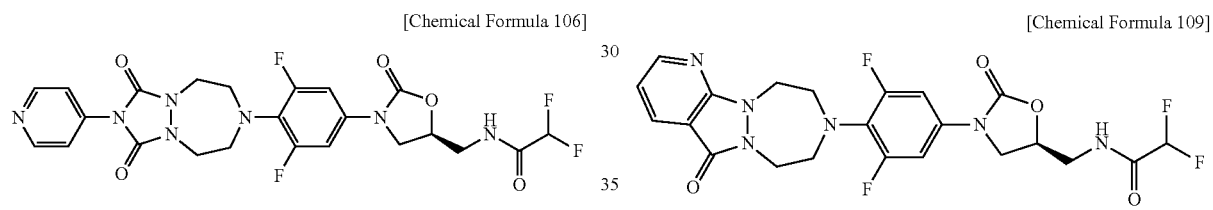

[Chemical Formula 108]

$^1$H NMR (CDCl$_3$) δ 2.04 (3H, s, Ac), 3.38-3.50 (4H, m), 3.64-3.71 (2H, m), 3.78 (1H, dd, J=6.9, 9.1 Hz), 4.01 (1H, t, J=9.1 Hz), 4.35-4.50 (4H, m), 4.76-4.86 (1H, m), 6.71 (1H, t, J=6.0 Hz, NHAc), 7.07 (1H, dd, J=4.8, 7.8 Hz), 7.13 (2H, d, J=10.7 Hz), 8.16 (1H, dd, J=1.7, 7.8 Hz), and 8.53 (1H, dd, J=1.7, 4.8 Hz).

Example 82

[Chemical Formula 109]

$^1$H NMR (CDCl$_3$) δ 3.38-3.49 (4H, m), 3.65-3.80 (2H, m), 3.83 (1H, ddd, J=3.9, 6.3, 14.6 Hz), 4.07 (1H, t, J=9.1 Hz), 4.35-4.49 (4H, m), 5.96 (1H, t, J=54.1 Hz, CHF$_2$), 7.07 (1H, dd, J=4.7, 8.0 Hz), 7.12 (2H, d, J=10.5 Hz), 7.53 (1H, br t, J=6 Hz, NHC=O), 8.16 (1H, dd, J=1.6, 8.0 Hz), and 8.53 (1H, dd, J=1.6, 4.7 Hz).

Example 83

[Chemical Formula 110]

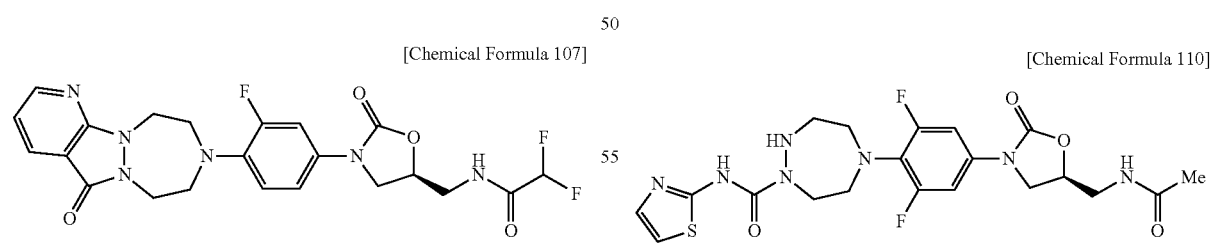

$^1$H NMR (CDCl$_2$) δ 2.03 (3H, s, Ac), 3.17-3.26 (2H, m), 3.29-3.36 (2H, m), 3.37-3.44 (2H, m), 3.62-3.70 (2H, m), 3.72 (1H, dd, J=6.5, 9.1 Hz), 3.84-3.95 (1H, m), 3.96 (1H, t, J=9.1 Hz), 4.14 (1H, br t, J=6 Hz), 4.74-4.84 (1H, m), 6.52 (1H, t, J=6.1 Hz, NHAc), 6.87 (1H, d, J=3.6 Hz), 7.09 (2H, d, J=10.7 Hz), 7.37 (1H, d, J=3.6 Hz), and 9.87 (1H, br s, Aryl-NHC=O).

Example 84

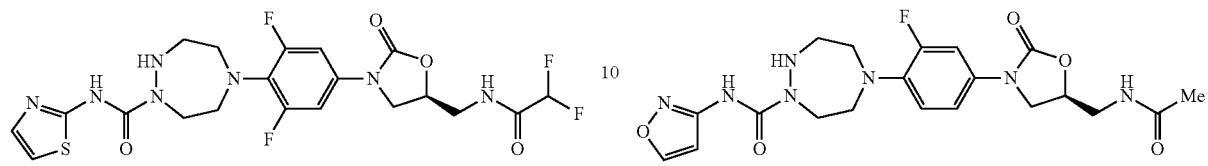

[Chemical Formula 111]

¹H NMR (CDCl₃) δ 3.18-3.26 (2H, m), 3.30-3.37 (2H, m), 3.37-3.45 (2H, m), 3.62-3.74 (2H, m), 3.78-3.96 (2H, m), 4.02-4.10 (2H, m), 4.78-4.88 (1H, m), 5.94 (1H, t, J=54.1 Hz, CHF₂), 6.88 (1H, d, J=3.6 Hz), 7.09 (2H, d, J=10.7 Hz), 7.19 (1H, br t, J=6 Hz, NHC=O), 7.37 (1H, d, J=3.6 Hz), and 9.85 (1H, s, Aryl-NHC=O).

Example 85

[Chemical Formula 112]

¹H NMR (CDCl₃) δ 2.03 (3H, s, Ac), 3.19-3.27 (2H, m), 3.32-3.44 (4H, m), 3.62-3.70 (3H, m), 3.74 (1H, dd, J=6.8, 9.1 Hz), 3.95-4.04 (2H, m), 4.73-4.83 (1H, m), 6.43 (1H, t, J=6.2 Hz, NHAc), 7.11 (2H, d, J=10.7 Hz), 7.44 (2H, d, J=4.8 Hz), and 8.42 (2H, d, J=4.8 Hz).

Example 86

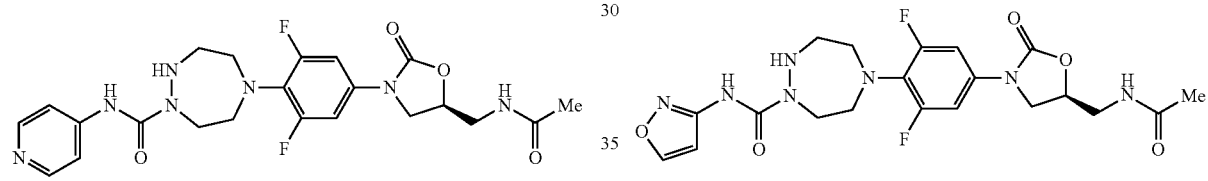

[Chemical Formula 113]

¹H NMR (CDCl₃) δ 3.19-3.28 (2H, m), 3.33-3.44 (4H, m), 3.61-3.74 (3H, m), 3.84 (1H, ddd, J=3.5, 6.3, 14.6 Hz), 3.96 (1H, t, J=6.3 Hz), 4.06 (1H, t, J=9.1 Hz), 4.78-4.88 (1H, m), 5.94 (1H, t, J=54.1 Hz, CHF₂), 7.07-7.14 (1H, br, Aryl-NHC=O), 7.10 (2H, d, J=10.7 Hz), 7.44 (2H, d, J=5.0 Hz), and 8.43 (2H, d, J=5.0 Hz).

Example 87

[Chemical Formula 114]

¹H NMR (CDCl₃) δ 2.02 (3H, s, Ac), 3.18-3.30 (2H, m), 3.36-3.46 (4H, m), 3.55-3.77 (3H, m), 3.87-4.05 (3H, m), 4.71-4.81 (1H, m), 6.28 (1H, br t, J=6 Hz, NHAc), 6.91 (1H, t, J=9.1 Hz), 7.00 (1H, d, J=1.6 Hz), 7.03 (1H, dd, 2.5, 9.1 Hz), 7.41 (1H, dd, J=2.5, 14.6 Hz), 8.23 (1H, d, J=1.6 Hz), and 9.22 (1H, s, Aryl-NHC=O).

Example 88

[Chemical Formula 115]

¹H NMR (CDCl₃) δ 2.03 (3H, s, Ac), 3.17-3.26 (2H, m), 3.30-3.42 (4H, m), 3.63-3.69 (2H, m), 3.74 (1H, dd, J=6.9, 9.1 Hz), 3.82-3.94 (1H, m), 3.96-4.04 (2H, m), 4.74-4.84 (1H, m), 6.36 (1H, t, J=6.1 Hz, NHAc), 7.02 (1H, d, J=1.7 Hz), 7.10 (2H, d, J=10.7 Hz), 8.24 (1H, d, J=1.7 Hz), and 9.26 (1H, s, Aryl-NHC=O).

Example 89

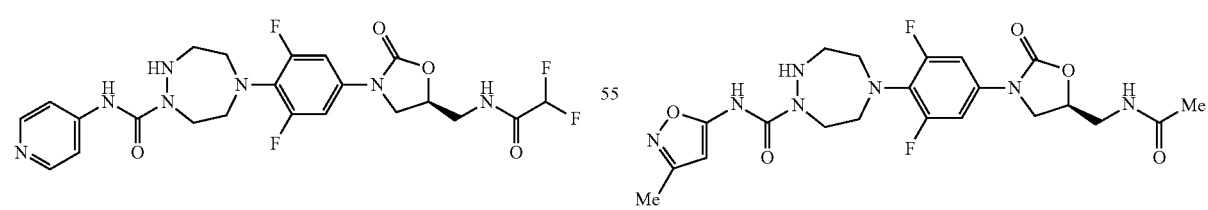

[Chemical Formula 116]

¹H NMR (CDCl₃) δ 2.03 (3H, s, Ac), 2.25 (3H, s, Aryl-Me), 3.18-3.26 (2H, m), 3.29-3.42 (4H, m), 3.62-3.70 (2H, m), 3.74 (1H, dd, J=6.6, 9.1 Hz), 3.80-3.94 (1H, m), 4.00 (1H, t, J=9.1 Hz), 4.07 (1H, t, J=6.1 Hz), 4.74-4.84 (1H, m), 6.03 (1H, s, O—C=CH), 6.48 (1H, t, J=6.3 Hz, NHAc), 7.10 (2H, d, J=10.7 Hz), and 9.34 (1H, s, Aryl-NHC=O).

Example 90

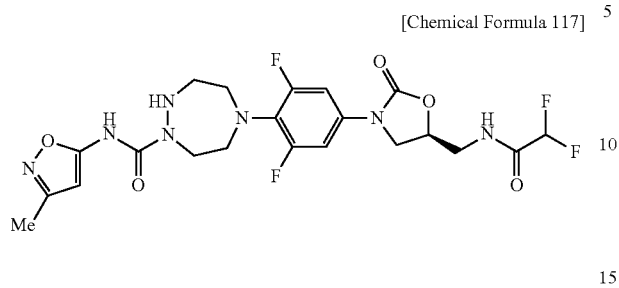
[Chemical Formula 117]

$^1$H NMR (CDCl$_3$) δ 2.26 (3H, s, Aryl-Me), 3.20-3.27 (2H, m), 3.30-3.43 (4H, m), 3.61-4.09 (6H, m), 4.78-4.88 (1H, m), 5.94 (1H, t, J=54.1 Hz), 6.24 (1H, s, O—C=CH), 6.96 (1H, br t, J=6 Hz, NHC=O), 7.10 (2H, d, J=10.7 Hz), and 9.34 (1H, s, Aryl-NHC=O).

Example 91

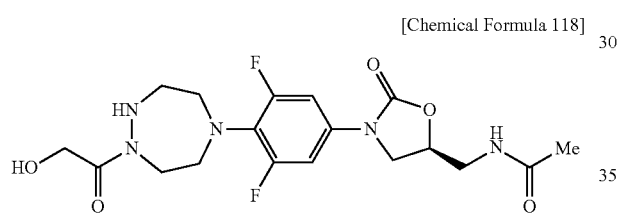
[Chemical Formula 118]

$^1$H NMR (CDCl$_3$) δ 2.03 (3H, s, Ac), 3.10-3.22 (2H, m), 3.25-3.31 (2H, m), 3.34-3.42 (2H, m), 3.63-3.70 (2H, m), 3.75 (1H, dd, J=6.6, 9.1 Hz), 3.88-3.93 (2H, m), 4.01 (1H, t, J=9.1 Hz), 4.39 (2H, s, CH$_2$OH), 4.75-4.85 (1H, m), 6.77 (1H, t, J=6.1 Hz, NHAc), and 7.09 (2H, d, J=10.7 Hz).

Example 92

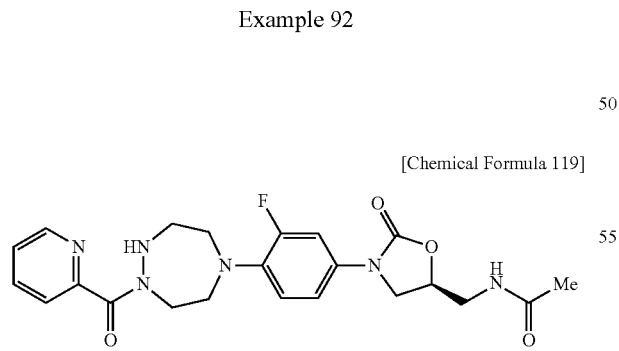
[Chemical Formula 119]

$^1$H NMR (CDCl$_3$) δ 2.01 (3H, s, Ac), 2.84-2.92 (1H, m), 3.26-3.32 (1H, m), 3.36-3.41 (1H, m), 3.49-3.54 (1H, m), 3.58-3.86 (6H, m), 3.95-4.08 (2H, m), 4.71-4.81 (1H, m), 6.73-6.82 (1H, m, NHAc), 6.84-7.04 (2H, m), 7.27-7.85 (3H, m), and 8.55 (1H, br d, J=5 Hz).

Example 93

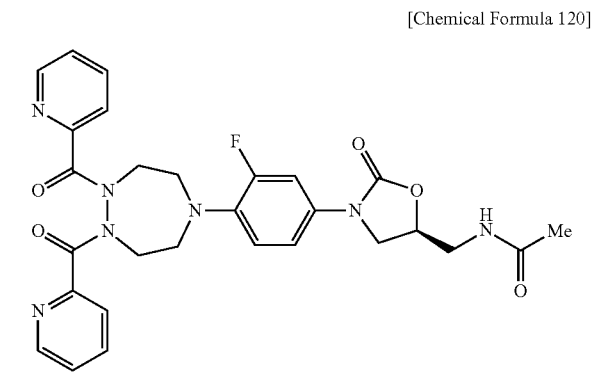 [SMILES: CC(=O)NC[C@H]1CN(c2ccc(N3CCN(C(=O)c4ccccn4)N(C(=O)c4ccccn4)CC3)c(F)c2)C(=O)O1]
[Chemical Formula 120]

$^1$H NMR (CDCl$_3$) δ 2.01 (3H, s, Ac), 3.46-3.82 (9H, m), 3.96-4.15 (2H, m), 4.46-4.57 (1H, m), 4.72-4.82 (1H, m), 6.54 (1H, t, J=6.0 Hz, NHAc), and 6.91-8.58 (9H, m).

Example 94

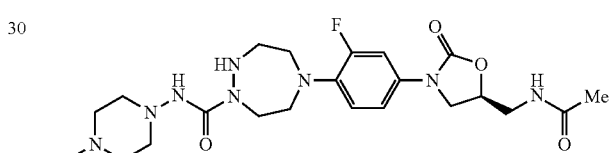
[Chemical Formula 121]

$^1$H NMR (CDCl$_3$) δ 2.03 (3H, s, Ac), 2.32 (3H, s, N-Me), 2.54-2.68 (4H, m), 2.76-2.93 (4H, m), 3.12-3.20 (2H, m), 3.33-3.40 (4H, m), 3.56-3.88 (5H, m), 4.00 (1H, t, J=9.1 Hz), 4.72-4.82 (1H, m), 6.54 (1H, t, J=6.1 Hz, NHAc), 6.88 (1H, t, J=9.1 Hz), 7.01 (1H, dd, J=2.4, 9.1 Hz), 7.19 (1H, s, N—NHC=O), and 7.39 (1H, dd, J=2.4, 14.6 Hz).

Example 95

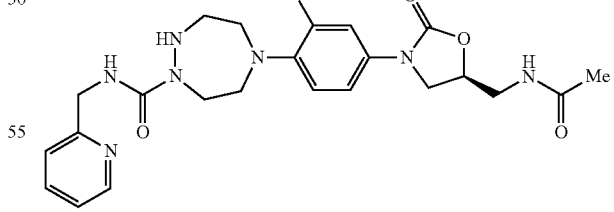
[Chemical Formula 122]

$^1$H NMR (CDCl$_3$) δ 2.02 (3H, s, Ac), 3.17-3.26 (2H, m), 3.36-3.44 (4H, m), 3.54-3.77 (4H, m), 3.84-3.93 (1H, m), 4.00 (1H, t, J=9.1 Hz), 4.54 (2H, AB, ArCH$_2$N), 4.71-4.81 (1H, m), 6.38 (1H, t, J=6.2 Hz, NHAc), 6.89 (1H, t, J=9.1 Hz), 7.01 (1H, dd, J=2.2, 9.1 Hz), 7.16 (1H, dd, J=4.9, 7.8 Hz), 7.24 (1H, t, J=5.8 Hz, CH$_2$NHC=O), 7.30 (1H, d, J=7.8 Hz), 7.39 (1H, dd, J=2.2, 14.6 Hz), 7.64 (1H, dt, J=1.9, 7.8 Hz), and 8.54 (1H, br d, J=5 Hz).

Example 96

[Chemical Formula 123]

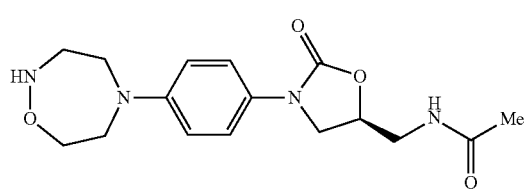

¹H-NMR in CDCl3: δ 2.02 (3H, s), 3.22 (2H, t, 6 Hz), 3.56 (1H, m), 3.68 (2H, t, 6 Hz), 3.74 (1H, m), 3.78 (2H, t, 6 Hz), 4.00 (1H, t, 9 Hz), 4.74 (1H, m), 6.07 (1H, bt), 6.73 (2H, d, 9 Hz), 7.31 (2H, d, 9 Hz)

Example 97

[Chemical Formula 124]

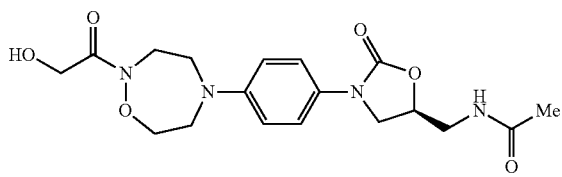

¹H-NMR in CDCl3: δ 2.03 (3H, s), 3.58 (1H, m), 3.76 (5H, m), 4.01 (3H, m), 4.12 (2H, t, 6 Hz), 4.29 (2H, bs), 4.75 (1H, m), 5.97 (1H, bt), 6.72 (2H, d, 9 Hz), 7.36 (2H, d, 9 Hz)

Example 98

[Chemical Formula 125]

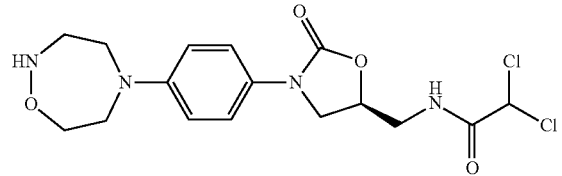

¹H-NMR in CDCl3: δ 3.22 (2H, t, 6 Hz), 3.60-3.84 (2H, m), 3.68 (2H, t, 6 Hz), 3.78 (2H, t, 6 Hz), 4.06 (1H, t, 9 Hz), 4.78 (1H, m), 5.95 (1H, s), 6.73 (2H, d, 9 Hz), 7.00 (1H, bt), 7.30 (2H, d, 9 Hz)

Example 99

[Chemical Formula 126]

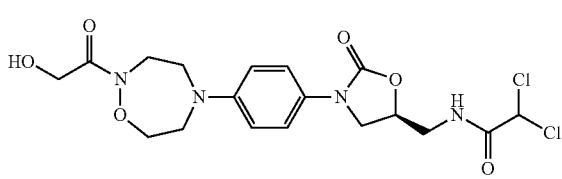

Example 100

[Chemical Formula 127]

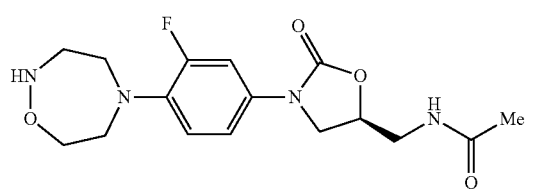

¹H-NMR in CDCl3: δ 2.03 (3H, s), 3.27 (2H, t, 6 Hz), 3.56 (2H, t, 6 Hz), 3.57-3.74 (4H, m), 3.93 (2H, t, 6 Hz), 4.01 (1H, t, 9 Hz), 4.75 (1H, m), 5.79 (1H, bs), 5.93 (1H, bt), 6.91 (1H, t, 9 Hz), 7.03 (1H, dd, 3, 9 Hz), 7.86 (1H, dd, 3, 9 Hz)

Example 101

[Chemical Formula 128]

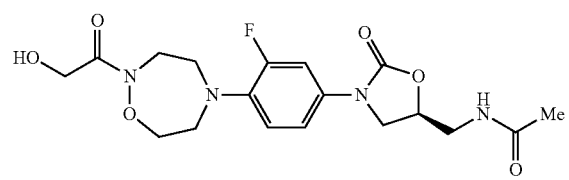

¹H-NMR in CDCl3: δ 2.03 (3H, s), 3.08 (1H, bs), 3.52 (4H, m), 3.58-3.76 (2H, m), 4.01 (3H, m), 4.13 (2H, t, 6 Hz), 4.33 (2H, s), 4.75 (1H, m), 5.96 (1H, bs), 6.90 (1H, t, 9 Hz), 7.05 (1H, dd, 3, 9 Hz), 7.43 (1H, dd, 3, 9 Hz)

Example 102

[Chemical Formula 129]

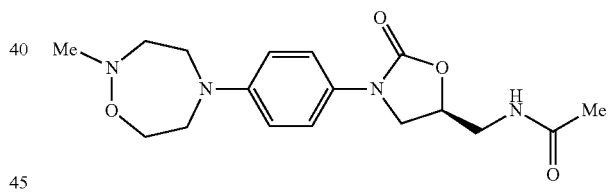

¹H-NMR in CDCl3: δ 2.03 (3H, s), 2.59 (3H, s), 2.93 (2H, t, 6 Hz), 3.55-3.69 (3H, m), 3.73 (4H, t, 6 Hz), 3.95 (2H, t, 6 Hz), 4.01 (1H, t, 9 Hz), 4.73 (1H, m), 6.00 (1H, bt), 6.73 (2H, d, 10 Hz), 7.31 (2H, d, 10 Hz)

Example 103

[Chemical Formula 130]

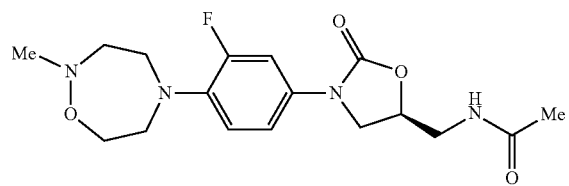

¹H-NMR in CDCl3: δ 2.03 (3H, s), 2.65 (3H, s), 2.96 (2H, t, 6 Hz), 3.55 (3H, t, 6 Hz), 3.61 (2H, t, 6 Hz), 3.69-3.75 (3H, m), 3.94 (2H, t, 6 Hz), 4.00 (1H, t, 9 Hz), 4.74 (1H, m), 5.93 (1H, bt), 6.89 (1H, t, 10 Hz), 7.02 (1H, dd, 10, 4 Hz), 7.35 (1H, dd, 10, 4 Hz)
Example 104
[Chemical Formula 131]
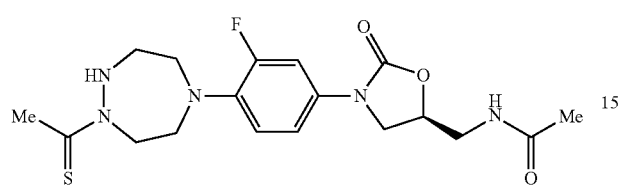
Example 105
[Chemical Formula 132]
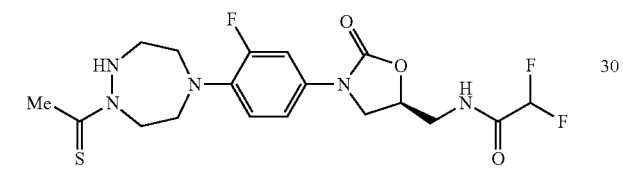
Example 106
[Chemical Formula 133]
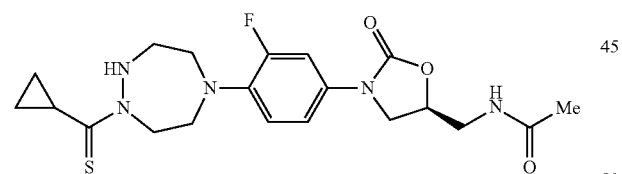
Example 107
[Chemical Formula 134]
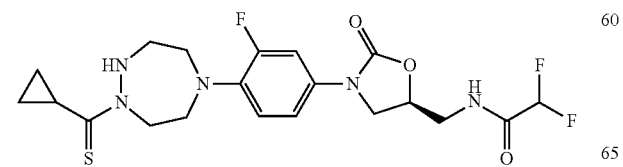
Example 108
[Chemical Formula 135]
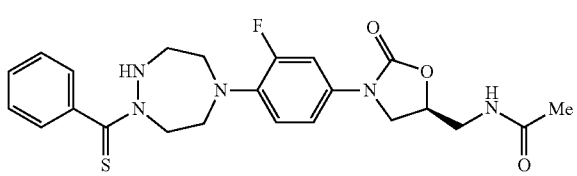
Example 109
[Chemical Formula 136]
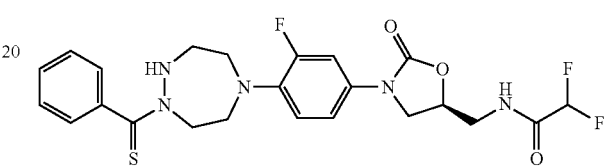
Example 110
[Chemical Formula 137]
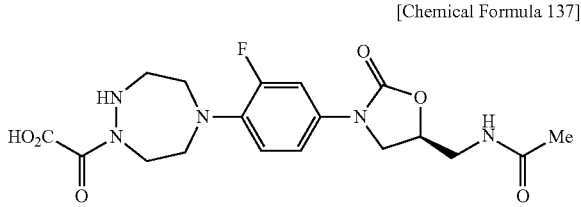 [SMILES: CC(=O)NC[C@H]1CN(c2ccc(N3CCNN(C(=O)C(=O)O)CC3)c(F)c2)C(=O)O1]
Example 111
[Chemical Formula 138]
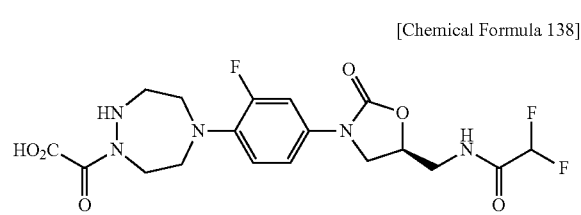 [SMILES: O=C(O)C(=O)N1CCN(c2ccc(N3C[C@H](CNC(=O)C(F)F)OC3=O)cc2F)CCN1]
Example 112
[Chemical Formula 139]
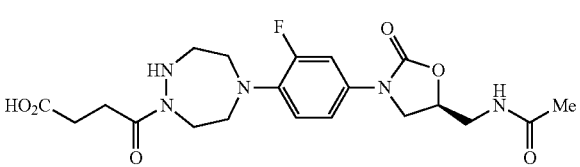

77
Example 113
78
Example 118
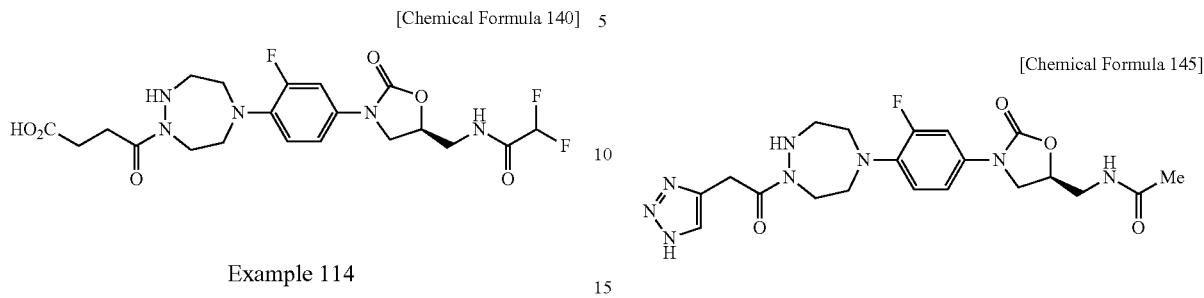
Example 114
Example 119
Example 115
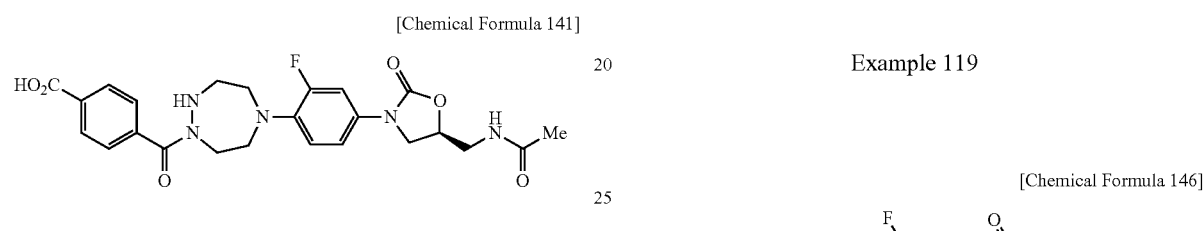
Example 120
Example 116
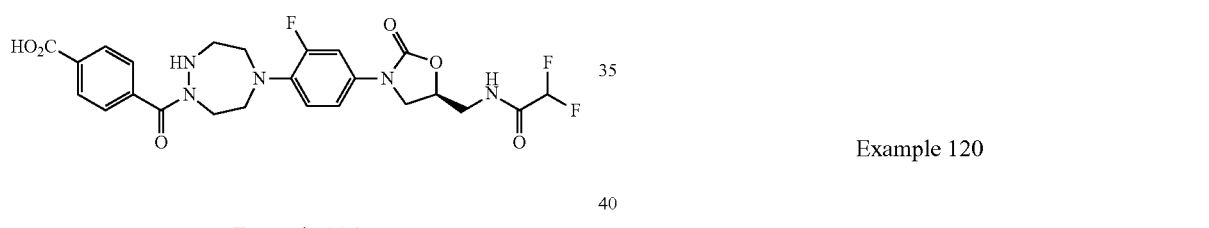
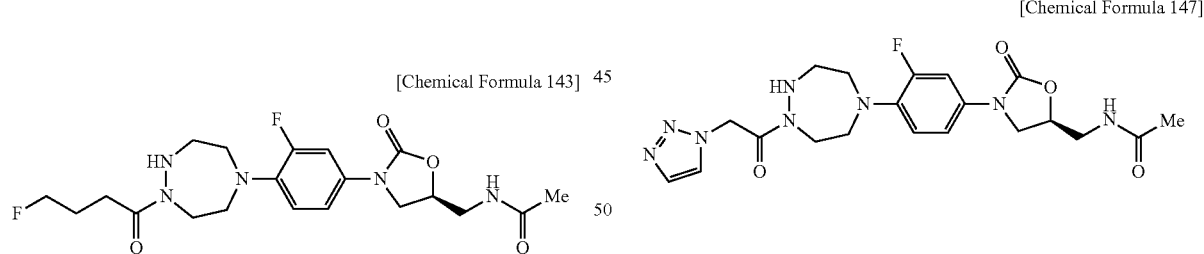
Example 117
Example 121
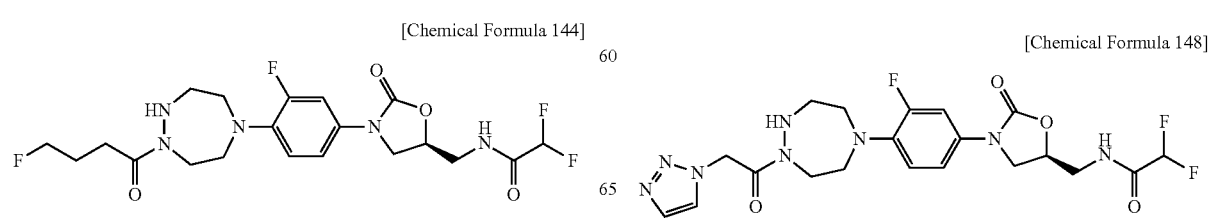

Example 122
[Chemical Formula 149]
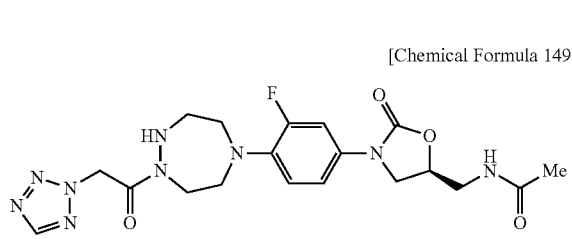
Example 124
[Chemical Formula 151]
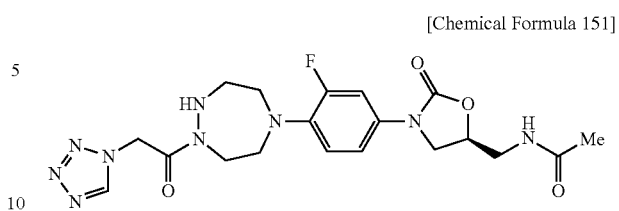
Example 125
[Chemical Formula 152]
Example 123
[Chemical Formula 150]
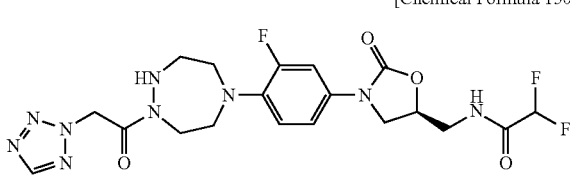
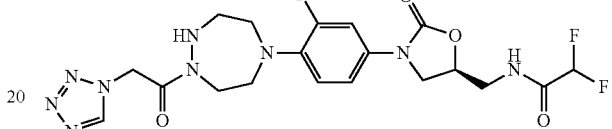
Example 126
[Chemical Formula 153]
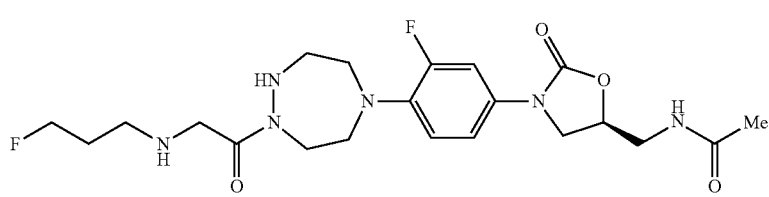
Example 127
[Chemical Formula 154]
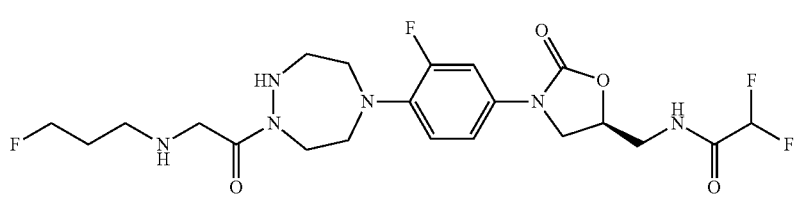
Example 128
[Chemical Formula 155]
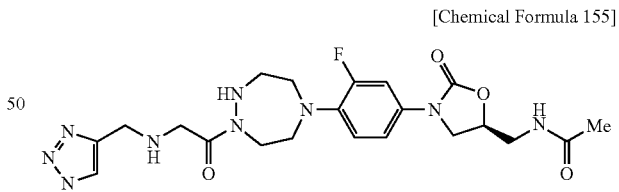
Example 129
[Chemical Formula 156]
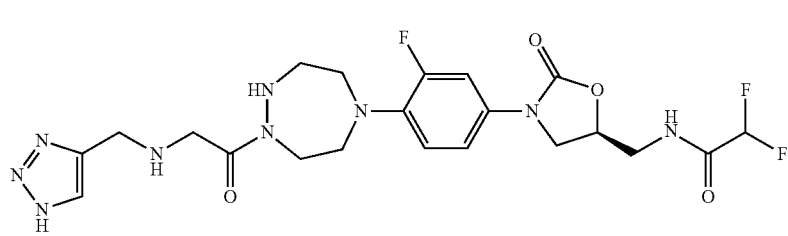

Example 130
[Chemical Formula 157]
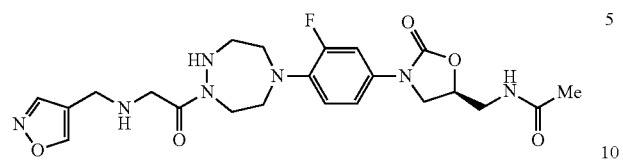
Example 131
[Chemical Formula 158]
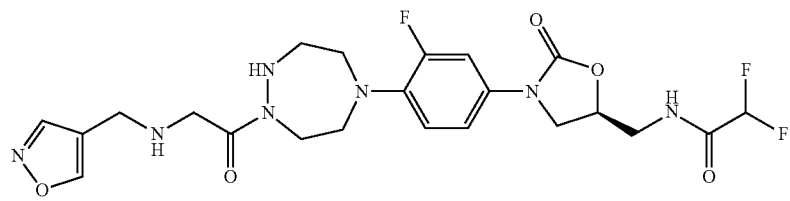
Example 132
[Chemical Formula 159]
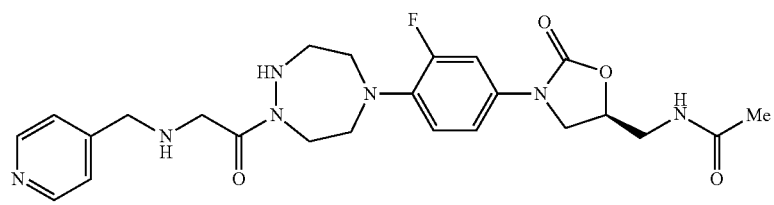
Example 133
[Chemical Formula 160]
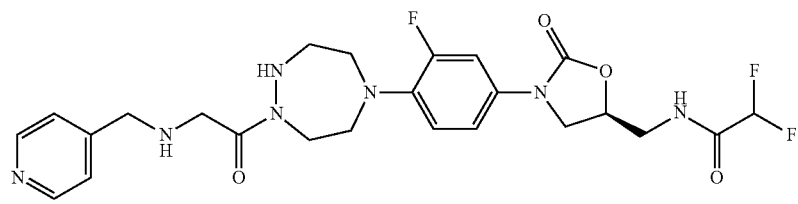
Example 134a
[Chemical Formula 161]
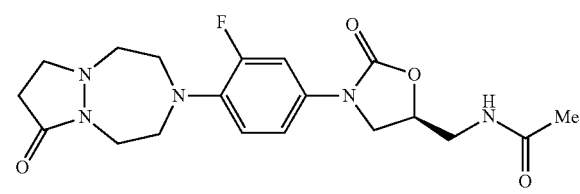
Example 134b
[Chemical Formula 162]
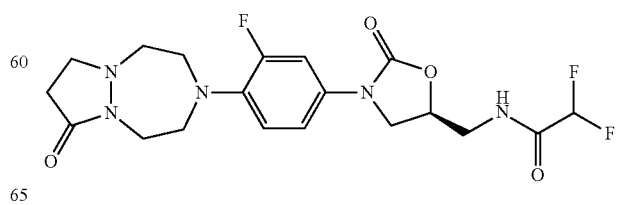

Example 135
[Chemical Formula 163]
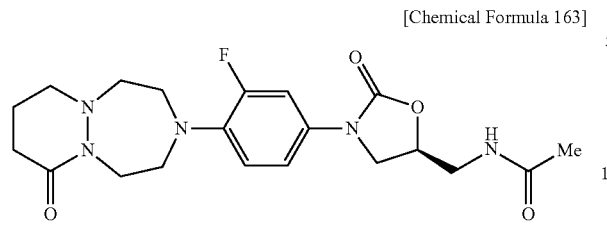
Example 136
[Chemical Formula 164]
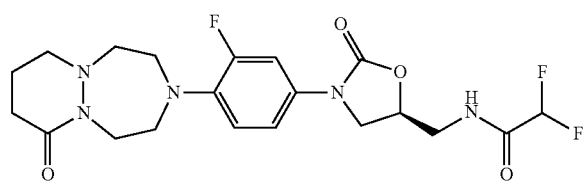
Example 137
[Chemical Formula 165]
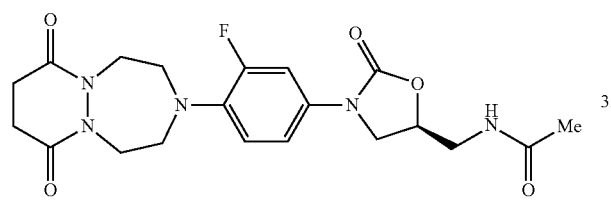
Example 138
[Chemical Formula 166]
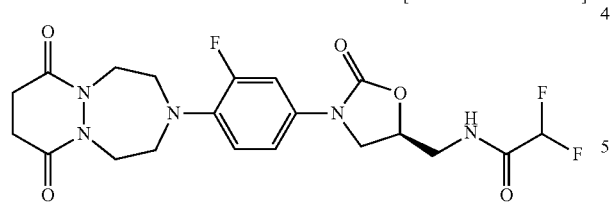
Example 139
[Chemical Formula 167]
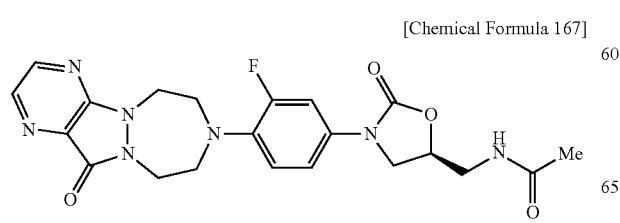
Example 140
[Chemical Formula 168]
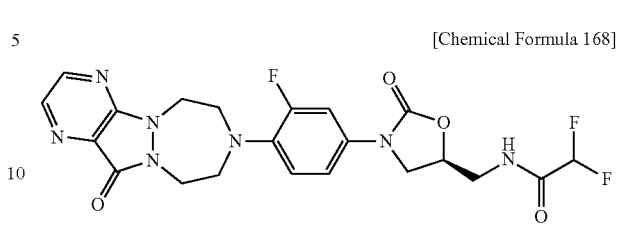
Example 141
[Chemical Formula 169]
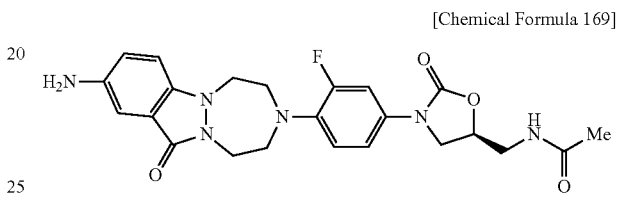
Example 142
[Chemical Formula 170]
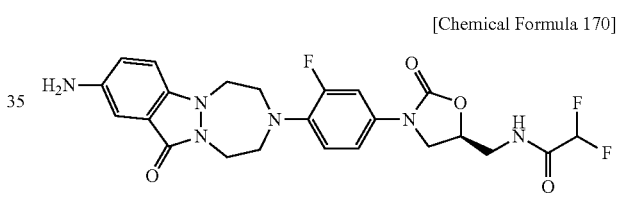
Example 143
[Chemical Formula 171]
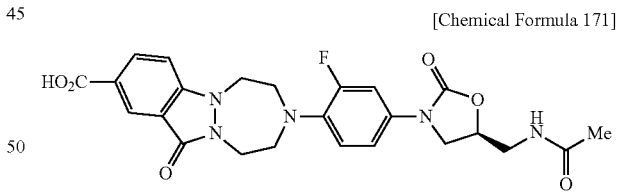
Example 144
[Chemical Formula 172]
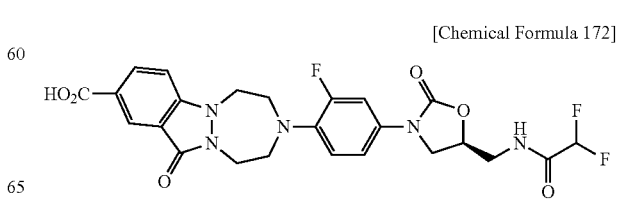

Example 145
Example 147
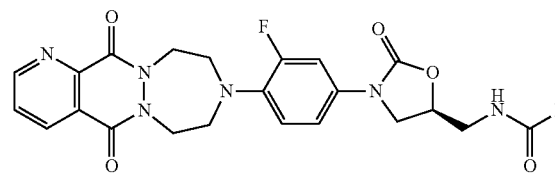
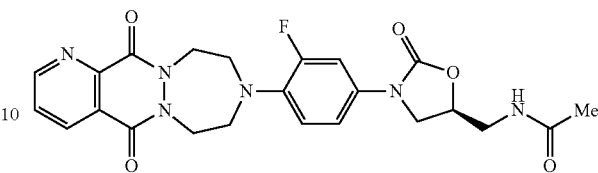
[Chemical Formula 173]
[Chemical Formula 175]
Example 146
Example 148
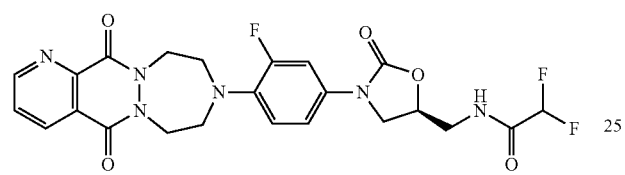
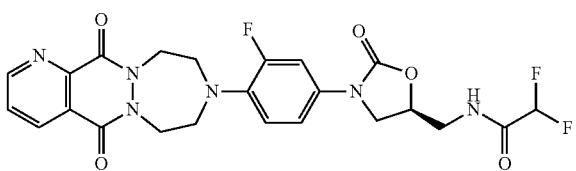
[Chemical Formula 174]
[Chemical Formula 176]
Example 149
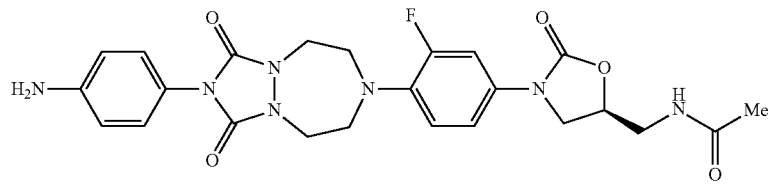
[Chemical Formula 177]
Example 150
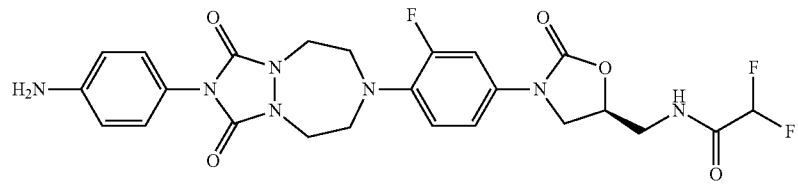
[Chemical Formula 178]
Example 151
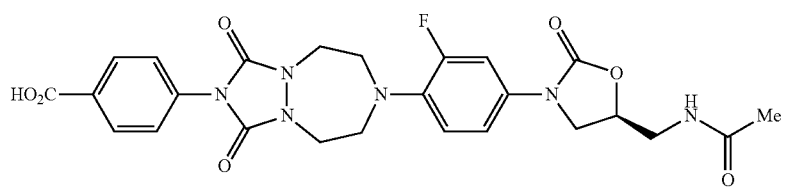
[Chemical Formula 179]

Example 152
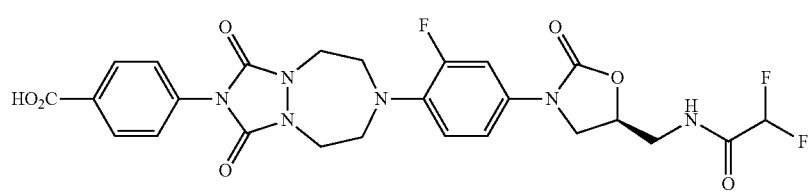
Example 153
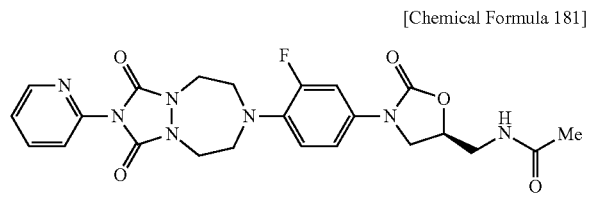 [SMILES: CC(=O)NC[C@H]1CN(c2ccc(N3CCn4c(=O)n(-c5ccccn5)c(=O)n4CC3)c(F)c2)C(=O)O1]
Example 154
[Chemical Formula 181]
Example 155
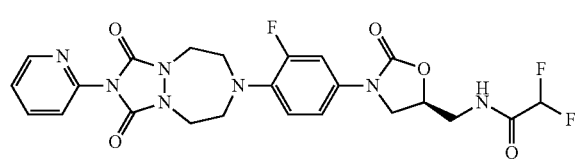
[Chemical Formula 182]
Example 156
[Chemical Formula 180]
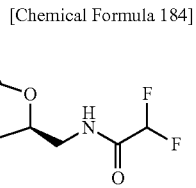
[Chemical Formula 184]
Example 157
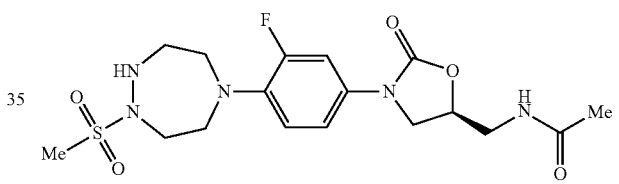
[Chemical Formula 185]
Example 158
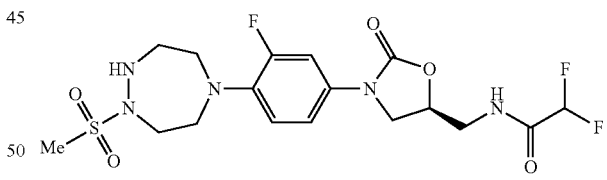
[Chemical Formula 186]
Example 159
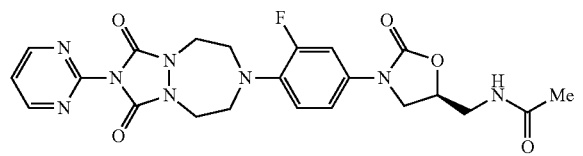
[Chemical Formula 183]
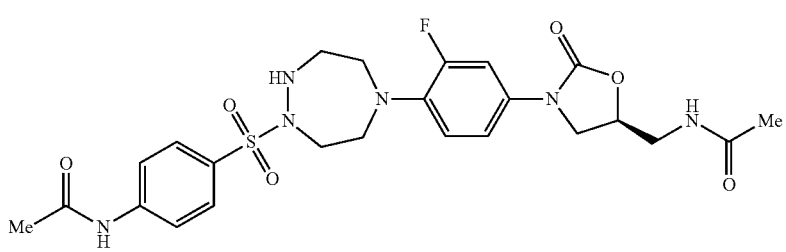
[Chemical Formula 187]

Example 160
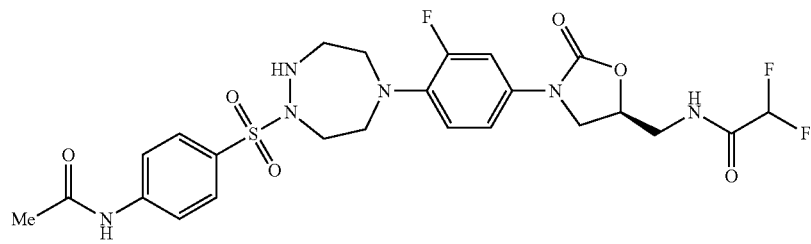
Example 161
[Chemical Formula 189]
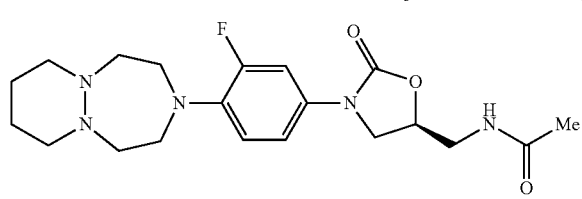
Example 162
[Chemical Formula 190]
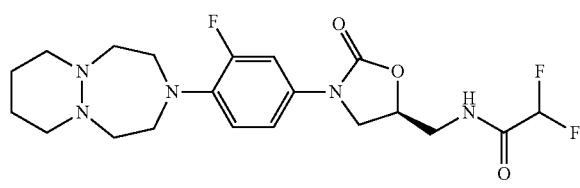
Example 163
[Chemical Formula 191]
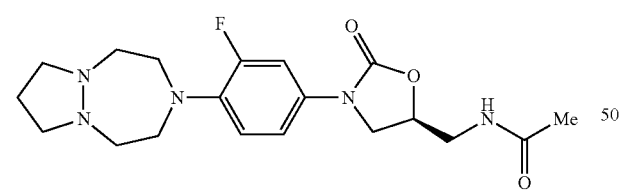
Example 164
[Chemical Formula 192]
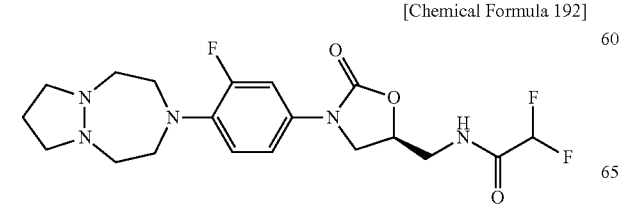
Example 165
[Chemical Formula 193]
Example 166
[Chemical Formula 194]
Example 167
[Chemical Formula 195]
Example 168
[Chemical Formula 196]

Example 169
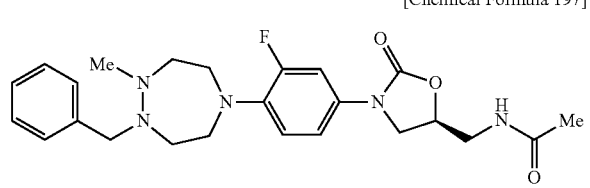
Example 170
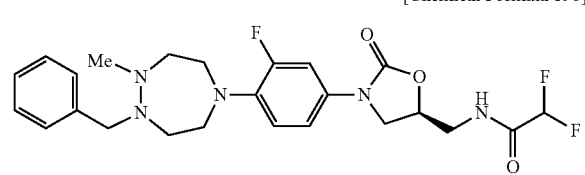
Example 171
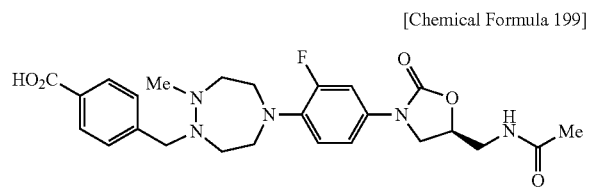 [SMILES: CC(=O)NC[C@H]1CN(c2ccc(N3CCN(C)N(Cc4ccc(C(=O)O)cc4)CC3)c(F)c2)C(=O)O1]
Example 172
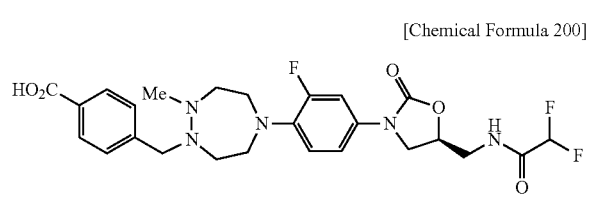 [SMILES: CN1CCN(c2ccc(N3C[C@H](CNC(=O)C(F)F)OC3=O)cc2F)CCN1Cc1ccc(C(=O)O)cc1]
Example 173
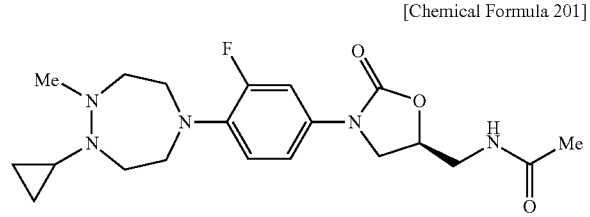 [SMILES: CC(=O)NC[C@H]1CN(c2ccc(N3CCN(C)N(C4CC4)CC3)c(F)c2)C(=O)O1]
Example 174
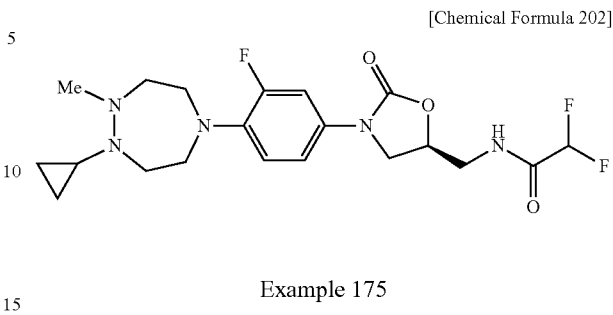
Example 175
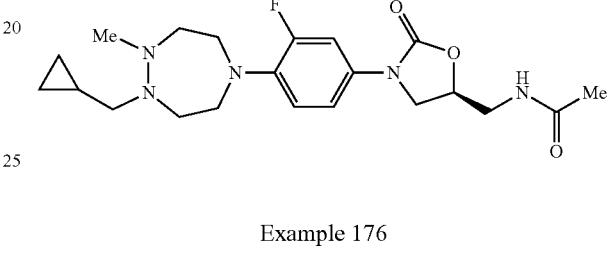
Example 176
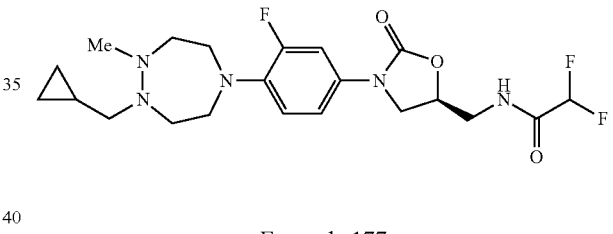
Example 177
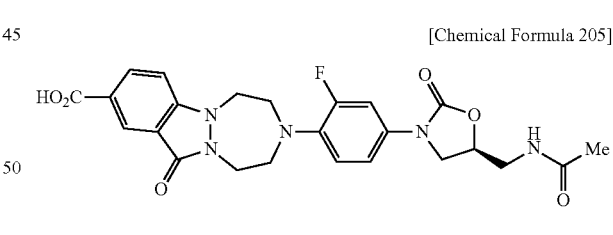
Example 178
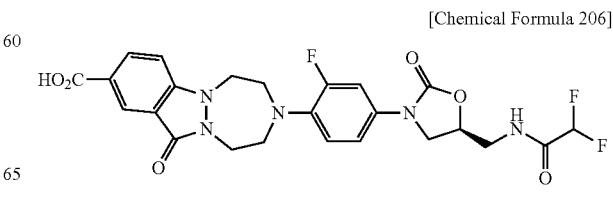

93
Example 179
[Chemical Formula 207]
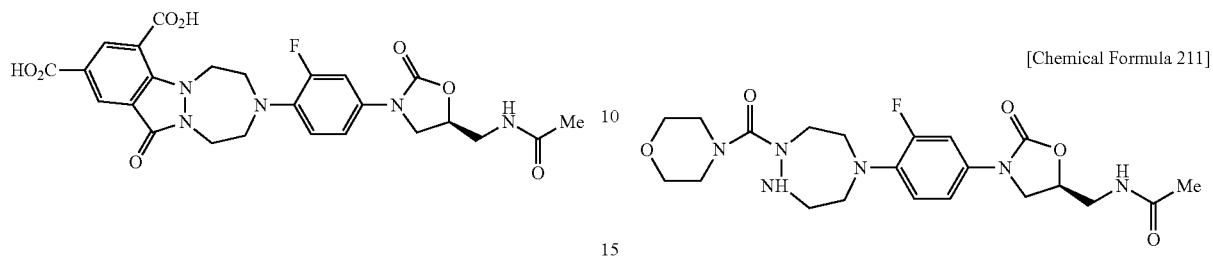
Example 180
[Chemical Formula 208]
Example 181
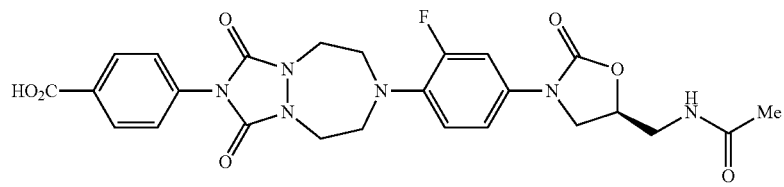
[Chemical Formula 209]
Example 182
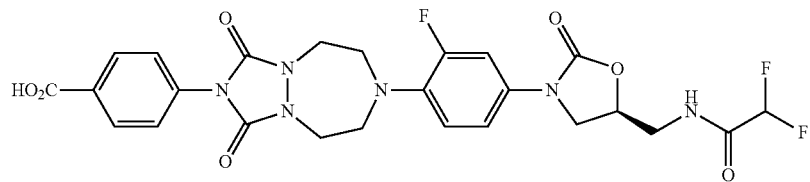
94
Example 183
[Chemical Formula 211]
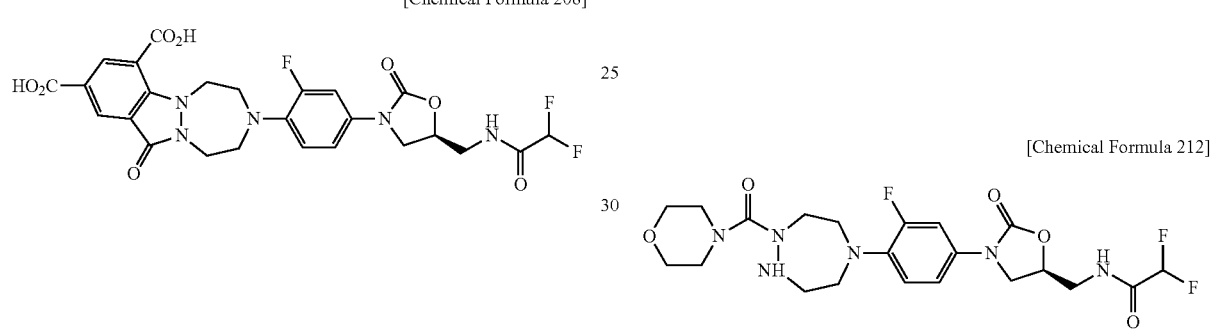
Example 184
[Chemical Formula 212]
[Chemical Formula 210]

Example 185
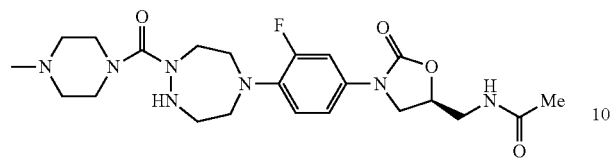
Example 186
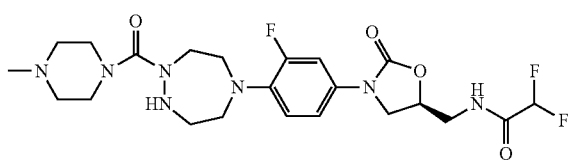
Example 187
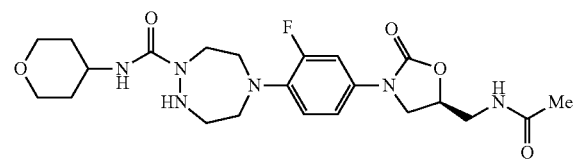
Example 188
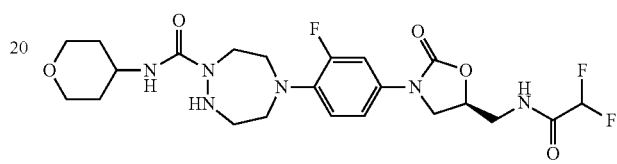
Example 189
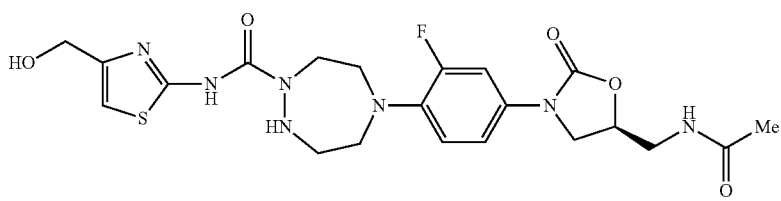
Example 190
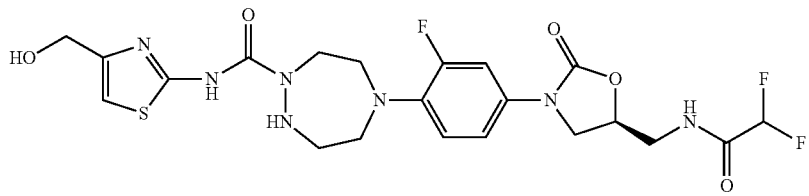
Example 191
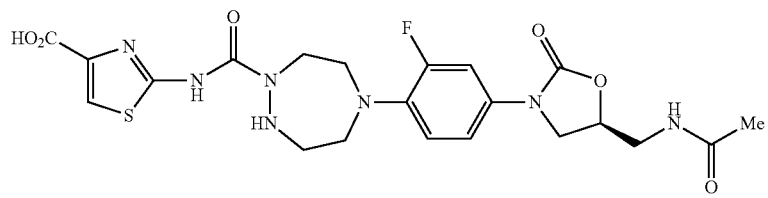

Example 192
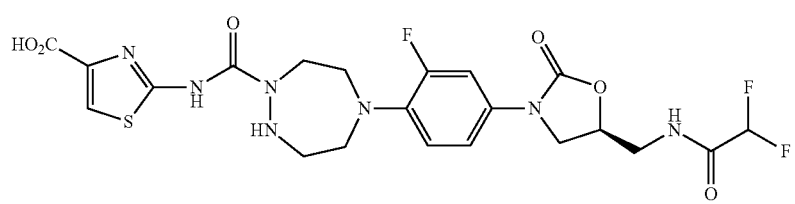
Example 193
[Chemical Formula 221]
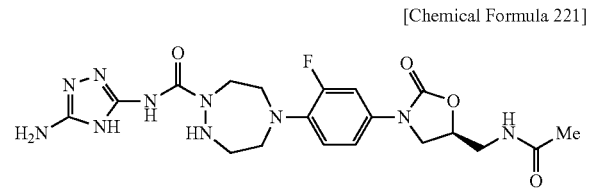 [SMILES: CC(=O)NC[C@H]1CN(c2ccc(N3CCNN(C(=O)Nc4nnc(N)[nH]4)CC3)c(F)c2)C(=O)O1]
Example 194
[Chemical Formula 222]
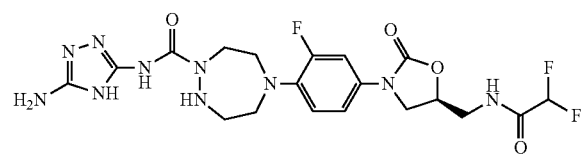
Example 195
[Chemical Formula 223]
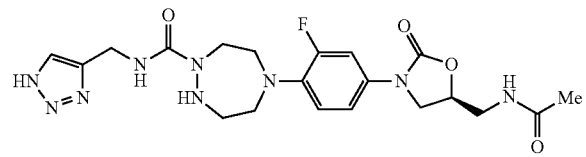
Example 196
[Chemical Formula 224]
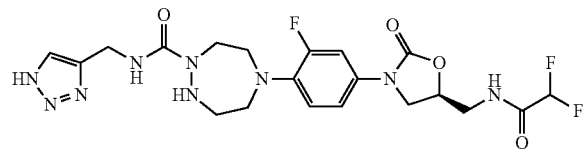
Example 197
[Chemical Formula 225]
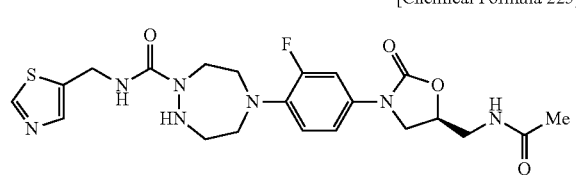
Example 198
[Chemical Formula 226]
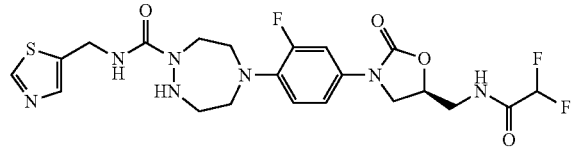
Example 199
[Chemical Formula 227]
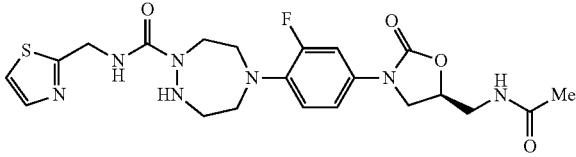
Example 200
[Chemical Formula 228]
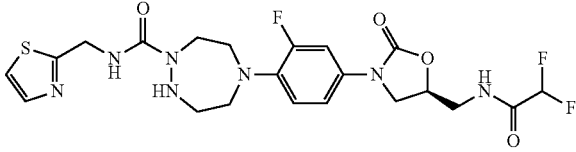

Example 201
[Chemical Formula 229]
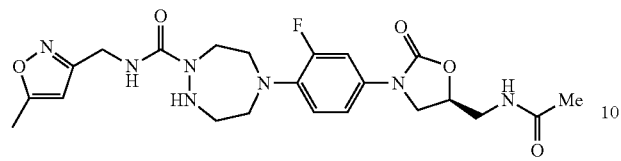
Example 202
[Chemical Formula 230]
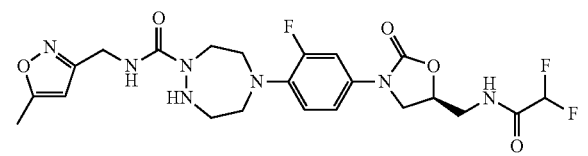
Example 203
[Chemical Formula 231]
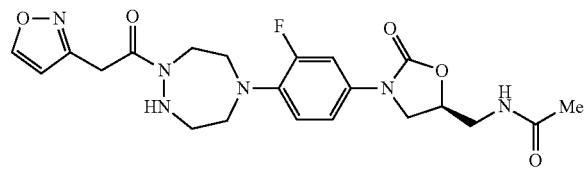
Example 204
[Chemical Formula 232]
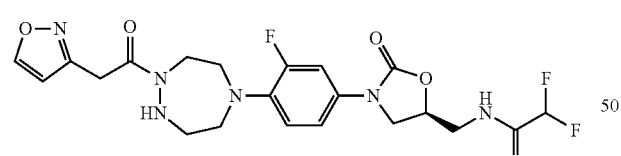
Example 205
[Chemical Formula 233]
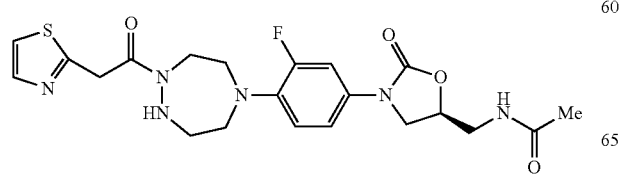
Example 206
[Chemical Formula 234]
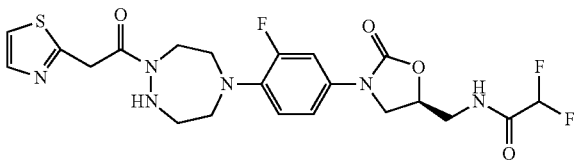
Example 207
[Chemical formula 235]
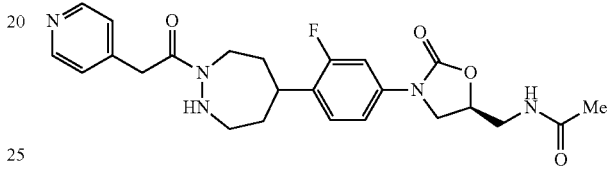
Example 208
[Chemical Formula 236]
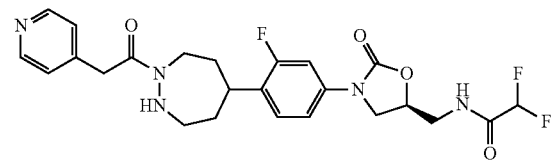
Example 209
[Chemical Formula 237]
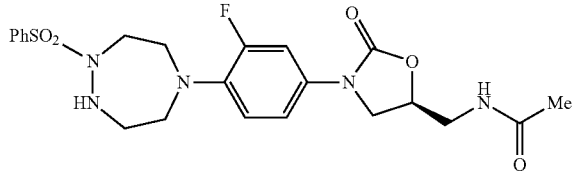
Example 210
[Chemical Formula 238]
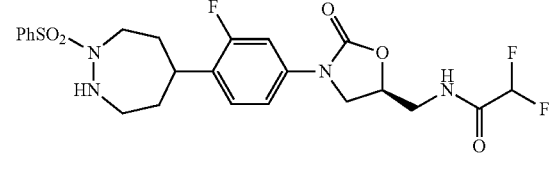

101
Example 211
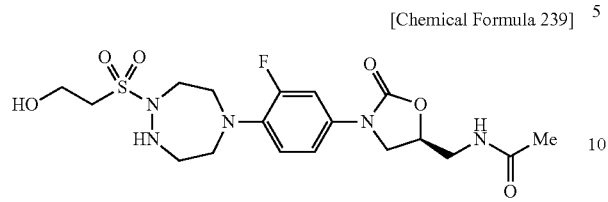
Example 212
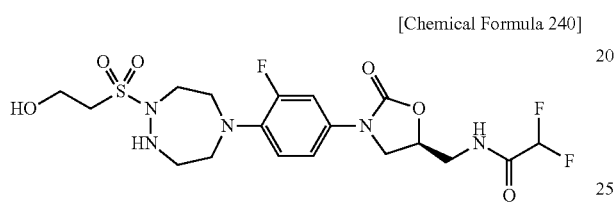
Example 213
[Chemical Formula 241]
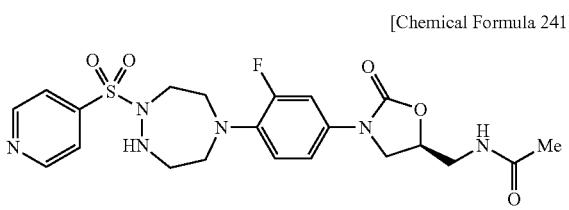
Example 214
[Chemical Formula 242]
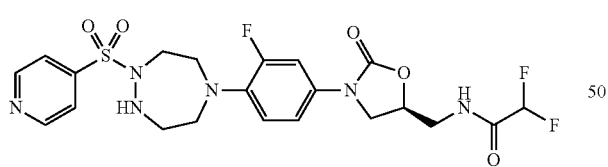
Example 215
[Chemical Formula 243]
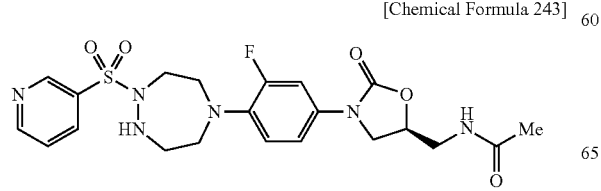
102
Example 216
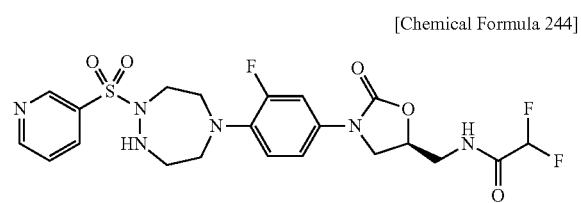 [SMILES: O=C(NC[C@H]1CN(c2ccc(N3CCNN(S(=O)(=O)c4cccnc4)CC3)c(F)c2)C(=O)O1)C(F)F]
Example 217
[Chemical Formula 245]
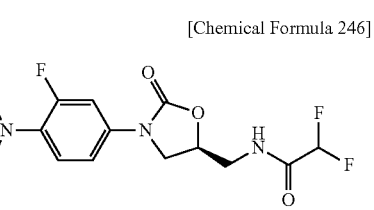
Example 218
[Chemical Formula 246]
Example 219
[Chemical Formula 247]
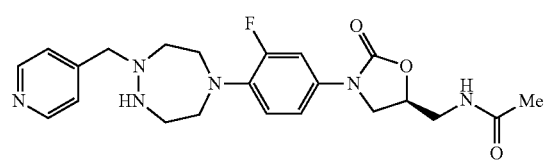
Example 220
[Chemical Formula 248]
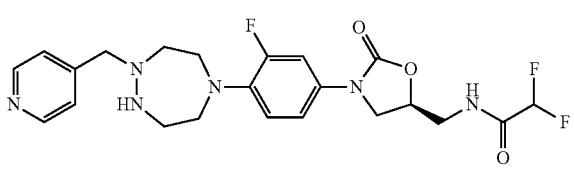

103
Example 221
[Chemical Formula 249]
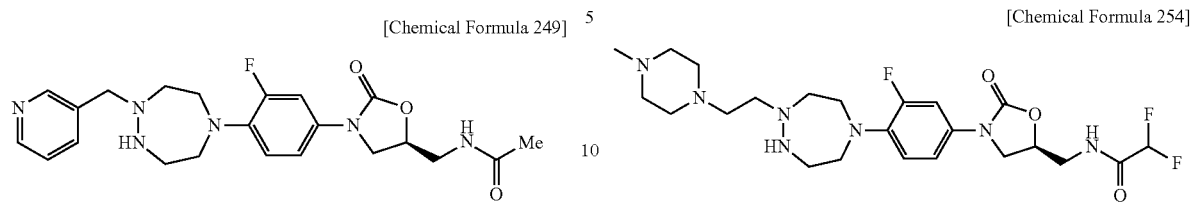
Example 222
[Chemical Formula 250]
Example 223
[Chemical Formula 251]
Example 224
[Chemical Formula 252]
Example 225
[Chemical Formula 253]
104
Example 226
[Chemical Formula 254]
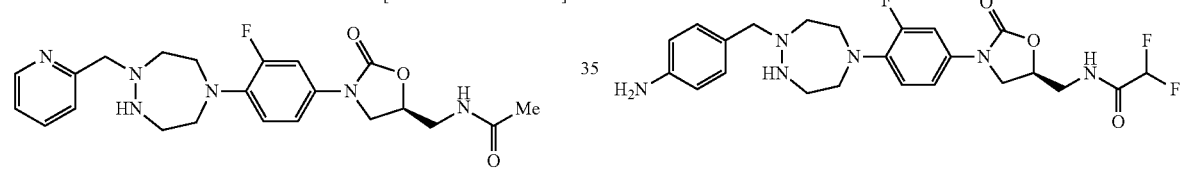
Example 227
[Chemical Formula 255]
Example 228
[Chemical Formula 256]
Example 229
[Chemical Formula 257]
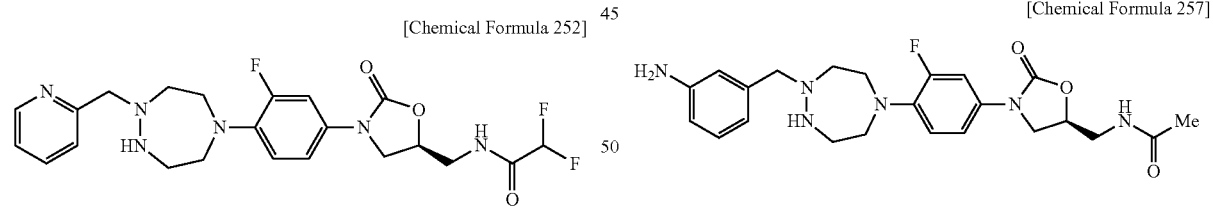
Example 230
[Chemical Formula 258]
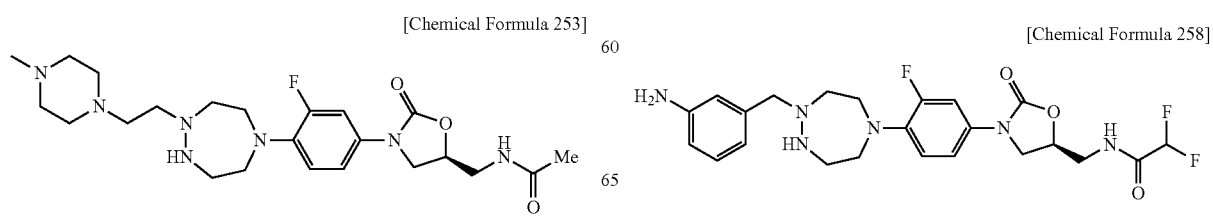

Example 231
[Chemical Formula 259]
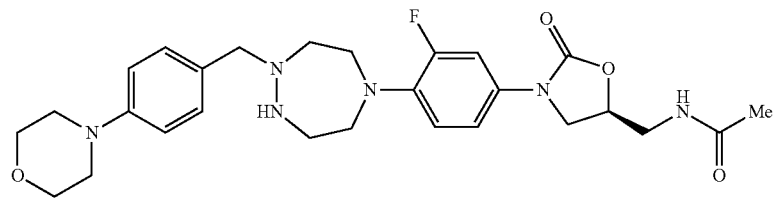
Example 232
[Chemical Formula 260]
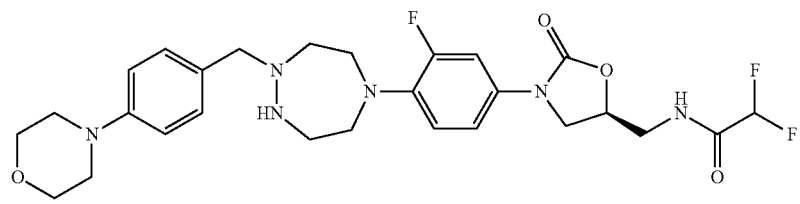
Example 233
[Chemical Formula 261]
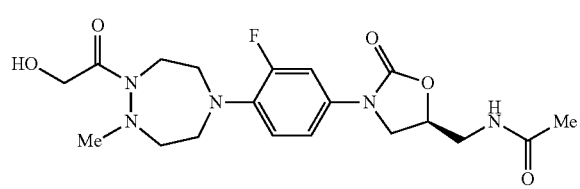
Example 234
[Chemical Formula 262]
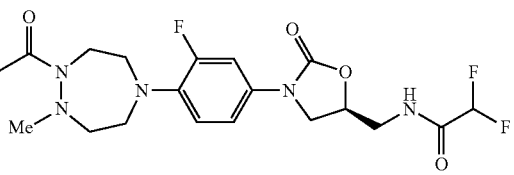
Example 235
[Chemical Formula 263]
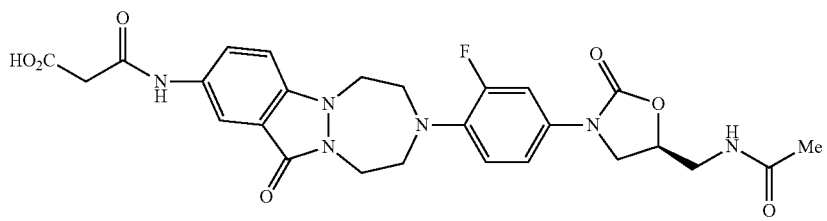
Example 236
[Chemical Formula 264]
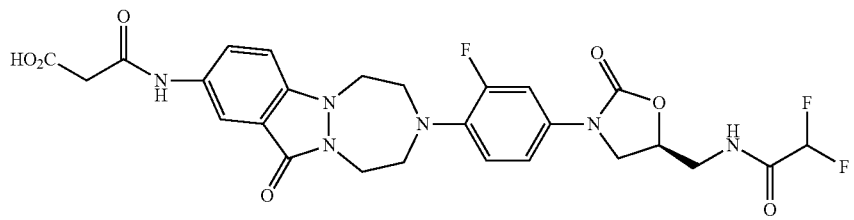

Example 237
[Chemical Formula 265]
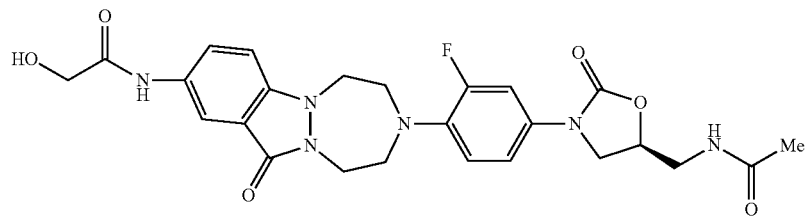
Example 238
[Chemical Formula 266]
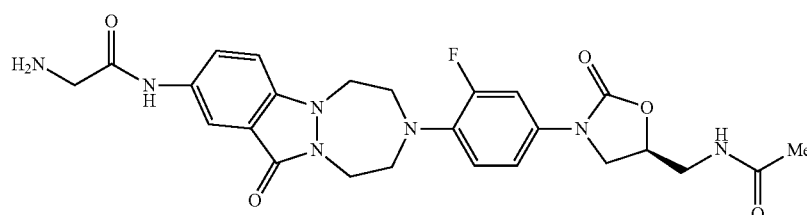
Example 239
[Chemical Formula 267]
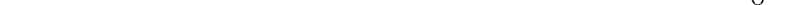
Example 240
[Chemical Formula 268]
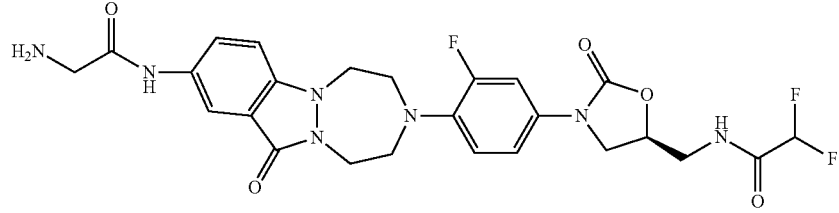
Example 241
[Chemical Formula 269]
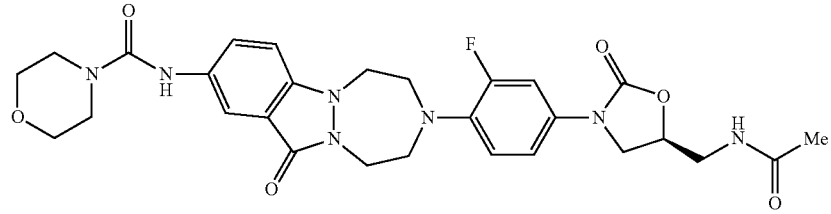

Example 242
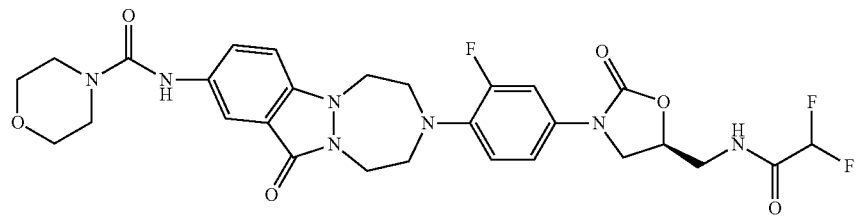
Example 243
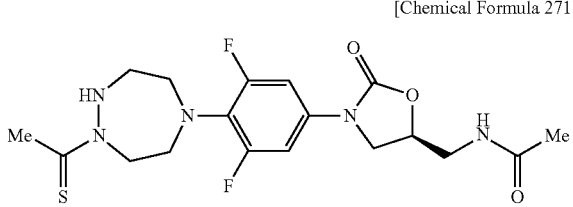
Example 244
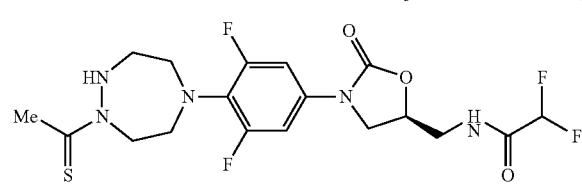
Example 245
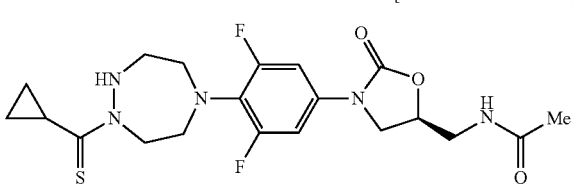
Example 246
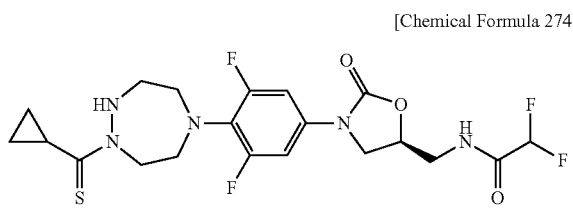 [SMILES: O=C(O)C(=O)N1CCN(c2c(F)cc(N3C[C@H](CNC(=O)C(F)F)OC3=O)cc2F)CCN1]
Example 247
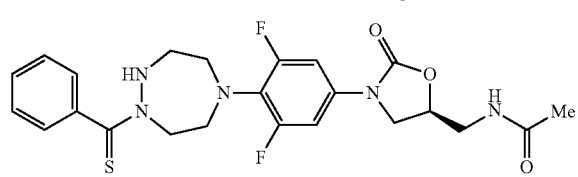
Example 248
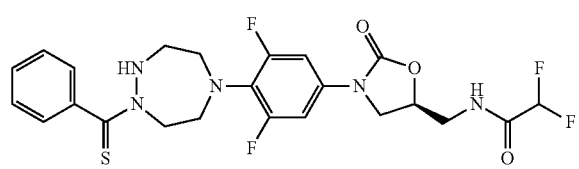
Example 249
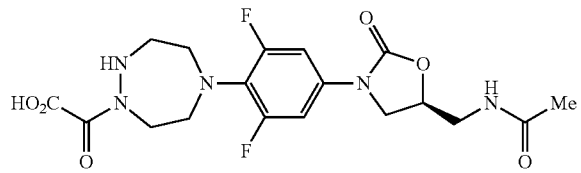
Example 250
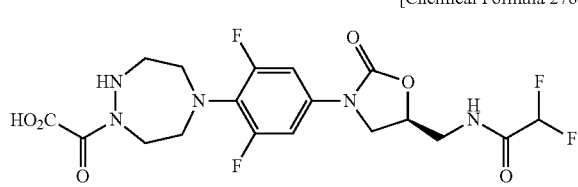

Example 251
[Chemical Formula 279]
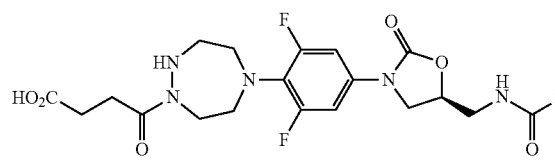
Example 252
[Chemical Formula 280]
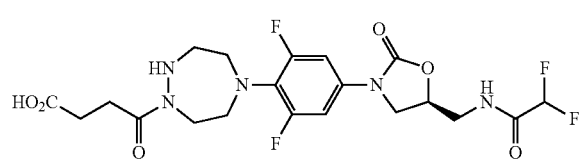
Example 253
[Chemical Formula 281]
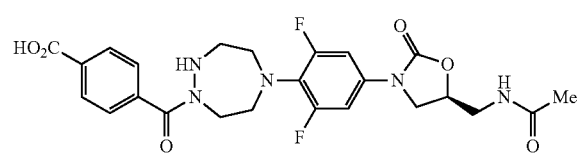
Example 254
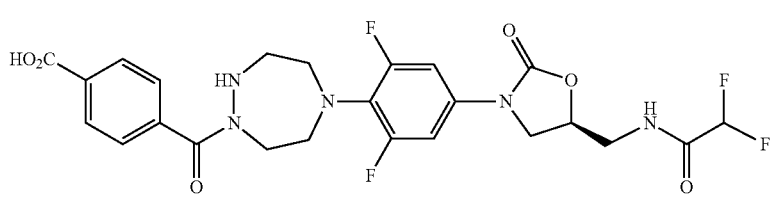
Example 255
[Chemical Formula 283]
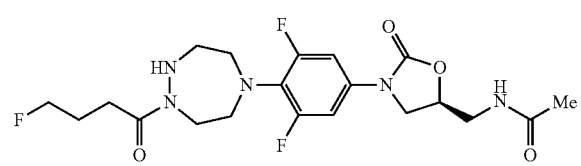
Example 256
[Chemical Formula 284]
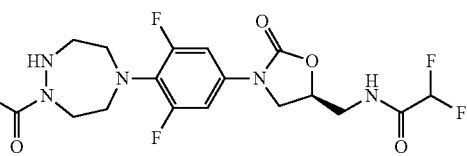
Example 257
[Chemical Formula 285]
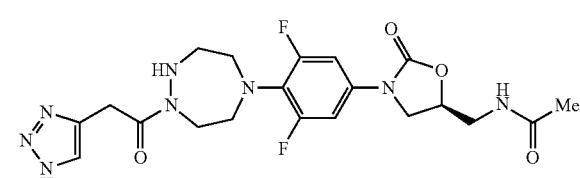
Example 258
[Chemical Formula 286]
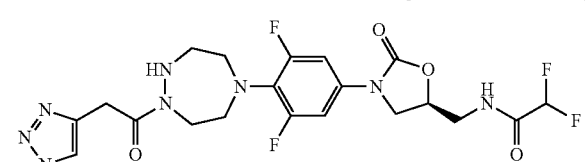
Example 259
[Chemical Formula 287]
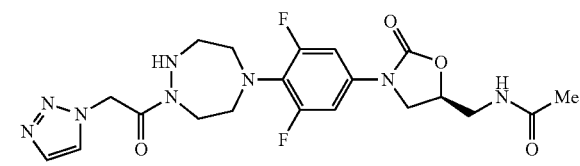

Example 260
[Chemical Formula 288]
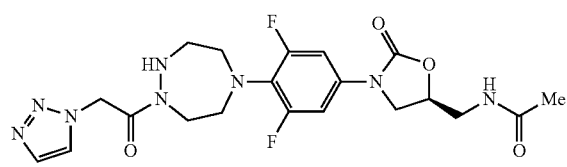
Example 261
[Chemical Formula 289]
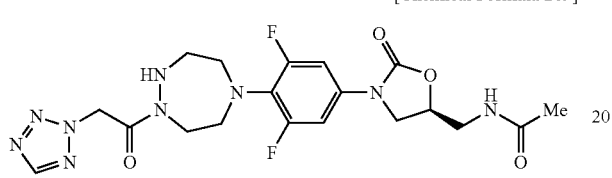
Example 262
[Chemical Formula 290]
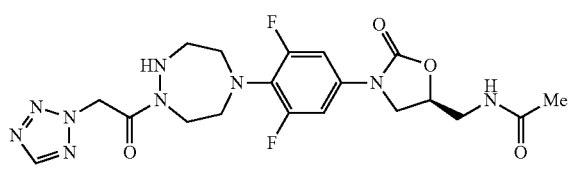
Example 263
[Chemical Formula 291]
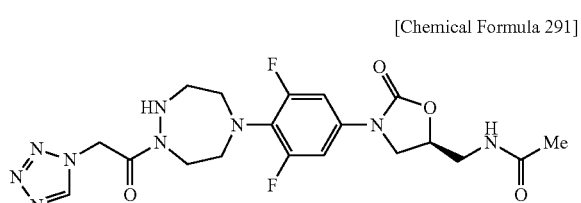
Example 264
[Chemical Formula 292]
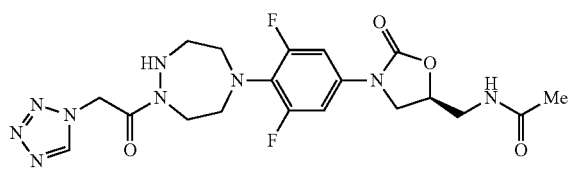
Example 265
[Chemical Formula 293]
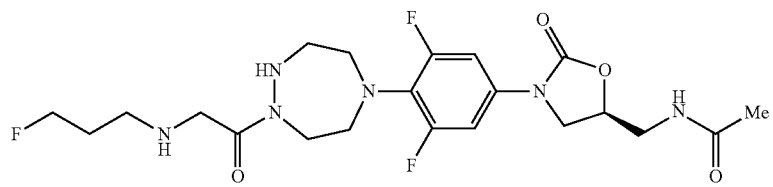
Example 266
[Chemical Formula 294]
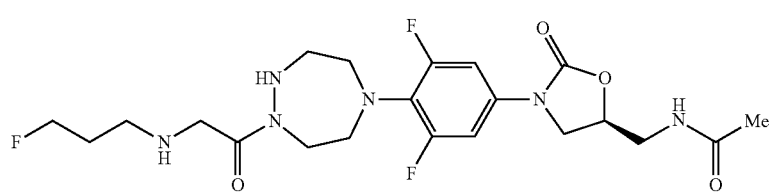

Example 267
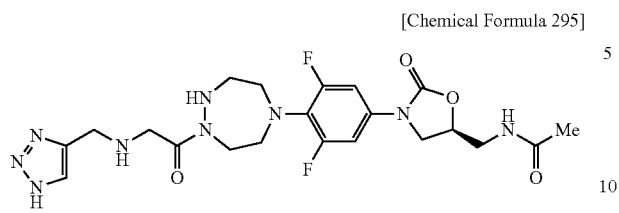
Example 268
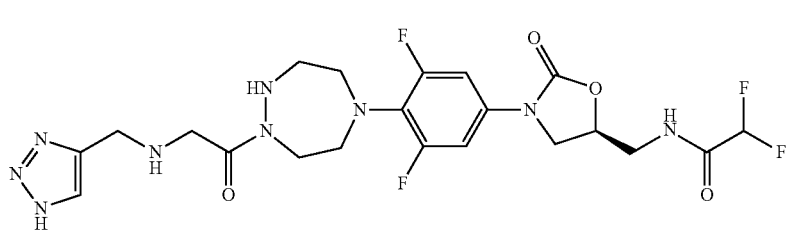
Example 269
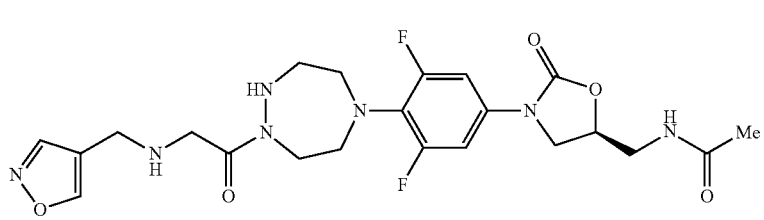
Example 270
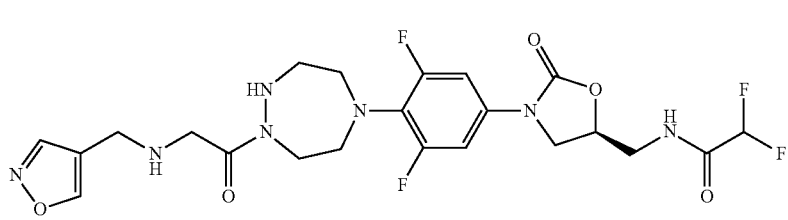
Example 271
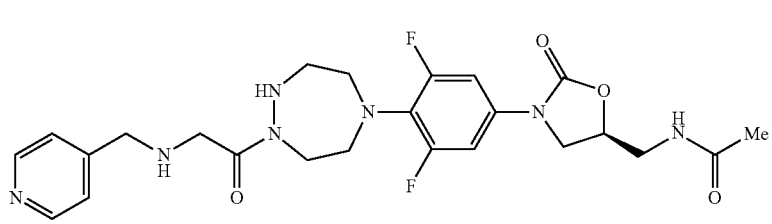

Example 272
[Chemical Formula 300]
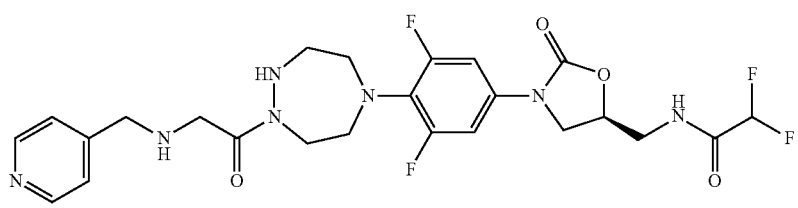
Example 273
[Chemical Formula 301]
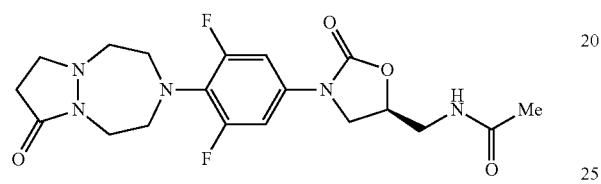
Example 274
[Chemical Formula 302]
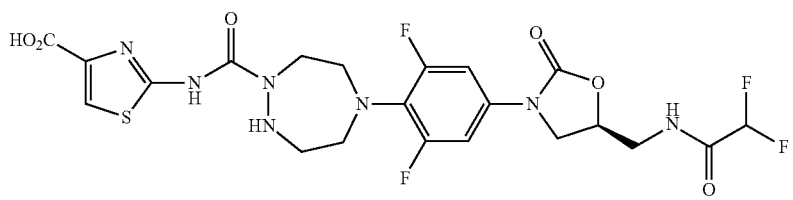
Example 275
[Chemical Formula 303]
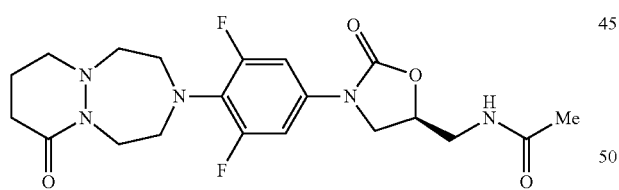
Example 276
[Chemical Formula 304]
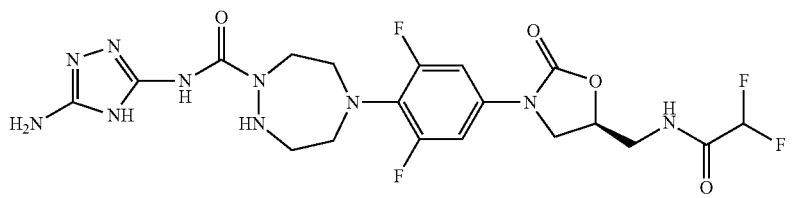

Example 277
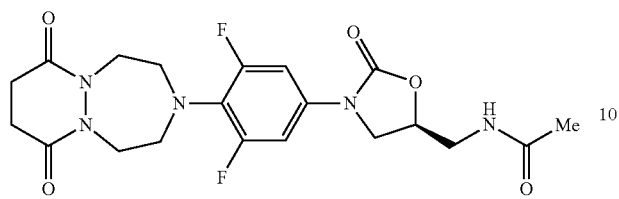
Example 278
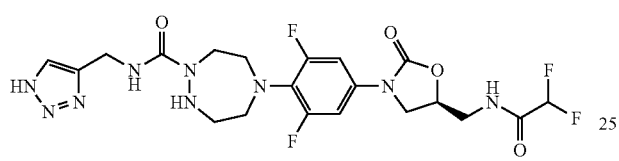
Example 279
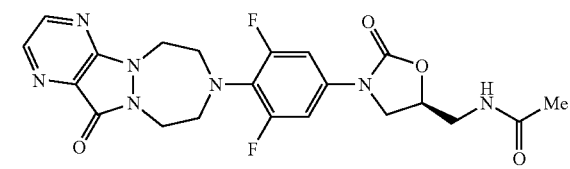
Example 280
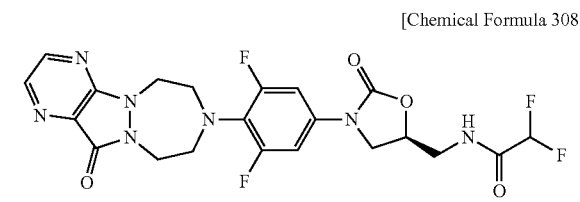 [SMILES: O=C(NC[C@H]1CN(c2cc(F)c(N3CCn4c(=O)c5nccnc5n4CC3)c(F)c2)C(=O)O1)C(F)F]
Example 281
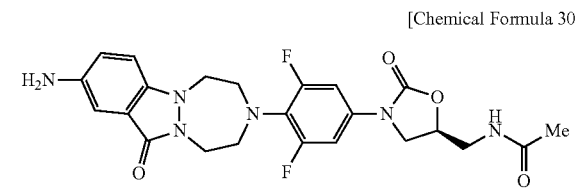
Example 282
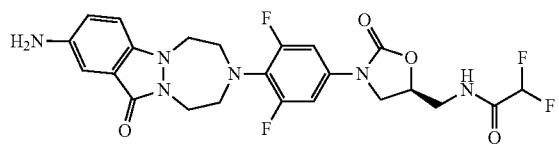
Example 283
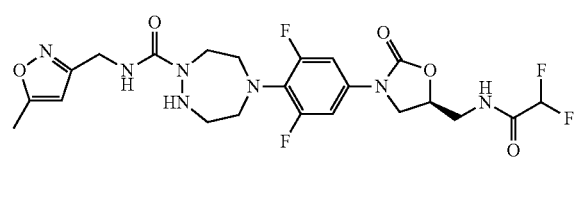
Example 284
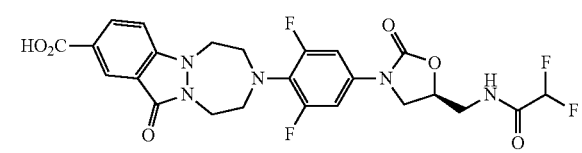
Example 285
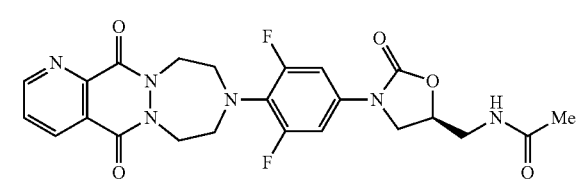
Example 286
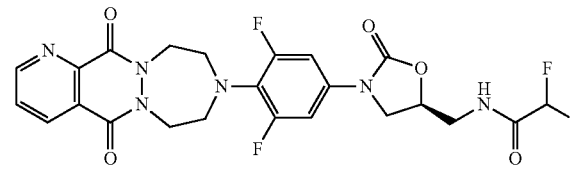

Example 287
[Chemical Formula 315]
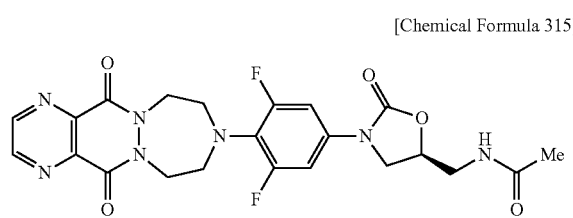
Example 288
[Chemical Formula 316]
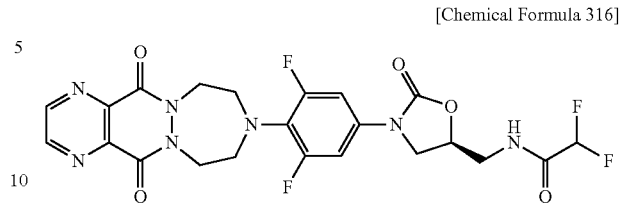
Example 289
[Chemical Formula 317]
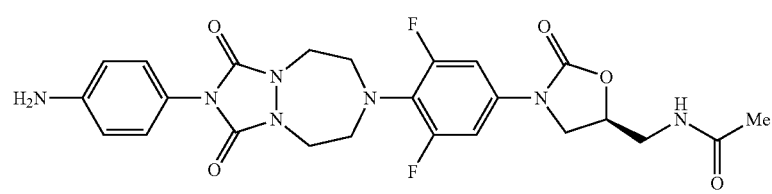
Example 290
[Chemical Formula 318]
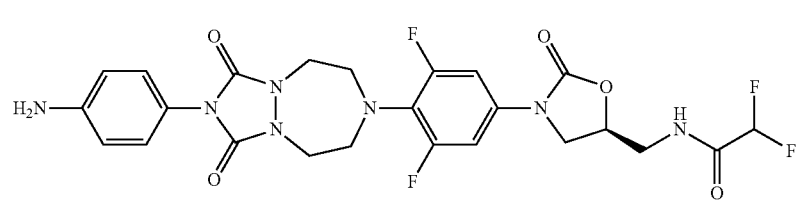
Example 291
[Chemical Formula 319]
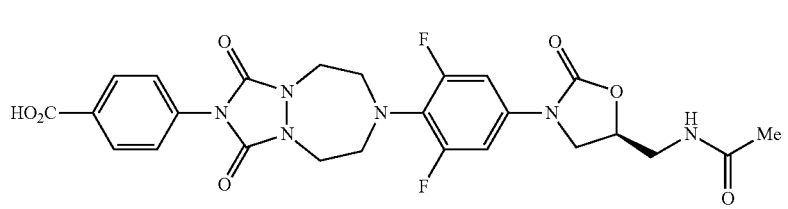
Example 292
[Chemical Formula 320]
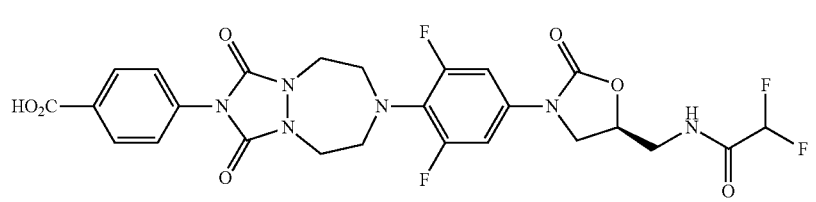

123
Example 293
[Chemical Formula 321]
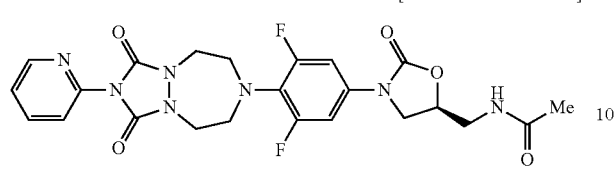
Example 294
[Chemical Formula 322]
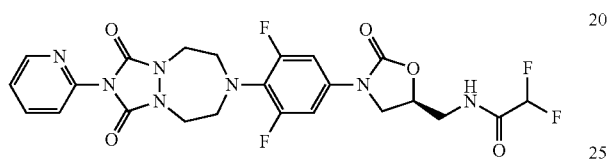
Example 295
[Chemical Formula 323]
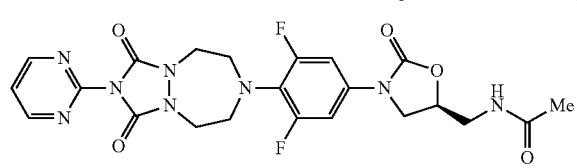
124
Example 296
[Chemical Formula 324]
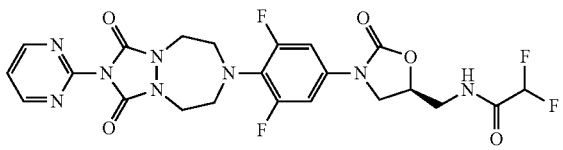
Example 297
[Chemical Formula 325]
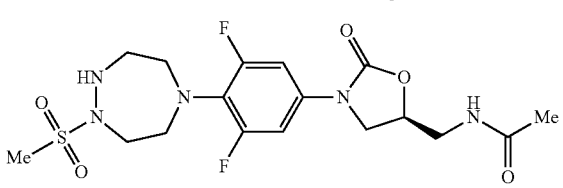
Example 298
[Chemical Formula 326]
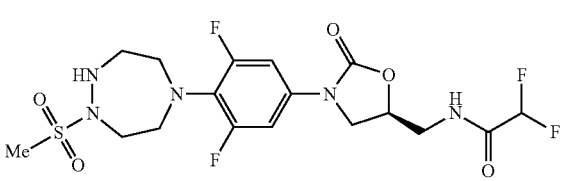
Example 299
[Chemical Formula 327]
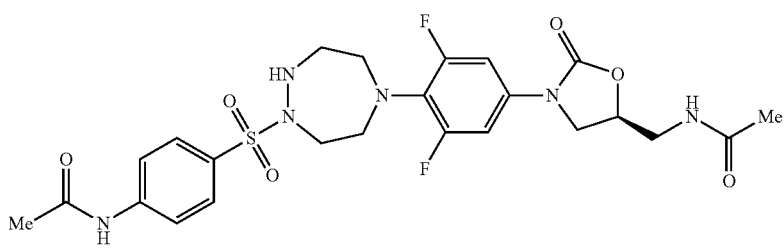
Example 300
[Chemical Formula 328]
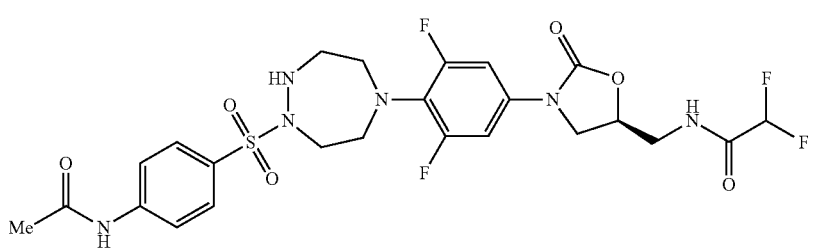

125
Example 301
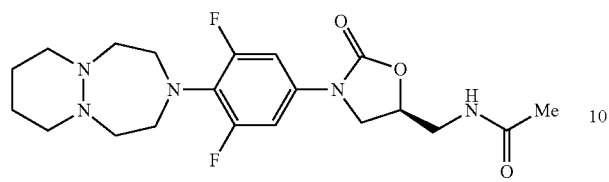
Example 302
[Chemical Formula 329]
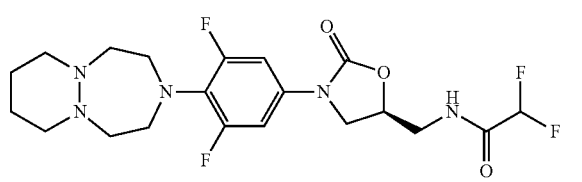
Example 303
[Chemical Formula 330]
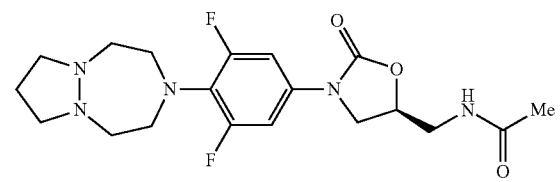
Example 304
[Chemical Formula 331]
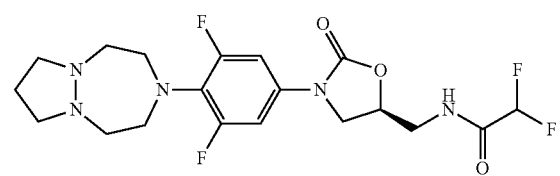
Example 305
[Chemical Formula 332]
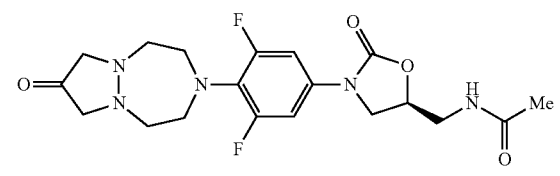
[Chemical Formula 333]
126
Example 306
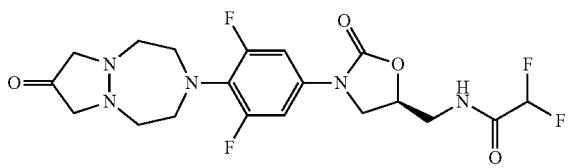
Example 307
[Chemical Formula 334]
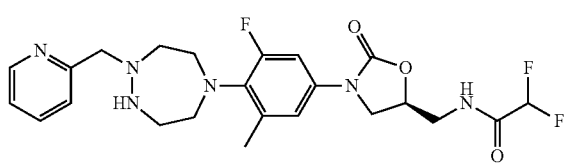
Example 308
[Chemical Formula 335]
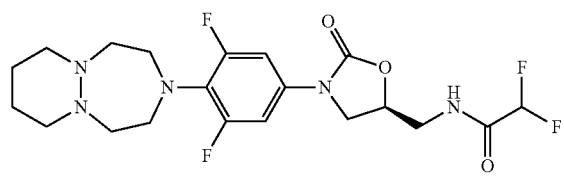
Example 309
[Chemical Formula 336]
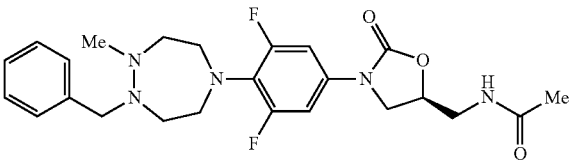
Example 310
[Chemical Formula 337]
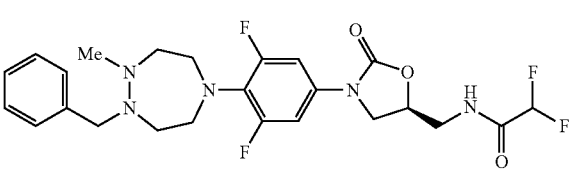
[Chemical Formula 338]

Example 311
[Chemical Formula 339]
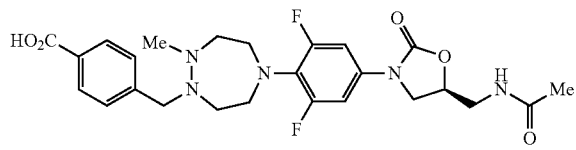
Example 312
Example 316
[Chemical Formula 344]
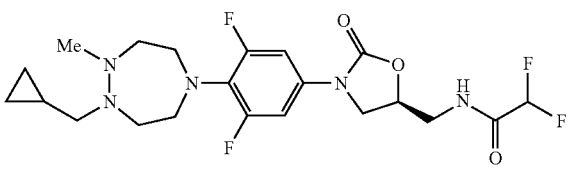
Example 317
[Chemical Formula 340]
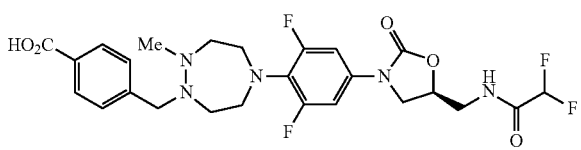
Example 313
[Chemical Formula 345]
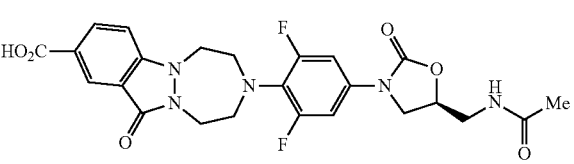
Example 318
[Chemical Formula 341]
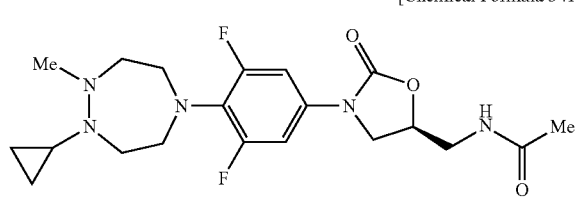
Example 314
[Chemical Formula 346]
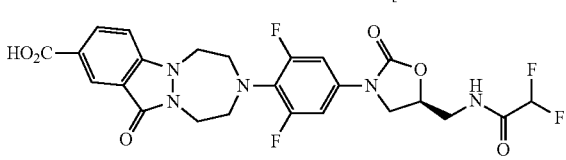
Example 319
[Chemical Formula 342]
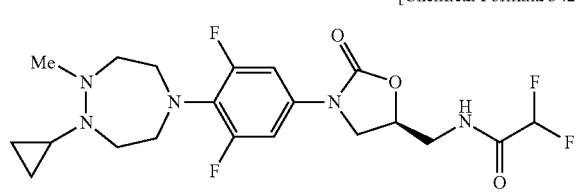
Example 315
[Chemical Formula 347]
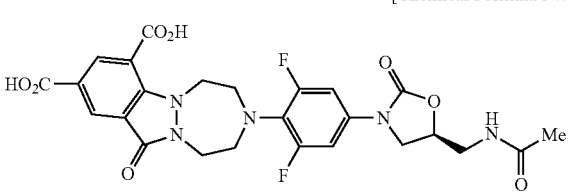
Example 320
[Chemical Formula 343]
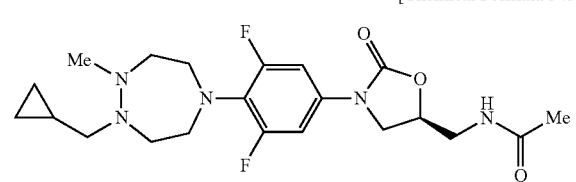
[Chemical Formula 348]
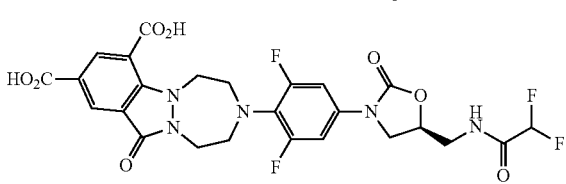

Example 321
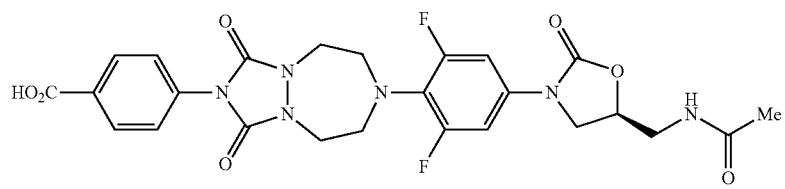
Example 322
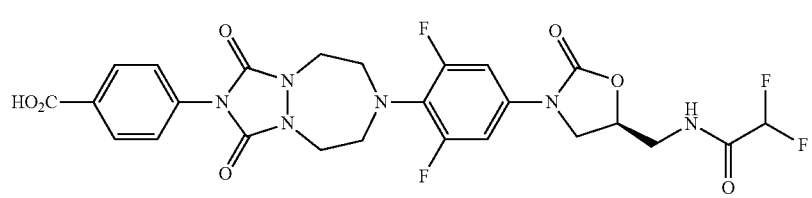
Example 323
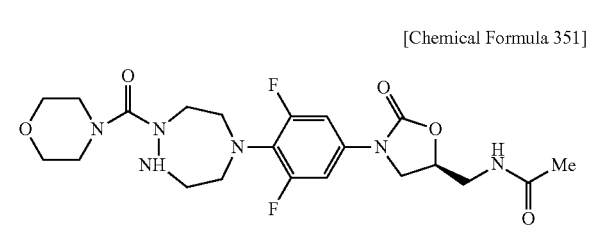 [SMILES: CC(=O)NC[C@H]1CN(c2cc(F)c(N3CCNN(C(=O)N4CCOCC4)CC3)c(F)c2)C(=O)O1]
Example 324
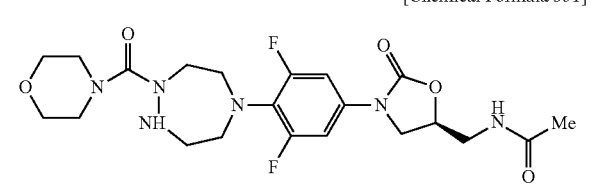
Example 325
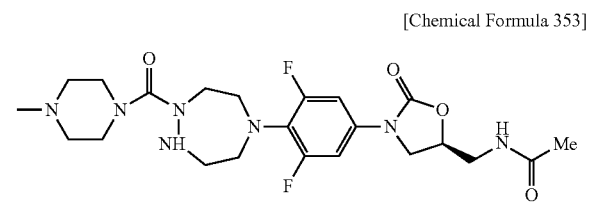 [SMILES: CC(=O)NC[C@H]1CN(c2cc(F)c(N3CCNN(C(=O)N4CCN(C)CC4)CC3)c(F)c2)C(=O)O1]
[Chemical Formula 349]
[Chemical Formula 350]
Example 326
[Chemical Formula 354]
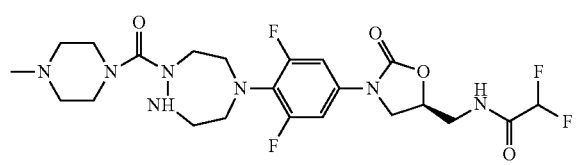
Example 327
[Chemical Formula 355]
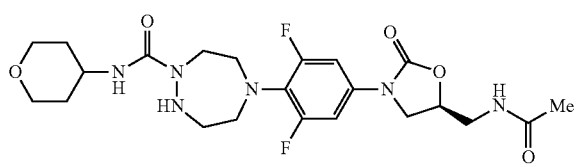
Example 328
[Chemical Formula 356]
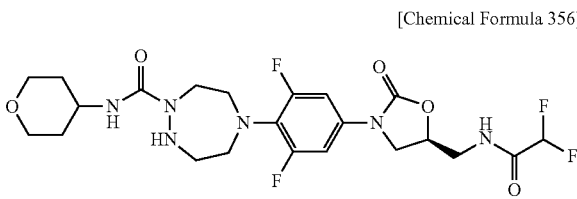 [SMILES: O=C(NC[C@H]1CN(c2cc(F)c(N3CCNN(C(=O)NC4CCOCC4)CC3)c(F)c2)C(=O)O1)C(F)F]

Example 329
[Chemical Formula 357]
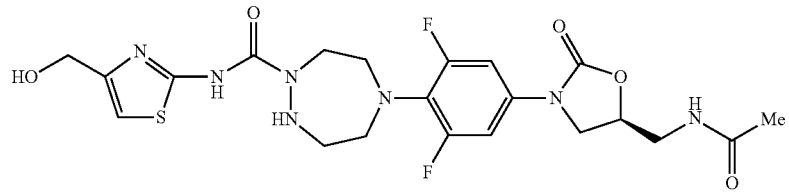
Example 330
[Chemical Formula 358]
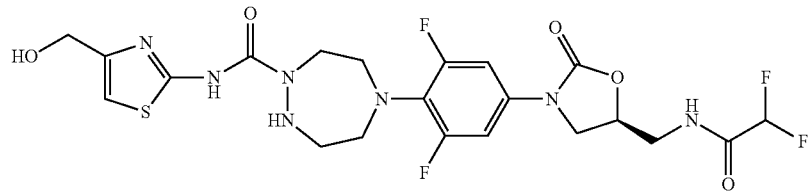
Example 331
[Chemical Formula 359]
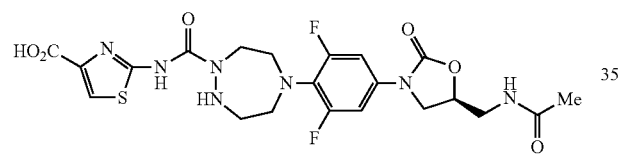
Example 332
[Chemical Formula 360]
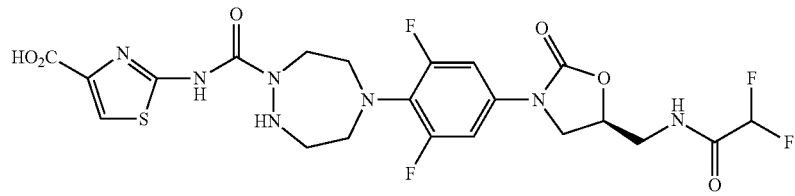
Example 333
[Chemical Formula 361]
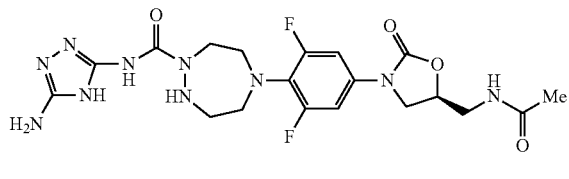
Example 334
[Chemical Formula 362]
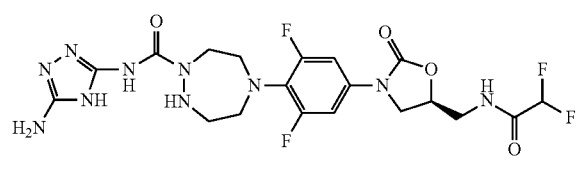

Example 335
[Chemical Formula 363]
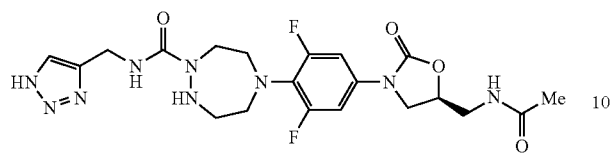
Example 336
[Chemical Formula 364]
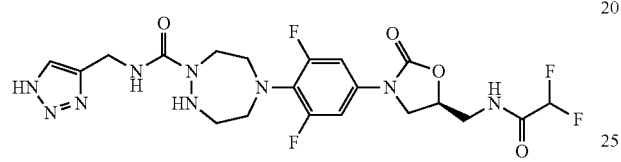
Example 337
[Chemical Formula 365]
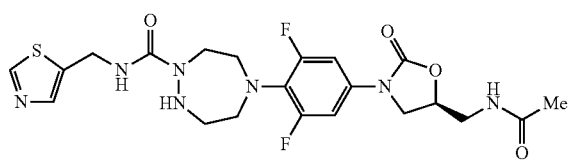
Example 338
[Chemical Formula 366]
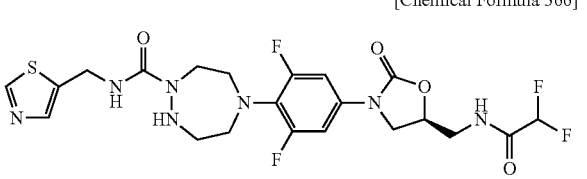
Example 339
[Chemical Formula 367]
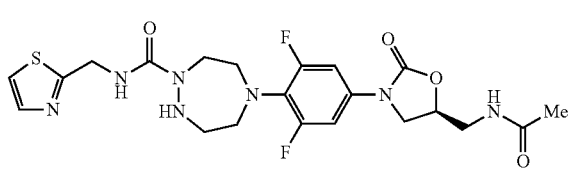
Example 340
[Chemical Formula 368]
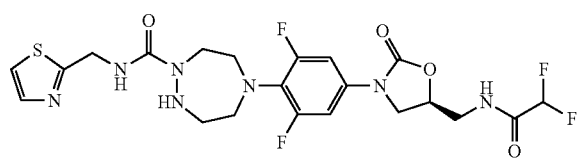
Example 341
[Chemical Formula 369]
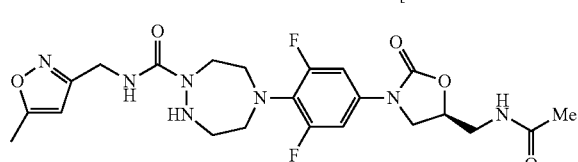
Example 342
[Chemical Formula 370]
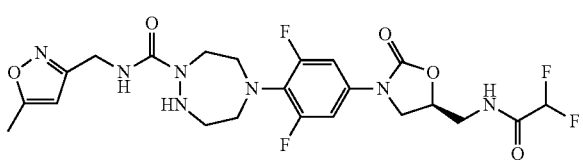
Example 343
[Chemical Formula 371]
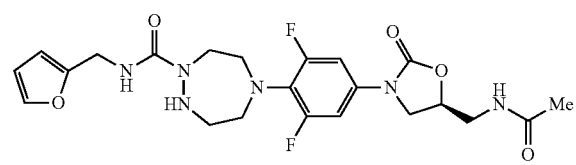
Example 344
[Chemical Formula 372]
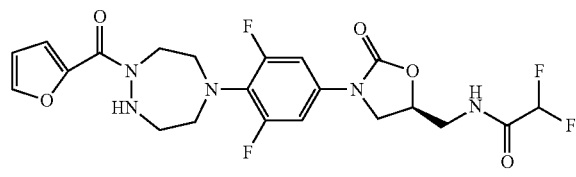

Example 345

[Chemical Formula 373]

Example 346

[Chemical Formula 374]

Example 347

[Chemical Formula 375]

Example 348

[Chemical Formula 376]

Example 349

[Chemical Formula 377]

Example 350

[Chemical Formula 378]

Example 351

[Chemical Formula 379]

Example 352

[Chemical Formula 380]

Example 353

[Chemical Formula 381]

Example 354

[Chemical Formula 382]

Example 355
[Chemical Formula 383]
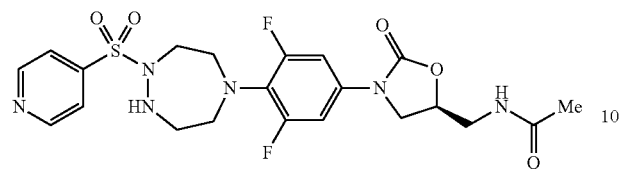
Example 356
Example 360
[Chemical Formula 388]
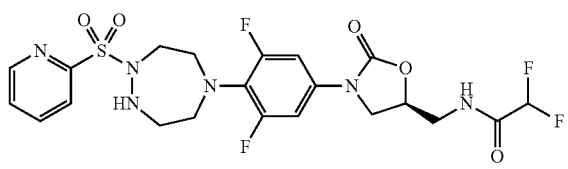
Example 361
[Chemical Formula 384]
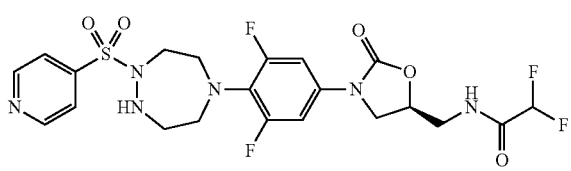
Example 357
[Chemical Formula 389]
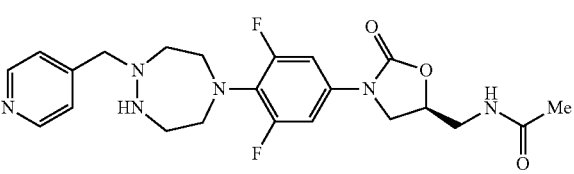
Example 362
[Chemical Formula 385]
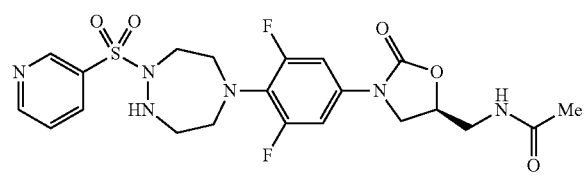
Example 358
[Chemical Formula 390]
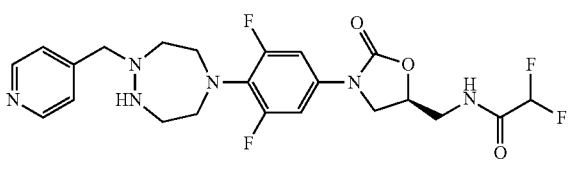
Example 363
[Chemical Formula 386]
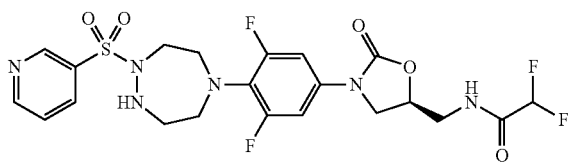
Example 359
[Chemical Formula 391]
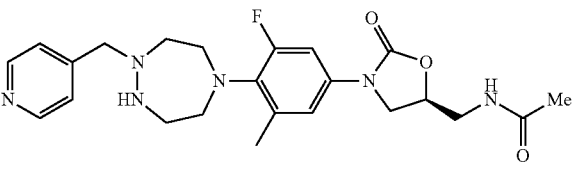
Example 364
[Chemical Formula 387]
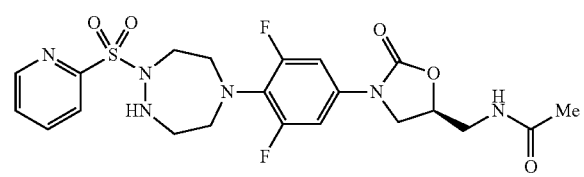
[Chemical Formula 392]
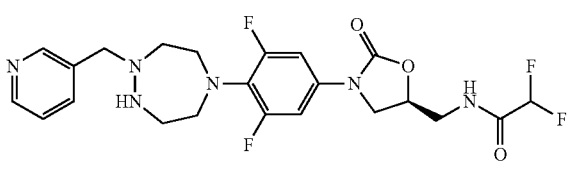

Example 365
Example 369
[Chemical Formula 393]
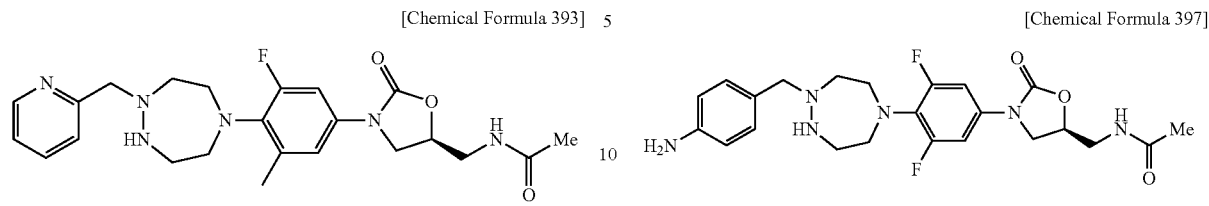
Example 366
[Chemical Formula 397]
Example 370
[Chemical Formula 394]
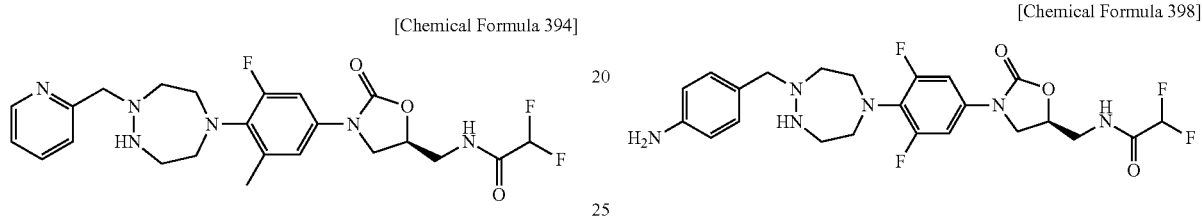
Example 367
[Chemical Formula 398]
Example 371
[Chemical Formula 395]
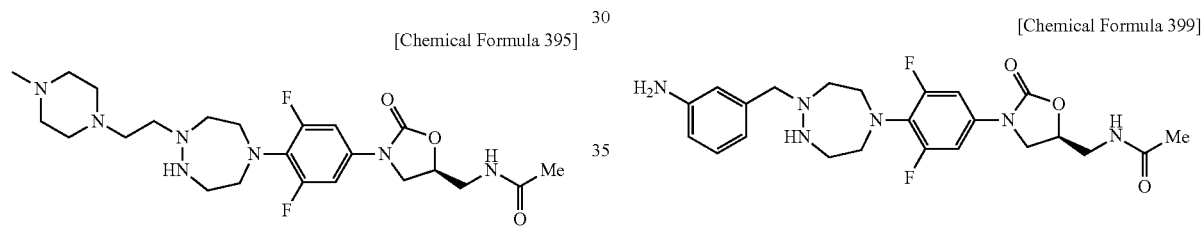
Example 368
[Chemical Formula 399]
Example 372
[Chemical Formula 396]
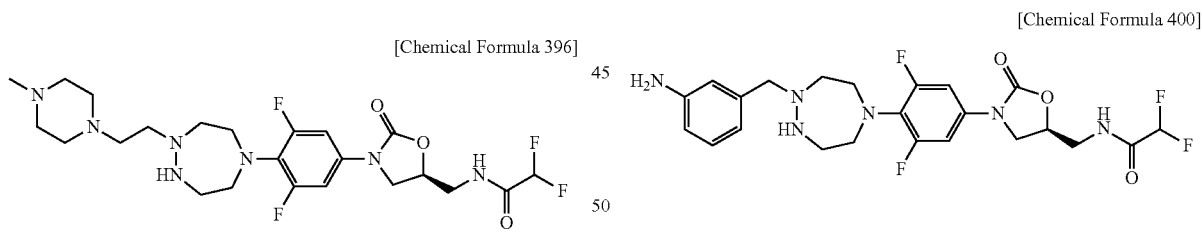
[Chemical Formula 400]
Example 373
[Chemical Formula 401]
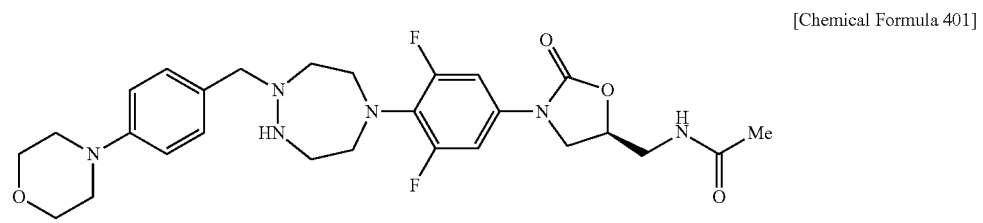

Example 374
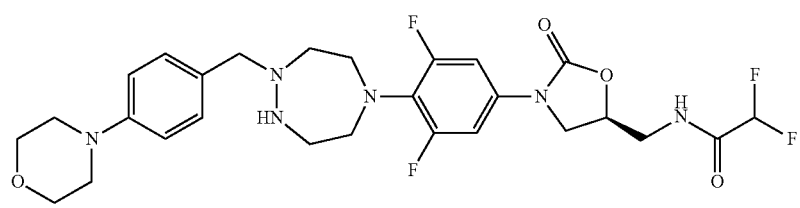
Example 375
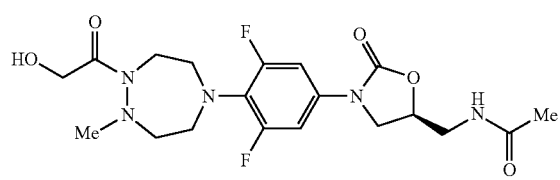
Example 376
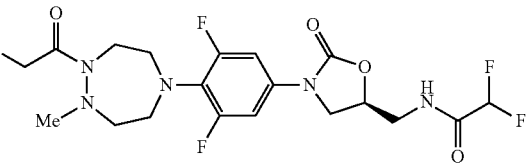
Example 377
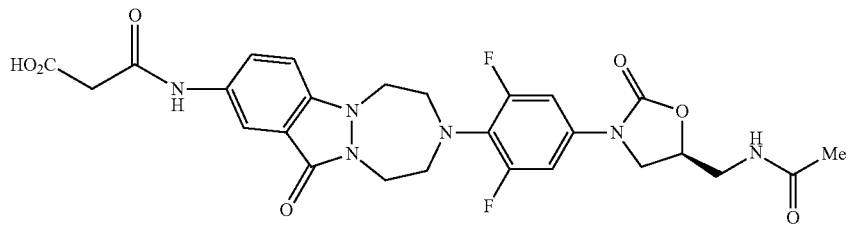
Example 378
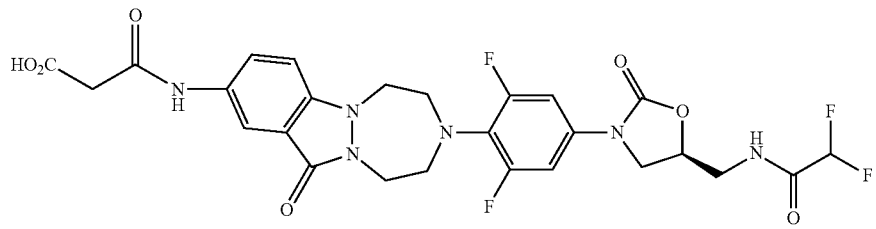
Example 379
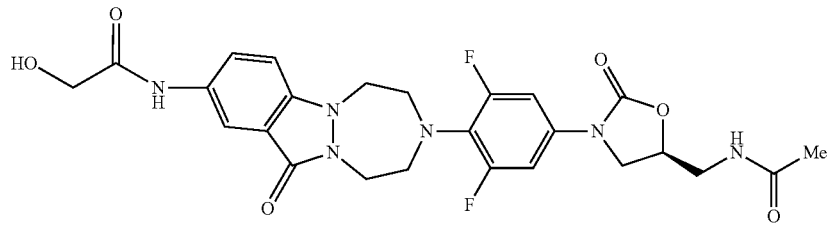

Example 380
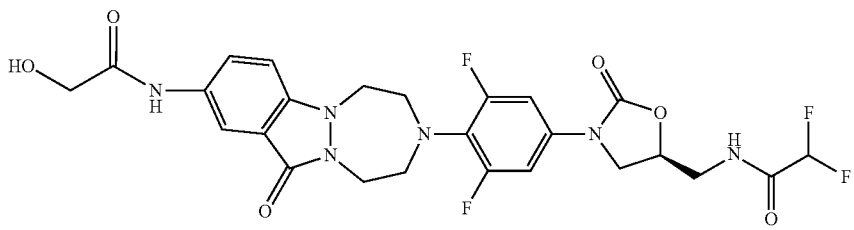
[Chemical Formula 408]
Example 381
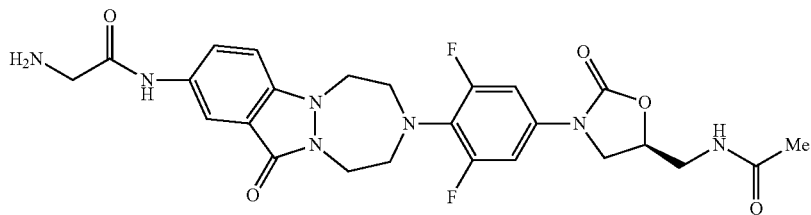
[Chemical Formula 409]
Example 382
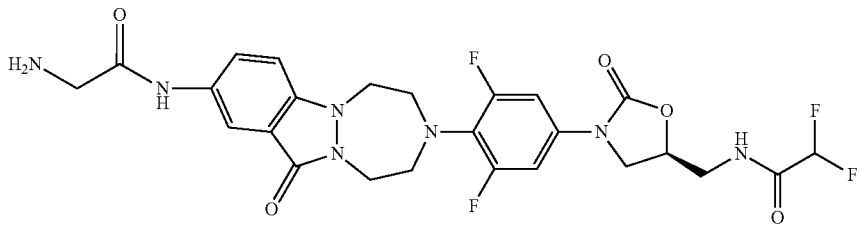
[Chemical Formula 410]
Example 383
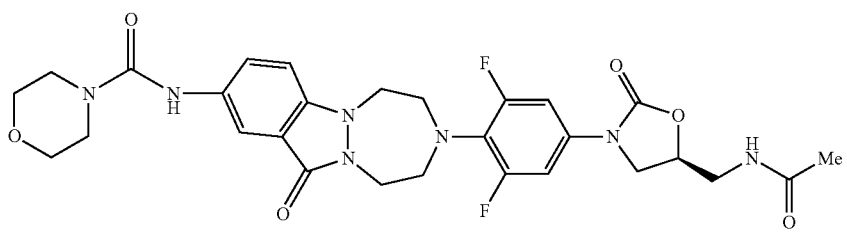
[Chemical Formula 411]
Example 384
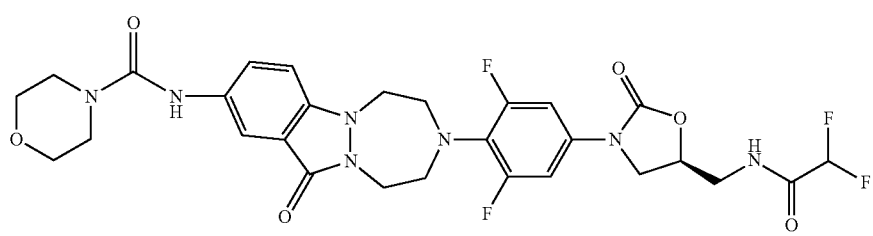
[Chemical Formula 412]

145
Example 385
[Chemical Formula 413]
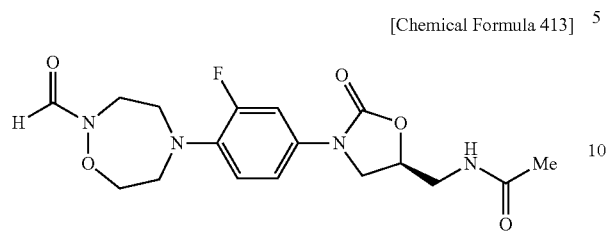
Example 386
[Chemical Formula 414]
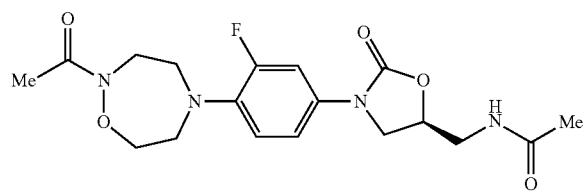
Example 387
[Chemical Formula 415]
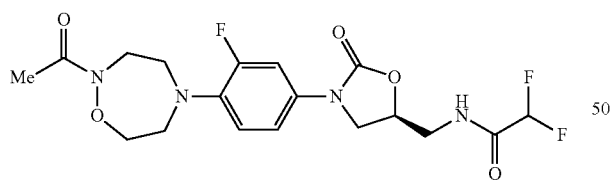
Example 388
[Chemical Formula 416]
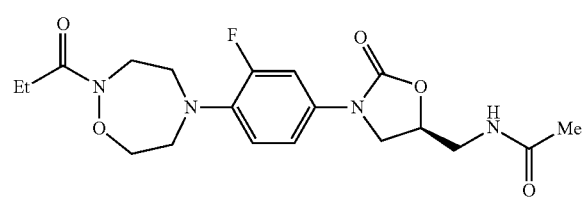
Example 389
[Chemical Formula 417]
146
Example 390
[Chemical Formula 418]
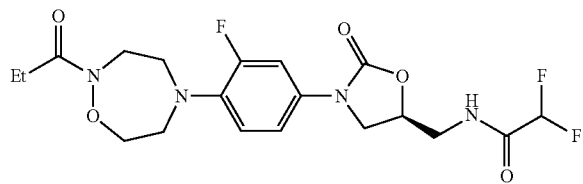
Example 391
[Chemical Formula 419]
Example 392
[Chemical Formula 420]
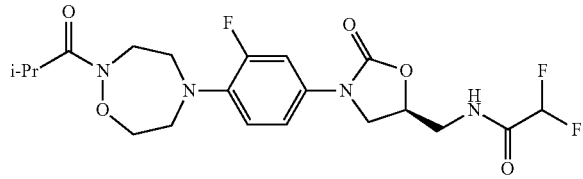
Example 393
[Chemical Formula 421]
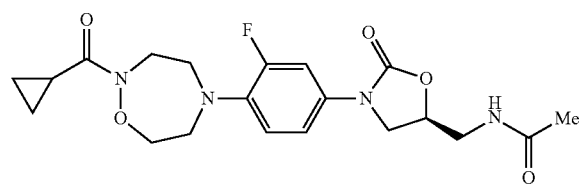
Example 394
[Chemical Formula 422]
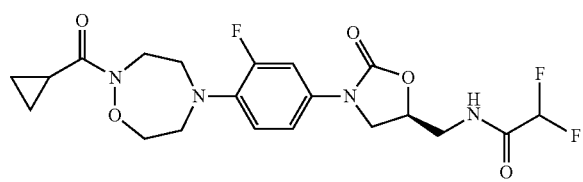

Example 395
[Chemical Formula 423]
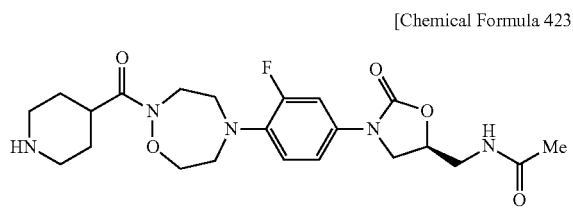
Example 396
[Chemical Formula 424]
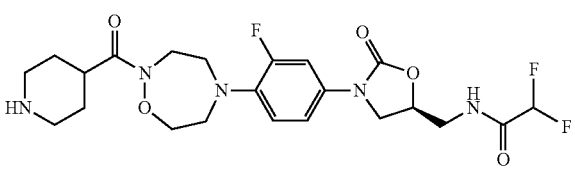
Example 397
[Chemical Formula 425]
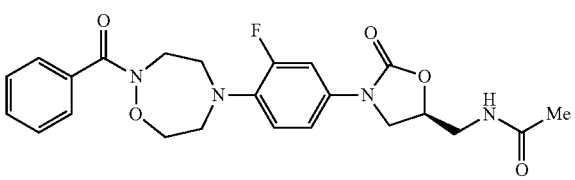
Example 398
[Chemical Formula 426]
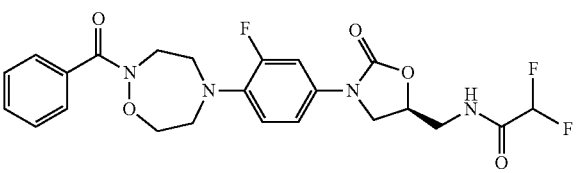
Example 399
[Chemical Formula 427]
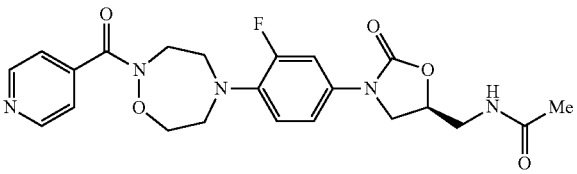
Example 400
[Chemical Formula 428]
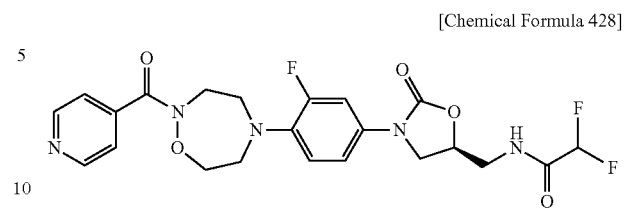
Example 401
[Chemical Formula 429]
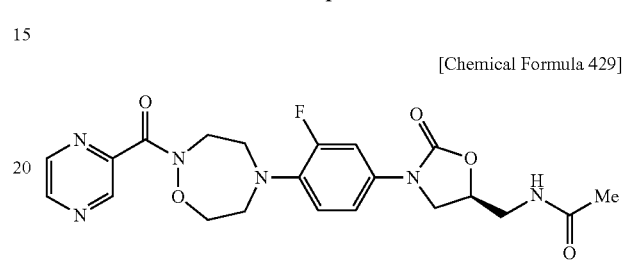
Example 402
[Chemical Formula 430]
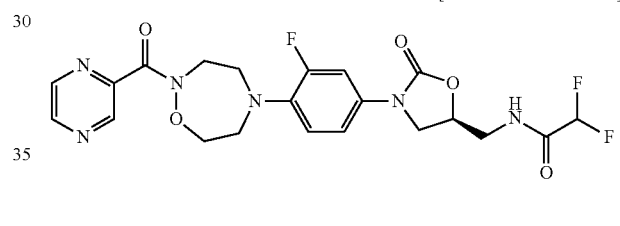
Example 403
[Chemical Formula 431]
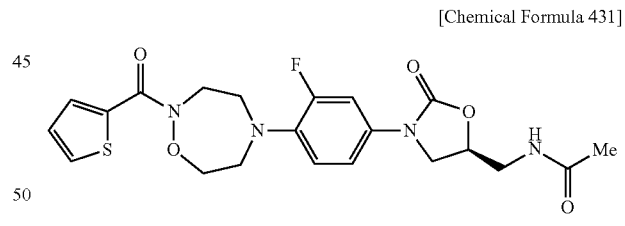
Example 404
[Chemical Formula 432]
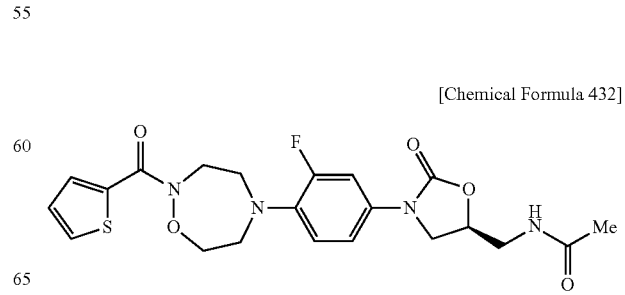

Example 405
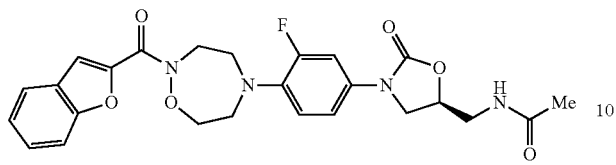
[Chemical Formula 433]
Example 406
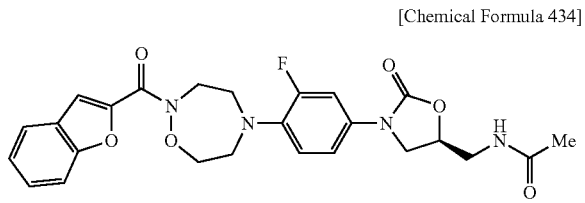 [SMILES: CC(=O)NC[C@H]1CN(c2ccc(N3CCON(C(=O)c4cc5ccccc5o4)CC3)c(F)c2)C(=O)O1]
[Chemical Formula 434]
Example 407
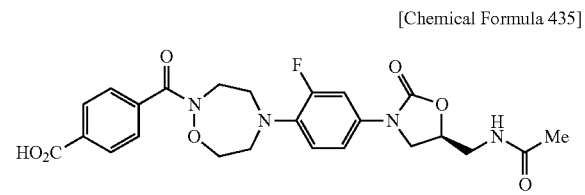 [SMILES: CC(=O)NC[C@H]1CN(c2ccc(N3CCON(C(=O)c4ccc(C(=O)O)cc4)CC3)c(F)c2)C(=O)O1]
[Chemical Formula 435]
Example 408
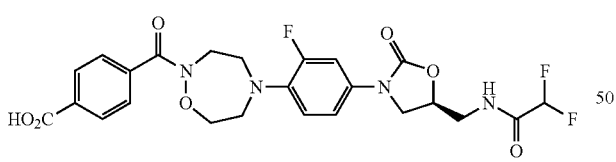
[Chemical Formula 436]
Example 409
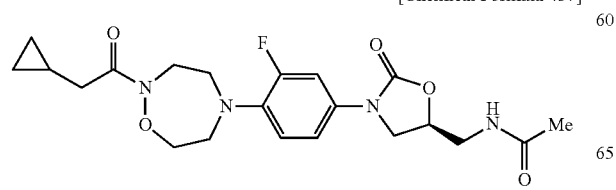
[Chemical Formula 437]
Example 410
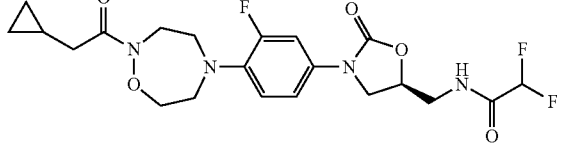
[Chemical Formula 438]
Example 411
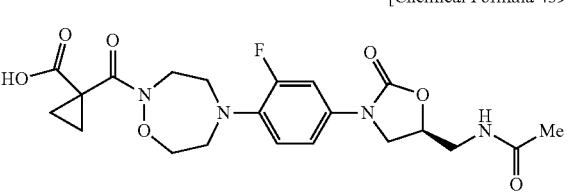
[Chemical Formula 439]
Example 412
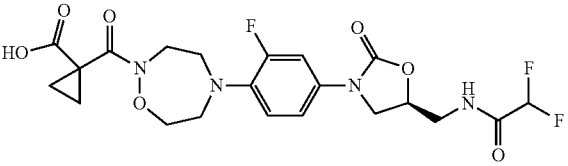
[Chemical Formula 440]
Example 413
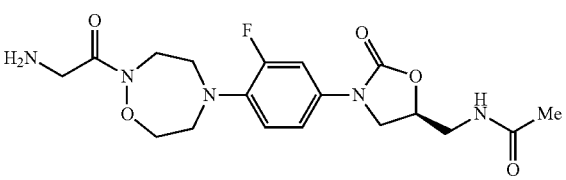
[Chemical Formula 441]
Example 414
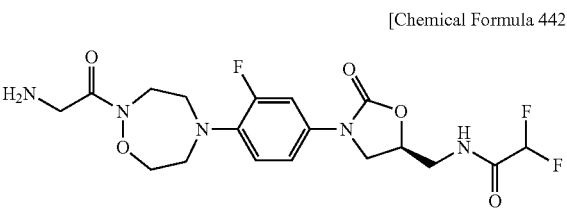
[Chemical Formula 442]

Example 415
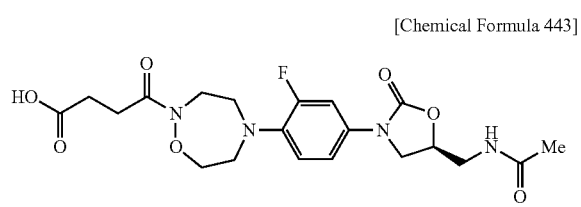 [SMILES: CC(=O)NC[C@H]1CN(c2ccc(N3CCON(C(=O)CCC(=O)O)CC3)c(F)c2)C(=O)O1]
Example 416
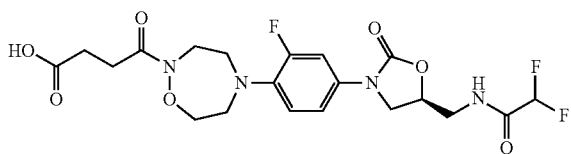
Example 417
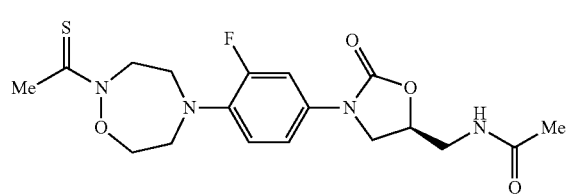
Example 418
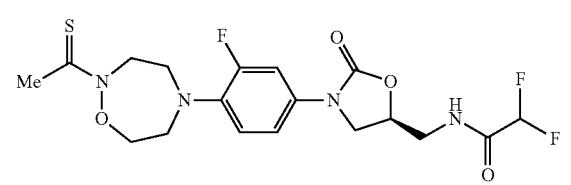
Example 419
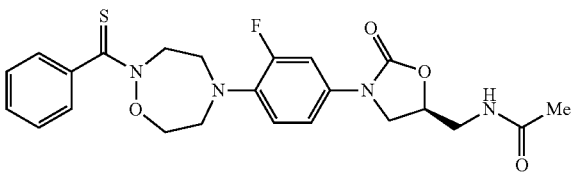
Example 420
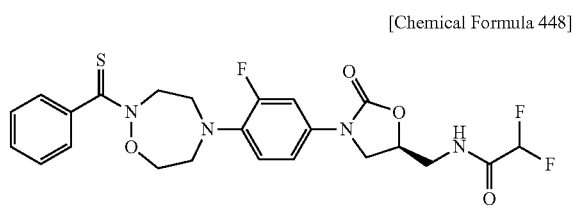 [SMILES: O=C(NC[C@H]1CN(c2ccc(N3CCON(C(=S)c4ccccc4)CC3)c(F)c2)C(=O)O1)C(F)F]
Example 421
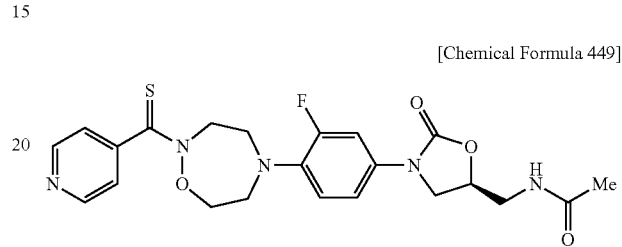
Example 422
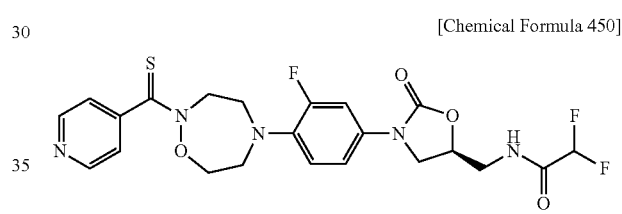
Example 423
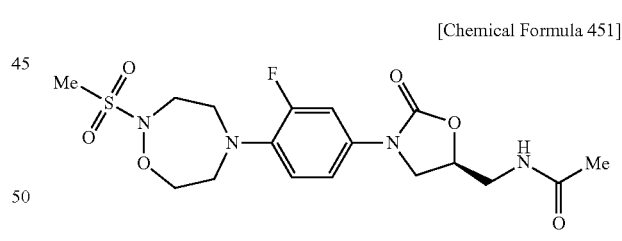
Example 424
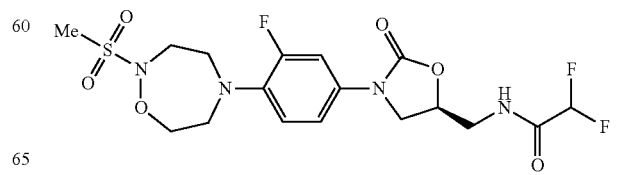

Example 425
[Chemical Formula 453]
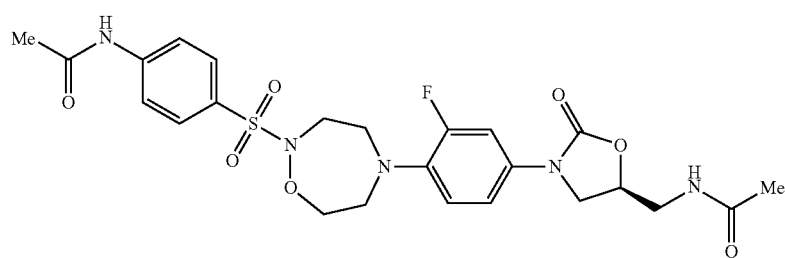
Example 426
[Chemical Formula 454]
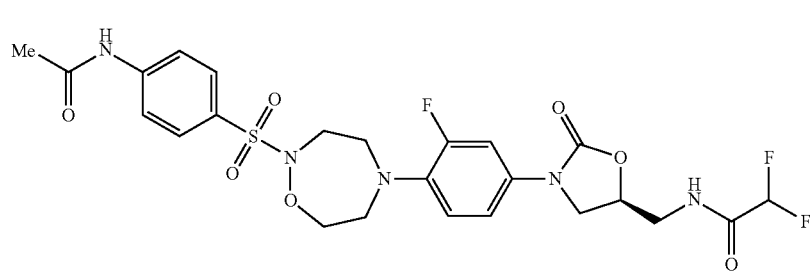
Example 427
Example 430
[Chemical Formula 455]
[Chemical Formula 458]
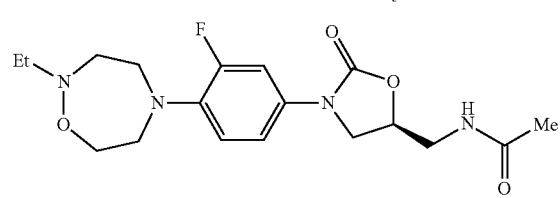 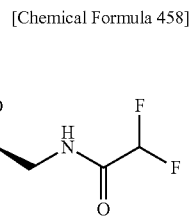
Example 428
Example 431
[Chemical Formula 456]
[Chemical Formula 459]
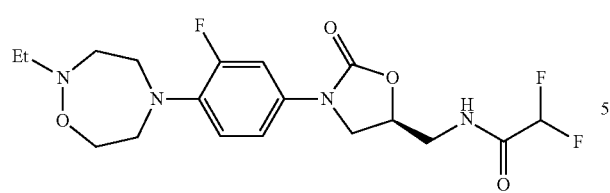 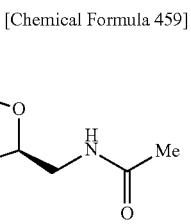
Example 429
Example 432
[Chemical Formula 457]
[Chemical Formula 460]
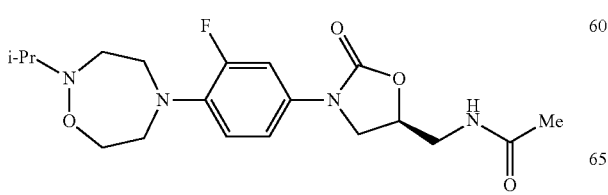 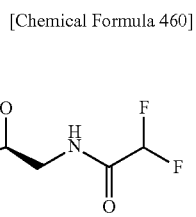

Example 433
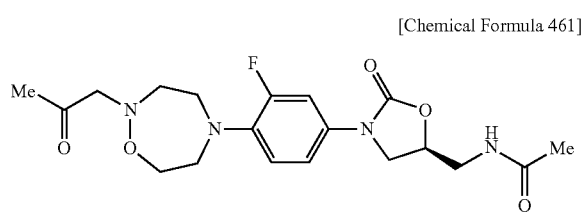
[Chemical Formula 461]
Example 434
Example 435
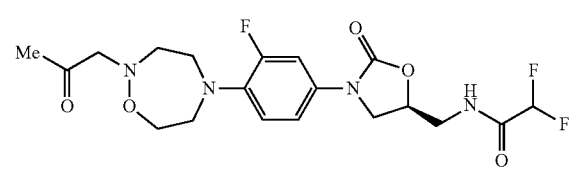
[Chemical Formula 462]
Example 436
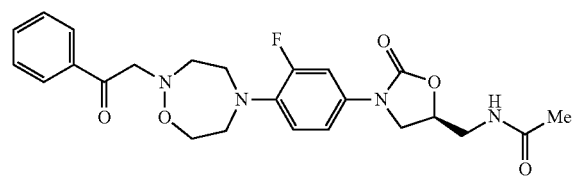
[Chemical Formula 463]
Example 437
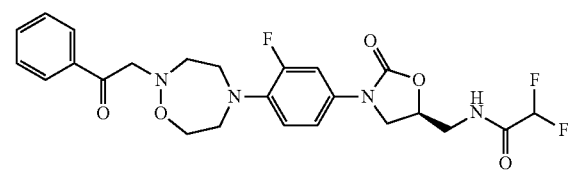
[Chemical Formula 464]
[Chemical Formula 465]
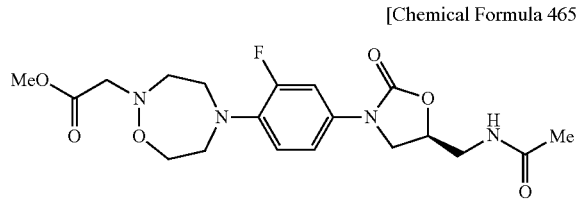
Example 438
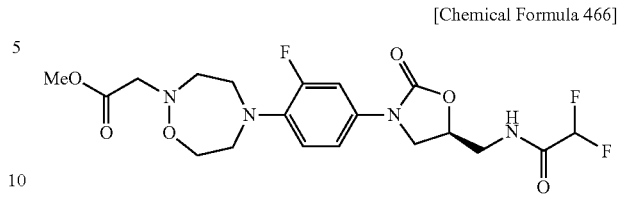
[Chemical Formula 466]
Example 439
[Chemical Formula 467]
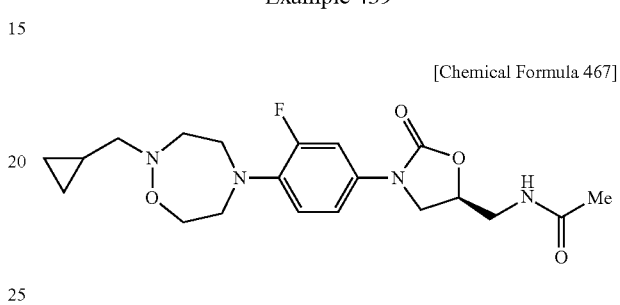
Example 440
[Chemical Formula 468]
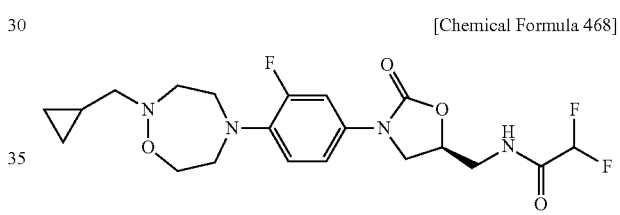
Example 441
[Chemical Formula 469]
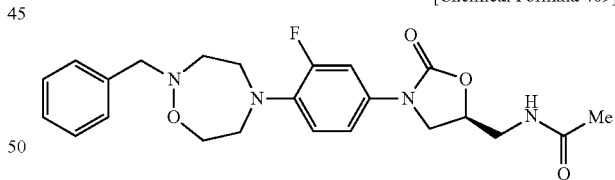
Example 442
[Chemical Formula 470]
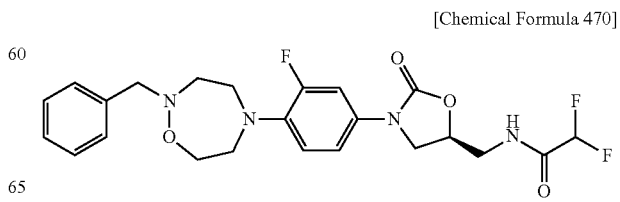

Example 443
Example 444
Example 445
Example 446
Example 447
Example 448
Example 449
Example 450
Example 451
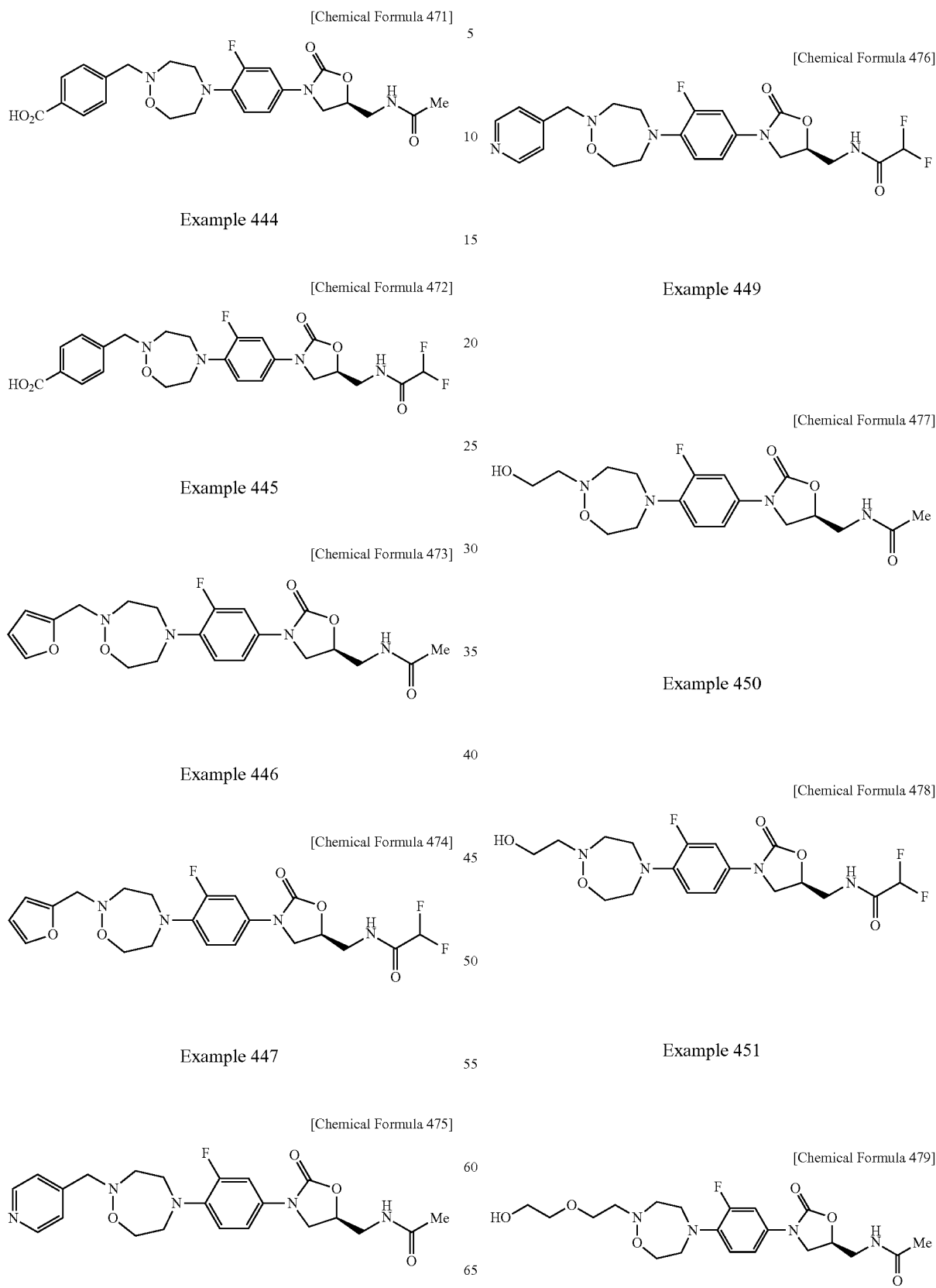

Example 452
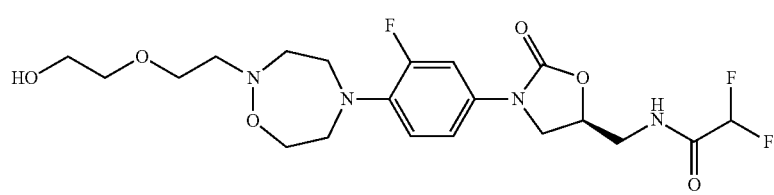
Example 453
[Chemical Formula 481]
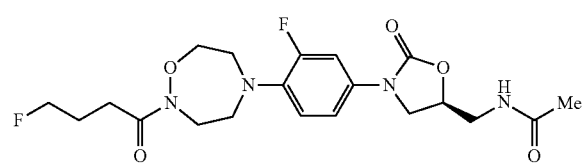
Example 454
[Chemical Formula 482]
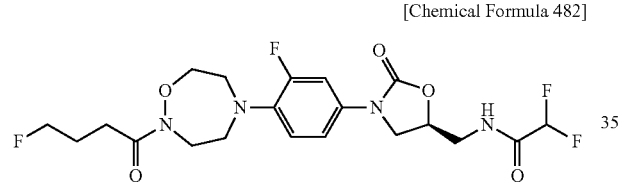
Example 455
[Chemical Formula 483]
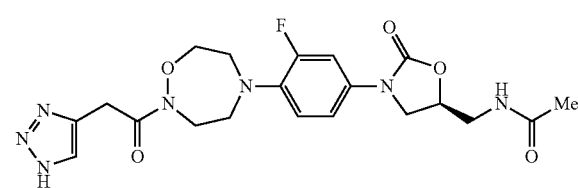
Example 456
[Chemical Formula 484]
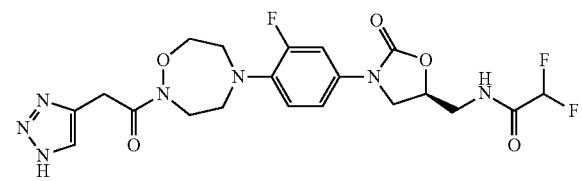
Example 457
[Chemical Formula 480]
Example 458
[Chemical Formula 485]
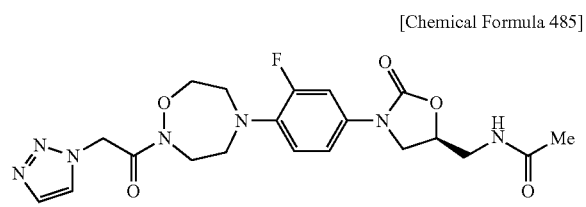 [SMILES: CC(=O)NC[C@H]1CN(c2ccc(N3CCON(C(=O)Cn4ccnn4)CC3)c(F)c2)C(=O)O1]
Example 459
[Chemical Formula 486]
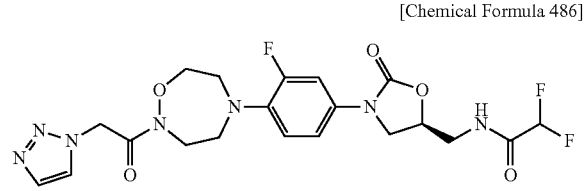 [SMILES: O=C(NC[C@H]1CN(c2ccc(N3CCON(C(=O)Cn4ccnn4)CC3)c(F)c2)C(=O)O1)C(F)F]
Example 460
[Chemical Formula 487]
[Chemical Formula 488]
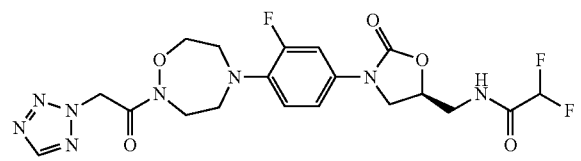

161 162
Example 461  Example 462
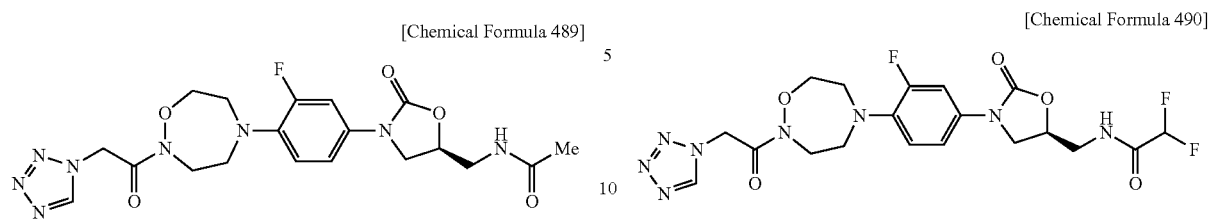
Example 463
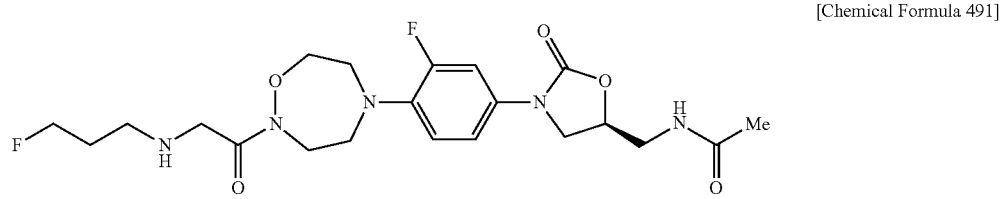 [SMILES: CC(=O)NC[C@H]1CN(c2ccc(N3CCON(C(=O)CNCCCF)CC3)c(F)c2)C(=O)O1]
Example 464
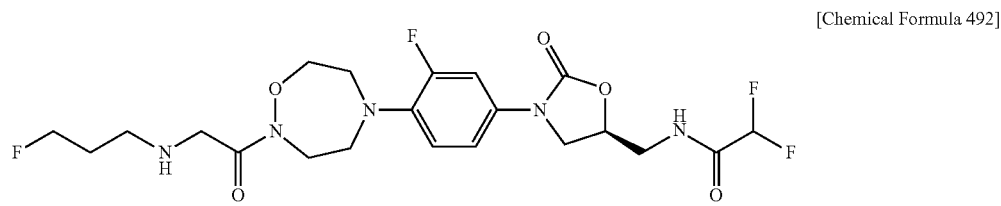 [SMILES: O=C(NC[C@H]1CN(c2ccc(N3CCON(C(=O)CNCCCF)CC3)c(F)c2)C(=O)O1)C(F)F]
Example 465
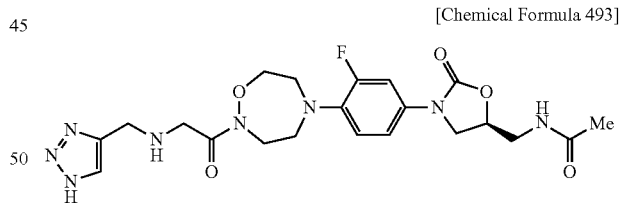
Example 466
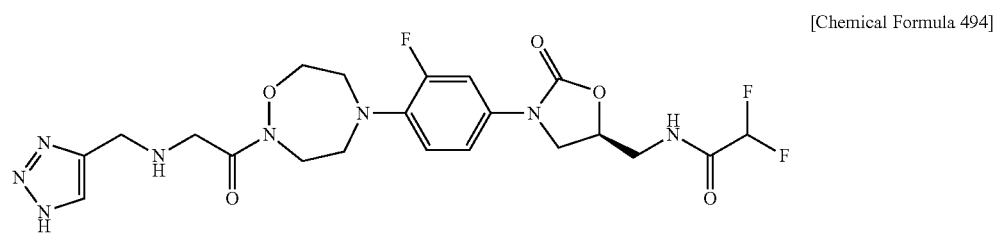 [SMILES: O=C(NC[C@H]1CN(c2ccc(N3CCON(C(=O)CNCc4c[nH]nn4)CC3)c(F)c2)C(=O)O1)C(F)F]

Example 467
[Chemical Formula 495]
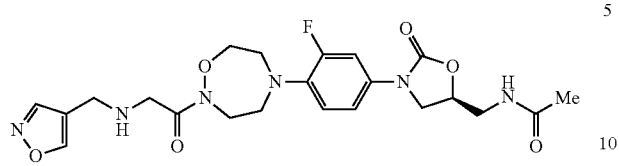
Example 468
[Chemical Formula 496]
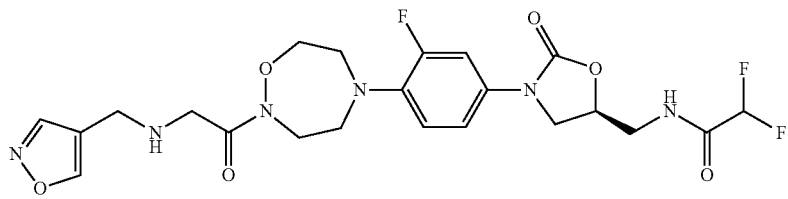
Example 469
[Chemical Formula 497]
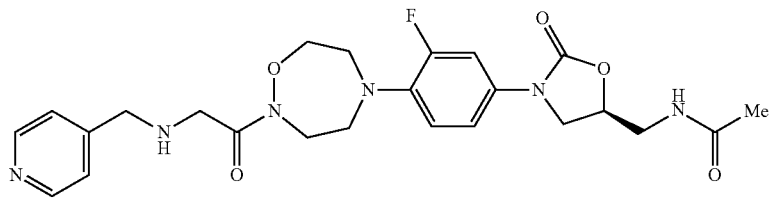
Example 470
[Chemical Formula 498]
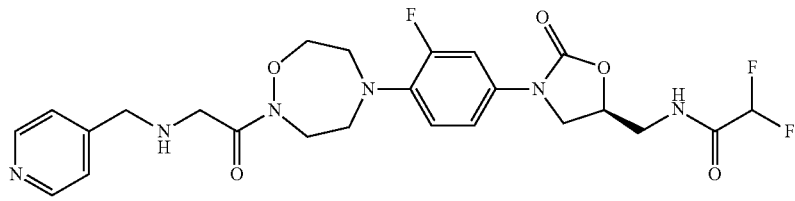
Example 471
[Chemical Formula 499]
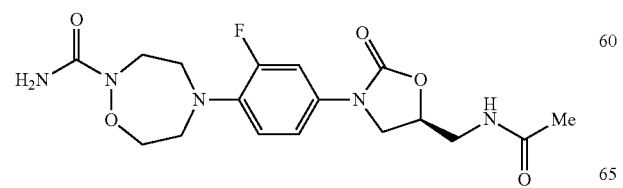

Example 472
[Chemical Formula 500]
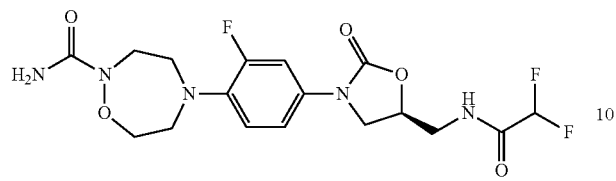
Example 473
[Chemical Formula 501]
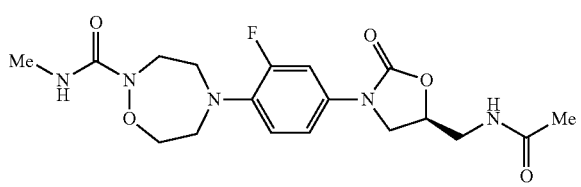
Example 474
[Chemical Formula 502]
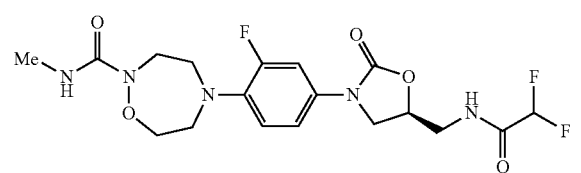
Example 475
[Chemical Formula 503]
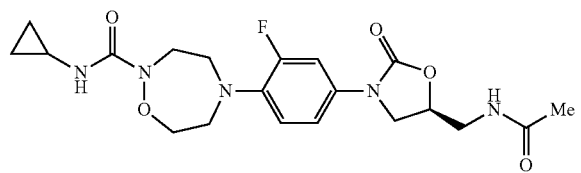
Example 476
[Chemical Formula 504]
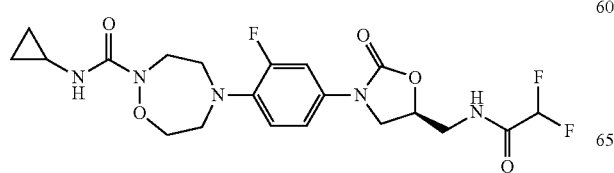
Example 477
[Chemical Formula 505]
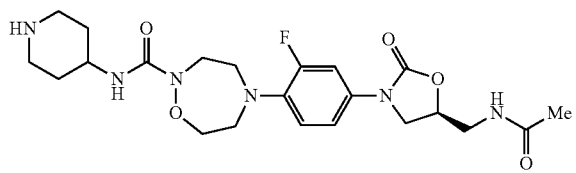
Example 478
[Chemical Formula 506]
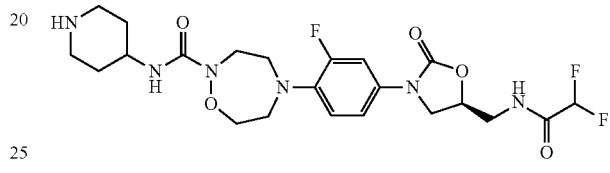
Example 479
[Chemical Formula 507]
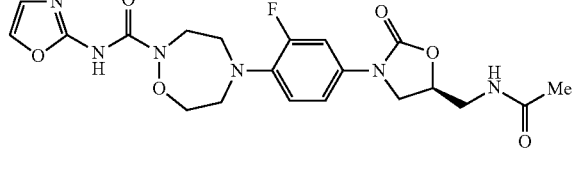
Example 480
[Chemical Formula 508]
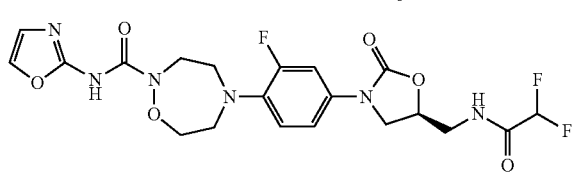
Example 481
[Chemical Formula 509]

Example 482
[Chemical Formula 510]
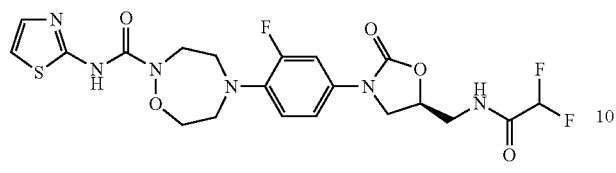
Example 483
[Chemical Formula 511]
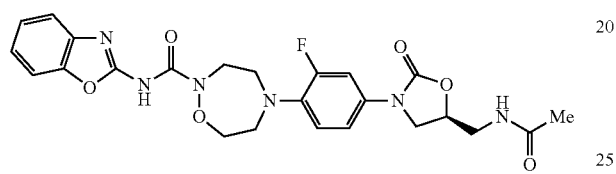
Example 484
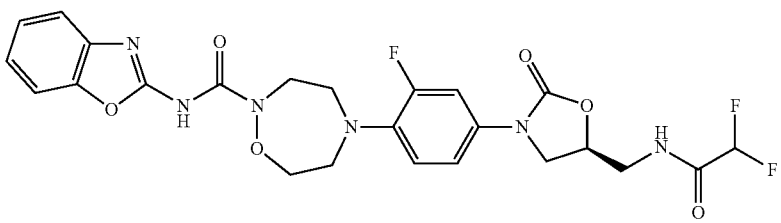
Example 485
[Chemical Formula 513]
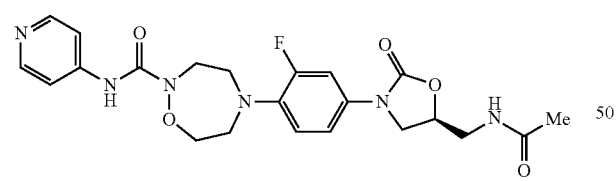
Example 486
[Chemical Formula 514]
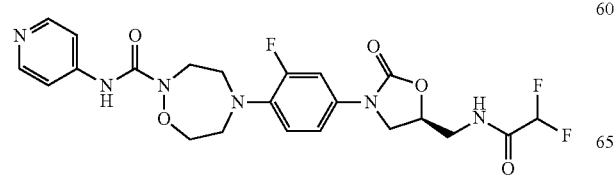
Example 487
[Chemical Formula 515]
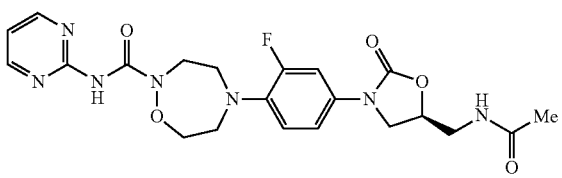
Example 488
[Chemical Formula 516]
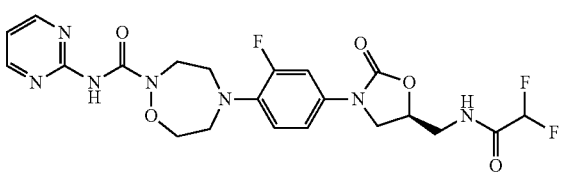
Example 489
[Chemical Formula 517]
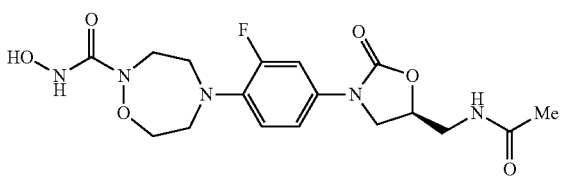
Example 490
[Chemical Formula 518]
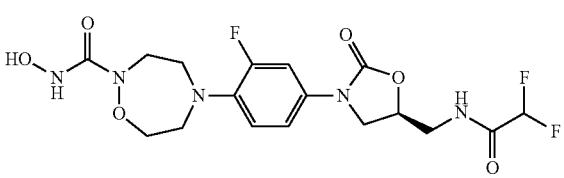

Example 491

[Chemical Formula 519]

Example 492

[Chemical Formula 520]

Example 493

[Chemical Formula 521]

Example 494

[Chemical Formula 522]

Example 495

[Chemical Formula 523]

Example 496

[Chemical Formula 524]

Example 497

[Chemical Formula 525]

Example 498

[Chemical Formula 526]

Example 499

[Chemical Formula 527]

| 171 | 172 |
|---|---|
| Example 500 | Example 505 |
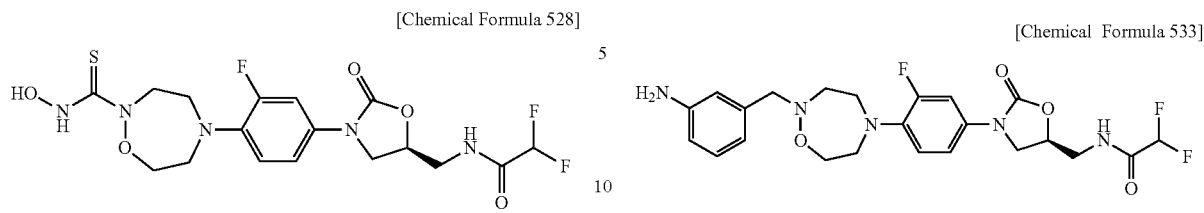
Example 501 | Example 506
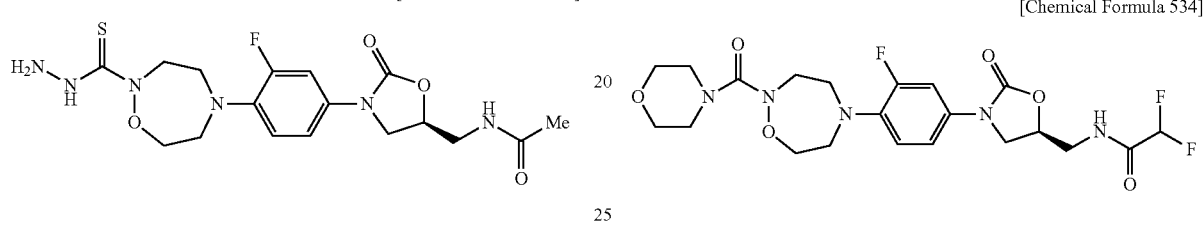
Example 502 | Example 507
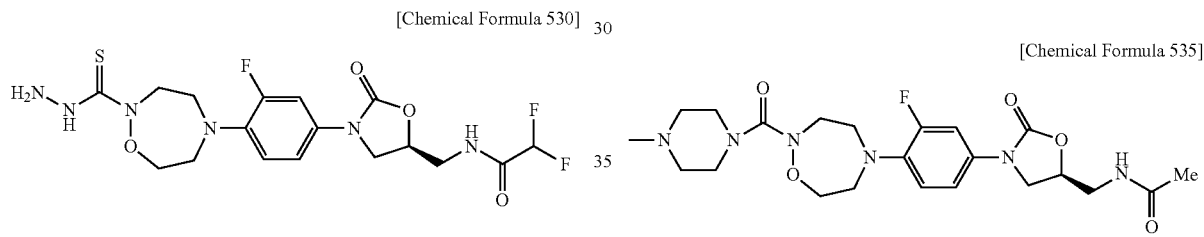
Example 503 | Example 508
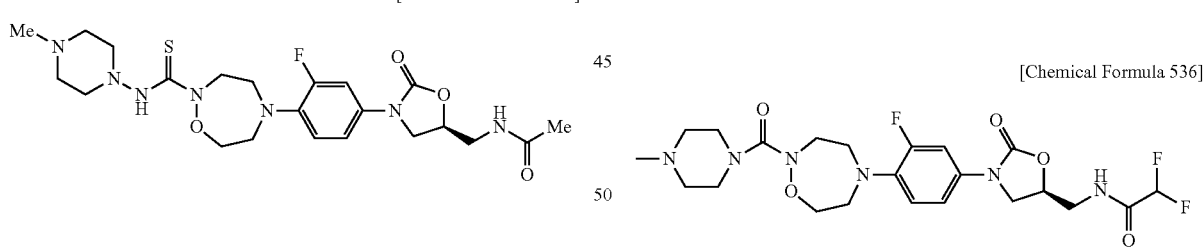
Example 504
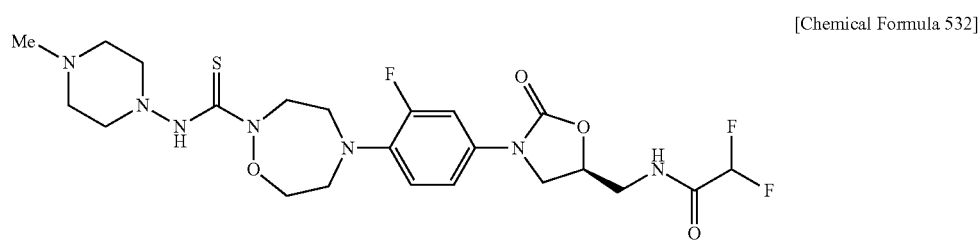 [SMILES: CN1CCN(NC(=S)N2CCN(c3ccc(N4C[C@H](CNC(=O)C(F)F)OC4=O)cc3F)CCO2)CC1]

Example 509
[Chemical Formula 537]
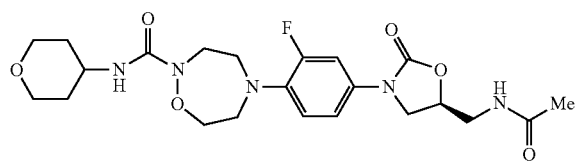
Example 510
[Chemical Formula 538]
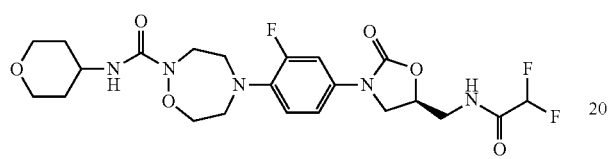
Example 511
[Chemical Formula 539]
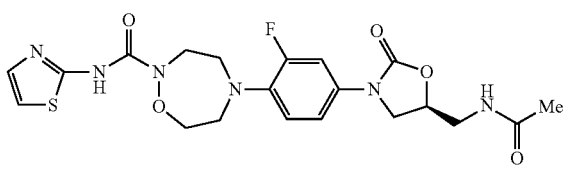
Example 512
[Chemical Formula 540]
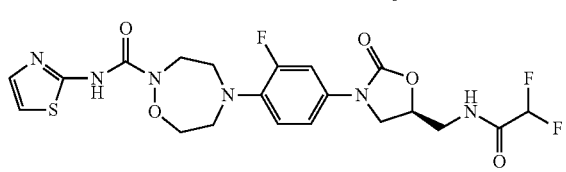
Example 513
[Chemical Formula 541]
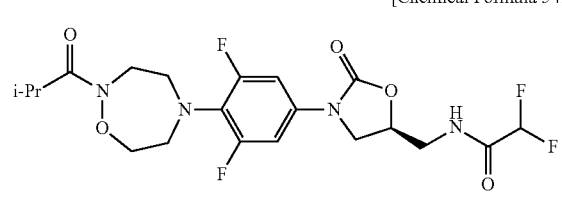
Example 514
[Chemical Formula 542]
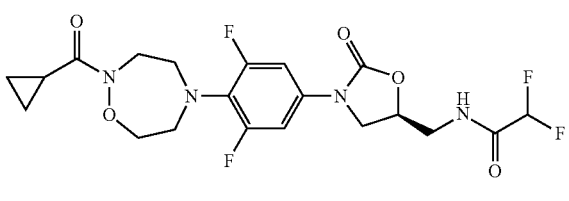
Example 515
[Chemical Formula 543]
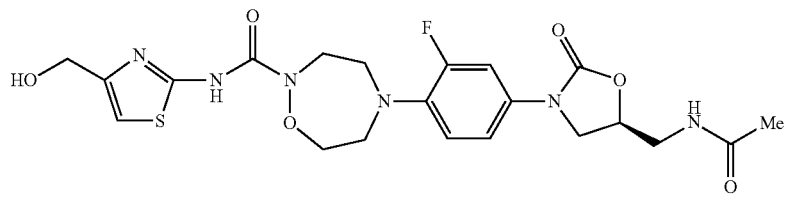
Example 516
[Chemical Formula 544]
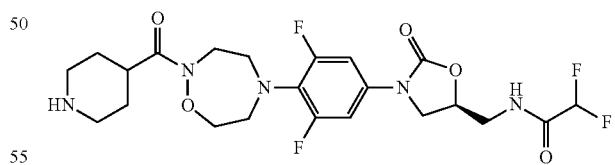
Example 517
[Chemical Formula 545]
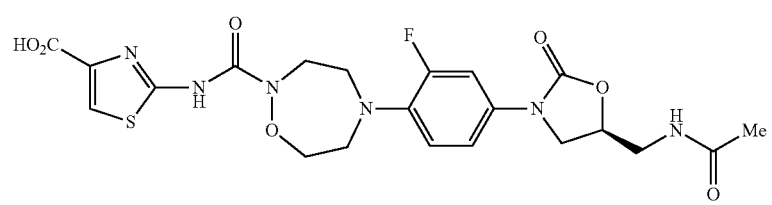

Example 518
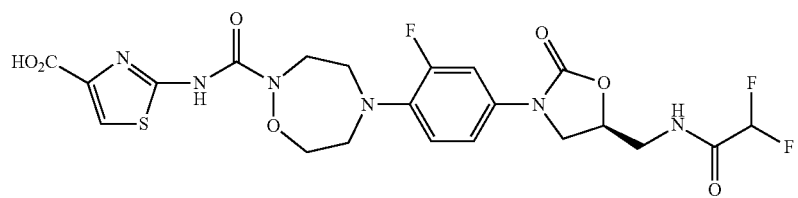
Example 519
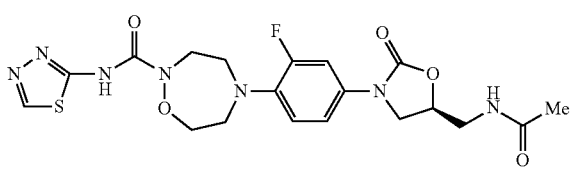
Example 520
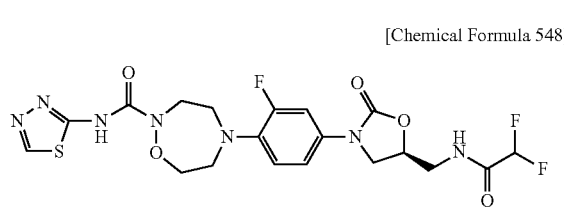 [SMILES: O=C(NC[C@H]1CN(c2ccc(N3CCON(C(=O)Nc4nncs4)CC3)c(F)c2)C(=O)O1)C(F)F]
Example 521
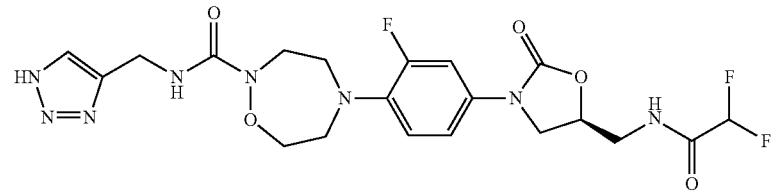
Example 522
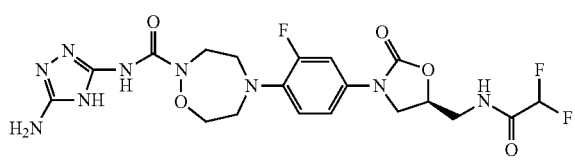
Example 523
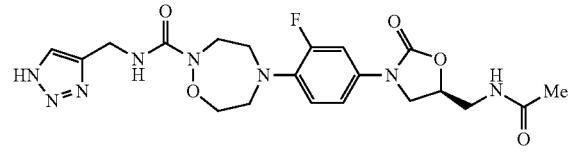
Example 524
[Chemical Formula 551]
Example 525
[Chemical Formula 552]
[Chemical Formula 549]
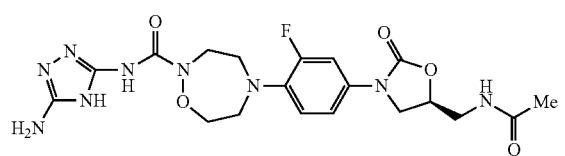
[Chemical Formula 553]
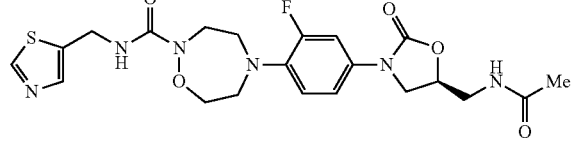

177
Example 526
[Chemical Formula 554]
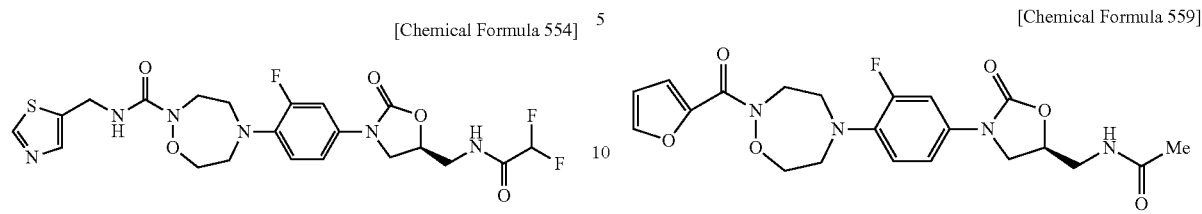
Example 527
[Chemical Formula 555]
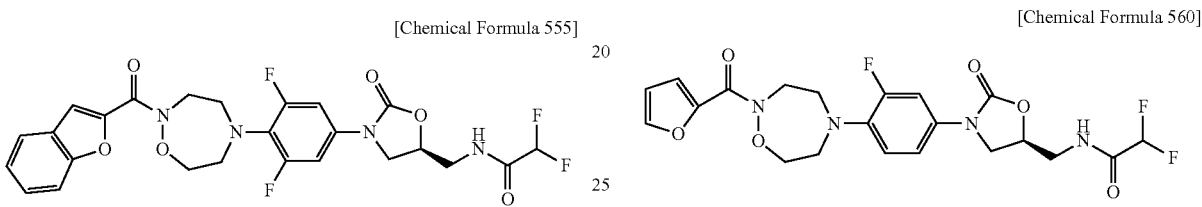
Example 528
[Chemical Formula 556]
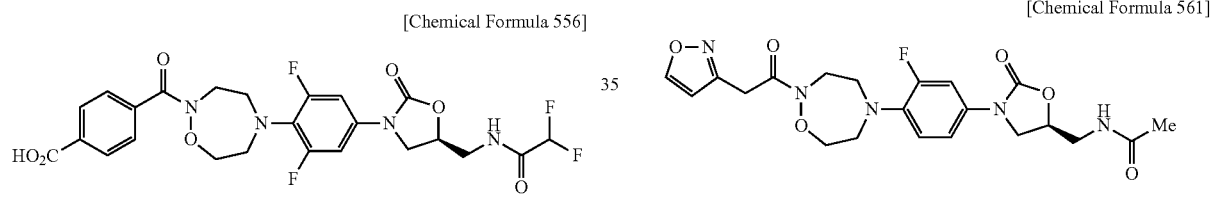
Example 529
[Chemical Formula 557]
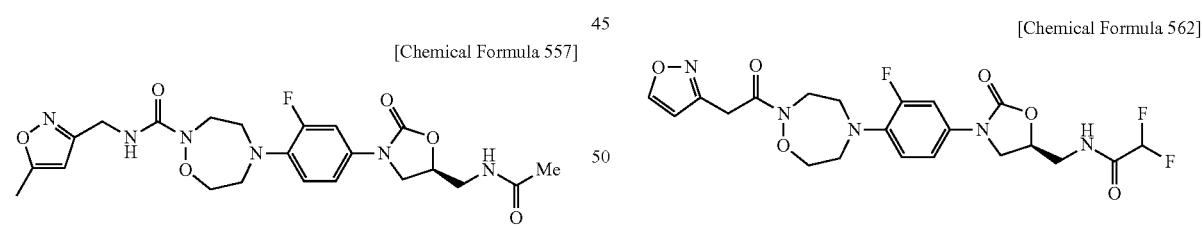
Example 530
[Chemical Formula 558]
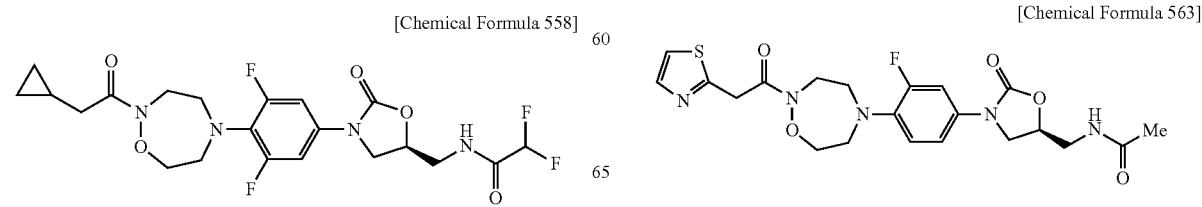
178
Example 531
[Chemical Formula 559]
Example 532
[Chemical Formula 560]
Example 533
[Chemical Formula 561]
Example 534
[Chemical Formula 562]
Example 535
[Chemical Formula 563]

Example 536

[Chemical Formula 564]

Example 537

[Chemical Formula 565]

Example 538

[Chemical Formula 566]

Example 539

[Chemical Formula 567]

Example 540

[Chemical Formula 568]

Example 541

[Chemical Formula 569]

Example 542

[Chemical Formula 570]

Example 543

[Chemical Formula 571]

Example 544

[Chemical Formula 572]

Example 545

[Chemical Formula 573]

181
Example 546
[Chemical Formula 574]
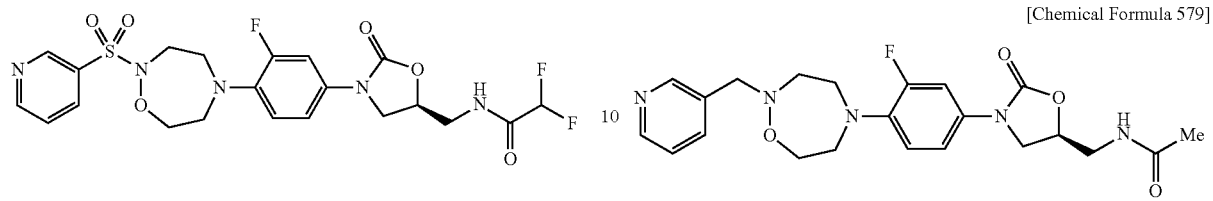
Example 547
[Chemical Formula 575]
Example 548
[Chemical Formula 576]
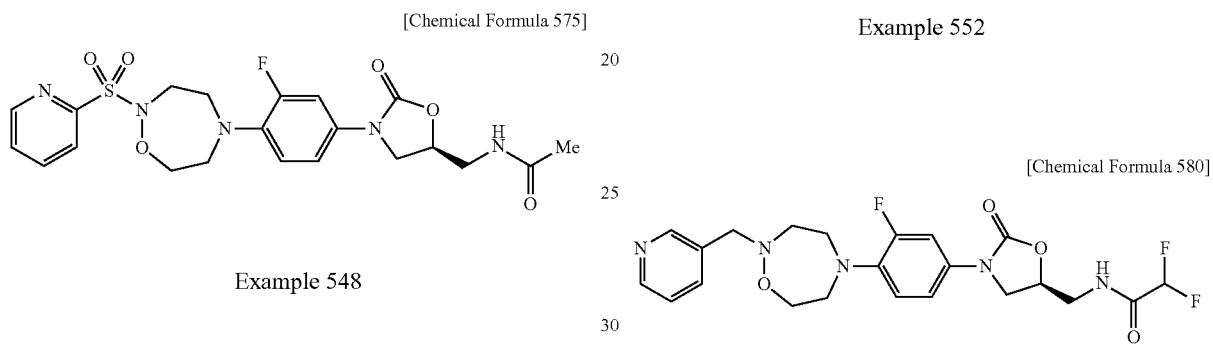
Example 549
[Chemical Formula 577]
Example 550
[Chemical Formula 578]
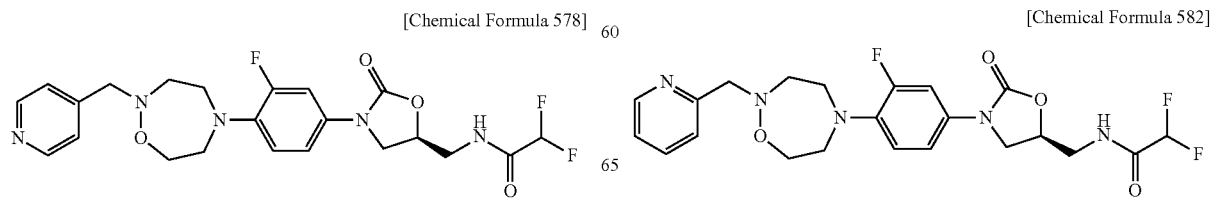
182
Example 551
[Chemical Formula 579]
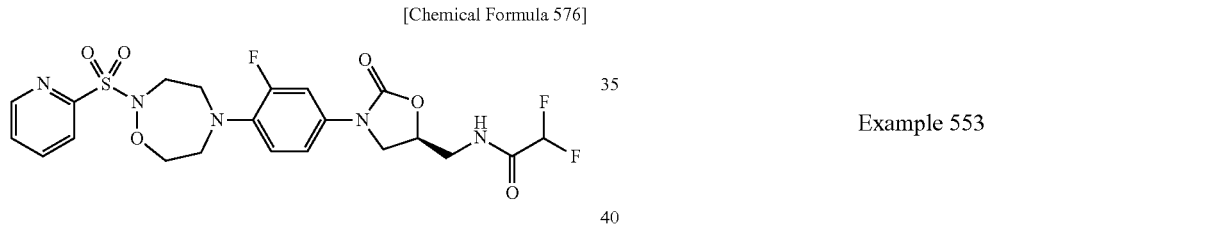
Example 552
[Chemical Formula 580]
Example 553
[Chemical Formula 581]
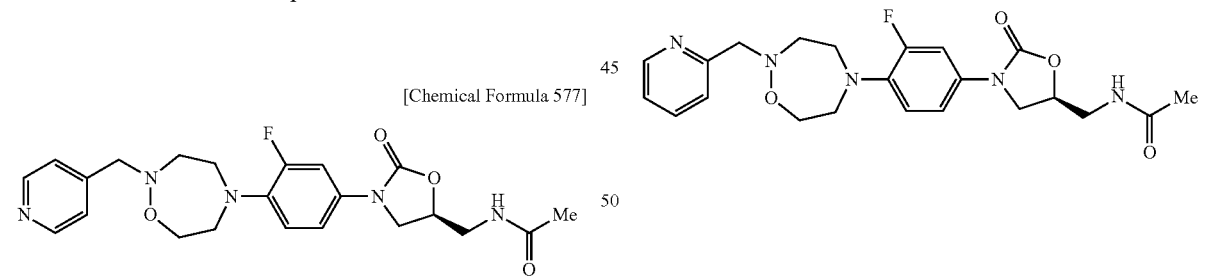
Example 554
[Chemical Formula 582]

Example 555
[Chemical Formula 583]
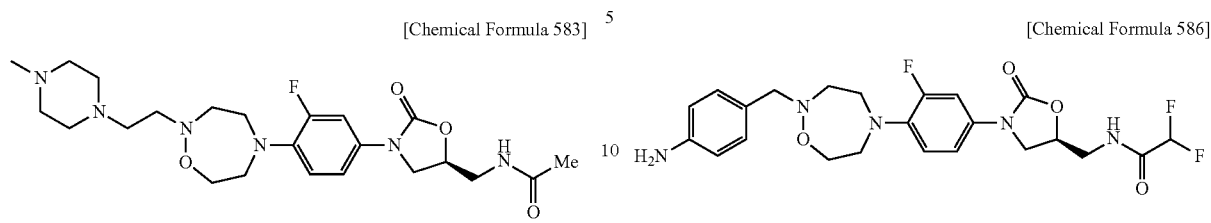
Example 556
[Chemical Formula 584]
Example 557
[Chemical Formula 585]
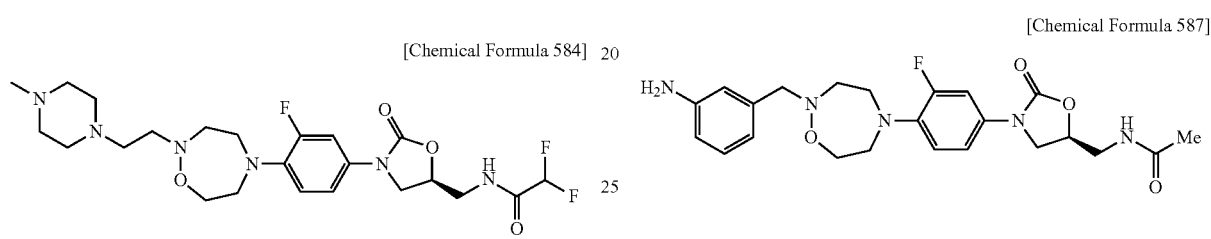
Example 558
[Chemical Formula 586]
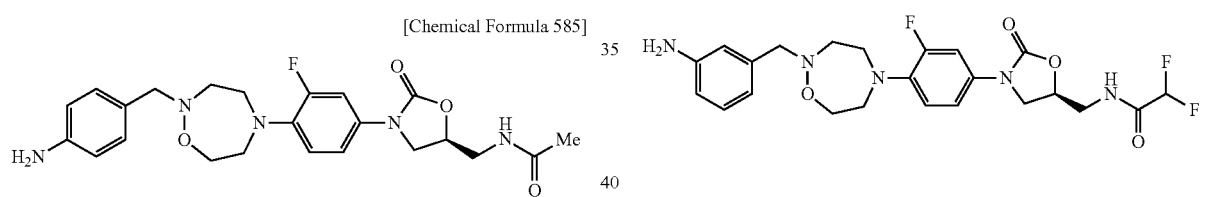
Example 559
[Chemical Formula 587]
Example 560
[Chemical Formula 588]
Example 561
[Chemical Formula 589]
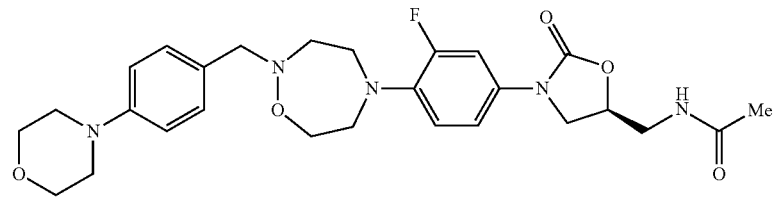
Example 562
[Chemical Formula 590]
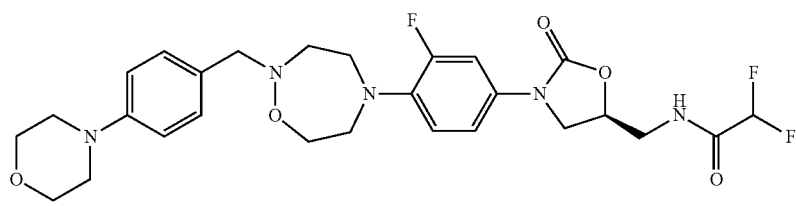

Example 563

Example 564

Example 565

Example 566

Example 567

Example 568

Example 569

Example 570

Example 571

Example 572

Example 573
[Chemical Formula 601]
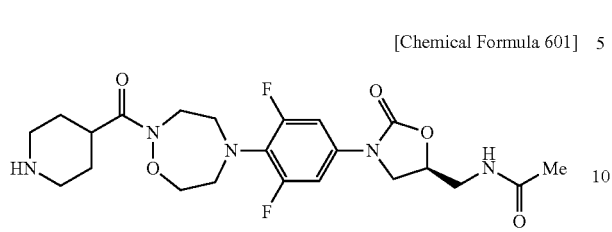
Example 574
Example 578
[Chemical Formula 606]
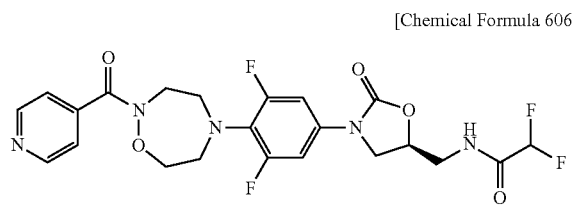
Example 579
[Chemical Formula 602]
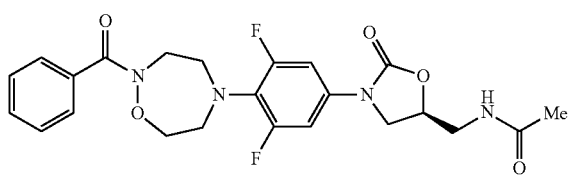
Example 575
[Chemical Formula 607]
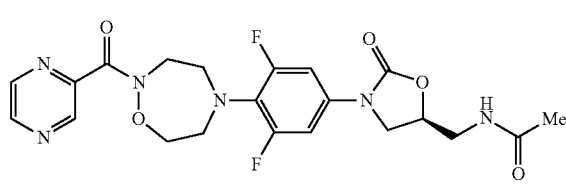
Example 580
[Chemical Formula 603]
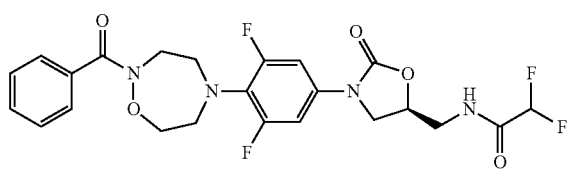
Example 576
[Chemical Formula 608]
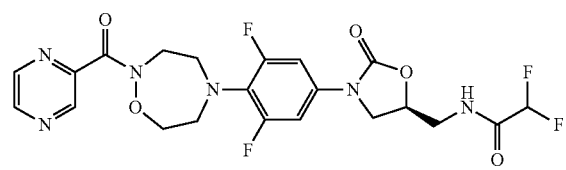
Example 581
[Chemical Formula 604]
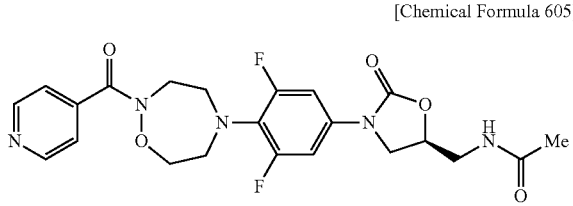
Example 577
[Chemical Formula 609]
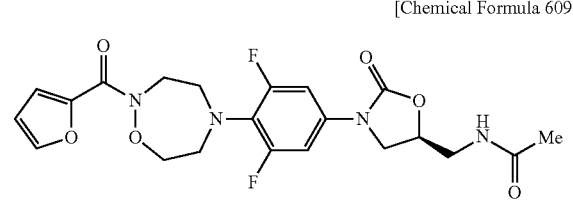
Example 582
[Chemical Formula 605]
[Chemical Formula 610]
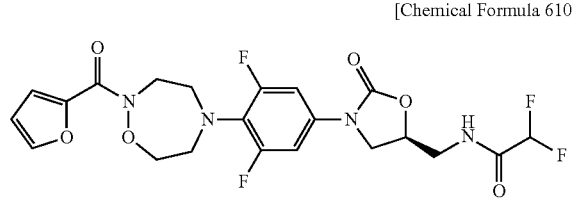 [SMILES: O=C(NC[C@H]1CN(c2cc(F)c(N3CCON(C(=O)c4cccs4)CC3)c(F)c2)C(=O)O1)C(F)F]

Example 583
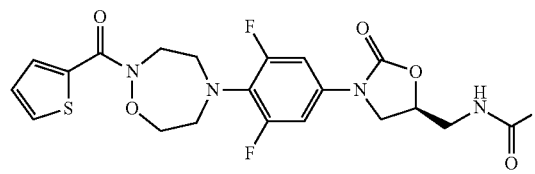
Example 584
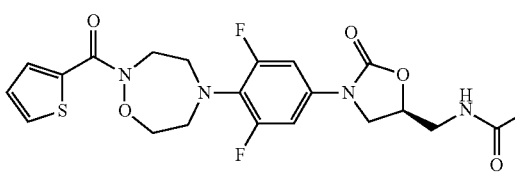
Example 585
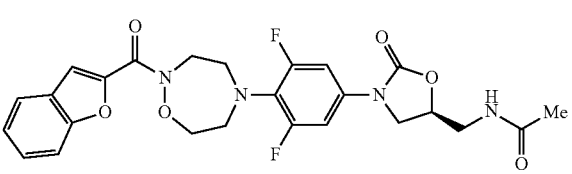
Example 586
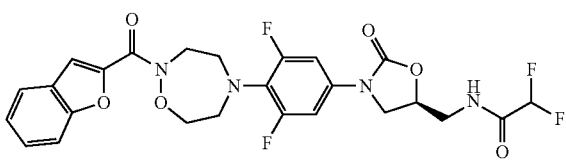
Example 587
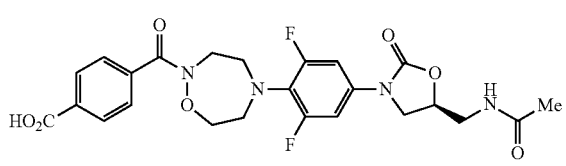
Example 588
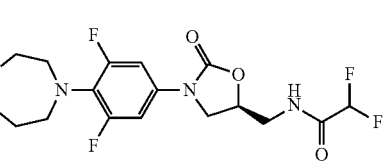
Example 589
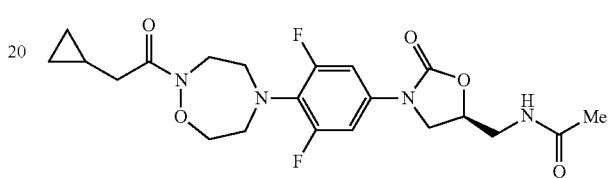
Example 590
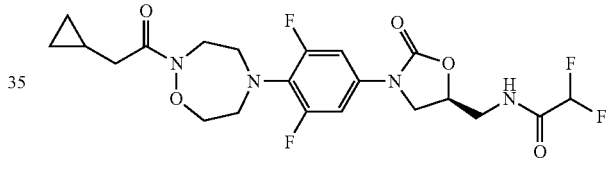
Example 591
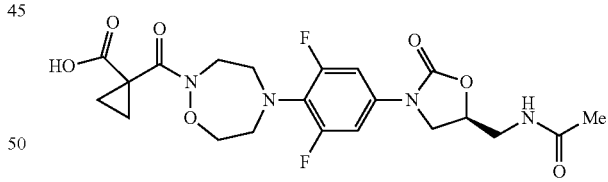
Example 592
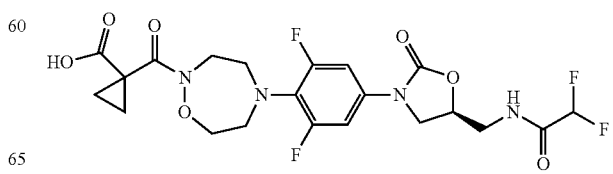

Example 593
Example 598
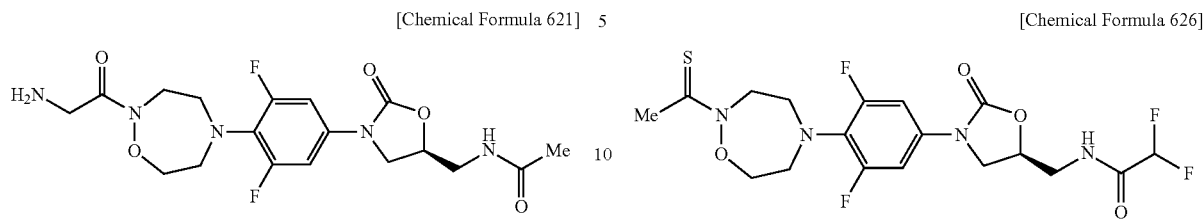
Example 594
Example 599
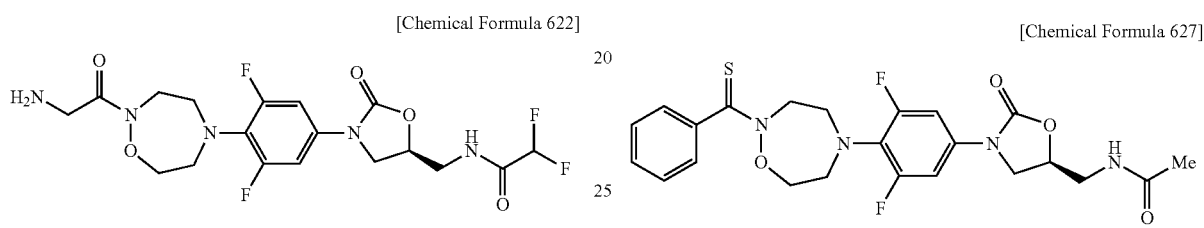
Example 595
Example 600
Example 596
Example 601
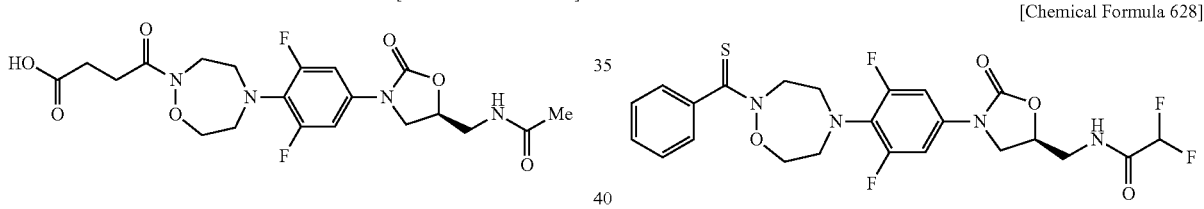
Example 597
Example 602
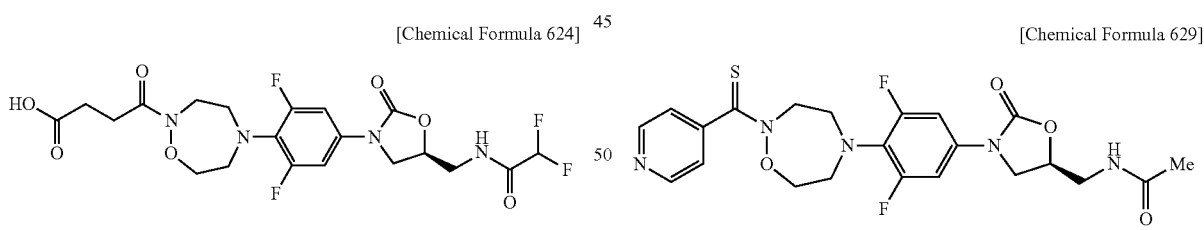
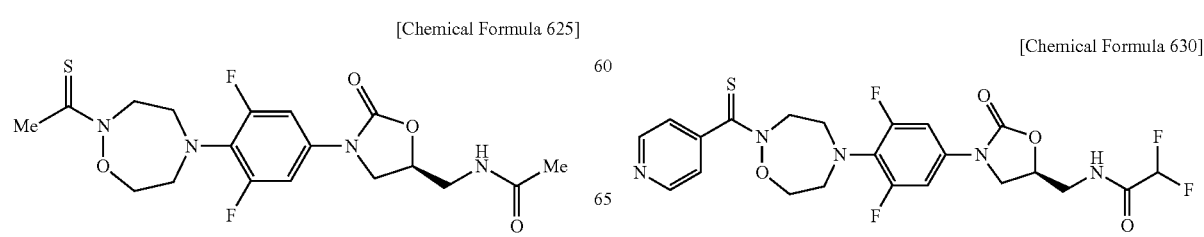

Example 603
[Chemical Formula 631]
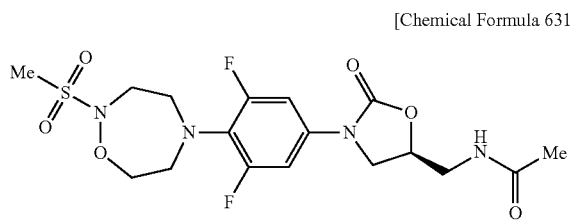
Example 604
[Chemical Formula 632]
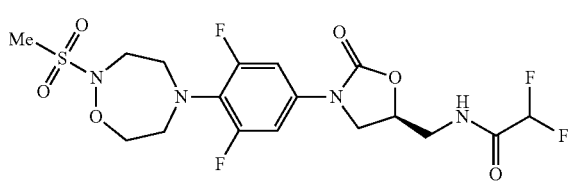
Example 605
[Chemical Formula 633]
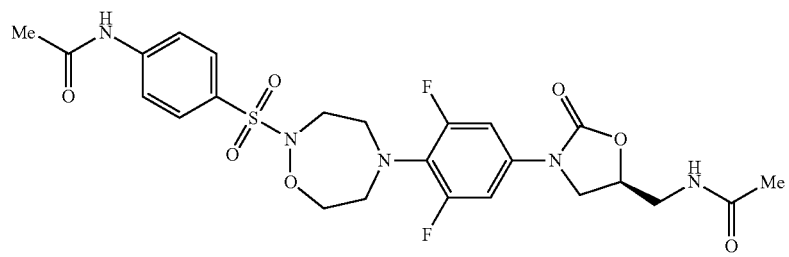
Example 606
[Chemical Formula 634]
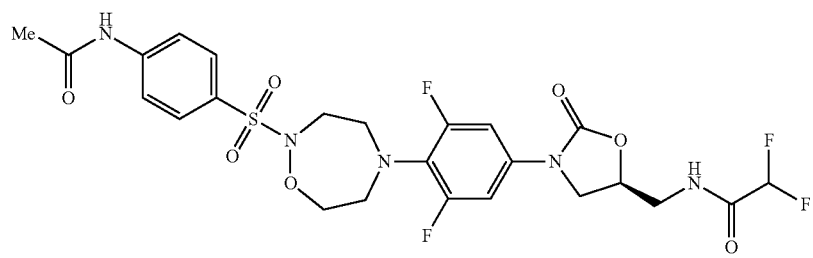
Example 607
[Chemical Formula 635]
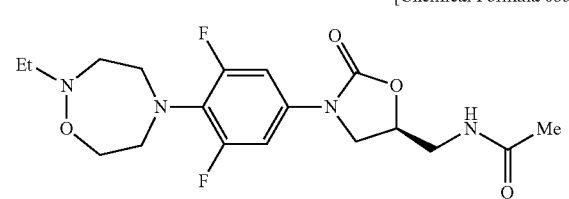
Example 608
[Chemical Formula 636]
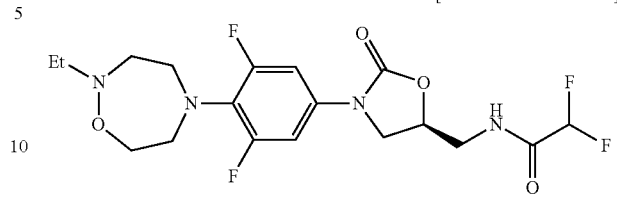
Example 609
[Chemical Formula 637]
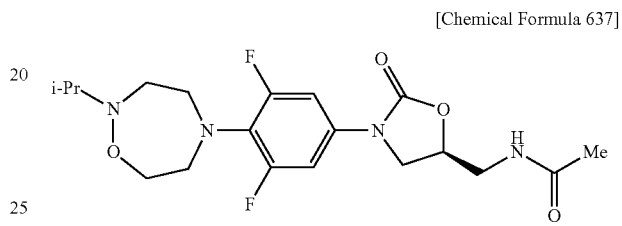
Example 610
[Chemical Formula 638]
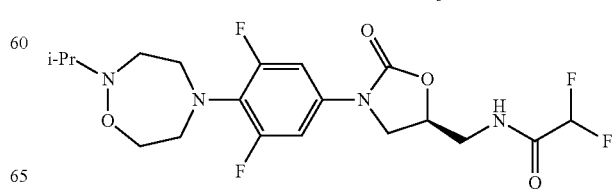

Example 611
[Chemical Formula 639]
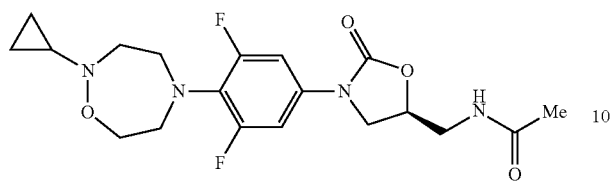
Example 612
[Chemical Formula 640]
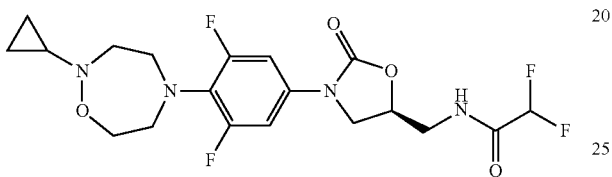
Example 613a
[Chemical Formula 641]
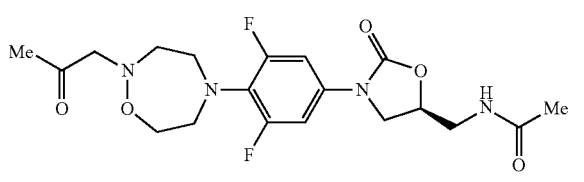
Example 613b
[Chemical Formula 642]
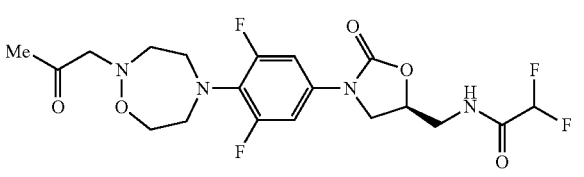
Example 614
[Chemical Formula 643]
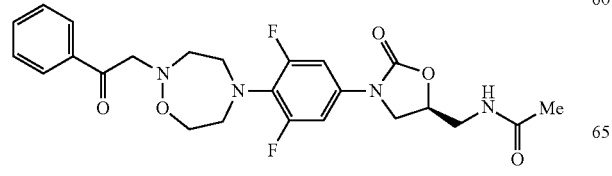
Example 615
[Chemical Formula 644]
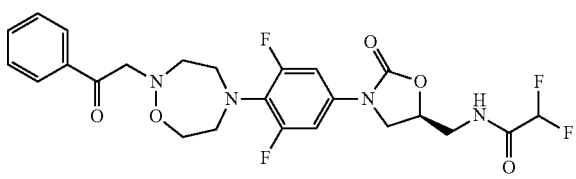
Example 616
[Chemical Formula 645]
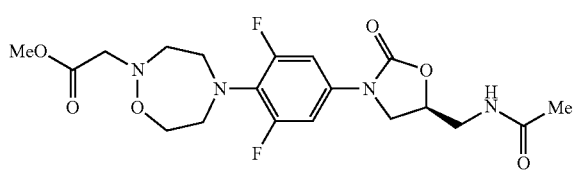
Example 617
[Chemical Formula 646]
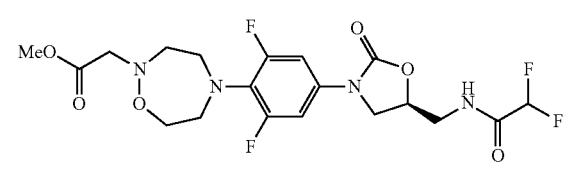
Example 618
[Chemical Formula 647]
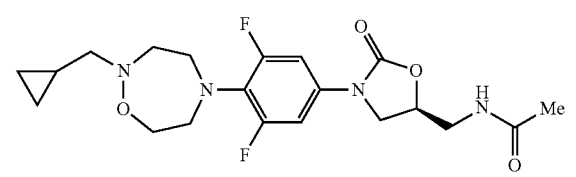
Example 619
[Chemical Formula 648]
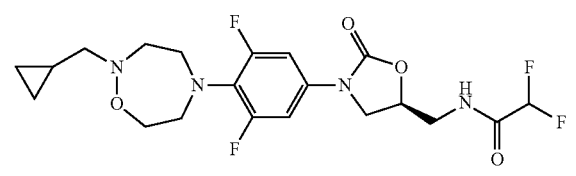

Example 620
[Chemical Formula 649]
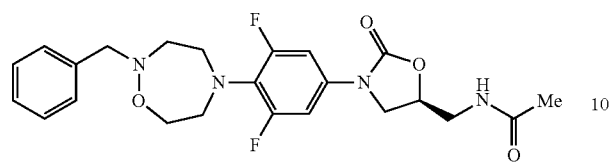
Example 621
Example 625
[Chemical Formula 654]
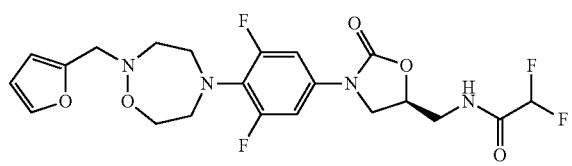
Example 626
[Chemical Formula 650]
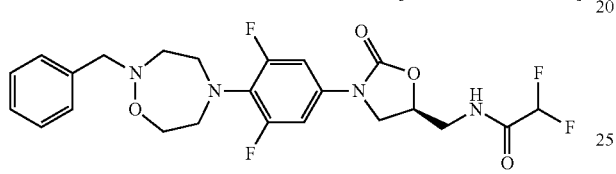
Example 622
[Chemical Formula 655]
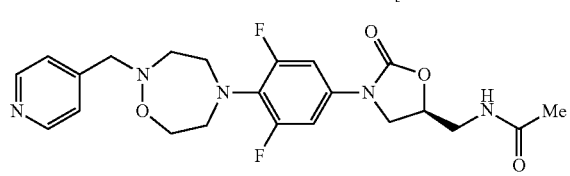
Example 627
[Chemical Formula 651]
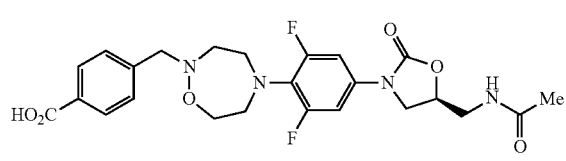
Example 623
[Chemical Formula 656]
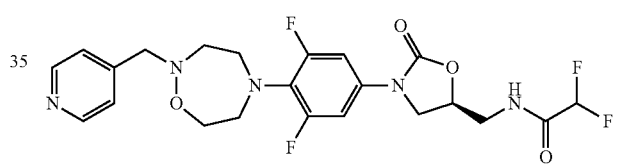
Example 628
[Chemical Formula 652]
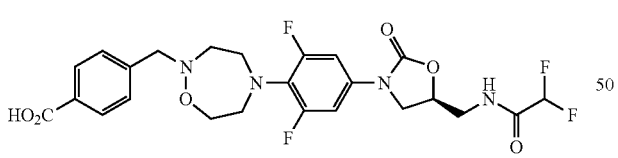
Example 624
[Chemical Formula 657]
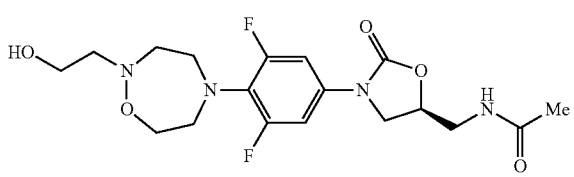
Example 629
[Chemical Formula 653]
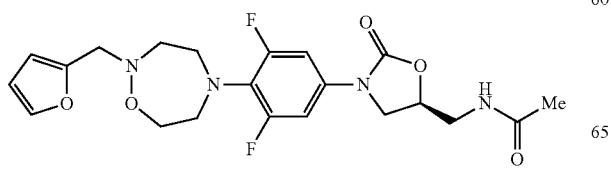
[Chemical Formula 658]
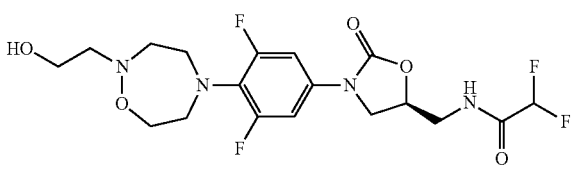

Example 630
[Chemical Formula 659]
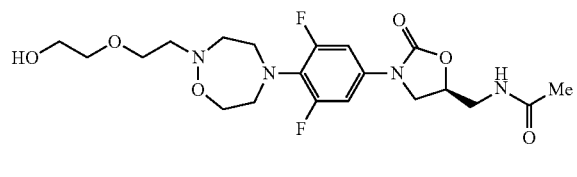
Example 631
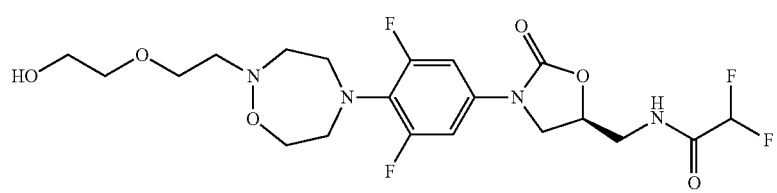
Example 632
[Chemical Formula 661]
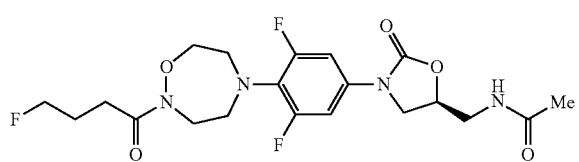
Example 633
[Chemical Formula 662]
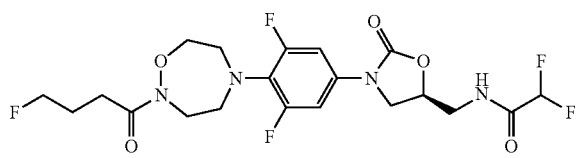
Example 634
[Chemical Formula 663]
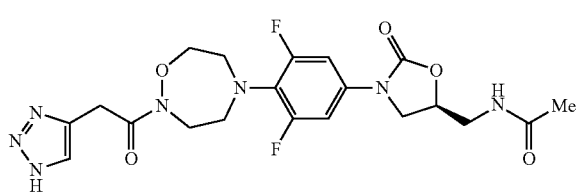
Example 635
[Chemical Formula 664]
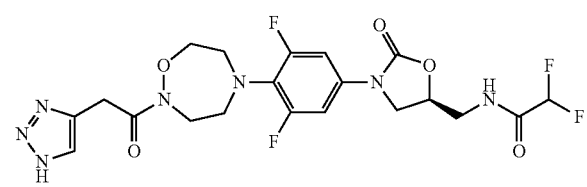
Example 636
[Chemical Formula 665]
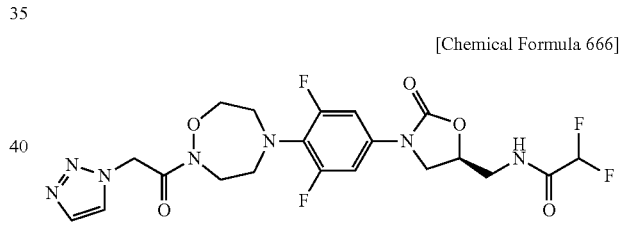
Example 637a
[Chemical Formula 666]
Example 637b
[Chemical Formula 667]
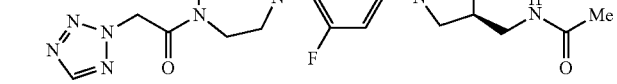
Example 638
[Chemical Formula 668]
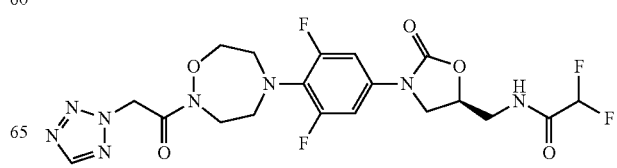

201 202
Example 639 Example 640
[Chemical Formula 669]
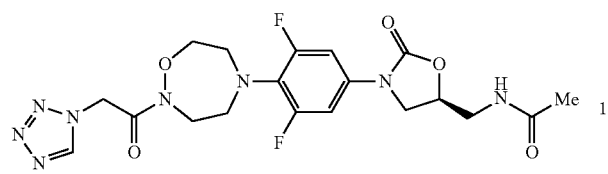
[Chemical Formula 670]
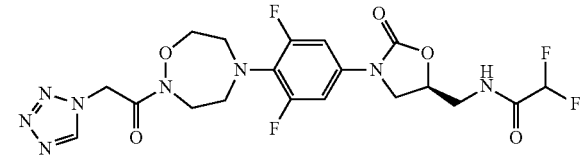
Example 641
[Chemical Formula 671]
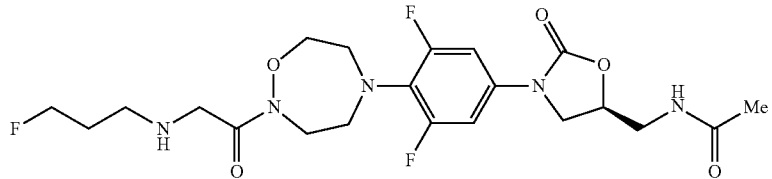
Example 642
[Chemical Formula 672]
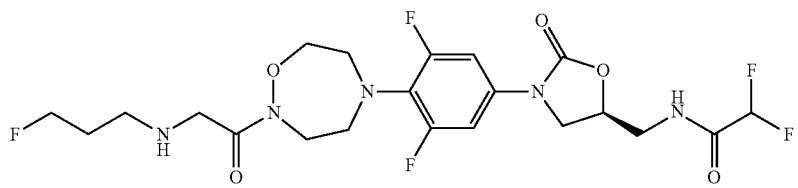
Example 643
[Chemical Formula 673]
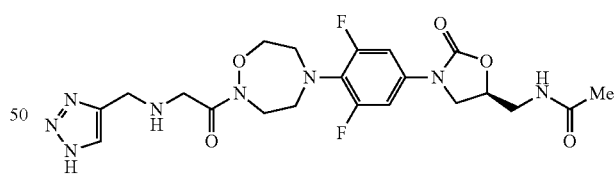
Example 644
[Chemical Formula 674]
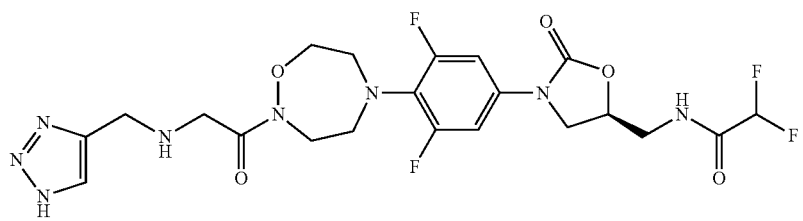

Example 645
[Chemical Formula 675]
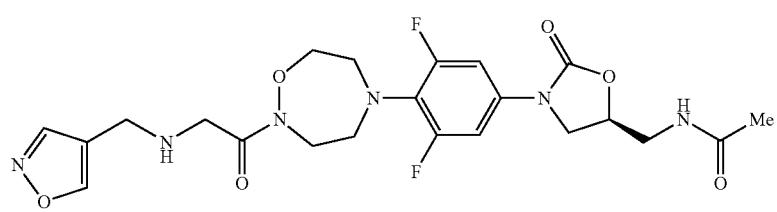
Example 646
[Chemical Formula 676]
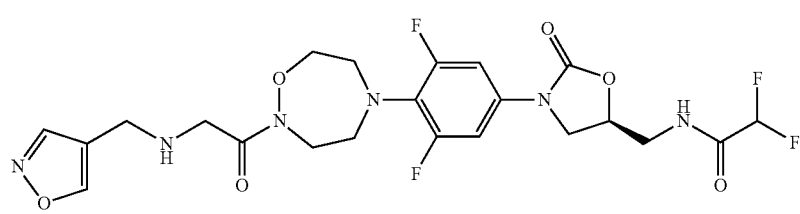
Example 647
[Chemical Formula 677]
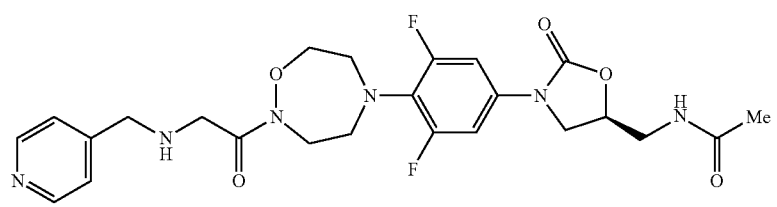
Example 648
[Chemical Formula 678]
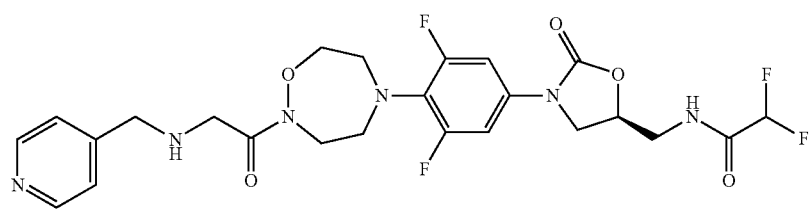
Example 64.9
Example 650
[Chemical Formula 679]
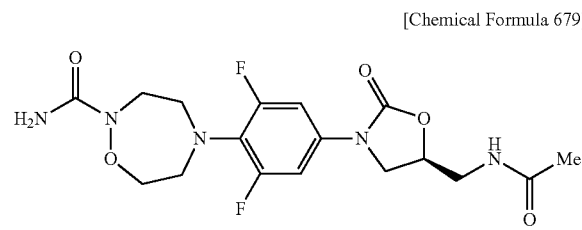 [SMILES: CC(=O)NC[C@H]1CN(c2cc(F)c(N3CCON(C(N)=O)CC3)c(F)c2)C(=O)O1]
[Chemical Formula 680]
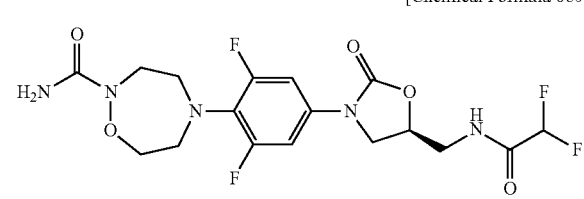

Example 651
[Chemical Formula 681]
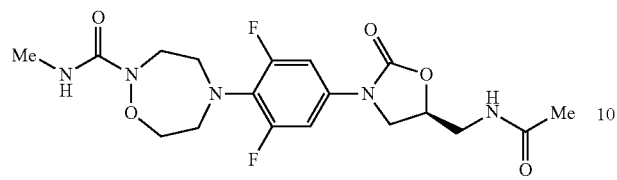
Example 652
[Chemical Formula 682]
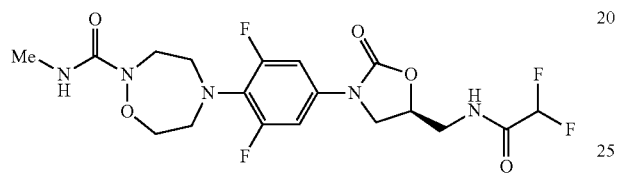
Example 653
[Chemical Formula 683]
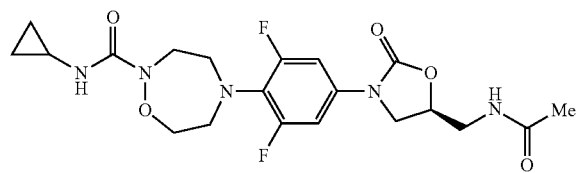
Example 654
[Chemical Formula 684]
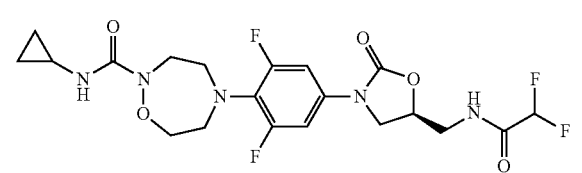
Example 655
[Chemical Formula 685]
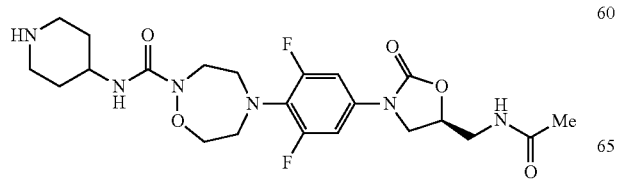
Example 656
[Chemical Formula 686]
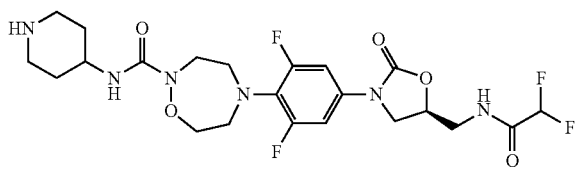
Example 657
[Chemical Formula 687]
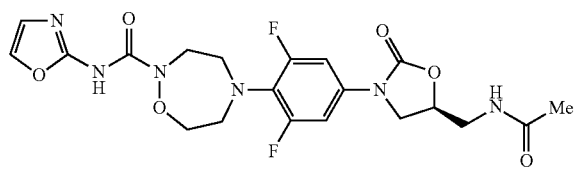
Example 658
[Chemical Formula 688]
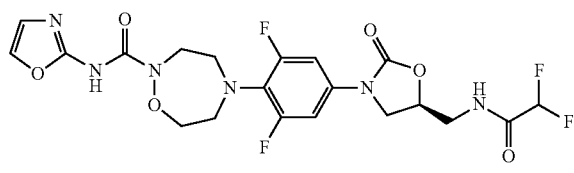
Example 659
[Chemical Formula 689]
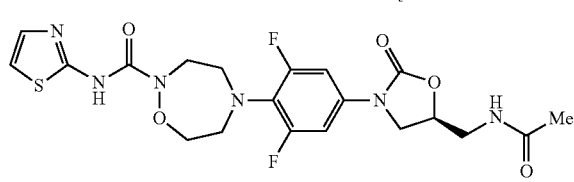
Example 660
[Chemical Formula 690]
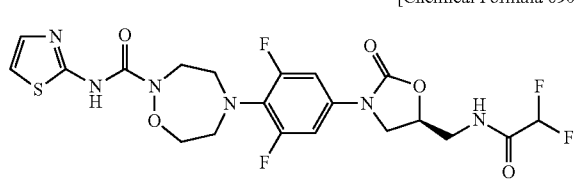

207
Example 661
[Chemical Formula 691]
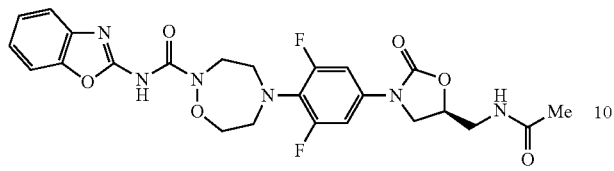
Example 662
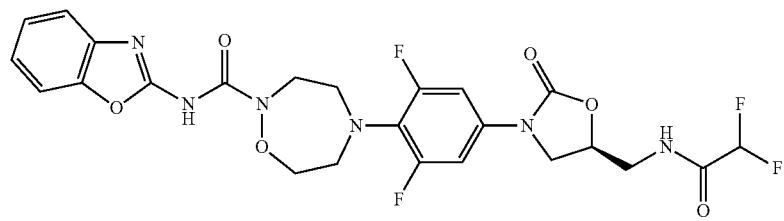
Example 663
[Chemical Formula 693]
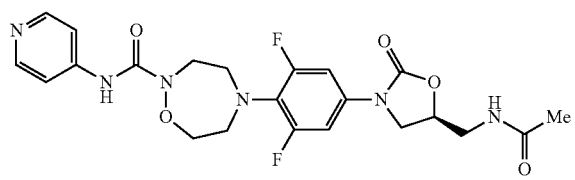
Example 664
[Chemical Formula 694]
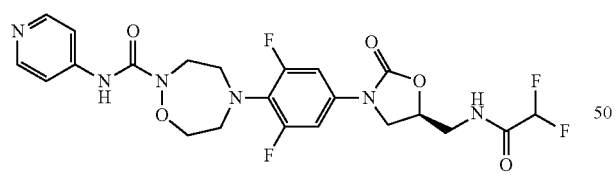
Example 665
[Chemical Formula 695]
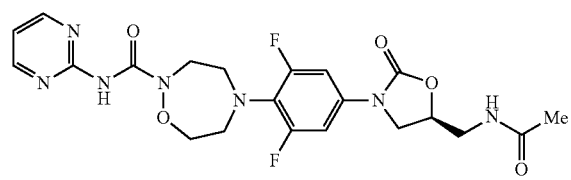
208
Example 666
[Chemical Formula 696]
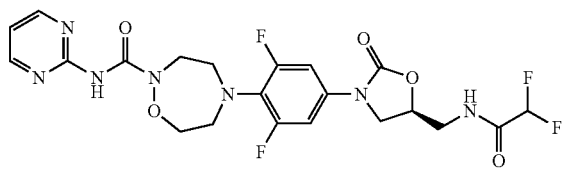
[Chemical Formula 692]
Example 667
[Chemical Formula 697]
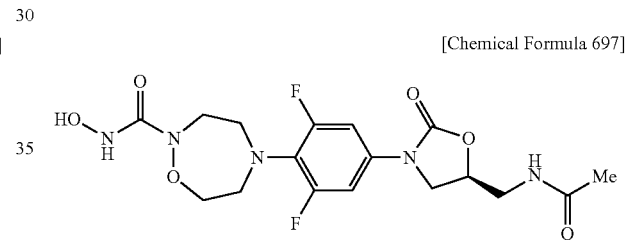
Example 668
[Chemical Formula 698]
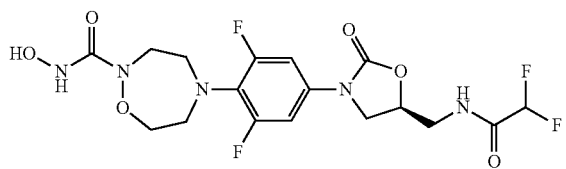
Example 669
[Chemical Formula 699]
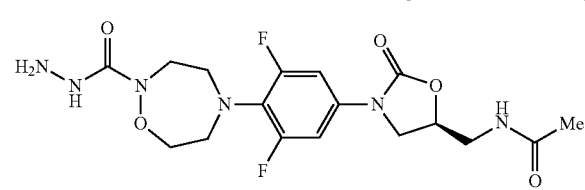

Example 670
[Chemical Formula 700]
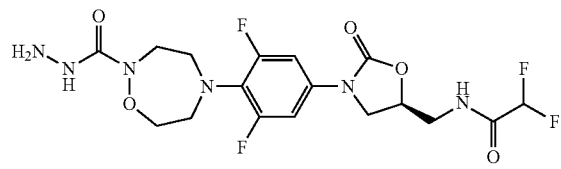
Example 671
[Chemical Formula 701]
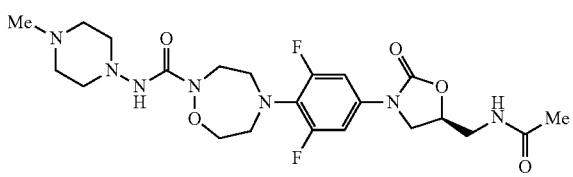
Example 672
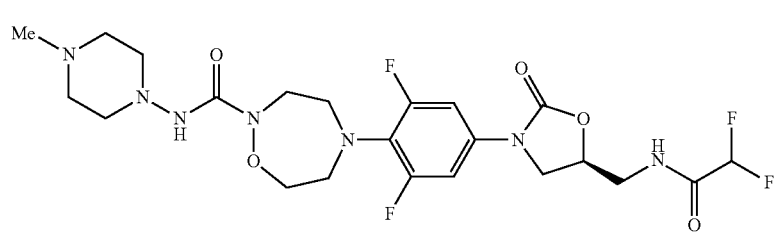
Example 673
[Chemical Formula 703]
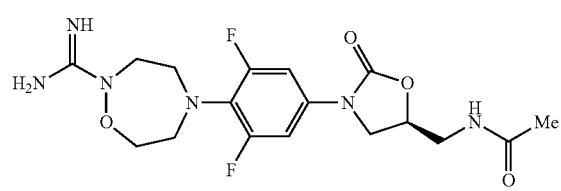
Example 674
[Chemical Formula 704]
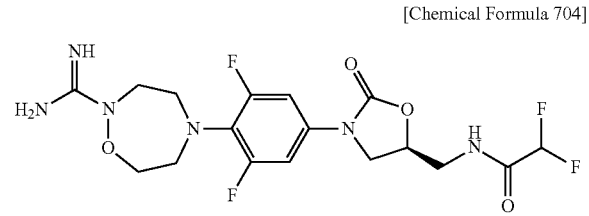 [SMILES: N=C(N)N1CCN(c2c(F)cc(N3C[C@H](CNC(=O)C(F)F)OC3=O)cc2F)CCO1]
Example 675
[Chemical Formula 705]
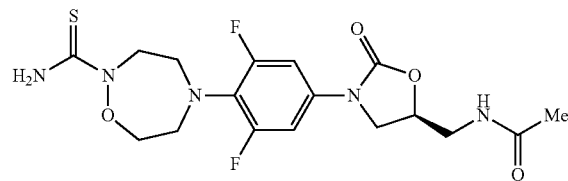
Example 676
[Chemical Formula 706]
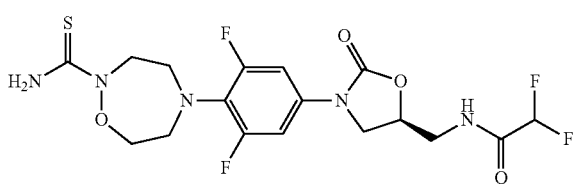
Example 677
[Chemical Formula 707]
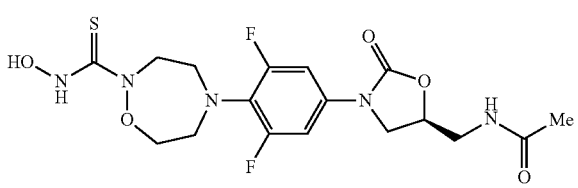
Example 678
[Chemical Formula 708]
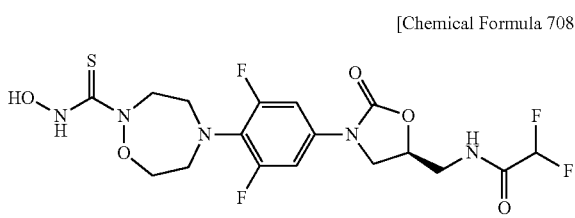

211
Example 679
[Chemical Formula 709]
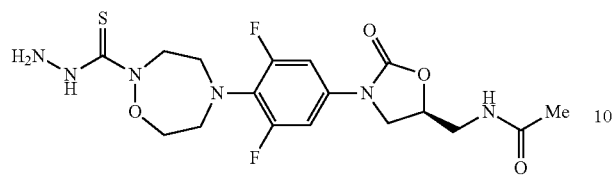
Example 680
[Chemical Formula 710]
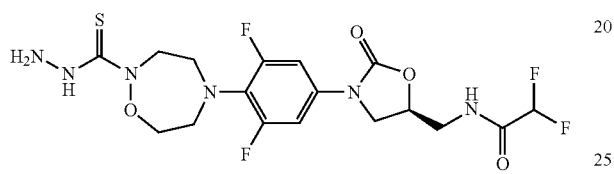
Example 681
[Chemical Formula 711]
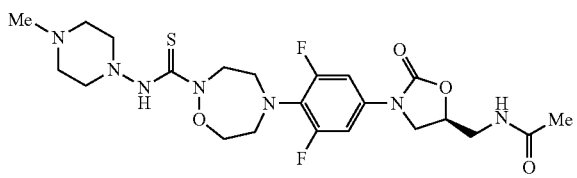
Example 682
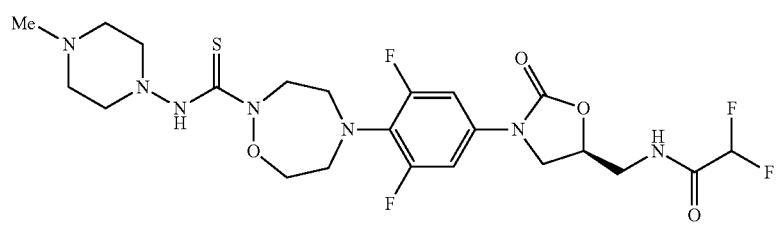
Example 683
[Chemical Formula 713]
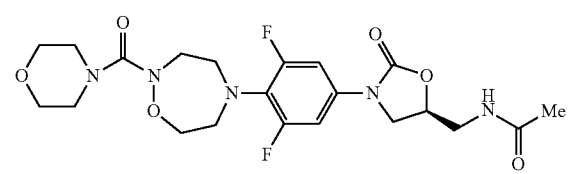
212
Example 684
[Chemical Formula 714]
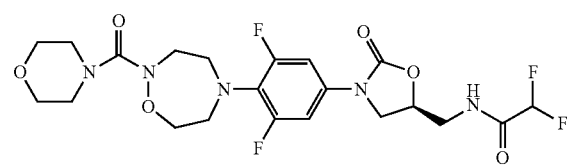
Example 685
[Chemical Formula 715]
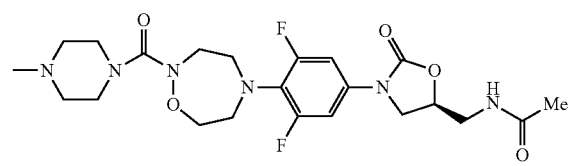
Example 686
[Chemical Formula 716]
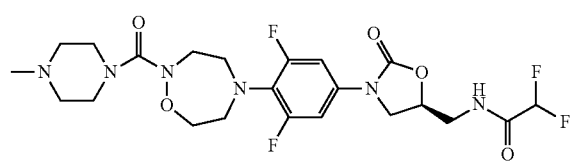
Example 687
[Chemical Formula 717]
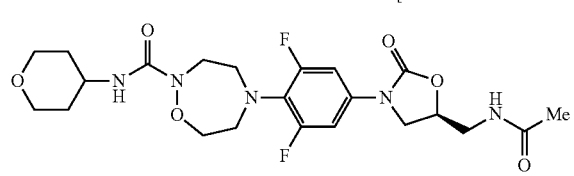

| 213 | 214 |
|---|---|
| Example 688 | Example 691 |
Example 689
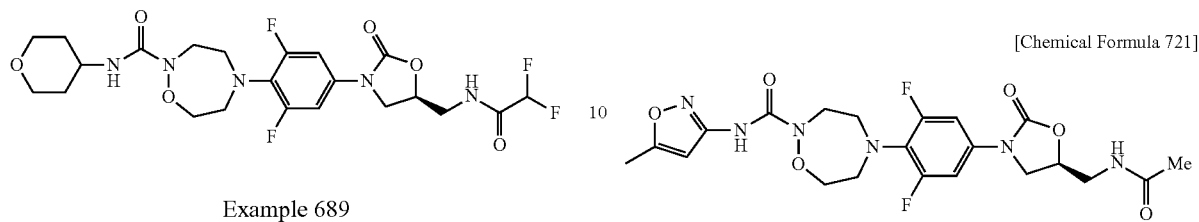
[Chemical Formula 718]
[Chemical Formula 721]
Example 692
Example 690
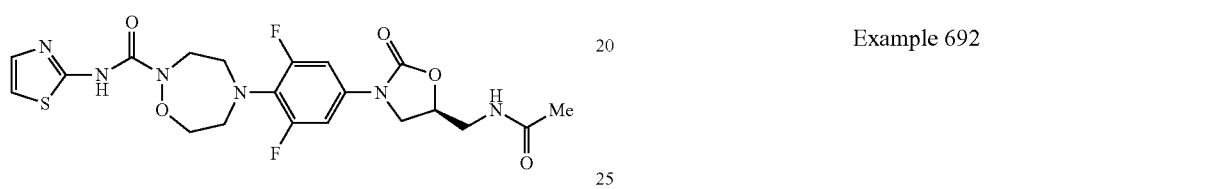
[Chemical Formula 719]
[Chemical Formula 722]
Example 693
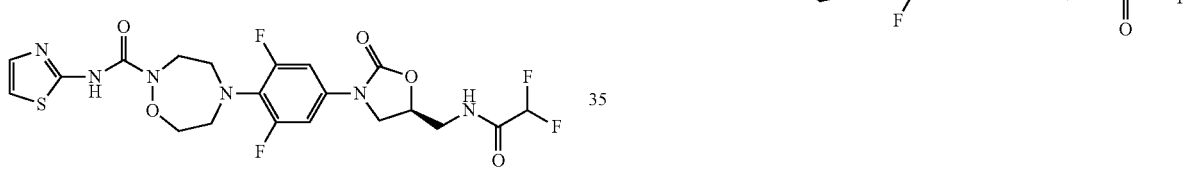
[Chemical Formula 720]
[Chemical Formula 723]
Example 694
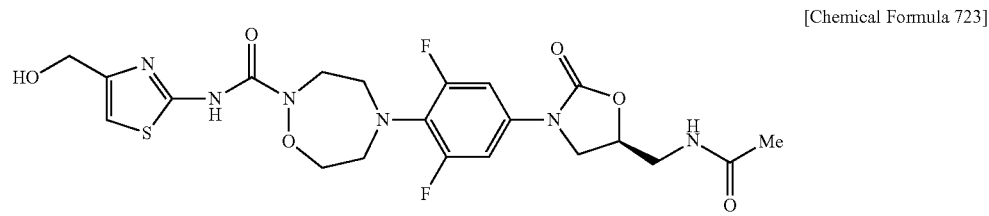 [SMILES: CC(=O)NC[C@H]1CN(c2cc(F)c(N3CCON(C(=O)Nc4nc(CO)cs4)CC3)c(F)c2)C(=O)O1]
[Chemical Formula 724]
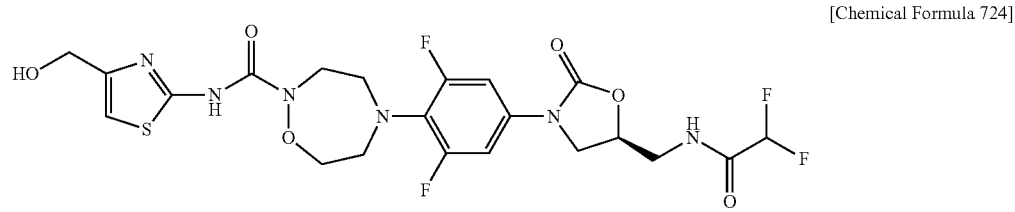 [SMILES: O=C(NC[C@H]1CN(c2cc(F)c(N3CCON(C(=O)Nc4nc(CO)cs4)CC3)c(F)c2)C(=O)O1)C(F)F]

Example 695
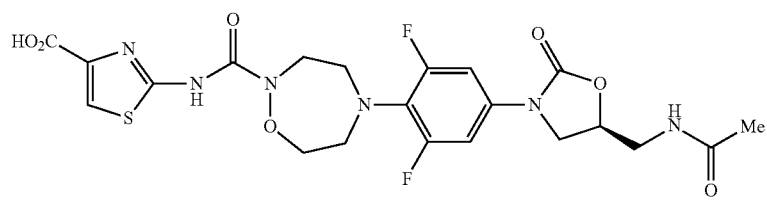
[Chemical Formula 725]
Example 696
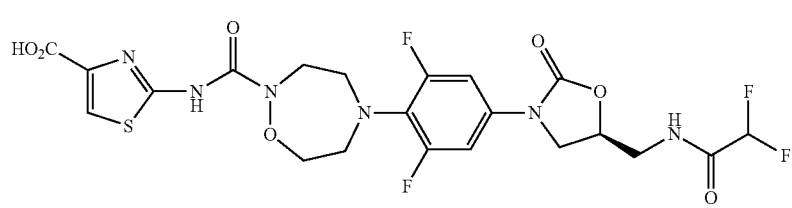
[Chemical Formula 726]
Example 697
[Chemical Formula 727]
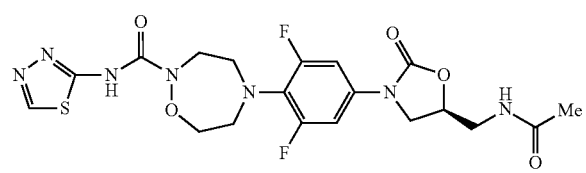
Example 698
[Chemical Formula 728]
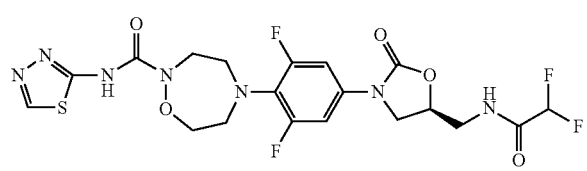
Example 699
[Chemical Formula 729]
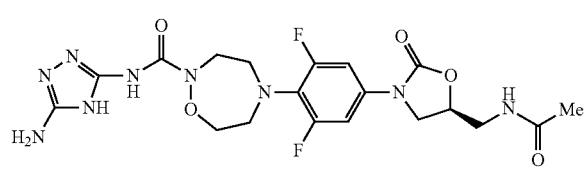
Example 700
[Chemical Formula 730]
Example 701
[Chemical Formula 731]
Example 702
[Chemical Formula 732]

217
Example 703
218
Example 708
[Chemical Formula 733]
Example 704
[Chemical Formula 738]
Example 709
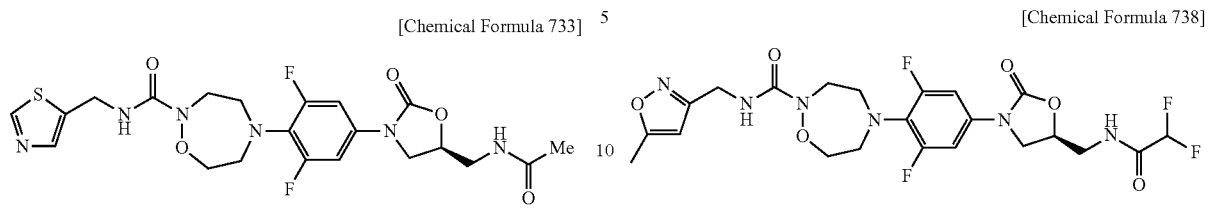
[Chemical Formula 734]
Example 705
[Chemical Formula 739]
Example 710
[Chemical Formula 735]
Example 706
[Chemical Formula 740]
Example 711
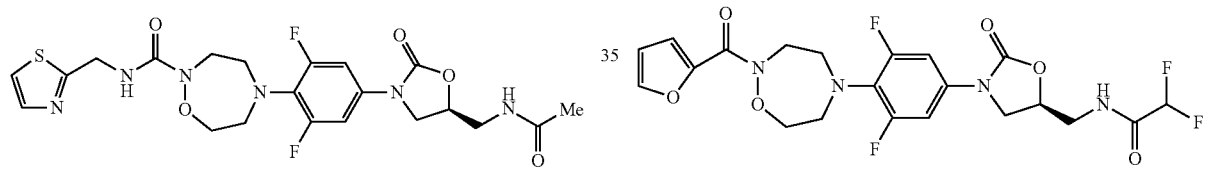
[Chemical Formula 736]
Example 707
[Chemical Formula 741]
Example 712
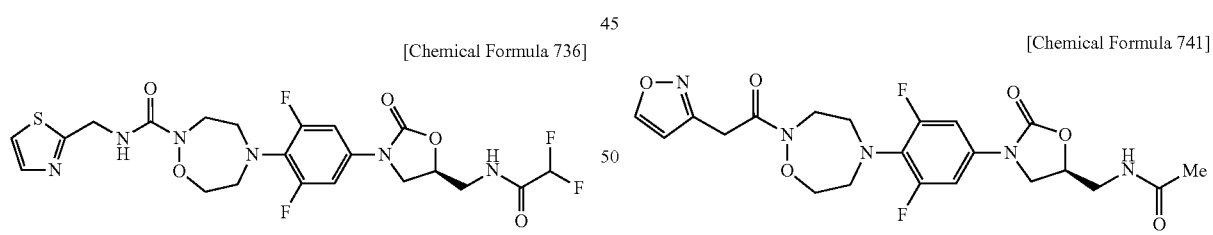
[Chemical Formula 737]
[Chemical Formula 742]
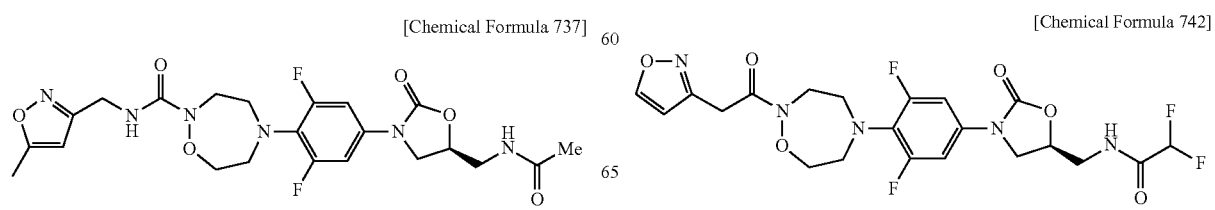

Example 713
[Chemical Formula 743]
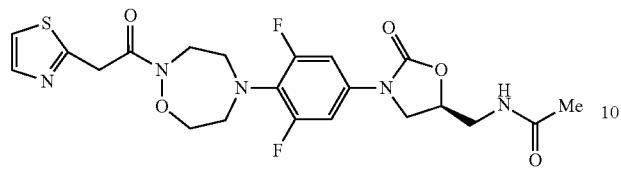
Example 714
Example 718
[Chemical Formula 748]
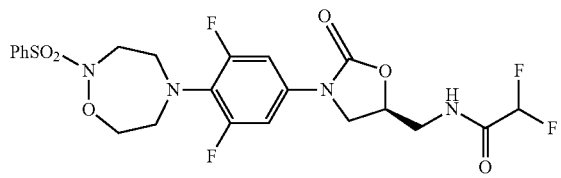
Example 719
[Chemical Formula 744]
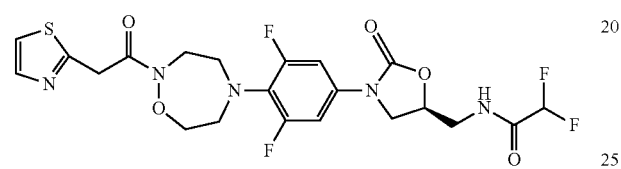
Example 715
[Chemical Formula 749]
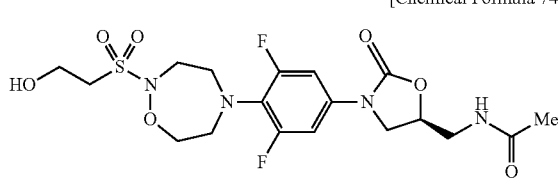
Example 720
[Chemical Formula 745]
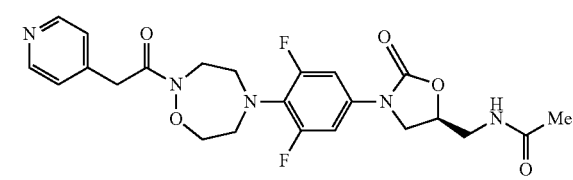
Example 716
[Chemical Formula 750]
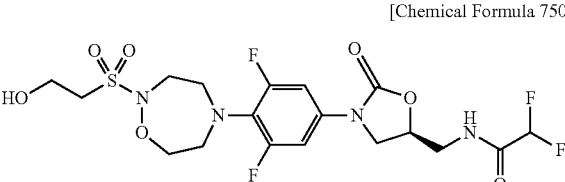
Example 721
[Chemical Formula 746]
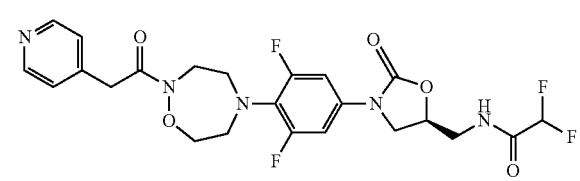
Example 717
[Chemical Formula 751]
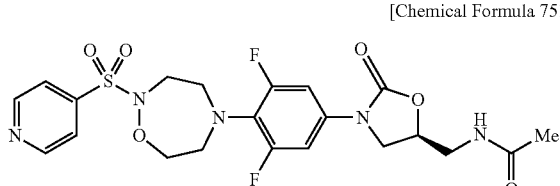
Example 722
[Chemical Formula 747]
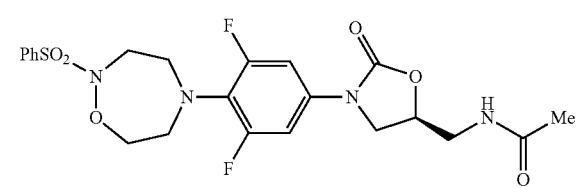
[Chemical Formula 752]
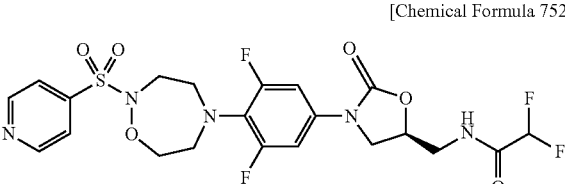

221
Example 723
[Chemical Formula 753]
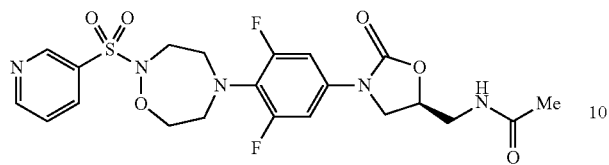
Example 724
[Chemical Formula 754]
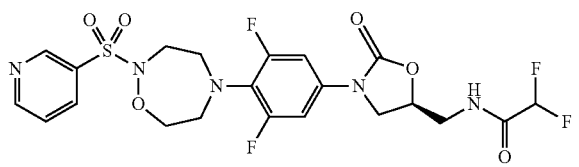
Example 725
[Chemical Formula 755]
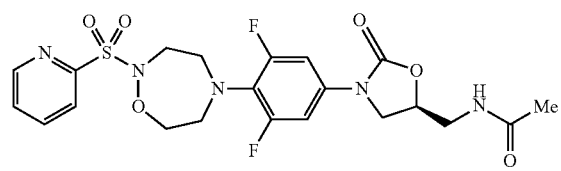
Example 726
[Chemical Formula 756]
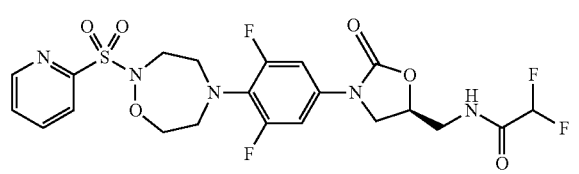
Example 727
[Chemical Formula 757]
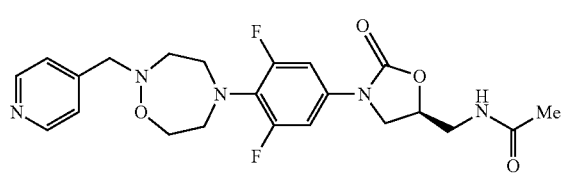
222
Example 728
[Chemical Formula 758]
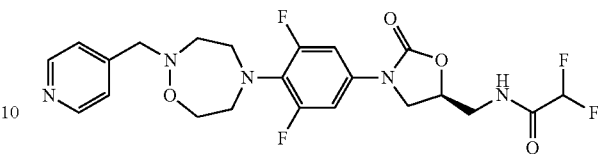
Example 729
[Chemical Formula 759]
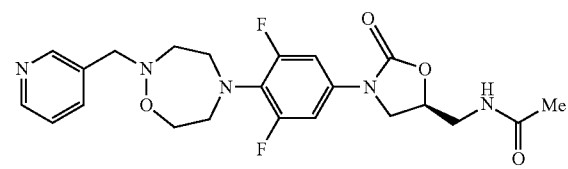
Example 730
[Chemical Formula 760]
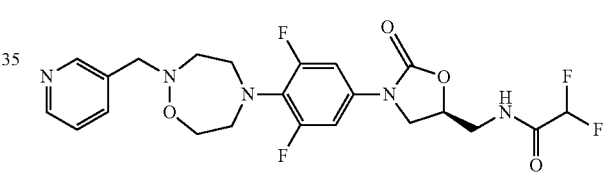
Example 731
[Chemical Formula 761]
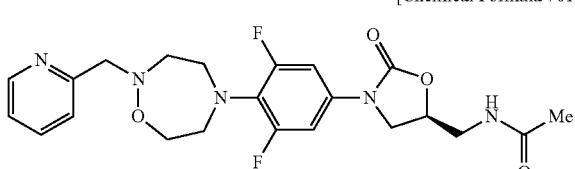
Example 732
[Chemical Formula 762]
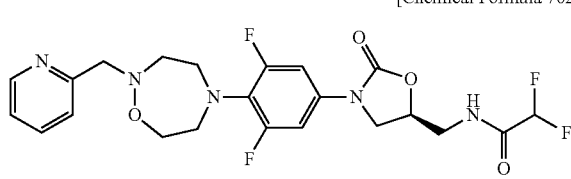

Example 733
[Chemical Formula 763]
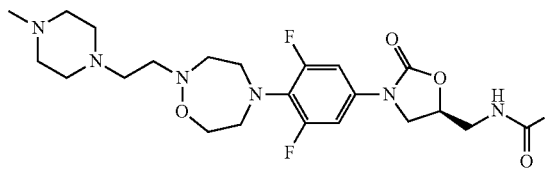
Example 734
[Chemical Formula 764]
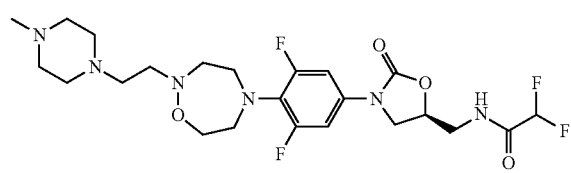
Example 735
[Chemical Formula 765]
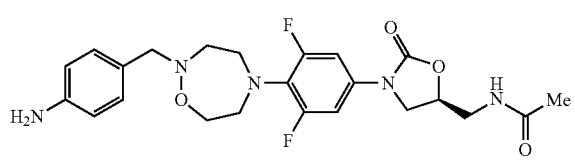
Example 736
[Chemical Formula 766]
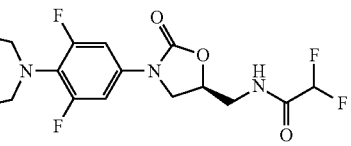
Example 737
[Chemical Formula 767]
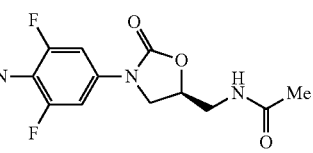
Example 738
[Chemical Formula 768]
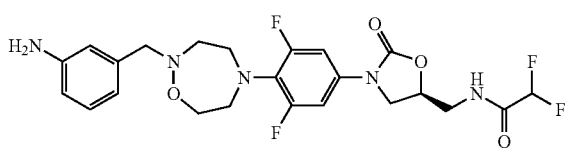
Example 739
[Chemical Formula 769]
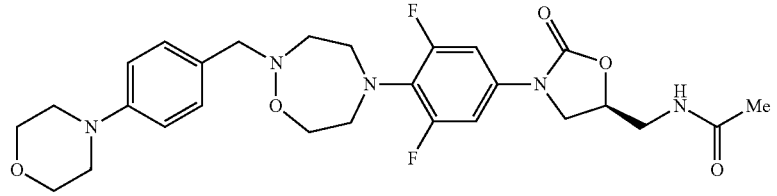
Example 740
[Chemical Formula 770]
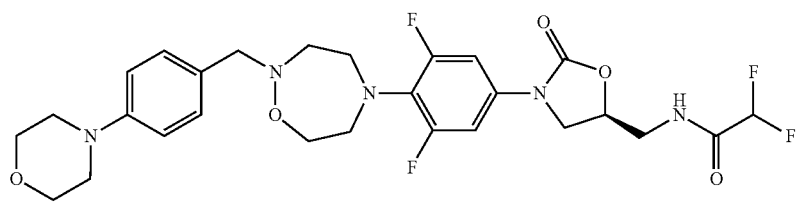

Example 741 to 743
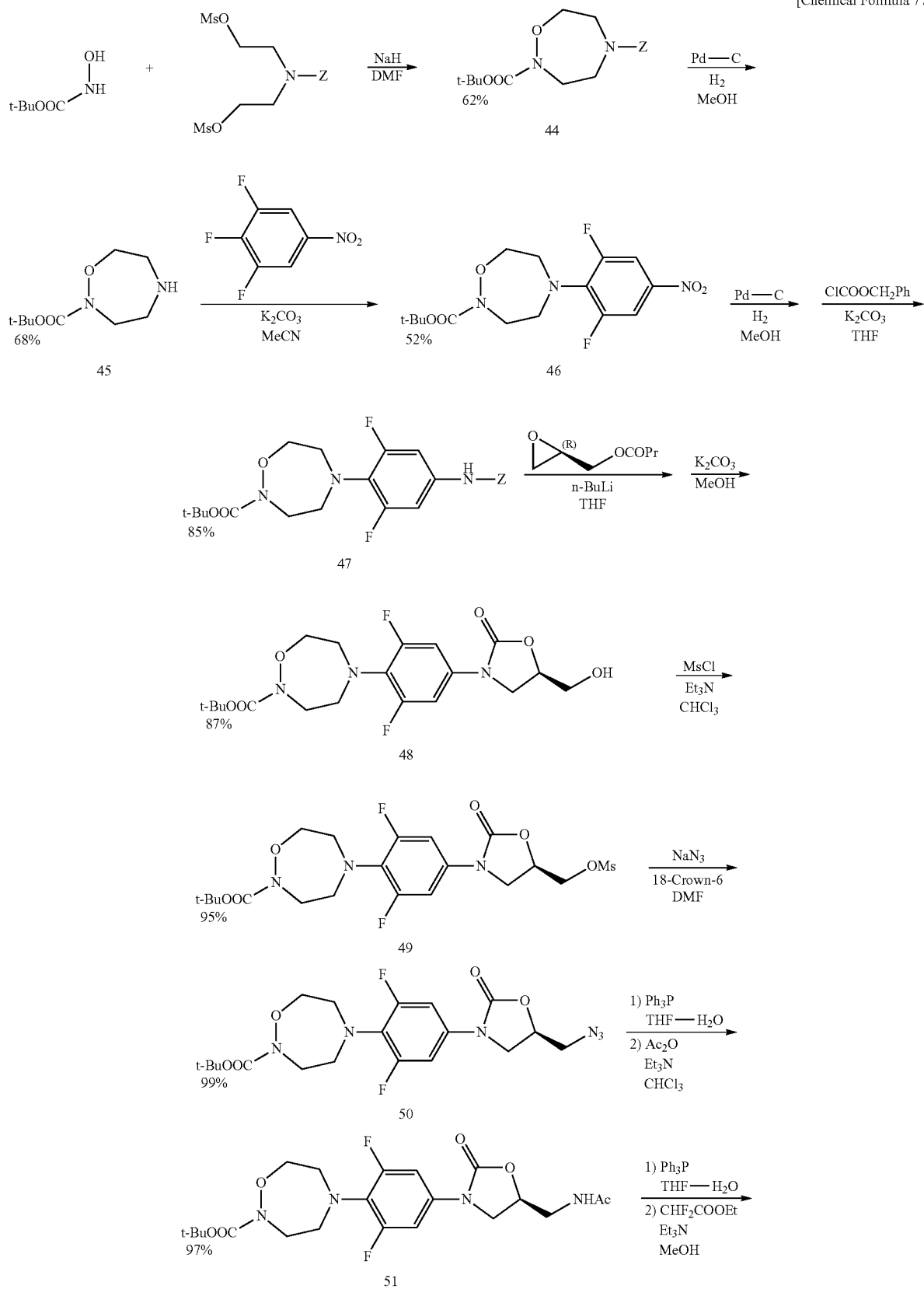

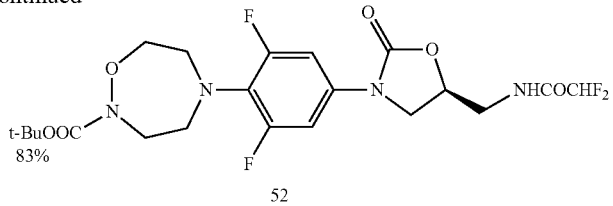

52

Synthesis of Compound (44)

To a solution of hydroxylamine-BOC compound (4.01 g) in DMF (40 ml), 60% NaH (2.61 g) is added portionwise at room temperature, and effervescence occurs simultaneously. After 15 minutes, mesyl compound (11.59 g) in DMF (40 ml) is dropped slowly, and stirred at room temperature for 15 minutes. The temperature is raised to 100-110° C. and continued stirring carefully for additional 15 minutes. After the reaction, under reduced pressure, solvent is removed and NH$_4$Cl aqueous solution is added and extracted with ethyl acetate. After dryness (Na$_2$SO$_4$), solvent is removed, and the residue is purified by silica gel chromatography (hexane-ethyl acetate (2:1)) to afford Compound (44) (6.11 g, 62%) as a colorless oil.

44: colorless oil; 1H-NMR (300 MHz, CDCl$_3$) δ 1.48 (s, 9H), 3.56-3.75 (m, 6H), 3.94-4.05 (m, 2H), 5.14 (s, 2H), 7.32 (s, 5H); IR (CHCl$_3$) ν$_{max}$ 1693 cm$^{-1}$; MS e/m 277 (3), 206 (3), 115 (10), 101 (29), 91 (99), 57 (100).

Synthesis of Compound (45)

To a solution of oxadiazepane compound (44, 6.84 g) in methanol (70 ml), 10% Pd—C (1.01 g) is added to subject to hydrogenation for 6 hours. After the reaction, the mixture is filtered, and solvent is removed. The residue is purified by silica gel chromatography (chloroform-methanol (9:1)). Recrystallization from ethanol affords a colorless amorphous Compound (45) (2.80 g, 68%).

45: colorless amorphous mp: 156.5-157.5° C. (EtOH) (decomp.); 1H-NMR (300 MHz, CDCl$_3$) δ 1.51 (s, 9H), 3.41-3.53 (m, 4H), 3.99 (t, 6, 2H), 4.32 (t, 5, 2H)); IR (KBr) ν$_{max}$ 1705, 1667 cm$^{-1}$; MS e/m 202 (M$^+$, 1), 129 (9), 99 (12), 72 (17), 57 (100), 43 (86).

Synthesis of Compound (46)

To a solution of amine compound (45, 6.84 g) and 3,4,5-trifluoronitro benzene (3.11 g) in acetonitrile (60 ml), potassium carbonate (3.19 g) is added, and the mixture is heated at reflux for 15 hours. After the reaction, NH$_4$Cl aqueous solution is added mad extracted with chloroform-methanol (9:1). After dryness (Na$_2$SO$_4$), solvent is removed, and the residue is purified by silica gel chromatography (hexane-ethyl acetate (2:1)). Recrystallization from hexane affords 3.31 g (52%) of Compound (46) as yellow needle-like crystal.

46: yellow needle-like crystal mp: 87-88° C. (Hexane); 1H-NMR (300 MHz, CDCl$_3$) δ 1.51 (s, 9H), 3.63-3.71 (m, 4H), 3.84 (t, 6, 2H), 4.13 (t, 5, 2H), 7.72-7.84 (m, 2H); IR (KBr) ν$_{max}$ 1678 cm$^{-1}$; MS e/m 359 (M$^+$, 0.3), 303 (1), 286 (1), 256 (4), 201 (7), 172 (7), 57 (100).

Synthesis of Compound (47)

To a solution of the nitro compound (46, 2.90 g) in methanol (40 ml), 10% Pd—C (646 mg) is added, and the mixture is subjected to hydrogenation for 2 hours. After the reaction, the mixture is filtered, and solvent is removed. After dryness, potassium carbonate (4.6 g) is added to a solution of the residue and carbobenzoxy chloride (3.0 ml) in THF (50 ml), and the solution is stirred for 15 hours. After the reaction, ice-cold water is added and extracted with chloroform. After dryness (Na$_2$SO$_4$), solvent is removed. The residue is purified by silica gel chromatography (hexane-ethyl acetate (2:1)). Recrystallization from chloroform-hexane affords 3.19 g (85%) of colorless prismatic Compound (47).

47: colorless prismatic mp: 100-101° C. (CHCl$_3$-Hexane); 1H-NMR (300 MHz, CDCl$_3$) δ 1.51 (s, 9H), 3.63-3.71 (m, 4H), 3.84 (t, 6, 2H), 4.13 (t, 5, 2H), 7.72-7.84 (m, 2H); IR (KBr) ν$_{max}$ 1731, 1687 cm$^{-1}$; MS e/m 463 (M$^+$, 4), 334 (4), 305 (4), 225 (6), 197 (6), 165 (14), 108 (10), 91 (91), 79 (12), 57 (100).

Synthesis of Compound (48)

To a solution of carbobenzoxy compound (47, 363 mg) in THF (10 ml), 1.54M BuLi hexane solution (0.60 ml) is added and stirred under argon atmosphere at −78°. After 10 minutes, (R)-glycidyl butyrate (241 mg) in THF (2 ml) is added and stirred at the temperature for 10 min. and additional 19 hours at room temperature. After the reaction, NH$_4$Cl aqueous solution is added and extracted with chloroform-methanol (9:1). After dryness (Na$_2$SO$_4$), solvent is removed.

The residue in methanol (10 ml) is added with potassium carbonate (173 mg) and stirred for 15 minutes. NH$_4$Cl aqueous solution is added and extracted with chloroform-methanol (9:1). After dryness (Na$_2$SO$_4$), solvent is removed. The residue is purified by silica gel chromatography (chloroform-methanol (9:1)) to afford 291 mg (87%) of Compound (48) as colorless syrup.

48: colorless syrup; 1H-NMR (300 MHz, CDCl$_3$) δ 1.51 (s, 9H), 3.33-3.43 (m, 4H), 3.71-3.82 (m, 3H), 3.90-4.02 (m, 3H), 4.07 (t, 5, 2H), 4.70-4.79 (m, 1H), 7.06-7.17 (m, 2H); IR (CHCl$_3$) ν$_{max}$ 1752, 1705, 1690 cm$^{-1}$; MS e/m 429 (M$^+$, 6), 326 (5), 299 (9), 271 (17), 242 (11), 168 (10), 154 (8), 57 (100).

Synthesis of Compound (49)

To a colorless solution of the hydroxy compound (48, 364 mg) and triethylamine (0.5 ml) in chloroform (10 ml), methanesulfonyl chloride (0.2 ml) is added and stirred under ice-cooling for 15 minutes. After the reaction, NaHCO$_3$ aqueous solution is added and extracted with chloroform-methanol (9:1). After dryness (Na$_2$SO$_4$), solvent is removed. The residue is purified by silica gel chromatography (chloroform-methanol (19:1)) to afford 409 mg (95%) of Compound (49) as colorless syrup.

49: colorless syrup; 1H-NMR (300 MHz, CDCl$_3$) δ 1.51 (s, 9H), 3.11 (s, 3H), 3.33-3.45 (m, 4H), 3.77 (t, 6, 2H), 3.89 (dd, 9, 6, 1H), 4.07 (t, 5, 2H), 4.13 (dd, 9, 9, 1H), 4.43 (dd, 12, 3.5, 1H), 4.53 (dd, 12, 3, 1H), 4.96 (dddd, 9, 6, 3.5, 3, 1H), 7.07-7.18 (m, 2H); IR (CHCl$_3$) ν$_{max}$ 1760, 1702, 1688 cm$^{-1}$; MS e/m 507 (M$^+$, 6), 404 (4), 378 (10), 349 (10), 335 (16), 320 (10), 180 (12), 79 (9), 57 (100).

Synthesis of Compound (50)

To a solution of the mesyl compound (49, 406 mg) and 18-Crown-6 (77 mg) in DMF (3 ml), NaN$_3$ (213 mg) is added and heated to 100-110° C. After 1 hour, solvent is removed. Water is added, and the mixture is extracted with chloroform. After dryness (Na$_2$SO$_4$), solvent is removed. The residue is purified by column chromatography (chloroform-methanol (19:1)) to afford 360 mg (99%) of colorless gummy Compound (50).

50: colorless gum; 1H-NMR (300 MHz, CDCl$_3$) δ 1.51 (s, 9H), 3.34-3.44 (m, 4H), 3.60 (dd, 13.5, 4, 1H), 3.71-3.85 (m, 4H), 4.01-4.13 (m, 3H), 4.78-4.88 (m, 1H), 7.08-7.19 (m, 2H); IR (CHCl$_3$) ν$_{max}$ 2105, 1757, 1690 cm$^{-1}$; MS e/m 454 (M$^+$, 5), 404 (4), 325 (4), 267 (5), 154 (11), 57 (100).

Synthesis of Compound (51)

A combined solution of the azido compound (50, 101 mg) and triphenylphosphine (123 mg) in THF (5 ml) and water (0.5 ml) is heated at reflux. After 1 hour, solvent is removed. The dried residue and triethylamine (1 ml) in chloroform (10 ml) is added dropwise with acetic anhydride (0.25 ml) and stirred for 1 hour. After the reaction, NaHCO$_3$ aqueous solution is added and the mixture is extracted with chloroform-methanol (9:1). After dryness (Na$_2$SO$_4$), solvent is removed. The residue is purified by preparative thin-layer chromatography (chloroform-methanol (19:1)) to afford 101 mg (97%) of colorless gummy compound (51).

51: colorless gum; 1H-NMR (300 MHz, CDCl$_3$) δ 1.51 (s, 9H), 2.03 (s, 3H), 3.34-3.43 (m, 4H), 3.60-3.71 (m, 2H), 3.72-3.81 (m, 3H), 4.01 (dd, 9, 9, 1H), 4.07 (t, 5, 2H), 4.76-4.85 (m, 1H), 6.99 (br t, 6, NH), 7.04-7.15 (m, 2H)); IR (CHCl$_3$) ν$_{max}$ 1750, 1673 cm$^{-1}$; MS e/m 470 (M$^+$, 14), 367 (6), 341 (9), 312 (10), 298 (10), 239 (14), 183 (9), 180 (13), 154 (9), 57 (100).

Synthesis of Compound (52)

A combined solution of the azido compound (50, 633 mg) and triphenylphosphine (579 mg) in THF (10 ml) and water (1 ml) is heated at reflux. After 30 minutes, solvent is removed. The dried residue and triethylamine (2 ml) in methanol (10 ml) is added dropwise with CHF$_2$COOEt (1 ml) and stirred for 3 hours. After the reaction, solvent is removed. The residue is purified by column chromatography (chloroform-methanol (19:1)) to afford 587 mg (83%) of colorless gummy compound (52).

52: colorless gum; 1H-NMR (300 MHz, CDCl$_3$) δ 1.51 (s, 9H), 3.33-3.43 (m, 4H), 3.63-3.82 (m, 5H), 4.02-4.11 (m, 3H), 4.80-4.90 (m, 1H), 5.96 (t, 54, 1H), 7.02-7.14 (m, 2H), 7.65-7.84 (br, NH); IR (CHCl$_3$) ν$_{max}$ 1758, 1706 cm$^{-1}$; MS e/m 506 (M$^+$, 5), 403 (4), 377 (9), 348 (9), 334 (12), 319 (7), 180 (11), 57 (100).

Example 741

Synthesis of Compound (53)

[Chemical Formula 772]

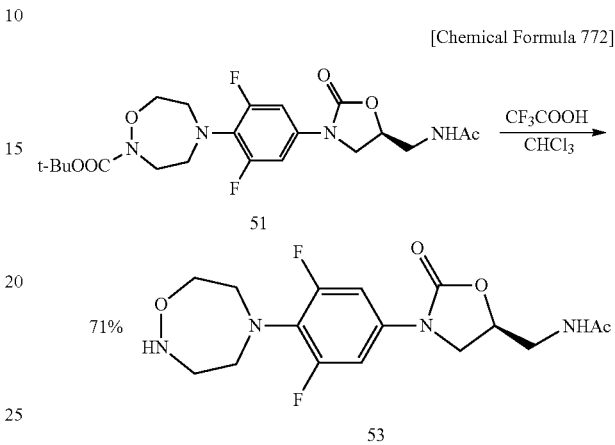

To a solution of BOC compound (51, 73 mg) in chloroform (10 ml), trifluoro acetic acid (0.5 ml) is added dropwise and stirred for 15 hours at room temperature. After the reaction, saturated aqueous NaHCO$_3$ is added, and the mixture is extracted with methanol-chloroform (1:9). After washing with water and dryness (Na$_2$SO$_4$), solvent is removed. The residue is purified by preparative thin-layer chromatography (methanol-chloroform (1:9)) to afford 41 mg (71%) of colorless glassy Compound (53).

53: colorless glass; 1H-NMR (300 MHz, CDCl$_3$) δ 2.03 (s, 3H), 3.22 (t, 6, 2H), 3.40 (br t, 6, 2H), 3.49 (t, 5.5, 2H), 3.66 (dd, 6, 4.5, 2H), 3.74 (dd, 9, 6.5, 1H), 3.90 (t, 5.5, 2H), 4.00 (dd, 9, 9, 1H), 4.79 (dddd, 9, 6.5, 4.5, 4.5, 1H), 6.68 (br t, 6, NH), 7.01-7.12 (m, 2H); IR (CHCl$_3$) ν$_{max}$ 1749, 1669 cm$^{-1}$; MS e/m 370 (M$^+$, 17), 341 (11), 312 (18), 298 (15), 256 (11), 239 (21), 195 (14), 183 (16), 180 (25), 168 (14), 126 (8), 85 (11), 56 (100), 43 (72).

Example 742

Synthesis of Compound (54)

[Chemical Formula 773]

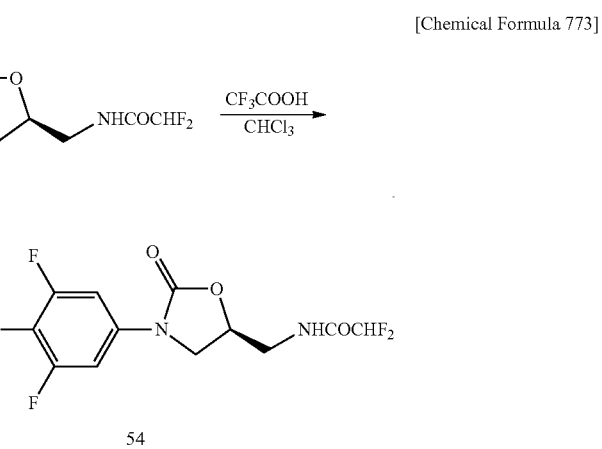

BOC Compound (52, 36 mg) in chloroform (5 ml) was added dropwise with trifluoro acetic acid (0.3 ml) and stirred for 15 hours at room temperature. After the reaction, saturated NaHCO₃ aqueous solution was added, ant the mixture is extracted with methanol-chloroform (1:9). After washing with water and dryness (Na₂SO₄), solvent is removed. The residue is purified by preparative thin-layer chromatography (methanol-chloroform (1:9)) and triturated with ether to afford 22 mg (76%) of Compound (54) as colorless powder.

54: colorless powders; 1H-NMR (300 MHz, CDCl₃) δ 3.22 (t, 5, 2H), 3.40 (br t, 5, 2H), 3.49 (t, 5.5, 2H), 3.66 (ddd, 14.5 6.5, 6.5, 1H), 3.70 (dd, 9, 6.5, 1H), 3.83 (ddd, 14.5, 6.5, 3, 1H), 3.90 (t, 5.5, 2H), 4.05 (dd, 9, 9, 1H), 4.78-4.88 (m, 1H), 5.94 (t, 54, 1H), 7.26 (br t, 6, NH), 7.00-7.11 (m, 2H); IR (CHCl₃) ν$_{max}$ 1755, 1706 cm$^{-1}$; MS e/m 406 (M⁺, 13), 388 (8), 377 (22), 361 (10), 348 (27), 334 (31), 319 (14), 195 (14), 180 (25), 168 (20), 154 (21), 56 (100).

Example 743

Synthesis of Compound (55)

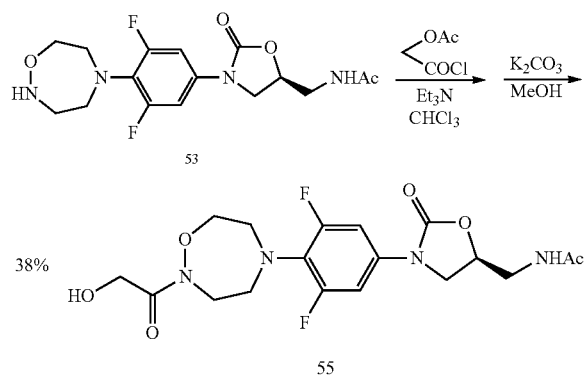

[Chemical Formula 774]

To a solution of amino compound (53, 41 mg) and triethylamine (0.3 ml) in chloroform (5 ml), acetoxy acetyl chloride (0.1 ml) is added, and the mixture is stirred under ice-cooling for 20 min. After the reaction, NaHCO₃ aqueous solution is added, and the mixture is extracted with methanol-chloroform (1:9). After washing with water and dryness, solvent is removed. The residue in methanol solution (5 ml) is added with K₂CO₃ (99 mg), and the mixture is stirred for 30 min. After the reaction, NH₄Cl aqueous solution is added, and the mixture is extracted with methanol-chloroform (1:9). After washing with water and dryness, solvent is removed. The residue is purified by preparative thin-layer chromatography (methanol-chloroform (1:9)) and triturated with ether to afford 18 mg (38%) of Compound (55) as colorless powders.

55: colorless powders; 1H-NMR (300 MHz, CDCl₃) δ 2.03 (s, 3H), 3.41 (t, 5, 2H), 3.47 (t, 5.5, 2H), 3.61-3.71 (m, 2H), 3.75 (dd, 9, 6.5, 1H), 3.95 (t, 5.5, 2H), 4.00 (dd, 9, 9, 1H), 4.12 (t, 5, 2H), 4.36 (s, 2H), 4.74-4.84 (m, 1H), 6.39 (br t, 6, NH), 7.06-7.17 (m, 2H); IR (CHCl₃) ν$_{max}$ 1753, 1662 cm$^{-1}$; MS e/m 428 (M⁺, 9), 384 (23), 323 (10), 309 (15), 298 (13), 239 (12), 213 (12), 183 (16), 180 (14), 169 (23), 85 (26), 56 (100), 44 (28), 43 (33).

Example 744

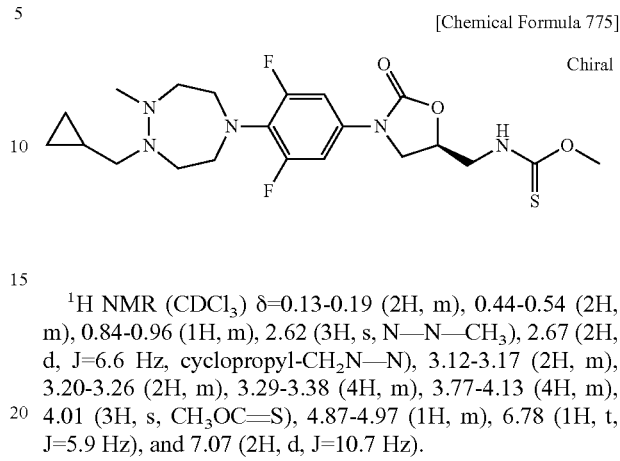

[Chemical Formula 775]

¹H NMR (CDCl₃) δ=0.13-0.19 (2H, m), 0.44-0.54 (2H, m), 0.84-0.96 (1H, m), 2.62 (3H, s, N—N—CH₃), 2.67 (2H, d, J=6.6 Hz, cyclopropyl-CH₂N—N), 3.12-3.17 (2H, m), 3.20-3.26 (2H, m), 3.29-3.38 (4H, m), 3.77-4.13 (4H, m), 4.01 (3H, s, CH₃OC=S), 4.87-4.97 (1H, m), 6.78 (1H, t, J=5.9 Hz), and 7.07 (2H, d, J=10.7 Hz).

Example 745

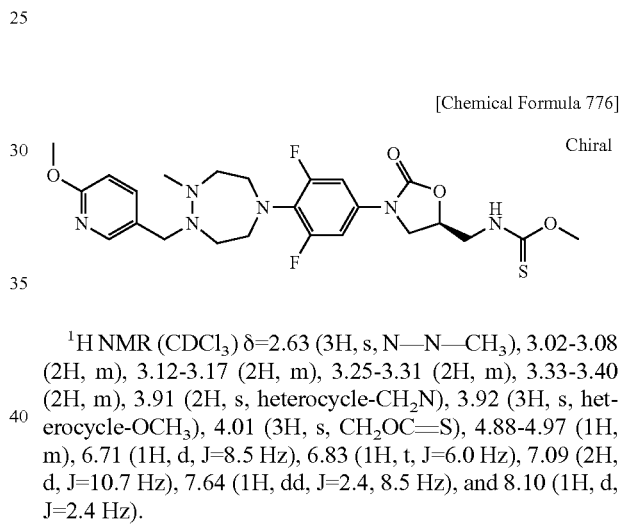

[Chemical Formula 776]

¹H NMR (CDCl₃) δ=2.63 (3H, s, N—N—CH₃), 3.02-3.08 (2H, m), 3.12-3.17 (2H, m), 3.25-3.31 (2H, m), 3.33-3.40 (2H, m), 3.91 (2H, s, heterocycle-CH₂N), 3.92 (3H, s, heterocycle-OCH₃), 4.01 (3H, s, CH₂OC=S), 4.88-4.97 (1H, m), 6.71 (1H, d, J=8.5 Hz), 6.83 (1H, t, J=6.0 Hz), 7.09 (2H, d, J=10.7 Hz), 7.64 (1H, dd, J=2.4, 8.5 Hz), and 8.10 (1H, d, J=2.4 Hz).

Example 746

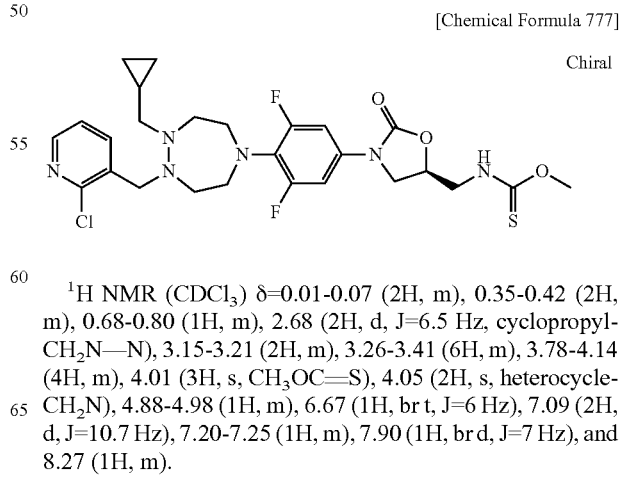

[Chemical Formula 777]

¹H NMR (CDCl₃) δ=0.01-0.07 (2H, m), 0.35-0.42 (2H, m), 0.68-0.80 (1H, m), 2.68 (2H, d, J=6.5 Hz, cyclopropyl-CH₂N—N), 3.15-3.21 (2H, m), 3.26-3.41 (6H, m), 3.78-4.14 (4H, m), 4.01 (3H, s, CH₃OC=S), 4.05 (2H, s, heterocycle-CH₂N), 4.88-4.98 (1H, m), 6.67 (1H, br t, J=6 Hz), 7.09 (2H, d, J=10.7 Hz), 7.20-7.25 (1H, m), 7.90 (1H, br d, J=7 Hz), and 8.27 (1H, m).

Example 747

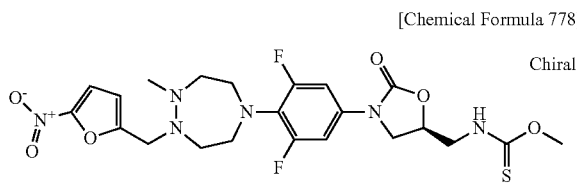

¹H NMR (CDCl₃) δ=2.61 (3H, s, N—N—CH₂), 3.09-3.14 (2H, m), 3.17-3.22 (2H, m), 3.32-3.39 (4H, m), 3.60-4.14 (4H, m), 4.01 (3H, s, CH₂OC=S), 4.05 (2H, s, heterocycle-CH₂N), 4.88-4.98 (1H, m), 6.52 (1H, d, J=3.6 Hz), 6.76 (1H, t, J=6.1 Hz), 7.10 (2H, d, J=10.7 Hz), and 7.29 (1H, d, J=3.6 Hz).

Example 748

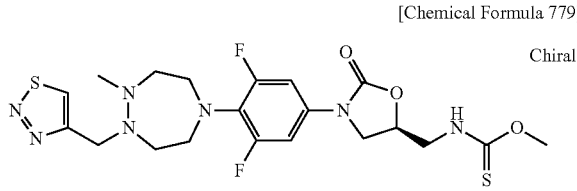 [SMILES: COC(=S)NC[C@H]1CN(c2cc(F)c(N3CCN(C)N(Cc4csnn4)CC3)c(F)c2)C(=O)O1]

¹H NMR (CDCl₃) δ=2.63 (3H, s, N—N—CH₃), 3.14-3.43 (8H, m), 3.61-4.15 (4H, m), 4.01 (3H, s, CH₃OC=S), 4.50 (2H, s, heterocycle-CH₂N), 4.87-4.97 (1H, m), 6.73 (1H, br t, J=6 Hz), 7.10 (2H, d, J=10.7 Hz), and 8.49 (1H, s, S—CH=C)

Example 749

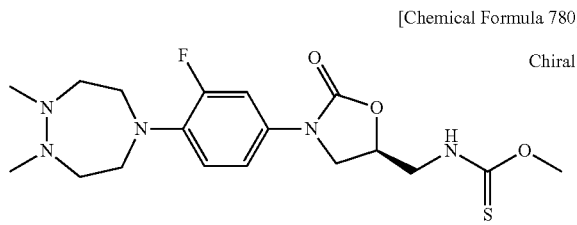

¹H NMR (CDCl₃) δ=2.53 (6H, s, CH₃N—NCH₃), 3.15-3.21 (4H, m), 3.37-3.43 (4H, m), 3.60-3.86 (2H, m), 3.91-4.11 (2H, m), 4.00 (3H, s, CH₃OC=S), 4.87-4.97 (1H, m), 6.85 (1H, t, J=9.3 Hz), 7.02 (1H, br d, J=9 Hz), 7.17 (1H, t, J=6.1 Hz, NHC=S), and 7.34 (1H, br d, J=15 Hz).

Example 750

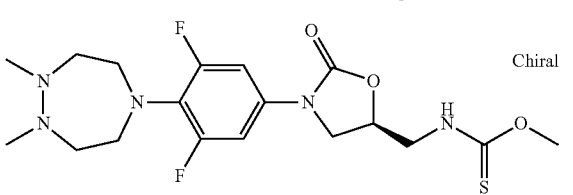

¹H NMR (CDCl₃) δ=2.60 (6H, s, CH₃N—NCH₃), 3.10-3.16 (4H, m), 3.32-3.38 (4H, m), 3.60-3.85 (2H, m), 3.94-4.13 (2H, m), 4.01 (3H, s, CH₃OC=S), 4.87-4.97 (1H, m), 6.81 (1H, t, J=6.1 Hz, NHC=S), and 7.08 (2H, d, J=10.7 Hz).

Example 751

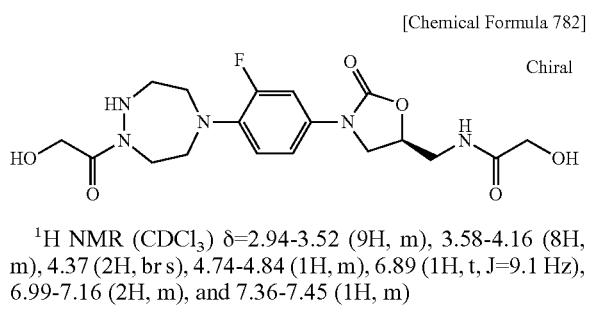

¹H NMR (CDCl₃) δ=2.94-3.52 (9H, m), 3.58-4.16 (8H, m), 4.37 (2H, br s), 4.74-4.84 (1H, m), 6.89 (1H, t, J=9.1 Hz), 6.99-7.16 (2H, m), and 7.36-7.45 (1H, m)

Example 752

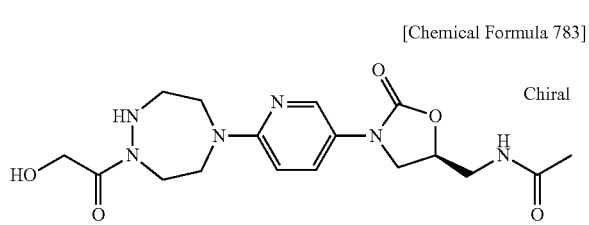 [SMILES: CC(=O)NC[C@H]1CN(c2ccc(N3CCNN(C(=O)CO)CC3)nc2)C(=O)O1]

¹H NMR (CDCl₃) δ=2.03 (3H, s, CH₃C=O), 3.00-4.04 (12H, m), 4.33 (2H, s, CH₂OH), 4.73-4.83 (1H, m), 6.37 (1H, t, J=6.0 Hz, NHC=O), 6.51-6.57 (1H, m), 7.75-7.82 (1H, m), and 8.09-8.12 (1H, m).

Example 753

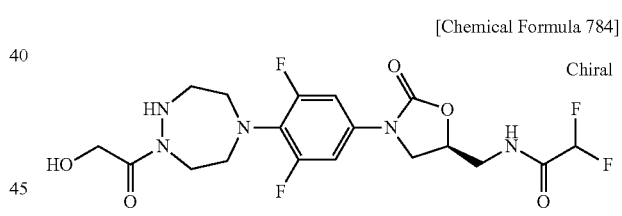

¹H NMR (CDCl₃) δ=3.11-3.19 (2H, m), 3.26-3.42 (4H, m), 3.63-3.90 (5H, m), 4.06 (1H, t, J=9.1 Hz), 4.39 (2H, s, CH₂OH), 4.79-4.90 (1H, m), 5.95 (1H, t, J=54.1 Hz, CHF₂), 7.08 (2H, d, J=10.7 Hz), and 7.45 (1H, t, J=6.2 Hz, NHC=O)

Example 754

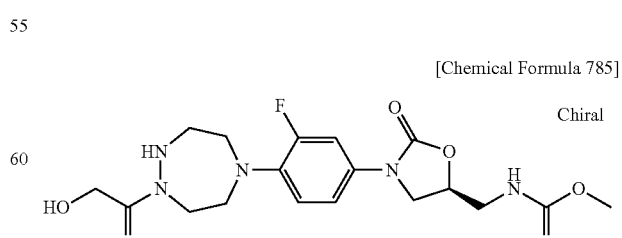

¹H NMR (CDCl₃) δ=3.12-3.48 (6H, m), 3.64-3.73 (2H, m), 3.81 (1H, dd, J=7.2, 9.1 Hz), 3.90-4.15 (3H, m) 4.01 (3H, s, CH₃OC=S), 4.37 (2H, br s, CH₂OH), 4.85-4.96 (1H, m), 6.73 (1H, br t, J=6 Hz, NHC=S), 6.90 (1H, t, J=9.1 Hz), 7.05 (1H, dd, J=2.5, 9.1 Hz), and 7.41 (1H, dd, J=2.5, 14.6 Hz).

Example 755

[Chemical Formula 786]

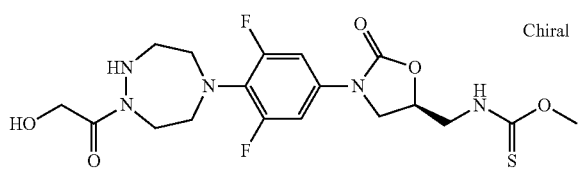

¹H NMR (CDCl₃) δ=3.12-3.18 (2H, m), 3.26-3.32 (2H, m), 3.35-3.41 (2H, m), 3.69-4.14 (6H, m), 4.01 (3H, s, CH₃OC=S), 4.39 (2H, s, CH₂OH), 4.88-4.98 (1H, m), 6.76 (1H, br t, J=6 Hz, NHC=S), and 7.11 (2H, d, J=10.7 Hz).

Example 756

[Chemical Formula 787]

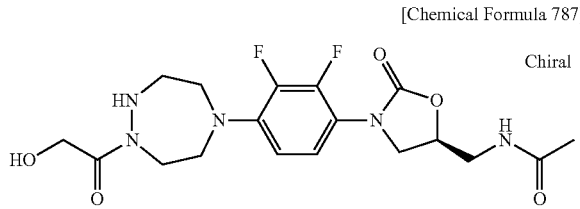 [SMILES: CC(=O)NC[C@H]1CN(c2ccc(N3CCNN(C(=O)CO)CC3)c(F)c2F)C(=O)O1]

¹H NMR (CDCl₃) δ=2.05 (3H, s, CH₃C=O), 3.17-3.25 (2H, m), 3.43-3.54 (4H, m), 3.62-3.71 (3H, m), 3.73 (1H, dd, J=6.3, 9.1 Hz), 3.93-3.99 (1H, m), 4.01 (1H, t, J=9.1 Hz), 4.37 (2H, s, CH₂OH), 4.76-4.86 (1H, m), 6.17 (1H, br t, J=6 Hz, NHC=O), 6.64 (1H, br t, J=9 Hz), and 7.05 (1H, br t, J=9 Hz).

Example 757

[Chemical Formula 788]

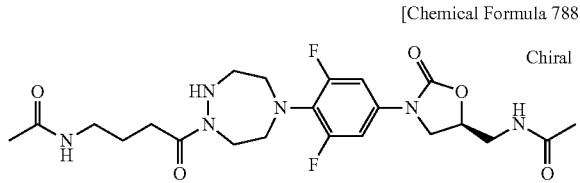

¹H NMR (CDCl₃) δ=1.76-1.88 (2H, m, NHCH₂CH₂CH₂C=O), 1.93 (3H, s, CH₂C=O), 1.99 (3H, s, CH₃C=O), 2.36 & 2.65 (2H, t, J=6.9 Hz, NHCH₂CH₂CH₂C=O), 2.92-3.82 (13H, m), 3.96 (1H, t, J=9.1 Hz), 4.71-4.81 (1H, m), 6.40-6.55 (1H, br, NHC=O), 6.88 (1H, t, J=6.1 Hz, NHC=O), and 7.06 (2H, d, J=10.7 Hz).

Example 758

¹H NMR (CDCl₃) δ=1.82-1.97 (2H, m, NHCH₂CH₂CH₂C=O), 2.02 (3H, s, CH₃C=O), 2.39 & 2.68 (2H, t, J=7.1 Hz, NHCH₂CH₂CH₂C=O), 2.96-4.10 (16H, m), 4.74-4.84 (1H, m), 6.54 (1H, br t, J=6 Hz, NHC=O), and 7.08 (2H, d, J=10.7 Hz).

Example 759

[Chemical Formula 790]

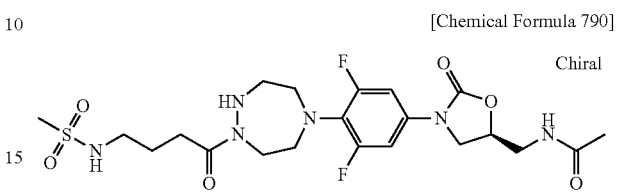

¹H NMR (CDCl₃) δ=1.84-1.98 (2H, m, NHCH₂CH₂CH₂C=O), 2.00 (3H, s, CH₃C=O), 2.42 & 2.71 (2H, t, J=6.9 Hz, NHCH₂CH₂CH₂C=O), 2.93 (3H, s, CH₃SO₂), 2.93-3.85 (13H, m), 3.97 (1H, t, J=9.1 Hz), 4.72-4.81 (1H, m), 5.38 & 5.40 (1H, t, J=5.8 Hz, NHCH₂CH₂CH₂C=O), 6.59 (1H, t, J=6.1 Hz, NHC=O), and 7.06 (2H, d, J=10.7 Hz).

Example 760

[Chemical Formula 791]

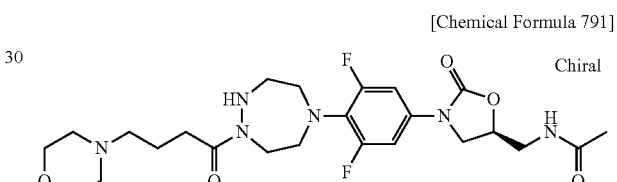

¹H NMR (CDCl₃) δ=1.78-1.92 (2H, m, NHCH₂CH₂CH₂C=O), 2.02 (3H, s, CH₃C=O), 2.35-2.65 (6H, m), 2.96-3.85 (17H, m), 4.00 (1H, t, J=9.1 Hz), 4.74-4.83 (1H, m), 6.78 (1H, br t, J=6 Hz, NHC=O), and 7.08 (2H, d, J=10.7 Hz).

Example 761

[Chemical Formula 792]

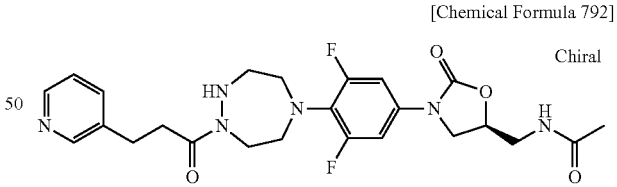

¹H NMR (CDCl₃) δ=2.02 (3H, s, CH₃C=O), 2.60-2.67 (1H, m), 2.90-3.86 (14H, m), 3.99 (1H, t, J=9.0 Hz), 4.73-4.83 (1H, m), 6.44 (1H, t, J=5.9 Hz, NHC=O), 7.08 (2H, d,

[Chemical Formula 789]

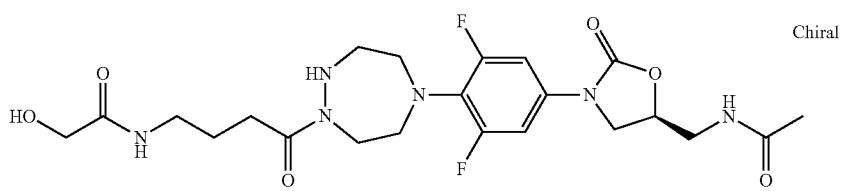

J=10.7 Hz), 7.21 (1H, dd, J=4.7, 7.8 Hz), 7.58 (1H, br d, J=8 Hz), 8.44 (1H, d, J=4.7 Hz), and 8.50 (1H, br s).

Example 762

[Chemical Formula 793]

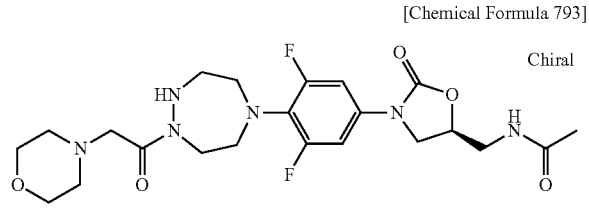 [SMILES: CC(=O)NC[C@H]1CN(c2cc(F)c(N3CCNN(C(=O)CN4CCOCC4)CC3)c(F)c2)C(=O)O1]

$^1$H NMR (CDCl$_3$) δ=2.03 (3H, s, CH$_3$C=O), 2.52-2.64 (4H, m, O[CH$_2$CH$_2$]$_2$N), 2.98-3.84 (17H, m), 3.99 (1H, t, J=9.1 Hz), 4.74-4.83 (1H, m), 6.38 (1H, br t, J=6 Hz, NHC=O), and 7.10 (2H, d, J=10.7 Hz).

Example 763

[Chemical Formula 794]

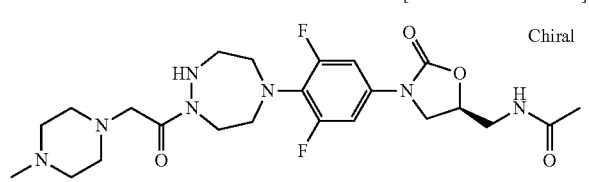

$^1$H NMR (CDCl$_3$) δ=2.03 (3H, s, CH$_3$C=O), 2.33 & 2.36 & 2.40 (3H, s, CH$_3$N), 2.51-2.75 (8H, m, CH$_3$N[CH$_2$CH$_2$]$_2$N), 2.98-3.83 (13H, m), 3.99 (1H, t, J=9.1 Hz), 4.74-4.83 (1H, m), 6.59 (1H, br t, J=6 Hz, NHC=O), and 7.08 (2H, d, J=10.7 Hz).

Example 764

[Chemical Formula 795]

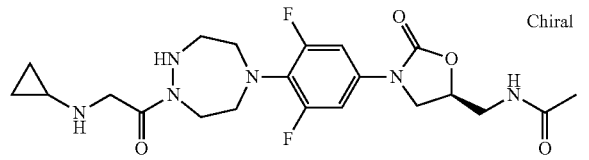

$^1$H NMR (CDCl$_3$) δ=0.37-0.48 (4H, m), 2.03 (3H, s, CH$_3$C=O), 2.18-2.27 (1H, m), 2.99-3.87 (13H, m), 3.99 (1H, t, J=9.1 Hz), 4.74-4.83 (1H, m), 6.79 (1H, br t, J=6 Hz, NHC=O), and 7.09 (2H, d, J=10.7 Hz).

Example 765

[Chemical Formula 796]

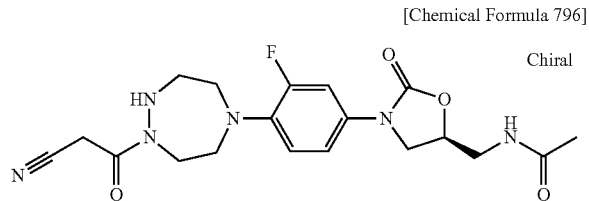 [SMILES: CC(=O)NC[C@H]1CN(c2ccc(N3CCNN(C(=O)CC#N)CC3)c(F)c2)C(=O)O1]

Example 766

[Chemical Formula 797]

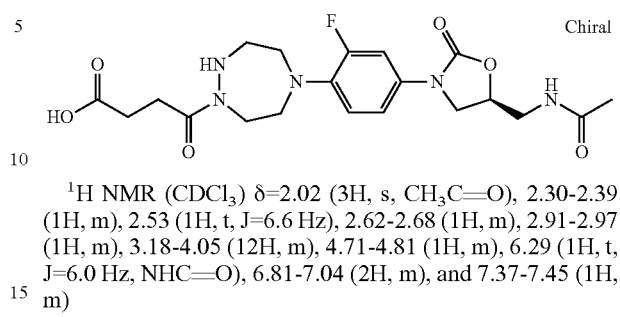

$^1$H NMR (CDCl$_3$) δ=2.02 (3H, s, CH$_3$C=O), 2.30-2.39 (1H, m), 2.53 (1H, t, J=6.6 Hz), 2.62-2.68 (1H, m), 2.91-2.97 (1H, m), 3.18-4.05 (12H, m), 4.71-4.81 (1H, m), 6.29 (1H, t, J=6.0 Hz, NHC=O), 6.81-7.04 (2H, m), and 7.37-7.45 (1H, m)

Example 767

[Chemical Formula 798]

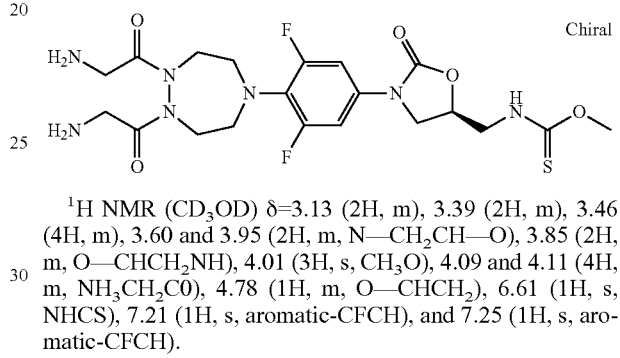

$^1$H NMR (CD$_3$OD) δ=3.13 (2H, m), 3.39 (2H, m), 3.46 (4H, m), 3.60 and 3.95 (2H, m, N—CH$_2$CH—O), 3.85 (2H, m, O—CHCH$_2$NH), 4.01 (3H, s, CH$_3$O), 4.09 and 4.11 (4H, m, NH$_3$CH$_2$C0), 4.78 (1H, m, O—CHCH$_2$), 6.61 (1H, s, NHCS), 7.21 (1H, s, aromatic-CFCH), and 7.25 (1H, s, aromatic-CFCH).

Example 768

[Chemical Formula 799]

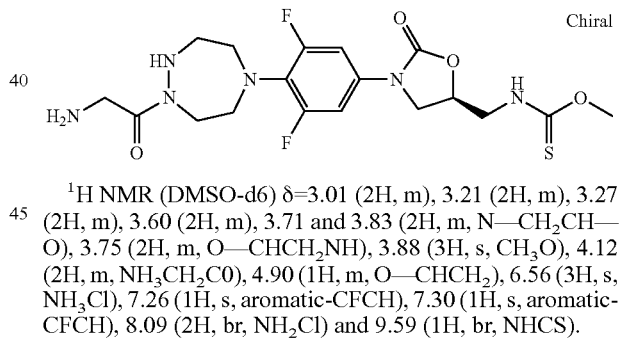

$^1$H NMR (DMSO-d6) δ=3.01 (2H, m), 3.21 (2H, m), 3.27 (2H, m), 3.60 (2H, m), 3.71 and 3.83 (2H, m, N—CH$_2$CH—O), 3.75 (2H, m, O—CHCH$_2$NH), 3.88 (3H, s, CH$_3$O), 4.12 (2H, m, NH$_3$CH$_2$C0), 4.90 (1H, m, O—CHCH$_2$), 6.56 (3H, s, NH$_3$Cl), 7.26 (1H, s, aromatic-CFCH), 7.30 (1H, s, aromatic-CFCH), 8.09 (2H, br, NH$_2$Cl) and 9.59 (1H, br, NHCS).

Example 769

[Chemical Formula 800]

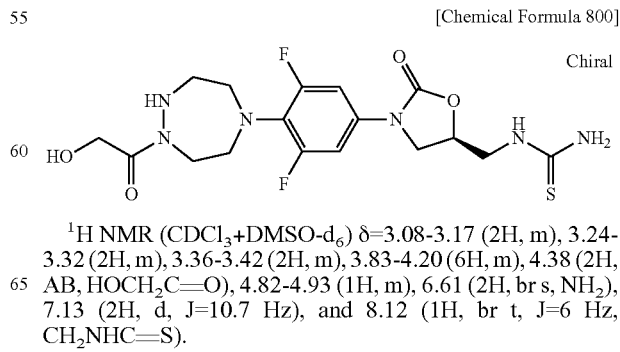

$^1$H NMR (CDCl$_3$+DMSO-d$_6$) δ=3.08-3.17 (2H, m), 3.24-3.32 (2H, m), 3.36-3.42 (2H, m), 3.83-4.20 (6H, m), 4.38 (2H, AB, HOCH$_2$C=O), 4.82-4.93 (1H, m), 6.61 (2H, br s, NH$_2$), 7.13 (2H, d, J=10.7 Hz), and 8.12 (1H, br t, J=6 Hz, CH$_2$NHC=S).

Example 770

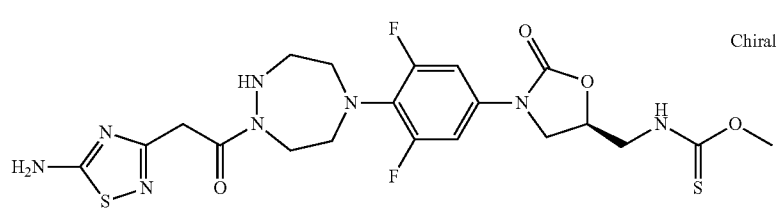

$^1$H NMR (CD$_3$OD) δ=1.42 (1H, s, NH$_2$), 1.47 (1H, s, NH$_2$), 3.05 (2H, m), 3.26 (2H, m), 3.31 (2H, m), 3.83 (2H, m), 3.63 and 4.10 (2H, m, N—CH$_2$CH—O), 3.90 (2H, m, O—CHCH$_2$NH), 3.95 (3H, s, CH$_3$O), 4.95 (1H, m, O—CHCH$_2$), 5.48 (1H, s, NHCS), 7.18 (1H, s, aromatic-CFCH), and 7.22 (1H, s, aromatic-CFCH).

Example 771

[Chemical Formula 802]

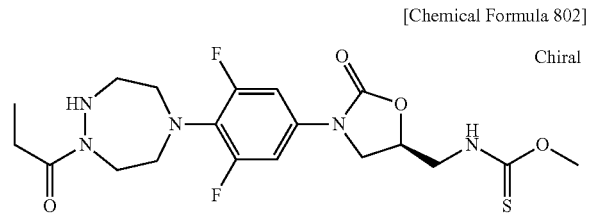 [SMILES: CCC(=O)N1CCN(c2c(F)cc(N3C[C@H](CNC(=S)OC)OC3=O)cc2F)CCN1]

$^1$H NMR (CDCl$_3$) δ=1.14 & 1.17 (3H, t, J=7.4 Hz, CH$_3$CH$_2$C=O, two conformers), 2.35 & 2.60 (2H, q, J=7.4 Hz, CH$_3$CH$_2$C=O, two conformers), 2.96-4.12 (12H, m), 4.00 (3H, s, CH$_3$OC=S), 4.88-4.98 (1H, m, NCH$_2$CHCH$_2$NHC=O), 7.05 (1H, br t, J=6 Hz, NHC=S), and 7.09 (2H, d, J=10.7 Hz).

Example 772

[Chemical Formula 803]

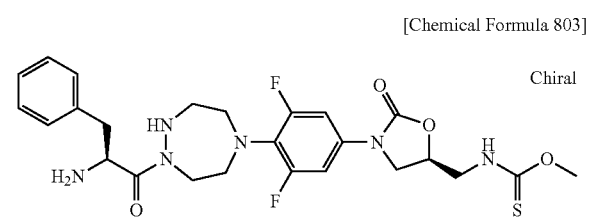 [SMILES: COC(=S)NC[C@H]1CN(c2cc(F)c(N3CCNN(C(=O)[C@@H](N)Cc4ccccc4)CC3)c(F)c2)C(=O)O1]

$^1$H NMR (CD$_3$OD) δ=2.95-3.15 (2H, dd, C$_6$H$_5$CH$_2$), 3.06 (2H, m), 3.25 (2H, m), 3.40 (2H, m), 3.50-3.80 (2H, m), 3.90 (2H, m, O—CHCH$_2$NH), 3.90-4.00 and 4.10 (2H, m, N—CH$_2$CH—O), 3.95 (3H, s, CH$_3$O), 4.77-4.90 (1H, m, NH$_2$CH—CO), 4.95-5.00 (1H, m, O—CHCH$_2$), 7.20-7.40 (5H, m, C$_6$H$_5$), 7.30 (1H, s, aromatic-CFCH) and 7.34 (1H, s, aromatic-CFCH).

Example 773

[Chemical Formula 804]

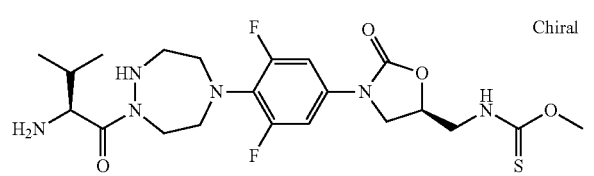

$^1$H NMR (CD$_3$OD) δ=1.00-1.20 (6H, d+d, CH$_3$CH), 1.52-1.54 (1H, m, CH$_3$CH), 3.17 (2H, m), 3.30 (2H, m), 3.42 (4H, m), 3.89 (2H, m, O—CHCH$_2$NH), 3.95 (3H, s, CH$_3$O), 3.96 and 4.14 (2H, m, N—CH$_2$CH—O), 4.80-4.85 (1H, m, NH$_3$CHCO), 4.95-5.00 (1H, m, O—CHCH$_2$), 7.21 (1H, s, aromatic-CFCH) and 7.25 (1H, s, aromatic-CFCH).

Example 774

[Chemical Formula 805]

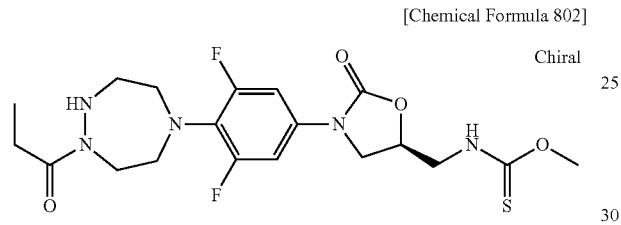

$^1$H NMR (CD$_3$OD) δ=1.96 (3H, s, CH$_3$CONH), 3.30-3.32 (2H, m), 3.35-3.43 (4H, m), 3.55 (2H, d, COCH$_2$CN), 3.79 and 4.11 (2H, dd+dd, N—CH$_2$CH—O), 3.94 (4H, m), 4.52 (2H, m, NHCO), 4.70-4.90 (1H, m, O—CHCH$_2$), 7.05-7.20 (2H, m, aromatic-CHCH), and 7.50 (1H, dd, aromatic-CFCH).

N-08

Example 775

[Chemical Formula 806]

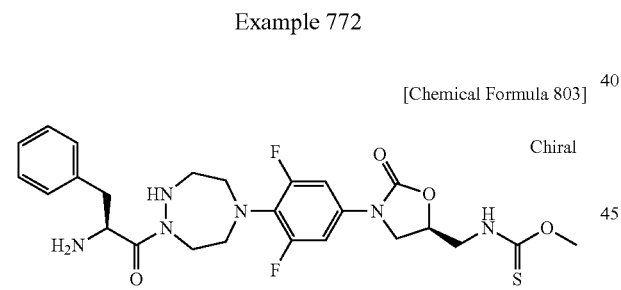

$^1$H NMR (CDCl$_3$) δ=2.03 (3H, s, CH$_3$C=O), 3.03-3.10 (2H, m), 3.24-3.31 (2H, m), 3.38-3.45 (2H, m), 3.58-3.76 (5H, m), 3.77 (3H, s, CH$_3$O), 3.99 (1H, t, J=8.8 Hz), 4.73-4.83 (1H, m), 6.32 (1H, t, J=6.0 Hz, NHC=O), and 7.07 (2H, d, J=10.7 Hz).

Example 776

[Chemical Formula 807]

¹H NMR (CDCl₃) δ=1.29 (3H, t, J=7.1 Hz, CH₃CH₂O), 2.03 (3H, s, CH₃C=O), 3.04-3.09 (2H, m), 3.25-3.30 (2H, m), 3.39-3.45 (2H, m), 3.58-3.76 (5H, m), 3.99 (1H, t, J=9.0 Hz), 4.21 (2H, q, J=7.1 Hz, CH₃CH₂O), 4.73-4.83 (1H, m), 6.33 (1H, t, J=6.0 Hz, NHC=O), and 7.07 (2H, d, J=10.7 Hz).

Example 777

[Chemical Formula 808]

¹H NMR (CDCl₃) δ=2.02 (3H, s, CH₃C=O), 3.10-3.90 (11H, m), 3.99 (1H, t, J=9.0 Hz), 4.73-4.83 (1H, m), 6.22 (1H, t, J=6.0 Hz, NHC=O), 6.97-7.08 (1H, br s, NHC=O), 7.12 (2H, d, =10.7 Hz), 7.34 (1H, dd, J=4.7, 8.2 Hz), 7.56 (1H, br d, J=8 Hz), and 8.44-8.50 (2H, m).

Example 778

[Chemical Formula 809]

¹H NMR (CDCl₃) δ=3.10-3.90 (12H, m), 4.77-4.88 (1H, m), 5.94 (1H, t, J=54.1 Hz, CHF₂C=O), 6.97-7.08 (1H, br s, NHC=O), 7.11 (2H, d, J=10.6 Hz), 7.36 (1H, dd, J=5.0, 8.0 Hz), 7.56 (1H, br d, J=8 Hz), and 8.43-8.51 (2H, m).

Example 779

[Chemical Formula 810]

¹H NMR (CDCl₃) δ=3.08-4.14 (12H, m), 4.01 (3H, s, CH₃OC=S), 4.88-4.98 (1H, m), 6.90 (1H, t, J=6.0 Hz, NHC=S), 7.12 (2H, d, J=10.5 Hz), 7.35 (1H, dd, J=4.7, 8.3 Hz), 7.56 (1H, br d, J=8 Hz), and 8.43-8.52 (2H, m).

Example 780

[Chemical Formula 811]

¹H NMR (CDCl₃) δ=3.10-3.17 (2H, m), 3.40-3.45 (2H, m), 3.54-3.75 (6H, m), 3.68 (3H, s, CH₃OC=O), 3.83 (1H, ddd, J=3.3, 6.3, 14.6 Hz), 4.06 (1H, t, J=9.1 Hz), 4.80 (1H, ddt, J=3.3, 9.1, 6.3 Hz, CHCH₂NHC=O), 5.94 (1H, t, J=54.1 Hz, CHF₂), 6.87 (1H, t, J=9.2 Hz), 7.00 (1H, dd, J=1.8, 9.2 Hz), 7.22 (1H, br t, J=6 Hz, NHC=O), and 7.32 (1H, dd, J=1.8, 14.8 Hz).

Example 781

[Chemical Formula 812]

¹H NMR (CD₃OD) δ=3.13-3.18 (2H, m), 3.34-3.39 (2H, m), 3.48-3.54 (2H, m), 3.70-3.97 (6H, m), 3.86 (3H, s, CH₃OC=O), 4.14 (1H, t, J=9.1 Hz), 4.75-4.85 (1H, m, NCH₂CHCH₂NHC=O), 5.94 (1H, t, J=54.0 Hz, CHF₂), 7.04 (2H, d, J=10.7 Hz), and 7.24 (1H, br t, J=6 Hz, NHC=O).

Example 782

[Chemical Formula 813]

¹H NMR (CDCl₃) δ=3.04-3.09 (2H, m), 3.25-3.30 (2H, m), 3.38-3.45 (2H, m), 3.62-3.69 (2H, m), 3.77 (3H, s, CH₃OC=O), 3.77-4.12 (4H, m), 4.01 (3H, s, CH₃OC=S), 4.88-4.98 (1H, m, CH₂CHCH₂NHC=O), 6.96 (1H, br t, J=8 Hz), and 7.08 (2H, d, J=10.7 Hz).

Example 783

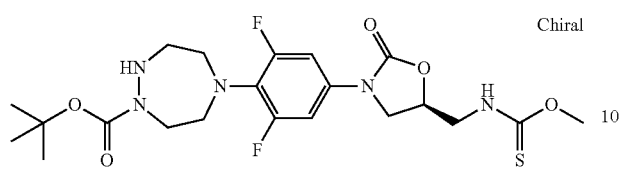
[Chemical Formula 814]
Chiral

¹H NMR (CDCl₃) δ=3.02-3.08 (2H, m), 3.24-3.30 (2H, m), 3.37-3.45 (2H, m), 3.57-3.63 (2H, m), 3.81 (1H, dd, J=7.1, 9.1 Hz), 3.93-4.14 (3H, m), 4.01 (3H, s, CH₃OC=S), 4.87-4.97 (1H, m, NCH₂CHCH₂NHC=O), 6.72 (1H, br t, J=6 Hz, NHC=S), and 7.08 (2H, d, J=10.7 Hz).

Example 784

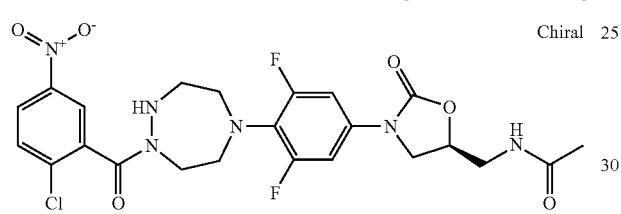
[Chemical Formula 815]
Chiral

¹H NMR (CDCl₃) δ=2.02 (3H, s, CH₃C=O), 2.93-4.11 (12H, m), 4.74-4.85 (1H, m), 6.42-6.53 (1H, m, NHC=O), 7.06-7.15 (2H, m), 7.54-7.62 (1H, m), and 8.13-8.21 (2H, m).

Example 785

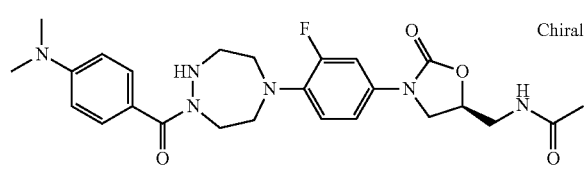
[Chemical Formula 816]
Chiral

¹H NMR (CDCl₃) δ=2.00 (3H, s, CH₃C=O), 2.97 (6H, s, CH₃NCH₃), 3.18-3.24 (2H, m), 3.44-3.50 (2H, m), 3.53-3.82 (7H, m), 3.98 (1H, t, J=9.1 Hz), 4.69-4.79 (1H, m), 6.55-6.65 (4H, m), 6.89 (1H, t, J=9.1 Hz), 6.99 (1H, dd, J=2.5, 9.1 Hz), 7.20 (1H, br s, NHC=O), and 7.38 (1H, dd, J=2.5, 14.6 Hz).

Example 786

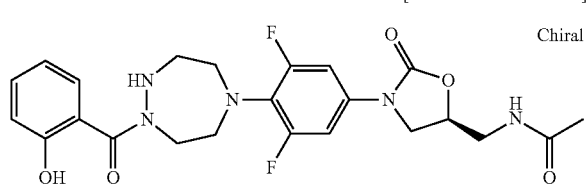
[Chemical Formula 817]
Chiral

¹H NMR (CDCl₃) δ=2.01 (3H, s, CH₃C=O), 3.10-3.17 (2H, m), 3.29-3.35 (2H, m), 3.46-3.52 (2H, m), 3.61-3.67 (2H, m), 3.72 (1H, dd, J=6.6, 9.1 Hz), 3.90-4.02 (3H, m), 4.72-4.83 (1H, m, NCH₂CHCH₂NHC=O), 6.48 (1H, br t, J=6 Hz, NHC=O), 6.85 (1H, br t, J=8 Hz), 6.97 (1H, br d, J=8 Hz), 7.09 (2H, d, J=10.7 Hz), 7.33 (1H, br t, J=8 Hz), and 7.76 (1H, br s).

Example 787

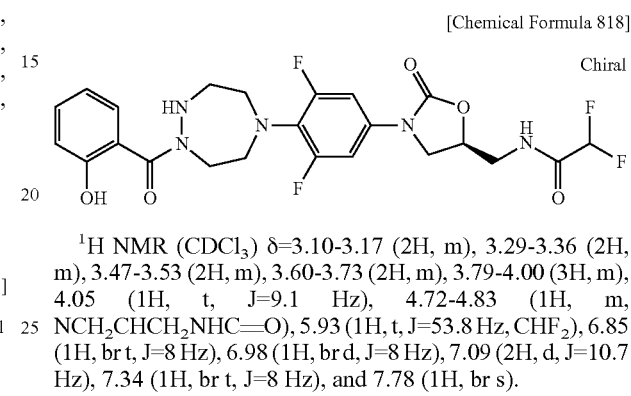
[Chemical Formula 818]
Chiral

¹H NMR (CDCl₃) δ=3.10-3.17 (2H, m), 3.29-3.36 (2H, m), 3.47-3.53 (2H, m), 3.60-3.73 (2H, m), 3.79-4.00 (3H, m), 4.05 (1H, t, J=9.1 Hz), 4.72-4.83 (1H, m, NCH₂CHCH₂NHC=O), 5.93 (1H, t, J=53.8 Hz, CHF₂), 6.85 (1H, br t, J=8 Hz), 6.98 (1H, br d, J=8 Hz), 7.09 (2H, d, J=10.7 Hz), 7.34 (1H, br t, J=8 Hz), and 7.78 (1H, br s).

Example 788

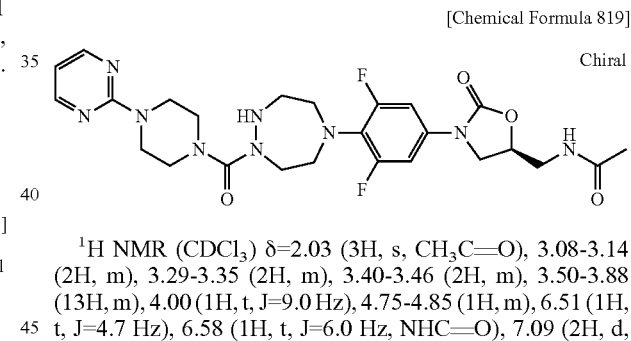
[Chemical Formula 819]
Chiral

¹H NMR (CDCl₃) δ=2.03 (3H, s, CH₃C=O), 3.08-3.14 (2H, m), 3.29-3.35 (2H, m), 3.40-3.46 (2H, m), 3.50-3.88 (13H, m), 4.00 (1H, t, J=9.0 Hz), 4.75-4.85 (1H, m), 6.51 (1H, t, J=4.7 Hz), 6.58 (1H, t, J=6.0 Hz, NHC=O), 7.09 (2H, d, J=10.7 Hz), and 8.32 (2H, d, J=4.7 Hz).

Example 789

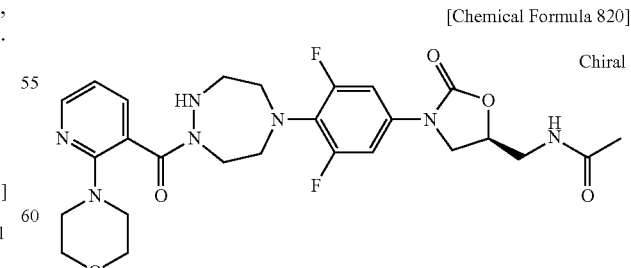
[Chemical Formula 820]
Chiral

¹H NMR (CDCl₃) δ=2.00 & 2.01 (3H, two singlet peaks, CH₃C=O), 3.04-4.02 (19H, m), 4.36-4.46 (1H, m), 4.71-4.81 (1H, m), 6.13-6.23 (1H, m, NHC=O), 6.79-7.15 (3H, m), and 7.47-8.54 (2H, m).

Example 790

[Chemical Formula 821]

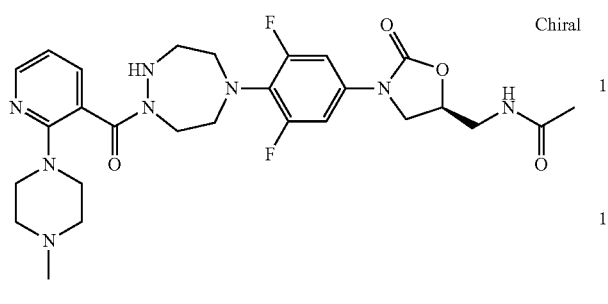

¹H NMR (CDCl₃) δ=1.94 & 1.95 (3H, two singlet peaks, CH₃C=O), 2.25 & 2.28 (3H, two singlet peaks, CH₃—N), 2.35-2.50 (4H, m), 2.96-3.93 (15H, m), 4.65-4.76 (1H, m), 6.29-6.39 (1H, m, NHC=O), 6.72 & 6.85 (1H, two dd peaks, J=4.4, 7.4 Hz), 6.96-7.05 (2H, m), 7.42 & 7.62 (1H, two dd peaks, J=1.9, 7.4 Hz), and 8.16 & 8.23 (1H, two dd peaks, J=1.9, 4.4 Hz).

Example 791

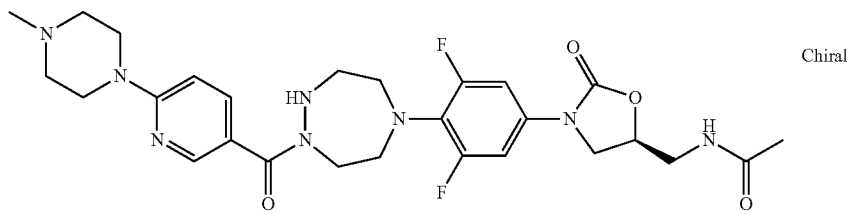

¹H NMR (CDCl₃) δ=2.02 (3H, s, CH₃C=O), 2.35 (3H, s, CH₃N), 2.51 (4H, t-like, J=5 Hz), 3.10-3.18 (2H, m), 3.28-3.35 (2H, m), 3.43-3.49 (2H, m), 3.56-3.75 (9H, m), 3.98 (1H, t, J=9.0 Hz), 4.72-4.82 (1H, m), 6.16 (1H, t, J=6.0 Hz, NHC=O), 6.62 (1H, d, J=8.8 Hz), 7.09 (2H, d, J=10.7 Hz), 7.70-7.85 (1H, br), and 8.51 (1H, br s).

Example 792

[Chemical Formula 823]

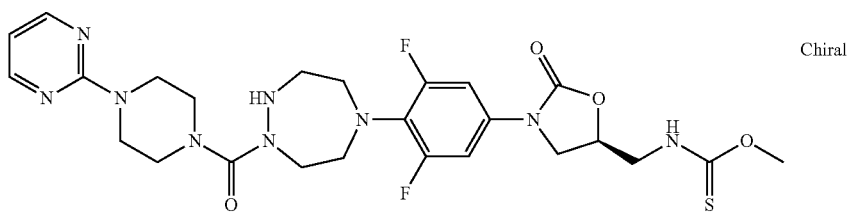

¹H NMR (CDCl₃) δ=3.08-3.15 (2H, m), 3.30-3.37 (2H, m), 3.40-3.46 (2H, m), 3.51-3.57 (4H, m), 3.63-3.69 (2H, m), 3.78-4.13 (8H, m), 4.01 (3H, s, CH₃OC=S), 4.88-4.98 (1H, m), 6.51 (1H, t, J=4.7 Hz), 6.86 (1H, t, J=6.0 Hz, NHC=S), 7.10 (2H, d, J=10.7 Hz), and 8.32 (2H, d, J=4.7 Hz).

Example 793

[Chemical Formula 824]

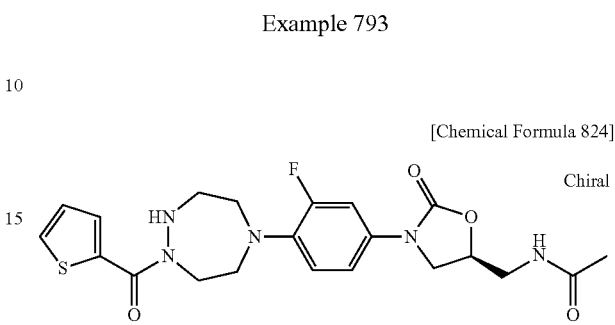

¹H NMR (CDCl₃+DMSO-d₆) δ=2.01 (3H, s, NHC=O), 3.28-3.42 (4H, m), 3.46-3.53 (2H, m), 3.58-3.66 (2H, m), 3.74 (1H, dd, J=7.1, 9.1 Hz), 4.00 (1H, t, J=9.1 Hz), 4.02-4.10 (2H, m), 4.71-4.81 (1H, m), 6.80 (1H, br t, J=6 Hz, NHC=O), 6.91 (1H, t, J=9.1 Hz), 7.03 (1H, br d, J=9 Hz), 7.07 (1H, t, J=4.5 Hz), 7.42 (1H, br d, J=15 Hz), 7.51 (1H, d, J=4.5 Hz), and 8.05 (1H, br s).

[Chemical Formula 822]

Example 794

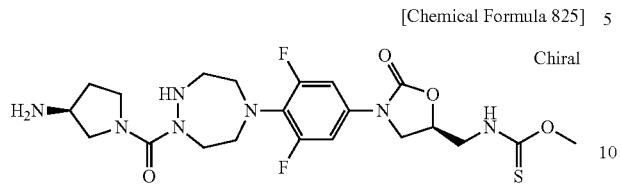
[Chemical Formula 825]

¹H NMR (CDCl₃) δ=1.60-1.74 (1H, m), 1.98-2.12 (1H, m), 2.86 (2H, br s, NH₂), 3.06-3.13 (2H, m), 3.23-3.39 (5H, m), 3.50-3.85 (8H, m), 3.93-4.14 (2H, m), 4.01 (3H, s, CH₃OC=S), 4.88-4.98 (1H, m), 6.72 (1H, br t, J=6 Hz, NHC=S), and 7.07 (2H, d, J=10.7 Hz).

Example 795

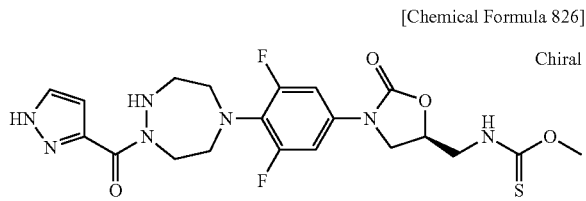 [SMILES: COC(=S)NC[C@H]1CN(c2cc(F)c(N3CCNN(C(=O)c4cc[nH]n4)CC3)c(F)c2)C(=O)O1]
[Chemical Formula 826]

¹H NMR (CD3OD) δ=3.14 (4H, m), 3.49 (4H, m), 3.89 (2H, m, O—CHCH₂NH), 3.94 (3H, s, CH3O), 4.10 (2H, m, N—CH₂CH—O), 4.93 (1H, m, O—CHCH₂), 6.70 (1H, s, NHCS), 7.01 (1H, br, aromatic-N—CHCH—), 7.21 (2H, s+s, aromatic-CFCH) and 7.66 (1H, br, aromatic-N—CHCH—)

Example 796

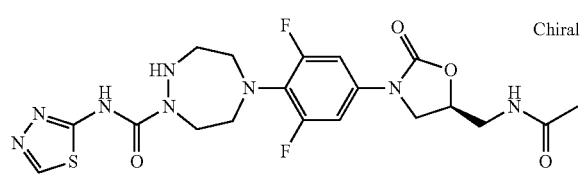
[Chemical Formula 827]

¹H NMR (CDCl₃) δ=2.03 (3H, s, CH₃C=O), 3.20-3.46 (6H, m), 3.63-3.71 (2H, m), 3.73 (1H, dd, J=6.8, 9.1 Hz), 3.86-3.96 (1H, m), 3.99 (1H, t, J=9.1 Hz), 4.14 (1H, t, J=6.0 Hz), 4.73-4.84 (1H, m), 6.37 (1H, t, J=6.3 Hz, NHC=O), 7.11 (2H, d, J=10.7 Hz), and 8.75 (1H, s, N=CH—S).

Example 797

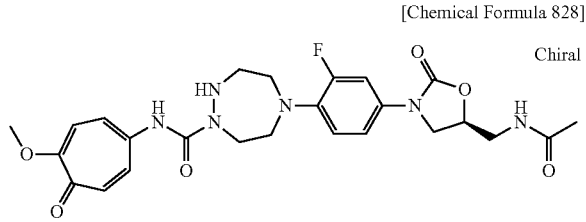 [SMILES: COc1ccc(NC(=O)N2CCN(c3ccc(N4C[C@H](CNC(C)=O)OC4=O)cc3F)CCN2)ccc1=O]
[Chemical Formula 828]

¹H NMR (CDCl₃) δ=2.02 (3H, s, CH₃C=O), 3.24-3.31 (2H, m), 3.39-3.47 (4H, m), 3.56-3.77 (3H, m), 3.83-4.04 (3H, m), 3.92 (3H, s, OMe), 4.72-4.81 (1H, m), 6.13 (1H, t, J=6.0 Hz, NHC=O), 6.78 (1H, d, J=11.3 Hz), 6.91 (1H, t, J=9.1 Hz), 7.03 (1H, dd, J=2.0, 9.1 Hz), 7.23-7.31 (1H, m), 7.42 (1H, dd, J=2.5, 14.6 Hz), 7.64 (1H, br d, J=11 Hz), and 8.71 (1H, s, NH-tropolone).

Example 798

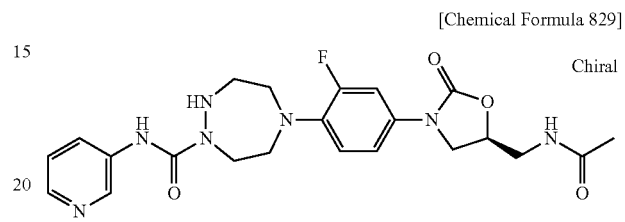
[Chemical Formula 829]

¹H NMR (CDCl₃) δ=2.02 (3H, s, CH₃C=O), 3.23-3.48 (6H, m), 3.56-3.78 (3H, m), 3.90-4.05 (3H, m), 4.71-4.81 (1H, m), 6.47 (1H, t, J=6.3 Hz, NHC=O), 6.86-7.05 (3H, m), 7.39 (1H, dd, J=2.5, 14.6 Hz), 7.64 (1H, ddd, J=1.9, 7.7, 8.5 Hz), 8.11 (1H, d, J=8.5 Hz), 8.22 (1H, br d, J=5 Hz), and 9.22 (1H, s, NH-heterocycle).

Example 799

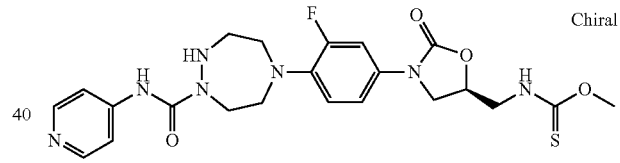
[Chemical Formula 830]

¹H NMR (CDCl₃) δ=3.24-3.31 (2H, m), 3.38-3.46 (4H, m), 3.59-4.10 (6H, m), 4.00 (3H, s, CH₃OC=S), 4.85-4.96 (1H, m), 6.90 (1H, t, J=8.8 Hz), 7.02 (1H, br d, J=9 Hz), 7.32 (1H, t, J=6.5 Hz, NHC=S), 7.36-7.44 (4H, m) 8.41 (2H, d-like, J=5 Hz), and 8.84 (1H, s, NH-heterocycle).

Example 800

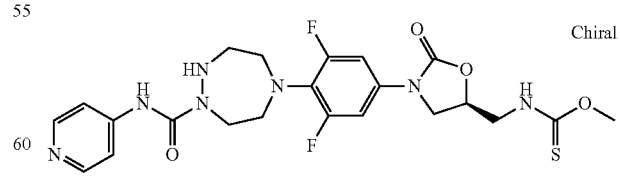
[Chemical Formula 831]

¹H NMR (CDCl₃) δ=3.19-3.27 (2H, m), 3.33-3.43 (4H, m), 3.61-4.13 (6H, m), 4.01 (3H, s, CH₃OC=S), 4.88-4.98 (1H, m), 6.85 (1H, br t, J=6 Hz, NHC=S), 7.11 (2H, d, J=10.7 Hz), 7.44 (2H, br d, J=5 Hz), 8.43 (2H, br d, J=5 Hz), and 8.87 (1H, s, NH-heterocycle).

Example 801

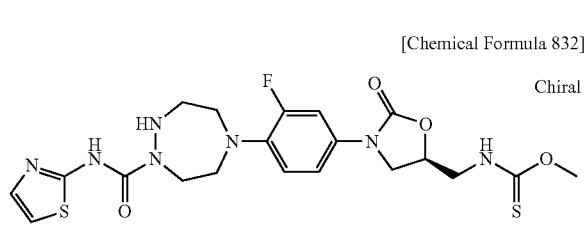 [SMILES: COC(=S)NC[C@H]1CN(c2ccc(N3CCNN(C(=O)Nc4nccs4)CC3)c(F)c2)C(=O)O1]
[Chemical Formula 832]
Chiral

¹H NMR (CDCl₃) δ=3.22-3.31 (2H, m), 3.34-3.48 (4H, m), 3.59-4.12 (6H, m), 4.00 (3H, s, CH₃OC=S), 4.85-4.96 (1H, m), 6.86 (1H, d, J=3.6 Hz), 6.90 (1H, t, J=8.8 Hz), 7.00-7.10 (2H, m), 7.36 (1H, d, J=3.6 Hz), 7.40 (1H, dd, J=2.5, 14.3 Hz), and 9.85 (1H, br s, NH-heterocycle).

Example 802

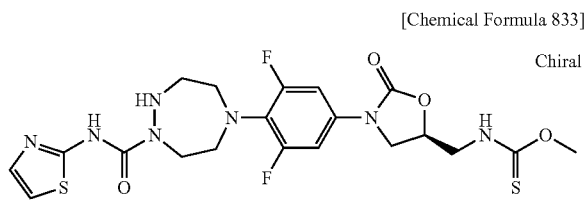 [SMILES: COC(=S)NC[C@H]1CN(c2cc(F)c(N3CCNN(C(=O)Nc4nccs4)CC3)c(F)c2)C(=O)O1]
[Chemical Formula 833]
Chiral

¹H NMR (CDCl₃) δ=3.19-3.26 (2H, m), 3.31-3.37 (2H, m), 3.38-3.44 (2H, m), 3.82 (1H, dd, J=7.1, 9.1 Hz), 3.86-4.16 (5H, m), 4.01 (3H, s, CH₃OC=S), 4.87-4.97 (1H, m), 6.71 (1H, br t, J=6 Hz, NHC=S), 6.88 (1H, d, J=3.6 Hz), 7.11 (2H, d, J=10.7 Hz), 7.37 (1H, d, J=3.6 Hz), and 9.83 (1H, br s, NH-heterocycle).

Example 803

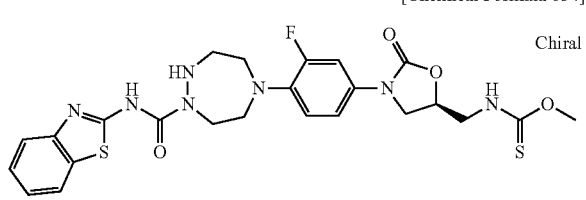
[Chemical Formula 834]
Chiral

¹H NMR (CDCl₃) δ=3.22-3.34 (2H, m), 3.38-3.44 (2H, m), 3.45-3.50 (2H, m), 3.82 (1H, dd, J=7.1, 9.1 Hz), 3.90-4.14 (5H, m), 4.00 (3H, s, CH₃OC=S), 4.85-4.95 (1H, m), 6.70 (1H, br t, J=6 Hz, NHC=S), 6.92 (1H, t, J=8.8 Hz), 7.05 (1H, br d, J=9 Hz), 7.21-7.33 (1H, m), 7.37-7.46 (2H, m), 7.71 (1H, d, J=8.0 Hz), 7.79 (1H, d, J=8.0 Hz), and 9.95 (1H, br s, NH-heterocycle).

Example 804

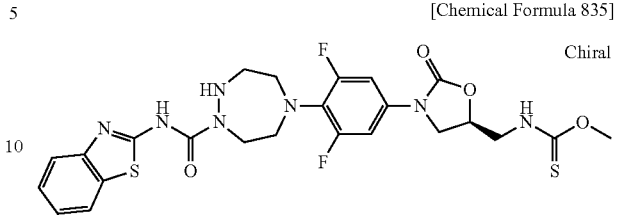
[Chemical Formula 835]
Chiral

¹H NMR (CDCl₃) δ=3.20-3.29 (2H, m), 3.31-3.38 (2H, m), 3.39-3.47 (2H, m), 3.81 (1H, dd, J=7.1, 9.1 Hz), 3.86-4.15 (5H, m), 4.01 (3H, s, CH₃OC=S), 4.88-4.97 (1H, m), 6.80 (1H, br t, J=6 Hz, NHC=S), 7.11 (2H, d, J=10.7 Hz), 7.21-7.33 (1H, m), 7.40 (1H, br t, J=8 Hz), 7.71 (1H, d, J=8.0 Hz), 7.79 (1H, d, J=8.0 Hz), and 10.00 (1H, br s, NH-heterocycle).

Example 805

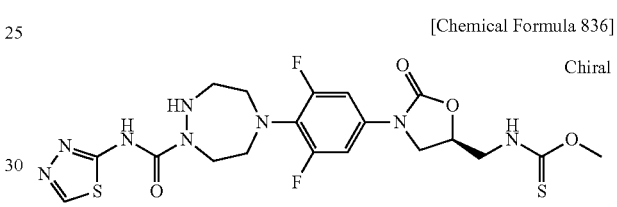
[Chemical Formula 836]
Chiral

¹H NMR (CDCl₃) δ=3.20-3.47 (6H, m), 3.59-4.13 (6H, m), 4.01 (3H, s, CH₃OC=S), 4.87-4.98 (1H, m), 6.74 (1H, br t, J=6 Hz, NHC=S), 7.12 (2H, d, J=10.5 Hz), 8.74 (1H, s, N=CH—S), and 10.09 (1H, s, NH-heterocycle).

Example 806

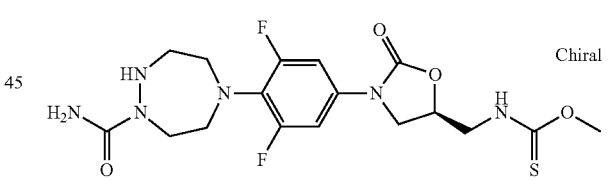
[Chemical Formula 837]
Chiral

¹H NMR (CDCl₃) δ=3.12-3.19 (2H, m), 3.28-3.36 (4H, m), 3.72-4.10 (6H, m), 4.01 (3H, s, CH₃OC=S), 4.88-4.98 (1H, m), 5.42 (2H, br s, H₂C=O), 7.05 (1H, t, J=6.0 Hz, NHC=S), and 7.11 (2H, d, J=10.7 Hz).

Example 807

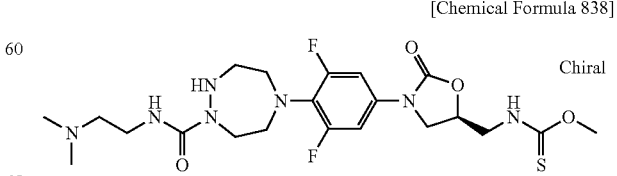
[Chemical Formula 838]
Chiral

¹H NMR (CDCl₃) δ=2.30 (6H, s, CH₃NCH₃), 2.48 (2H, t, J=6.3 Hz, Me₂NCH₂), 3.07-3.15 (2H, m), 3.26-3.38 (6H, m), 3.64-4.10 (6H, m), 4.00 (3H, s, CH$_3$OC=S), 4.88-4.98 (1H, m), 6.72 (1H, t, J=5.5 Hz), 7.09 (2H, d, J=10.7 Hz), and 7.29 (1H, br t, J=6 Hz).

Example 808

[Chemical Formula 839]

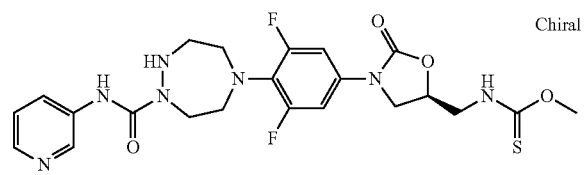

$^1$H NMR (CDCl$_3$) δ=3.20-4.11 (12H, m), 4.00 (3H, s, CH$_3$OC=S), 4.34-4.47 (1H, m, CHNHC=O), 4.88-4.98 (1H, m), 7.07 (1H, t-like, J=6 Hz, NHC=S), 7.09 (2H, d, J=10.7 Hz), 7.23 (1H, dd, J=4.7, 8.4 Hz), 8.14 (1H, br d, J=8 Hz), 8.24 (1H, br d, J=5 Hz), 8.51 (1H, br s), and 8.74 (1H, s, heteroaryl-NHC=O).

Example 809

[Chemical Formula 840]

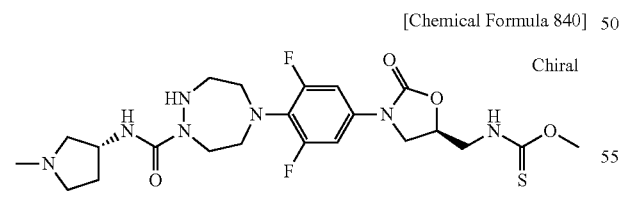

$^1$H NMR (CDCl$_3$) δ=1.69-1.84 (1H, m), 2.00-2.58 (3H, m), 2.47 (3H, s, N—CH$_3$), 2.68-2.86 (2H, m), 3.00-3.15 (2H, m), 3.25-3.36 (4H, m), 3.61-4.14 (6H, m), 4.01 (3H, s, CH$_3$OC=S), 4.34-4.47 (1H, m, CHNHC=O), 4.87-4.97 (1H, m), 6.81 (1H, d, J=7.7 Hz, CHNHC=O), 6.94 (1H, t-like, J=6 Hz, NHC=S), and 7.09 (2H, d, J=10.7 Hz).

Example 810

[Chemical Formula 841]

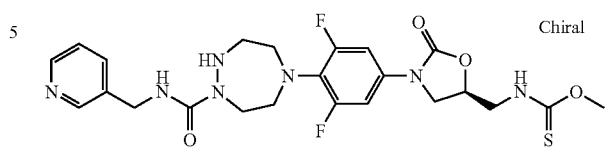

$^1$H NMR (CDCl$_3$) δ=3.12-3.20 (2H, m), 3.28-3.36 (4H, m), 3.75-4.08 (6H, m), 3.99 (3H, s, CH$_3$OC=S), 4.55 (2H, d, J=5.9 Hz, heteroaryl-CH$_2$NHC=O), 4.88-4.98 (1H, m), 7.09 (2H, d, J=10.7 Hz), 7.17 (1H, ddd, J=1.1, 4.9, 7.5 Hz), 7.27 (1H, t, J=5.8 Hz), 7.32 (1H, d, J=7.5 Hz), 7.48 (1H, t, J=6.2 Hz), 7.65 (1H, dt, J=1.9, 7.5 Hz), and 8.54 (1H, ddd, J=1.1, 1.9, 4.9 Hz).

Example 811

[Chemical Formula 842]

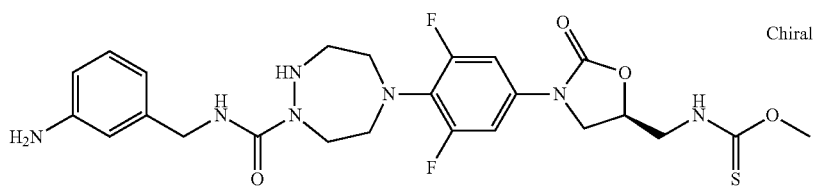

$^1$H NMR (CDCl$_3$) δ=3.07-3.14 (2H, m), 3.28-3.37 (4H, m), 3.59-4.16 (6H, m), 4.00 (3H, s, CH$_3$OC=S), 4.34 (2H, d, J=5.8 Hz, aryl-CH$_2$NHC=O), 4.86-4.96 (1H, m), 6.55-6.92 (5H, m), and 7.03-7.14 (3H, m).

Example 812

[Chemical Formula 843]

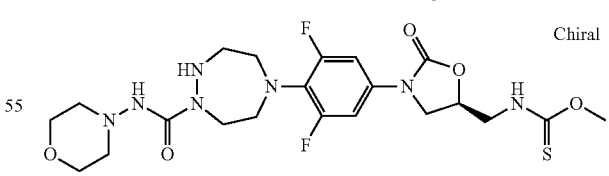

$^1$H NMR (CDCl$_3$) δ=2.75-2.87 (4H, m), 3.08-3.15 (2H, m), 3.25-3.32 (4H, m), 3.64-4.12 (10H, m), 4.00 (3H, s, CH$_3$OC=S), 4.90-5.00 (1H, m), 7.09 (2H, d, J=10.7 Hz), 7.31 (1H, s, N—NHC=O), and 7.45 (1H, t, J=5.9 Hz, NHC=S).

Example 813

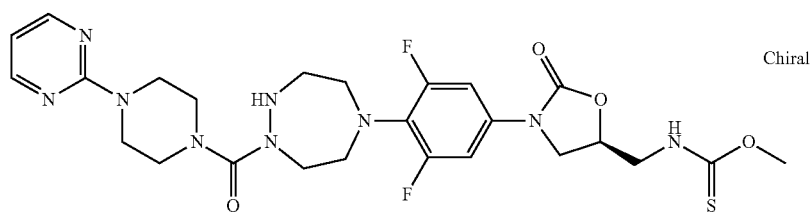

[Chemical Formula 844]

¹H NMR (CDCl₃) δ=3.08-3.15 (2H, m), 3.30-3.37 (2H, m), 3.40-3.46 (2H, m), 3.51-3.57 (4H, m), 3.63-3.69 (2H, m), 3.78-4.13 (8H, m), 4.01 (3H, s, CH₃OC=S), 4.88-4.98 (1H, m), 6.51 (1H, t, J=4.7 Hz), 6.86 (1H, t, J=6.0 Hz, NHC=S), 7.10 (2H, d, J=10.7 Hz), and 8.32 (2H, d, J=4.7 Hz).

Example 814

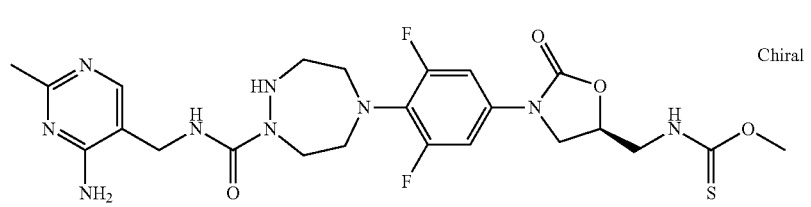

[Chemical Formula 845]

¹H NMR (CDCl₃) δ=2.47 (3H, s, CH₃-heteroaryl), 3.05-3.14 (2H, m), 3.25-3.36 (4H, m), 3.60-4.13 (6H, m), 4.01 (3H, s, CH₃OC=S), 4.26 (2H, d, J=6.9 Hz, heteroaryl-CH₂NHC=O), 4.88-4.98 (1H, m), 6.21 (2H, br s, heteroaryl-NH₂), 6.82 (1H, t, J=6.0 Hz), 7.10 (2H, d, J=10.7 Hz), 7.14 (1H, t, J=6.0 Hz), and 7.96 (1H, s).

Example 815

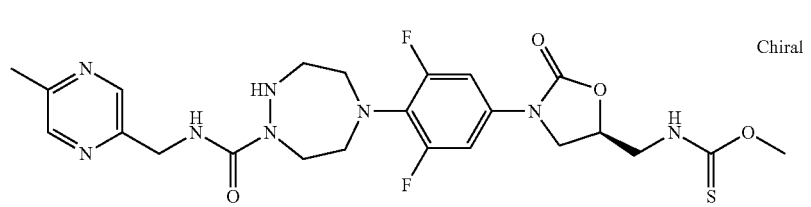

[Chemical Formula 846]

¹H NMR (CDCl₃) δ=2.56 (3H, s, CH₃-heteroaryl), 3.10-3.19 (2H, m), 3.29-3.37 (4H, m), 3.63-4.13 (6H, m), 4.00 (3H, s, CH₃OC=S), 4.56 (2H, d, J=5.9 Hz, heteroaryl-CH₂NHC=O), 4.87-4.97 (1H, m), 6.92 (1H, t, J=6.0 Hz), 7.10 (2H, d, J=10.7 Hz), 7.16 (1H, t, J=6.0 Hz), 8.39 (1H, s), and 8.52 (1H, s).

Example 816

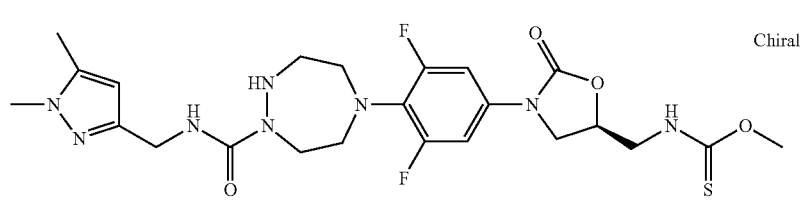

[Chemical Formula 847]

¹H NMR (CDCl₃) δ=2.23 (3H, s, CH₃—C=C—), 3.05-3.14 (2H, m), 3.27-3.36 (4H, m), 3.62-4.12 (6H, m), 3.73 (3H, CH₃—N—N=C), 4.00 (3H, s, CH₃OC=S), 4.35 (2H, d, J=5.9 Hz, heterocycle-CH₂NHC=O), 4.87-4.97 (1H, m), 5.98 (1H, s, Me-C=CH—C), 6.80 (1H, t, J=6.0 Hz), 6.89 (1H, t, J=6.0 Hz), and 7.09 (2H, d, J=10.7 Hz).

Example 817

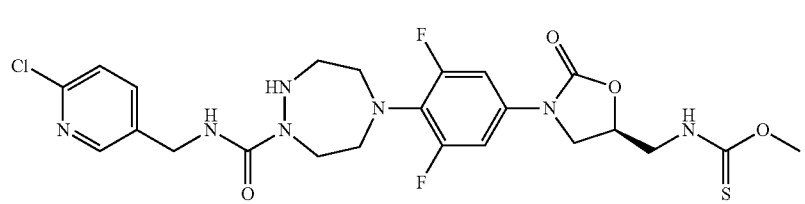

[Chemical Formula 848]

¹H NMR (CDCl₃) δ=3.07-3.15 (2H, m), 3.27-3.38 (4H, m), 3.62-4.13 (6H, m), 4.00 (3H, s, CH₃OC=S), 4.42 (2H, d, J=6.3 Hz, heteroaryl-CH₂NHC=O), 4.87-4.97 (1H, m), 6.86 (1H, t, J=6.0 Hz), 6.88 (1H, t, J=6.0 Hz), 7.10 (2H, d, J=10.7 Hz), 7.29 (1H, d, J=8.0 Hz), 7.66 (1H, dd, J=2.5, 8.0 Hz), and 8.33 (1H, d, J=2.5 Hz).

Example 818

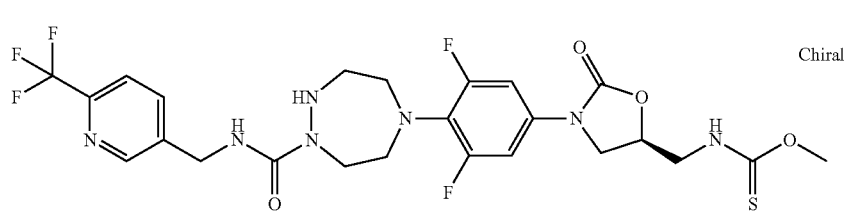

[Chemical Formula 849]

¹H NMR (CDCl₃) δ=3.09-3.16 (2H, m), 3.29-3.38 (4H, 3.60-4.13 (6H, m), 4.01 (3H, s, CH₃OC=S), 4.52 (2H, d, J=6.1 Hz, heteroaryl-CH₂NHC=O), 4.87-4.97 (1H, m), 6.81 (1H, t, J=6.0 Hz), 6.94 (1H, t, J=6.0 Hz), 7.10 (2H, d, J=10.7 Hz), 7.65 (1H, d, J=8.2 Hz), 7.87 (1H, br d, J=8 Hz), and 8.67 (1H, br s).

Example 819

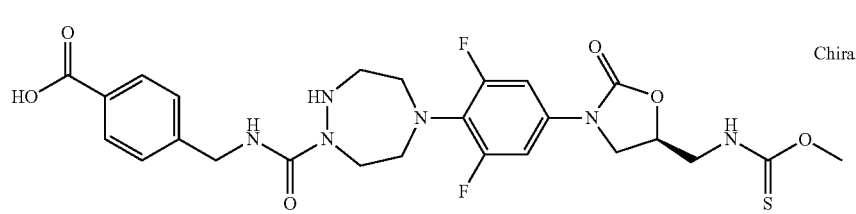

[Chemical Formula 850]

¹H NMR (CDCl₃) δ=3.08-3.17 (2H, m), 3.30-3.41 (4H, m), 3.65-4.13 (6H, m), 4.01 (3H, s, CH₃OC=S), 4.51 (2H, d, J=6.0 Hz, aryl-CH₂NHC=O), 4.87-4.97 (1H, m), 6.77 (1H, t, J=6.0 Hz), 6.93 (1H, t, J=6.0 Hz), 7.10 (2H, d, J=10.7 Hz), 7.40 (2H, d, J=8.5 Hz), and 8.02 (2H, d, J=8.5 Hz).

Example 820

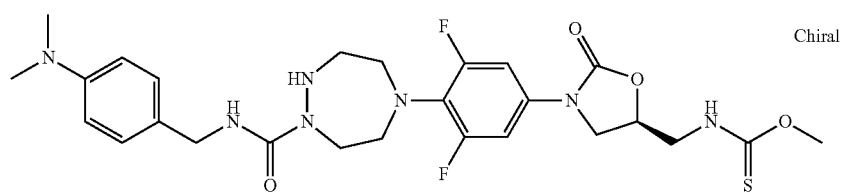

[Chemical Formula 851]

¹H NMR (CDCl₃) δ=2.93 (6H, s, CH₃NCH₃), 3.04-3.12 (2H, m), 3.26-3.37 (4H, m), 3.58-4.09 (6H, m), 3.99 (3H, s, CH₃OC=S), 4.32 (2H, d, J=5.8 Hz, aryl-CH₂NHC=O), 4.86-4.96 (1H, m), 6.67 (1H, t, J=6.0 Hz), 6.71 (2H, d, J=8.8 Hz), 7.06 (1H, t, J=6.0 Hz), 7.09 (2H, d, J=10.7 Hz), and 7.20 (2H, d, J=8.8 Hz).

Example 821

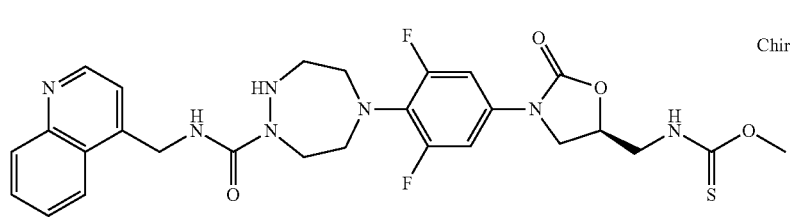

[Chemical Formula 852]

¹H NMR (CDCl₃) δ=3.09-3.18 (2H, m), 3.29-3.41 (4H, m), 3.60-4.10 (6H, m), 3.99 (3H, s, CH₃OC=S), 4.87-4.97 (1H, m), 4.93 (2H, d, J=6.0 Hz, heteroaryl-CH₂NHC=O), 6.94 (1H, t, J=6.0 Hz), 7.01 (1H, t, J=6.0 Hz), 7.10 (2H, d, J=10.7 Hz), 7.39 (1H, d, J=4.4 Hz), 7.60 (1H, t-like, J=8 Hz), 7.73 (1H, t-like, J=8 Hz), 8.07 (1H, br d, J=8 Hz), 8.11 (1H, br d, J=8 Hz), and 8.88 (1H, d, J=4.4 Hz).

Example 822

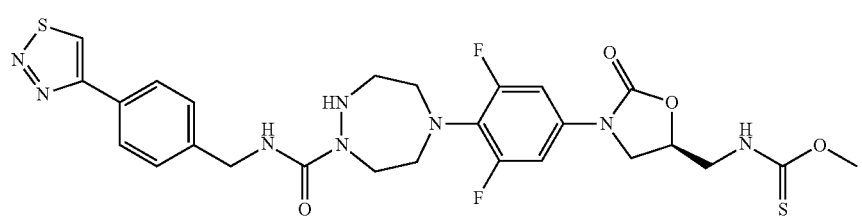

[Chemical Formula 853]

¹H NMR (CDCl₃) δ=3.09-3.17 (2H, m), 3.30-3.39 (4H, m), 3.62-4.10 (6H, m), 4.01 (3H, s, CH₃OC=S), 4.50 (2H, d, J=6.0 Hz, aryl-CH₂NHC=O), 4.87-4.97 (1H, m), 6.90 (1H, t, 6.0 Hz), 6.97 (1H, t, J=6.0 Hz), 7.09 (2H, d, J=10.7 Hz), 7.46 (2H, d, J=8.3 Hz), 8.00 (2H, d, J=8.3 Hz), and 8.64 (1H, s).

Example 823

[Chemical Formula 854]

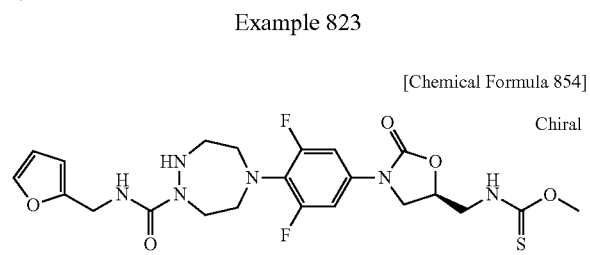

¹H NMR (CDCl₃) δ=3.08-3.15 (2H, m), 3.27-3.37 (4H, m), 3.60-4.12 (6H, m), 4.01 (3H, s, CH₃OC=S), 4.42 (2H, d, J=6.0 Hz, heterocycle-CH₂NHC=O), 4.87-4.97 (1H, m), 6.21 (1H, d, J=3.0 Hz), 6.32 (1H, dd, J=1.9, 3.0 Hz), 6.76 (2H, br t, J=6 Hz), 7.09 (2H, d, J=10.7 Hz), and 7.36 (1H, d, J=1.9 Hz).

Example 824

[Chemical Formula 855]

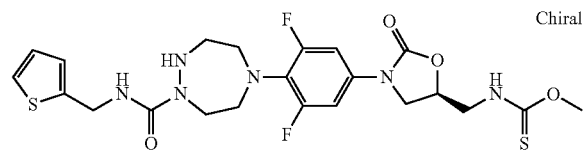

¹H NMR (CDCl₃) δ=3.07-3.15 (2H, m), 3.27-3.38 (4H, m), 3.65-4.12 (6H, m), 4.00 (3H, s, CH₃OC=S), 4.60 (2H, d, J=6.0 Hz, heterocycle-CH₂NHC=O), 4.87-4.97 (1H, m), 6.77-6.86 (2H, m), 6.92-7.00 (2H, m), 7.10 (2H, d, J=10.7 Hz), and 7.20 (1H, dd, J=1.4, 4.9 Hz).

Example 825

[Chemical Formula 856]

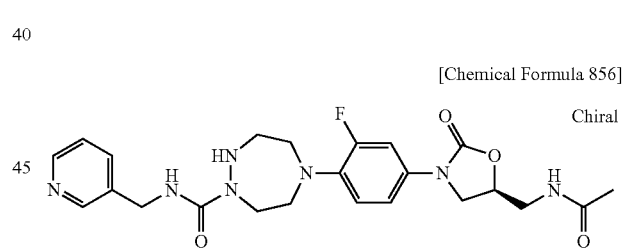

¹H NMR (CDCl₃) δ=2.00 (1H, s, CH₃C=O), 3.10-3.20 (2H, m), 3.34-3.43 (4H, m), 3.55-3.92 (5H, m), 3.99 (1H, t, J=9.1 Hz), 4.42 (2H, d, J=6.2 Hz, heteroaryl-CH₂NHC=O), 4.73-4.83 (1H, m), 6.84-6.93 (2H, m), 7.01 (1H, br d, J=9 Hz), 7.22-7.26 (1H, m), 7.06 (1H, t, J=6.1 Hz), 7.24 (1H, dd, J=5.0, 7.4 Hz), 7.38 (1H, br d, J=15 Hz), 7.64 (1H, br d, J=7 Hz), 8.48 (1H, br d, J=5 Hz), and 8.54 (1H, br s).

Example 826

[Chemical Formula 857]

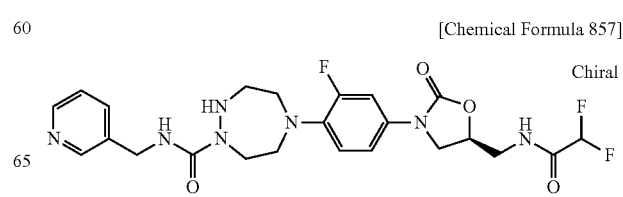

$^1$H NMR (CDCl$_3$) δ=3.12-3.20 (2H, m), 3.36-3.45 (4H, m), 3.57-3.94 (5H, m), 4.07 (1H, t, J=9.1 Hz), 4.43 (2H, d, J=6.3 Hz, heteroaryl-CH$_2$NHC=O), 4.75-4.86 (1H, m), 5.93 (1H, t, J=54.0 Hz, CHF$_2$), 6.83 (1H, t, J=6.1 Hz, NHC=O), 6.90 (1H, t, J=9.1 Hz), 7.01 (1H, dd, J=2.8, 9.1 Hz), 7.22-7.26 (1H, m), 7.38 (1H, dd, J=2.8, 14.6 Hz), 7.65 (1H, br d, J=7 Hz), 8.50 (1H, dd, J=1.4, 4.7 Hz), and 8.55 (1H, d, J=1.4 Hz).

Example 827

[Chemical Formula 858]

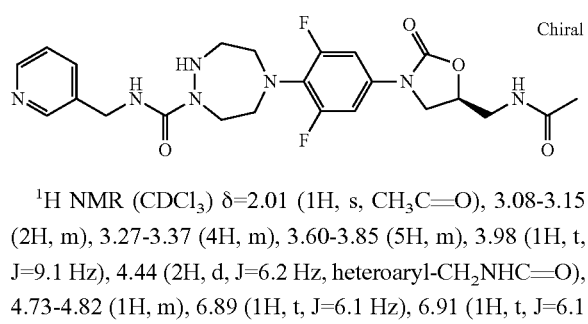

$^1$H NMR (CDCl$_3$) δ=2.01 (1H, s, CH$_3$C=O), 3.08-3.15 (2H, m), 3.27-3.37 (4H, m), 3.60-3.85 (5H, m), 3.98 (1H, t, J=9.1 Hz), 4.44 (2H, d, J=6.2 Hz, heteroaryl-CH$_2$NHC=O), 4.73-4.82 (1H, m), 6.89 (1H, t, J=6.1 Hz), 6.91 (1H, t, J=6.1 Hz), 7.08 (2H, d, J=10.6 Hz), 7.26 (1H, dd, J=4.9, 7.6 Hz), 7.68 (1H, br d, J=8 Hz), 8.49 (1H, br d, J=5 Hz), and 8.56 (1H, br s).

Example 828

[Chemical Formula 859]

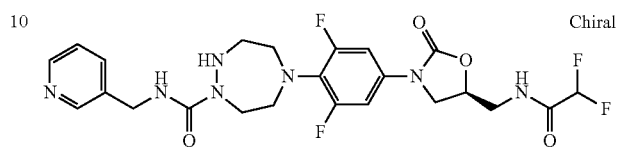

$^1$H NMR (CDCl$_3$) δ=3.08-3.15 (2H, m), 3.28-3.38 (4H, m), 3.60-3.87 (5H, m), 4.05 (1H, t, J=9.1 Hz), 4.45 (2H, d, J=6.3 Hz, heteroaryl-CH$_2$NHC=O), 4.77-4.87 (1H, m), 5.93 (1H, t, J=54.0 Hz, CHF$_2$), 6.87 (1H, t, J=6.1 Hz, NHC=O), 6.90 (1H, t, J=9.1 Hz), 7.08 (2H, d, J=10.6 Hz), 7.22-7.40 (2H, m), 7.67 (1H, br d, J=8 Hz), 8.50 (1H, dd, J=1.5, 4.7 Hz), and 8.57 (1H, d, J=1.5 Hz).

Example 829

[Chemical Formula 860]

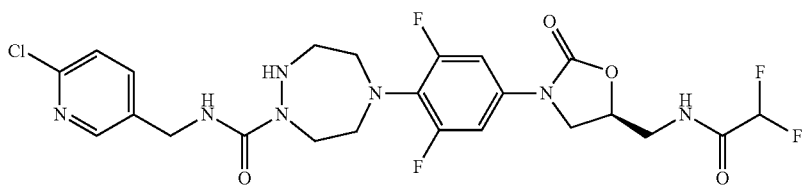

$^1$H NMR (CDCl$_3$) δ=3.07-3.15 (2H, m), 3.28-3.38 (4H, m), 3.60-3.87 (5H, m), 4.05 (1H, t, J=9.1 Hz), 4.41 (2H, d, J=6.3 Hz, heteroaryl-CH$_2$NHC=O), 4.77-4.84 (1H, m), 5.93 (1H, t, J=54.0 Hz, CHF$_2$), 6.88 (1H, t, J=6.1 Hz, NHC=O), 7.08 (2H, d, J=10.6 Hz), 7.29 (1H, d, J=8.2 Hz), 7.66 (1H, dd, J=2.5, 8.2 Hz), and 8.33 (1H, d, J=2.5 Hz).

Example 830

[Chemical Formula 861]

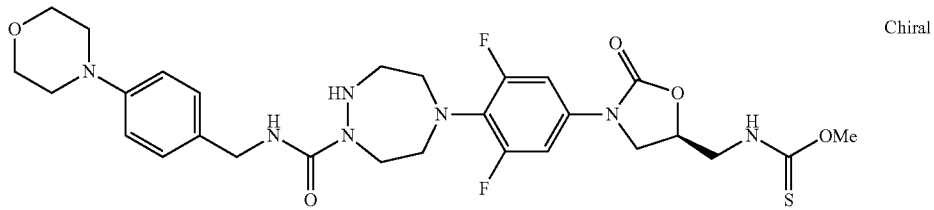

¹H NMR (CDCl₃) δ=3.05-4.12 (20H, m), 4.35 (2H, d, J=6.0 Hz, aryl-CH₂NHC=O), 4.86-4.97 (1H, m), 6.71 (1H, t, J=6.0 Hz), 6.79 (1H, t, J=6.0 Hz), 6.88 (2H, d, J=8.9 Hz), 7.10 (2H, d, J=10.7 Hz), and 7.24 (2H, d, J=8.9 Hz)

Example 831

¹H NMR (CD₃OD) δ=2.38 (3H, s, heterocycle-CH₃), 2.55 (3H, s, heterocycle-CH₃), 3.26-3.40 (6H, m), 3.81-3.92 (5H, m), 3.94 (3H, s, CH₃OC=S), 4.10 (1H, t, J=9.1 Hz), 4.26 (2H, s, NHCH₂-heterocycle), 4.90-5.00 (1H, m, NCH₂CHCH₂NHC=O), and 7.23 (2H, d, J=11.0 Hz).

Example 834

[Chemical Formula 862]

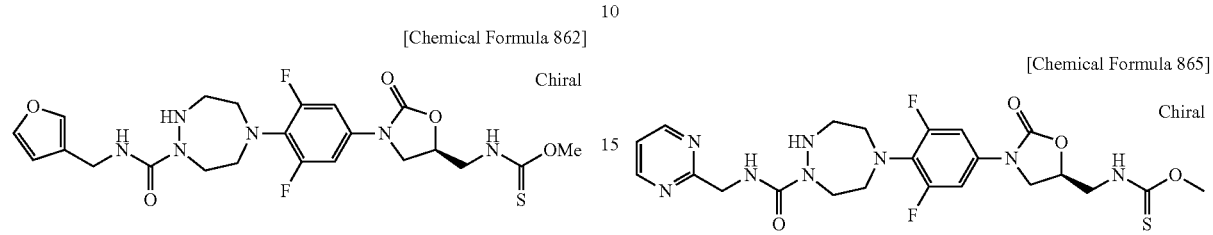

[Chemical Formula 865]

¹H NMR (CDCl₃) δ=3.05-3.13 (2H, m), 3.27-3.36 (4H, m), 3.63-4.11 (6H, m), 4.00 (3H, s, CH₃OC=S), 4.27 (2H, d, J=6.0 Hz, heterocycle-CH₂NHC=O), 4.87-4.97 (1H, m), 6.40 (1H, br s), 6.63 (1H, t, J=6.1 Hz), 6.97 (1H, t, J=6.1 Hz), 7.09 (2H, d, J=10.7 Hz), and 7.37 (2H, br s).

Example 832

¹H NMR (CDCl₃) δ=3.18-3.25 (2H, m), 3.32-3.38 (4H, m), 3.75-4.14 (6H, m), 4.01 (3H, s, CH₃OC=S), 4.72 (2H, d, J=5.8 Hz, NHCH₂-heterocycle), 4.87-4.97 (1H, m, NCH₂CHCH₂NHC=O), 6.74 (1H, t, J=5.8 Hz), 7.10 (2H, d, J=10.4 Hz), 7.19 (1H, t, J=5.0 Hz), 7.38 (1H, t, J=6.0 Hz), and 8.72 (2H, d, J=5.0 Hz).

[Chemical Formula 863]

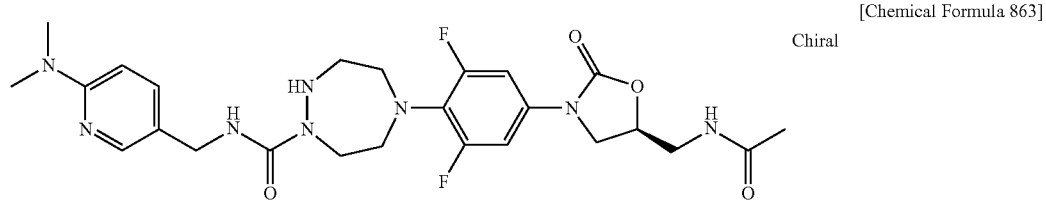 [SMILES: CC(=O)NC[C@H]1CN(c2cc(F)c(N3CCNN(C(=O)NCc4ccc(N(C)C)nc4)CC3)c(F)c2)C(=O)O1]

¹H NMR (CDCl₃) δ=2.02 (3H, s, CH₃C=O), 3.02-3.13 (2H, m), 3.08 (6H, s, CH₃NCH₃), 3.26-3.38 (4H, m), 3.56-3.85 (5H, m), 3.98 (1H, t, J=9.8 Hz), 4.28 (2H, d, J=5.8 Hz, NHCH₂-heterocycle), 4.72-4.83 (1H, m, NCH₂CHCH₂NHC=O), 6.24 (1H, t, J=6.0 Hz), 6.51 (1H, d, J=8.8 Hz), 6.65 (1H, t, J=5.8 Hz), 7.09 (2H, d, J=10.7 Hz), 7.48 (1H, dd, J=2.5, 8.8 Hz), and 8.10 (1H, d, J=2.5 Hz).

Example 833

[Chemical Formula 864]

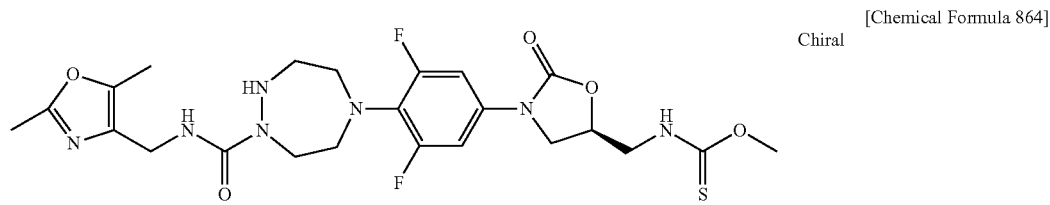

Example 835

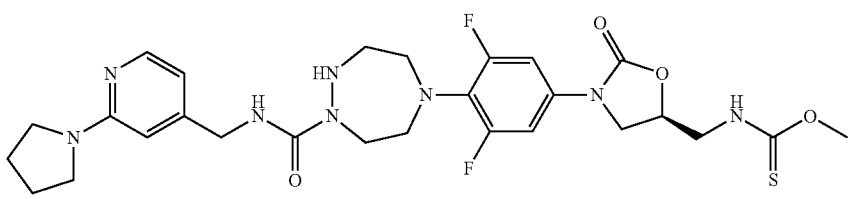
[Chemical Formula 866]
Chiral $^1$H NMR (CDCl$_3$) δ=1.97-2.03 (4H, m, NCH$_2$CH$_2$CH$_2$CH$_2$N), 3.09-3.17 (2H, m), 3.30-3.38 (4H, m), 3.42-3.50 (4H, m, NCH$_2$CH$_2$CH$_2$CH$_2$N), 3.65-4.14 (6H, m), 4.01 (3H, s, CH$_3$OC=S), 4.37 (2H, d, J=6.1 Hz, NHCH$_2$-heterocycle), 4.87-4.97 (1H, m, NCH$_2$CHCH$_2$NHC=O), 6.30 (1H, s), 6.48 (1H, d, J=5.2 Hz), 6.81 (2H, br t, J=6 Hz), 7.10 (2H, d, J=10.7 Hz), and 8.09 (1H, d, J=5.2 Hz).

Example 836

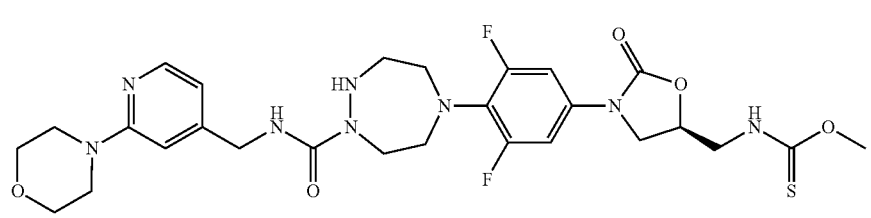
[Chemical Formula 867]
Chiral $^1$H NMR (CDCl$_3$) δ=3.09-3.17 (2H, m), 3.30-3.39 (4H, m), 3.46-3.54 (4H, m, NCH$_2$CH$_2$OCH$_2$CH$_2$N), 3.65-4.12 (6H, m), 3.78-3.86 (4H, m, NCH$_2$CH$_2$OCH$_2$CH$_2$N), 4.01 (3H, s, CH$_3$OC=S), 4.36 (2H, d, J=6.2 Hz, NHCH$_2$-heterocycle), 4.87-4.97 (1H, m, NCH$_2$CHCH$_2$NHC=O), 6.59 (1H, s), 6.62 (1H, d, J=5.2 Hz), 6.76 (1H, br t, J=6 Hz), 6.84 (1H, br t, J=6 Hz), 7.09 (2H, d, J=10.7 Hz), and 8.14 (1H, d, J=5.2 Hz).

Example 837

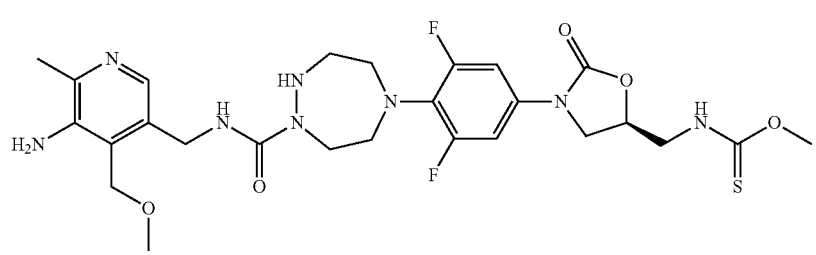
[Chemical Formula 868]
Chiral $^1$H NMR (CDCl$_3$) δ=2.43 (3H, s, heterocycle-CH$_3$), 3.01-3.08 (2H, m), 3.24-3.38 (4H, m), 3.40 (3H, s, heterocycle-CH$_2$OCH$_3$), 3.60-4.14 (6H, m), 4.01 (3H, s, CH$_3$OC=S), 4.27 (2H, br s, hererocycle-NH$_2$), 4.41 (2H, d, J=5.5 Hz, NHCH$_2$-heterocycle), 4.60 (2H, s, heterocycle-CH$_2$OCH$_3$), 4.88-4.97 (1H, m, NCH$_2$CHCH$_2$NHC=O), 6.57 (1H, br t, J=6 Hz), 6.87 (1H, br t, J=6 Hz), 7.10 (2H, d, J=10.7 Hz), and 7.88 (1H, s).

Example 838

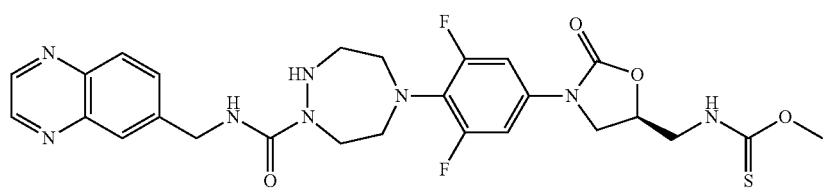

[Chemical Formula 869]

¹H NMR (CDCl₃) δ=3.08-3.20 (2H, m), 3.32-3.41 (4H, m), 3.72-4.14 (6H, m), 4.01 (3H, s, CH₃OC=S), 4.70 (2H, d, J=6.0 Hz, NHCH₂-heterocycle), 4.88-4.98 (1H, m, NCH₂CHCH₂NHC=O), 6.75 (1H, br t, J=6 Hz), 7.05 (1H, br t, J=6 Hz), 7.11 (2H, d, J=10.7 Hz), 7.78 (1H, br d, J=9 Hz), 8.00 (1H, s), 8.09 (1H, d, J=8.6 Hz), and 8.82-8.86 (2H, m).

Example 839

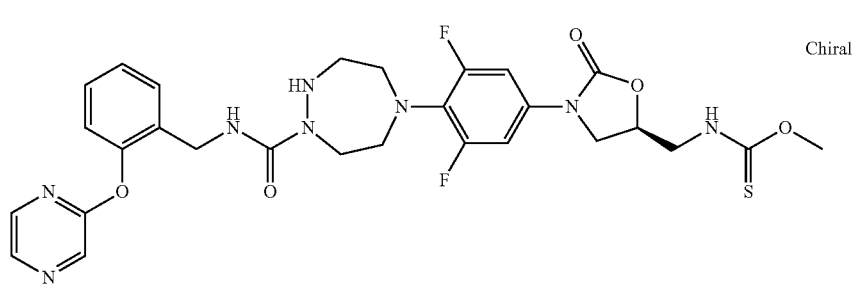

[Chemical Formula 870]

¹H NMR (CDCl₃) δ=2.97-3.05 (2H, m), 3.22-3.33 (4H, m), 3.48-4.12 (6H, m), 4.00 (3H, s, CH₃OC=S), 4.40 (2H, d, J=6.0 Hz, NHCH₂-heterocycle), 4.87-4.97 (1H, m, NCH₂CHCH₂NHC=O), 6.69-6.80 (2H, m), 7.06 (1H, br t, J=6 Hz), 7.09 (2H, d, J=10.7 Hz), 7.28-7.38 (2H, m), 7.49 (1H, dd, J=1.7, 7.4 Hz), 8.08 (1H, br s), 8.26 (1H, d, J=2.8 Hz), and 8.47 (1H, br s).

Example 840

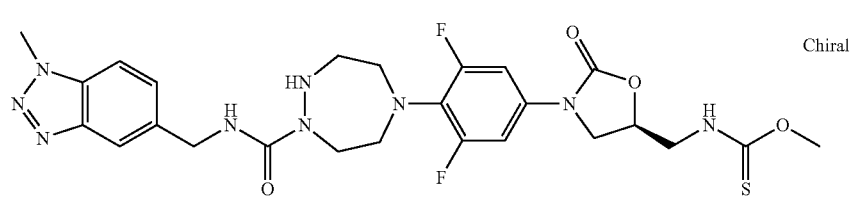

[Chemical Formula 871]

¹H NMR (CDCl₃) δ=3.08-3.15 (2H, m), 3.29-3.38 (4H, m), 3.64-4.16 (6H, m), 4.00 (3H, s, CH₃OC=S), 4.29 (3H, s, N=N—N—CH₃), 4.60 (2H, br d, J=6 Hz, NHCH₂-heterocycle), 4.88-4.98 (1H, m, NCH₂CHCH₂NHC=O), 6.88-6.98 (2H, m), 7.10 (2H, d, J=10.5 Hz), 7.44-7.54 (2H, m), and 7.94 (1H, s).

Example 841

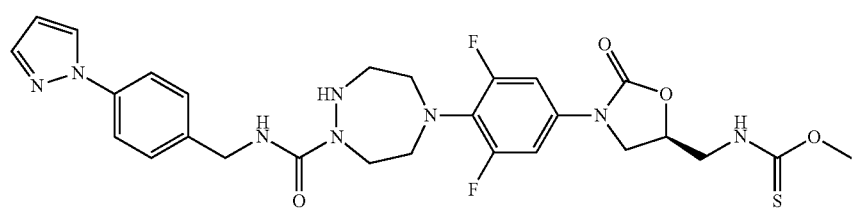

[Chemical Formula 872]

¹H NMR (CDCl₃) δ=3.08-3.15 (2H, m), 3.29-3.39 (4H, m), 3.60-4.16 (6H, m), 4.01 (3H, s, CH₃OC=S), 4.46 (2H, d, J=6.0 Hz, NHCH₂-heterocycle), 4.87-4.97 (1H, m, NCH₂CHCH₂NHC=O), 6.46 (1H, dd, J=1.7, 2.5 Hz), 6.75 (1H, br t, J=6 Hz), 6.85 (1H, br t, J=6 Hz), 7.10 (2H, d, J=10.7 Hz), 7.41 (2H, d, J=8.5 Hz), 7.65 (2H, d, J=8.5 Hz), 7.72 (1H, d, J=1.7 Hz), and 7.91 1H, d, J=2.5 Hz).

Example 842

[Chemical Formula 873]

Chiral

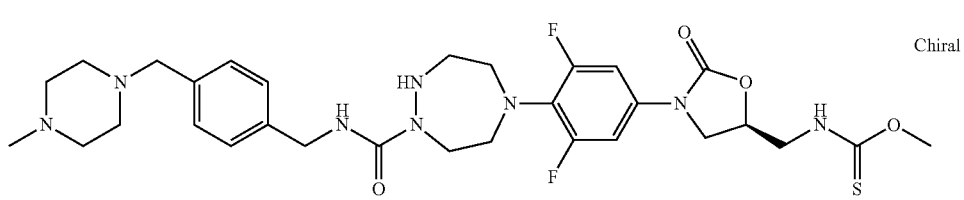

¹H NMR (CDCl₃) δ=2.28 (3H, s, CH₃N), 2.08-2.80 (8H, m), 3.06-3.20 (2H, m), 3.26-3.38 (4H, m), 3.49 (2H, br NCH₂Ph), 3.66-3.12 (6H, m), 3.99 (3H, s, CH₃OC=S), 4.41 (2H, br s, NHCH₂-heterocycle), 4.87-4.97 (1H, m, NCH₂CHCH₂NHC=O), 6.79 (1H, br t, J=6 Hz), 7.10 (2H, d, J=10.7 Hz), and 7.26 (1H, br t, J=6 Hz).

Example 843

[Chemical Formula 874]

Chiral

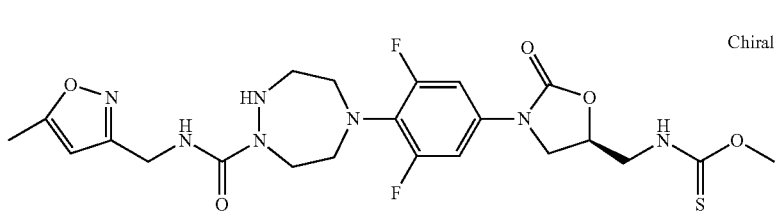

¹H NMR (CDCl₃) δ=2.40 (3H, s, heterocycle-CH₃), 3.08-3.15 (2H, m), 3.26-3.37 (4H, m), 3.65-4.16 (6H, m), 4.01 (3H, s, CH₃OC=S), 4.44 (2H, d, J=6.0 Hz, NHCH₂-heterocycle), 4.87-4.97 (1H, m, NCH₂CHCH₂NHC=O), 6.01 (1H, s), 6.81 (1H, br t, J=6 Hz), 6.90 (1H, br t, J=6 Hz), and 7.10 (2H, d, J=10.7 Hz).

Example 844

[Chemical Formula 875]

Chiral

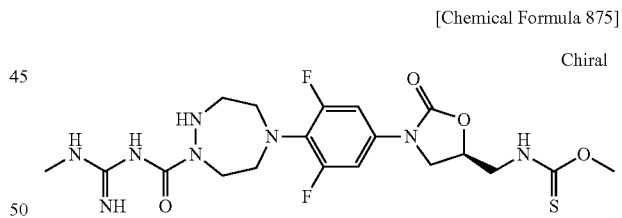

¹H NMR (CDCl₃+DMSO-d₆) δ=2.97 (3H, d, J=4.0 Hz, NHCH₃), 3.15-3.29 (4H, m), 3.34-3.41 (2H, m), 3.76-3.82 (2H, m), 3.82-4.04 (4H, m), 4.00 (3H, s, CH₃OC=S), 4.88-4.98 (1H, m, NCH₂CHCH₂NHC=O), 7.12 (2H, d, J=10.5 Hz), 8.16 (1H, br t, J=6 Hz), and 9.85 (1H, br s).

Example 845

[Chemical Formula 876]

Chiral

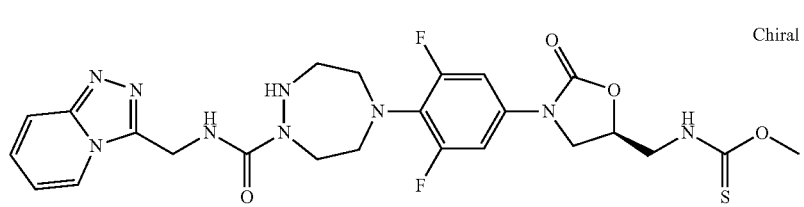

¹H NMR (CDCl₃) δ=2.40 (3H, s, heterocycle-CH₃), 3.03-3.11 (2H, m), 3.21-3.28 (2H, m), 3.31-3.37 (2H, m), 3.68-4.12 (6H, m), 4.00 (3H, s, CH₃OC=S), 4.90-5.00 (1H, m, NCH₂CHCH₂NHC=O), 4.99 (2H, d, J=6.2 Hz, NHCH₂-heterocycle), 6.87 (1H, br t, J=6 Hz), 7.09 (2H, d, J=10.7 Hz), 7.11 (1H, br t, J=6 Hz), 7.25-7.36 (2H, m), 7.73 (1H, br d, J=10 Hz), and 8.59 (1H, br d, J=7 Hz).

¹H NMR (CDCl₃) δ=3.19-3.26 (2H, m), 3.37-3.43 (4H, m), 3.59-3.67 (2H, m), 3.78-4.14 (4H, m), 4.00 (3H, s, CH₃OC=S), 4.59 (2H, d, J=5.6 Hz, NHCH₂-heteroaryl), 4.86-4.96 (1H, m, NCH₂CHCH₂NHC=O), 6.79 (1H, br t, J=6 Hz, NHC=S), 6.90 (1H, t, J=9.1 Hz), 7.02 (1H, br d, J=9 Hz), 7.14-7.30 (2H, m), 7.39 (1H, dd, J=2.8, 14.7 Hz), and 8.26-8.30 (1H, m).

Example 846

[Chemical Formula 877]

Chiral

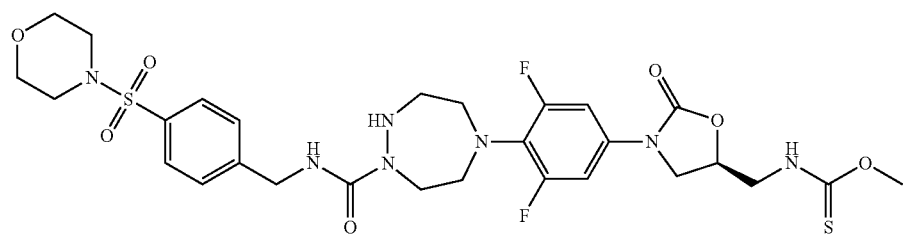

¹H NMR (CDCl₃) δ=2.95-3.02 (4H, m, NCH₂CH₂OCH₂CH₂N), 3.11-3.18 (2H, m), 3.30-3.39 (4H, m), 3.64-4.12 (6H, m), 3.71-3.78 (4H, m, NCH₂CH₂OCH₂CH₂N), 4.00 (3H, s, CH₃OC=S), 4.52 (2H, d, J=6.2 Hz, NHCH₂-heterocycle), 4.88-4.98 (1H, m, NCH₂CHCH₂NHC=O), 6.93-7.00 (2H, m), 7.10 (2H, d, J=10.7 Hz), 7.50 (2H, br d, J=8 Hz), and 7.70 (2H, br d, J=8 Hz).

Example 847

[Chemical Formula 878]

Chiral

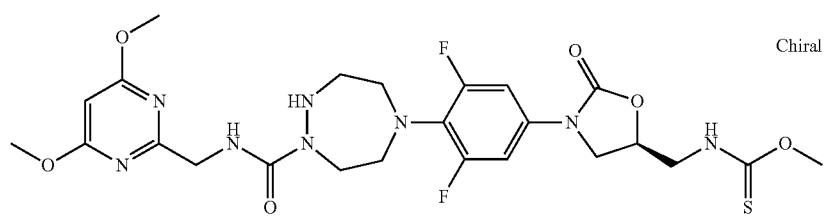

¹H NMR (CDCl₃) δ=3.16-3.24 (2H, m), 3.31-3.38 (4H, m), 3.65-4.10 (6H, m), 3.93 & 3.95 (6H, s, heterocycle-OCH₃×2, two conformers), 4.01 (3H, s, CH₃OC=S), 4.50 & 4.51 (2H, d, J=5.5 Hz, NHCH₂-heterocycle, two conformers), 4.89-4.99 (1H, m, NCH₂CHCH₂NHC=O), 5.73 & 7.18 (1H, br t, J=6 Hz, two conformers), 5.91 (1H, br s), 7.10 (2H, d, J=10.7 Hz), and 7.45 (1H, br t, J=6 Hz).

Example 848

[Chemical Formula 879]

Chiral

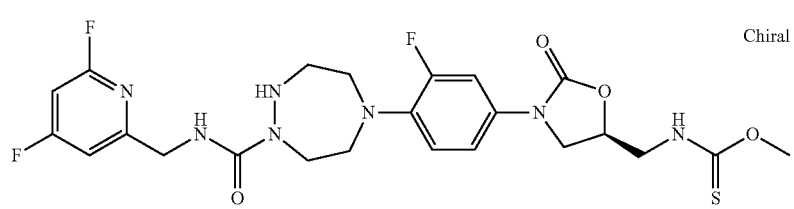

Example 849

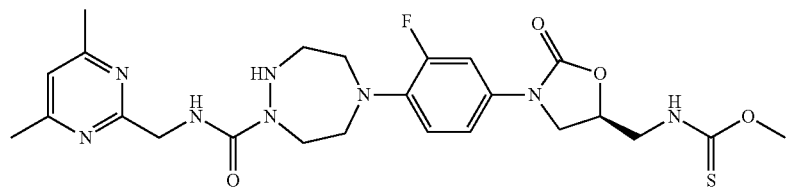

[Chemical Formula 880]

¹H NMR (CDCl₃) δ=2.45 (6H, s, CH₃-heteroaryl×2), 3.24-3.32 (2H, m), 3.39-3.47 (4H, m), 3.61-3.68 (2H, m), 3.78-4.14 (4H, m), 4.00 (3H, s, CH₃OC=S), 4.60 (2H, d, J=5.4 Hz, NHCH₂-heteroaryl), 4.85-4.95 (1H, m, NCH₂CHCH₂NHC=O), 6.72 (1H, br t, J=6 Hz, NHC=S), 6.89 (1H, s), 6.91 (1H, t, J=9.1 Hz), 7.02 (1H, dd, J=2.5, 9.1 Hz), 7.38 (1H, t, J=5.4 Hz, NHCH₂-heteroaryl), and 7.40 (1H, dd, J=2.5, 14.6 Hz).

Example 850

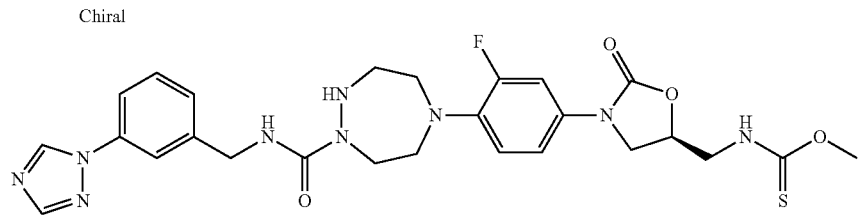

[Chemical Formula 881]

¹H NMR (CDCl₃) δ=3.15-3.23 (2H, m), 3.35-3.45 (4H, m), 3.62-3.71 (2H, m), 3.78-4.11 (4H, m), 4.00 (3H, s, CH₃OC=S), 4.50 (2H, d, J=6.2 Hz, NHCH₂-aryl), 4.86-4.96 (1H, m, NCH₂CHCH₂NHC=O), 6.85-6.95 (2H, m), 7.02 (1H, dd, J=2.5, 9.1 Hz), 7.17 (1H, t, J=6.2 Hz), 7.32-7.49 (3H, m), 7.55 (1H, br d, J=8 Hz), 7.64 (1H, s), 8.09 (1H, s), and 8.57 (1H, s).

Example 851

[Chemical Formula 882]

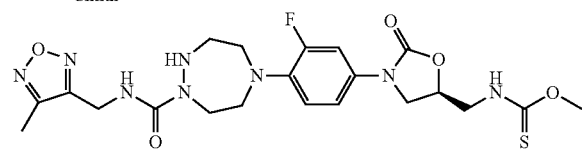

¹H NMR (CDCl₃) δ=2.39 (3H, s, CH₃-heteroaryl), 3.14-3.22 (2H, m), 3.35-3.42 (4H, m), 3.63-3.75 (2H, m), 3.78-4.12 (4H, m), 4.00 (3H, s, CH₃OC=S), 4.55 (2H, d, J=6.1 Hz, NHCH₂-heteroaryl), 4.86-4.97 (1H, m, NCH₂CHCH₂NHC=O), 6.88 (1H, t, J=9.1 Hz), 6.94 (1H, br t, J=6 Hz, NHC=S), 7.01 (1H, dd, J=2.5, 9.1 Hz), 7.11 (1H, t, J=6.1 Hz, NHCH₂-heteroaryl), and 7.38 (1H, dd, J=2.5, 14.6 Hz).

Example 852

[Chemical Formula 883]

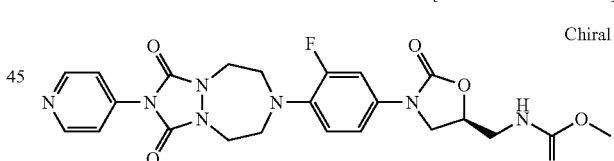

¹H NMR (CDCl₃) δ=3.43-3.50 (4H, m), 3.85 (1H, dd, J=7.1, 9.1 Hz), 3.91-4.21 (7H, m), 4.01 (3H, s, OMe), 4.87-4.98 (1H, m), 6.96-7.13 (3H, m), 7.48 (1H, dd, J=2.5, 15.0 Hz), 7.78 (2H, d, J=4.7 Hz), and 8.70 (2H, d, J=4.7 Hz).

Example 853

[Chemical Formula 884]

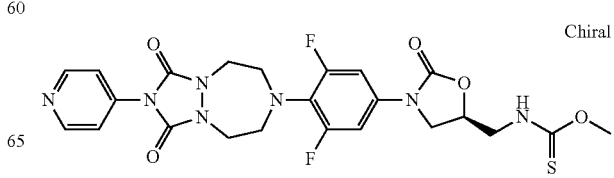

¹H NMR (CDCl₃) δ=3.42-3.49 (4H, m), 3.84 (1H, dd, J=7.1, 9.1 Hz), 3.90-4.19 (7H, m), 4.01 (3H, s, OMe), 4.88-4.99 (1H, m), 6.79 (1H, t, J=6.3 Hz, NHC=S), 7.16 (2H, d, J=10.7 Hz), 7.79 (2H, d, J=4.7 Hz), and 8.71 (2H, d, J=4.7 Hz).

Example 854

[Chemical Formula 885]

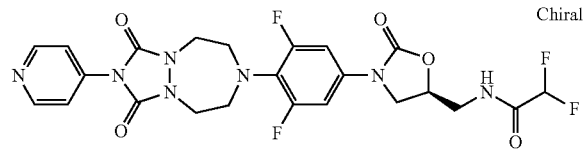

¹H NMR (CDCl₃) δ=3.41-3.50 (4H, m), 3.63-3.76 (2H, m), 3.84 (1H, ddd, J=3.3, 6.3, 14.6 Hz), 4.07 (1H, t, J=9.1 Hz), 4.10-4.16 (4H, m), 4.79-4.89 (1H, m), 5.94 (1H, t, J=54.1 Hz, CHF₂), 7.07-7.15 (1H, br, NHC=O), 7.14 (2H, J=10.7 Hz), 7.78 (2H, d, J=4.7 Hz), and 8.71 (2H, d, J=4.7 Hz).

Example 855

[Chemical Formula 886]

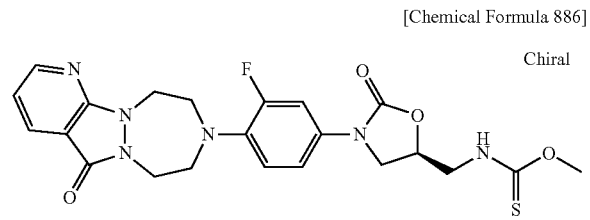 [SMILES: COC(=S)NC[C@H]1CN(c2ccc(N3CCn4c(=O)c5cccnc5n4CC3)c(F)c2)C(=O)O1]

¹H NMR (CDCl₃) δ=3.38-3.50 (4H, m), 3.62-4.14 (4H, m), 4.00 (3H, s, CH₃OC=S), 4.37-4.48 (4H, m), 4.88-4.98 (1H, m), 6.95 (1H, t, J=6.0 Hz, NHC=S), 7.00 (1H, t, J=9.1 Hz), 7.05-7.12 (2H, m), 7.47 (1H, dd, J=2.5, 14.0 Hz), 8.18 (1H, dd, J=1.7, 7.7 Hz), and 8.54 (1H, dd, J=1.7, 4.7 Hz).

Example 856

[Chemical Formula 887]

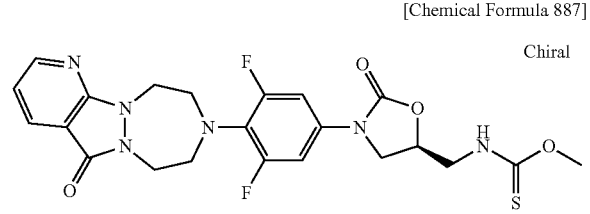 [SMILES: COC(=S)NC[C@H]1CN(c2cc(F)c(N3CCn4c(=O)c5cccnc5n4CC3)c(F)c2)C(=O)O1]

¹H NMR (CDCl₃) δ=3.35-3.50 (4H, m), 3.62-4.14 (4H, m), 4.00 (3H, s, CH₃OC=S), 4.34-4.49 (4H, m), 4.88-5.01 (1H, m), 7.02-7.19 (4H, m), 8.17 (1H, d, J=1.7, 7.7 Hz), and 8.53 (1H, dd, J=1.7, 4.7 Hz)

Example 857

[Chemical Formula 888]

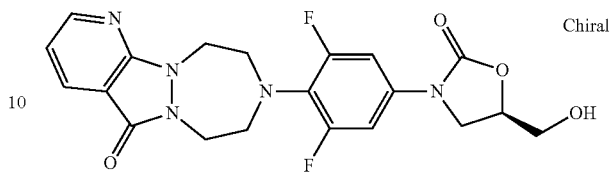

¹H NMR (CDCl₃) δ=2.55 (1H, br t, J=6 Hz, OH), 3.38-3.50 (4H, m), 3.77 (1H, ddd, J=3.6, 7.1, 12.6 Hz), 3.95-4.06 (3H, m), 4.37-4.48 (4H, m), 4.72-4.81 (1H, m), 7.07 (1H, dd, J=4.7, 7.7 Hz), 7.17 (2H, d, J=10.8 Hz), 8.18 (1H, dd, J=1.7, 7.7 Hz), and 8.53 (1H, dd, J=1.7, 4.7 Hz).

Example 858

[Chemical Formula 889]

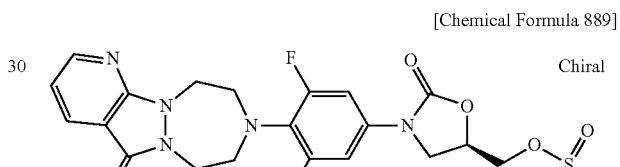

¹H NMR (CDCl₃) δ=3.02 (3H, s, CH₃SO₂), 3.38-3.52 (4H, m), 3.84-3.95 (1H, m), 4.11 (1H, t, J=9.1 Hz), 4.37-4.54 (6H, m), 4.89-4.99 (1H, m), 7.07 (1H, dd, J=4.7, 7.7 Hz), 7.17 (2H, d, J=10.8 Hz), 8.18 (1H, dd, J=1.7, 7.7 Hz), and 8.53 (1H, dd, J=1.7, 4.7 Hz).

Example 859

[Chemical Formula 890]

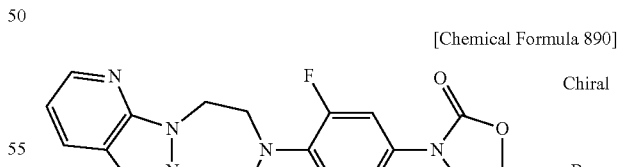

¹H NMR (CDCl₃) δ=3.39-3.51 (4H, m), 3.58 (1H, dd, J=7.1, 10.7 Hz, CHHBr), 3.65 (1H, dd, J=3.8, 10.7 Hz, CHHBr), 3.83 (1H, dd, J=5.8, 9.1 Hz), 4.12 (1H, t, J=9.1 Hz), 4.37-4.48 (4H, m), 4.84-4.95 (1H, m), 7.07 (1H, dd, J=4.7, 7.7 Hz), 7.18 (2H, d, J=10.7 Hz), 8.18 (1H, dd, J=1.7, 7.7 Hz), and 8.53 (1H, dd, J=1.7, 4.7 Hz).

Example 860

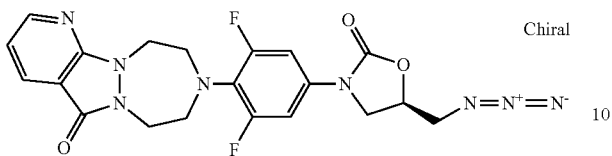
[Chemical Formula 891]

¹H NMR (CDCl₃) δ=3.39-3.51 (4H, m), 3.87-4.15 (4H, m), 4.37-4.52 (4H, m), 4.85-4.95 (1H, m), 7.11 (1H, dd, J=4.7, 7.7 Hz), 7.17 (2H, d, J=10.7 Hz), 8.18 (1H, dd, J=1.6, 7.7 Hz), and 8.53 (1H, dd, J=1.6, 4.7 Hz).

Example 861

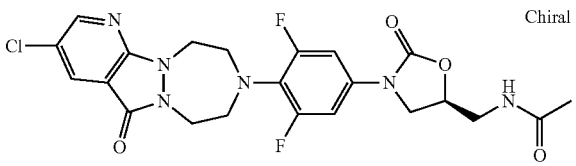
[Chemical Formula 892]

¹H NMR (CDCl₃) δ=2.02 (3H, s, CH₃C=O), 3.36-3.48 (4H, m), 3.61-3.77 (3H, m), 3.99 (1H, t, J=9.1 Hz), 4.35-4.45 (4H, m), 4.73-4.83 (1H, m, NCH₂CHCH₂NHC=O), 6.11 (1H, br t, J=6 Hz), 7.13 (2H, d, J=10.7 Hz), 8.12 (1H, dd, J=1.4, 2.5 Hz), and 8.45 (1H, dd, J=1.4, 2.5 Hz).

Example 862

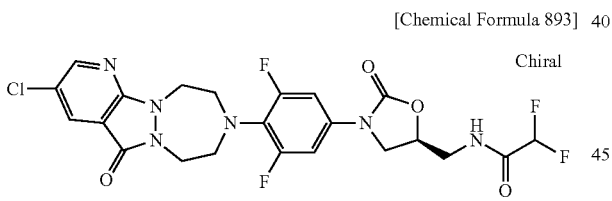
[Chemical Formula 893]

¹H NMR (CDCl₃) δ=3.30-3.40 (4H, m), 3.54-3.83 (3H, m), 4.00 (1H, t, J=9.1 Hz), 4.28-4.39 (4H, m), 4.72-4.82 (1H, m, NCH₂CHCH₂NHC=O), 5.87 (1H, t, J=59.0 Hz, CHF₂), 6.96 (1H, br t, J=6 Hz, NHC=O), 7.07 (2H, d, J=10.7 Hz), 8.06 (1H, dd, J=1.4, 2.5 Hz), and 8.39 (1H, dd, J=1.4, 2.5 Hz).

Example 863

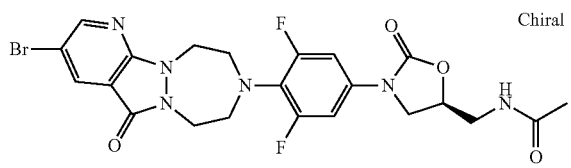
[Chemical Formula 894]

¹H NMR (CDCl₃) δ=2.03 (3H, s, CH₃C=O), 3.37-3.49 (4H, m), 3.63-3.82 (3H, m), 4.00 (1H, t, J=9.1 Hz), 4.35-4.46 (4H, m), 4.74-4.84 (1H, m, NCH₂CHCH₂NHC=O), 6.38 (1H, br t, J=6 Hz, NHC=O), 7.13 (2H, d, J=10.7 Hz), 8.26 (1H, br s), and 8.54 (1H, br s)

Example 864

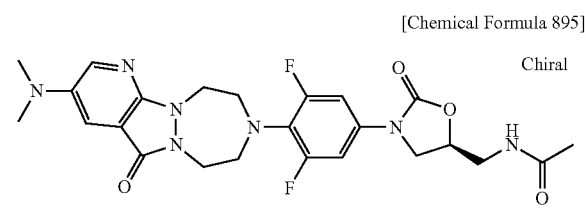 [SMILES: CC(=O)NC[C@H]1CN(c2cc(F)c(N3CCn4c(=O)c5cc(N(C)C)cnc5n4CC3)c(F)c2)C(=O)O1]
[Chemical Formula 895]

¹H NMR (CDCl₃) δ=2.03 (3H, s, CH₃C=O), 2.98 (6H, s, CH₃NCH₃), 3.35-3.52 (4H, m), 3.63-3.79 (3H, m), 4.00 (1H, t, J=9.1 Hz), 4.20-4.35 (4H, m), 4.75-4.84 (1H, m, NCH₂CHCH₂NHC=O), 6.32 (1H, br t, J=6 Hz, NHC=O), 7.13 (2H, d, J=10.7 Hz), 7.45 (1H, d, J=3.0 Hz), and 8.24 (1H, d, J=3.0 Hz).

Example 865

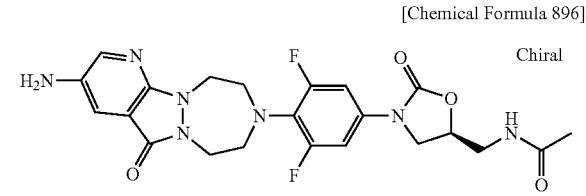 [SMILES: CC(=O)NC[C@H]1CN(c2cc(F)c(N3CCn4c(=O)c5cc(N)cnc5n4CC3)c(F)c2)C(=O)O1]
[Chemical Formula 896]

¹H NMR (CDCl₃) δ=2.03 (3H, s, CH₃C=O), 3.35-3.52 (4H, m), 3.61-3.79 (3H, m), 4.00 (1H, t, J=9.1 Hz), 4.20-4.35 (4H, m), 4.75-4.84 (1H, m, NCH₂CHCH₂NHC=O), 6.19 (1H, br t, J=6 Hz, NHC=O), 7.13 (2H, d, J=10.7 Hz), 7.46 (1H, d, J=2.2 Hz), and 8.13 (1H, d, J=2.2 Hz).

Example 866

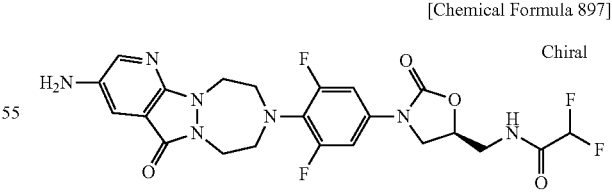
[Chemical Formula 897]

¹H NMR (CDCl₃) δ=3.35-3.52 (4H, m), 3.61-3.90 (3H, m), 4.07 (1H, t, J=9.1 Hz), 4.20-4.35 (4H, m), 4.79-4.88 (1H, m, NCH₂CHCH₂NHC=O), 5.94 (1H, t, J=54.0 Hz, CHF₂), 7.01 (1H, br t, J=6 Hz, NHC=O), 7.13 (2H, d, J=10.7 Hz), 7.46 (1H, d, J=2.8 Hz), and 8.13 (1H, d, J=2.8 Hz).

Example 867

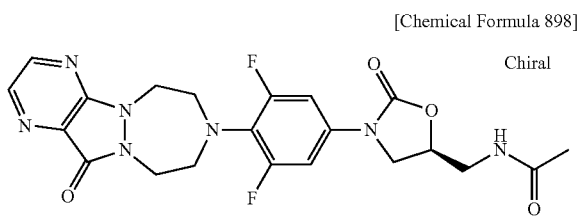 [SMILES: CC(=O)NC[C@H]1CN(c2cc(F)c(N3CCn4c(=O)c5nccnc5n4CC3)c(F)c2)C(=O)O1]

[Chemical Formula 898]

$^1$H NMR (CDCl$_3$) δ=2.05 (3H, s, CH$_3$C=O), 3.40-3.52 (4H, m), 3.68 (2H, dd, J=4.7, 6.1 Hz), 3.79 (1H, dd, J=6.7, 9.1 Hz), 4.00 (1H, t, J=9.1 Hz), 4.44-4.50 (4H, m), 4.75-4.85 (1H, m, NCH$_2$CHCH$_2$NHC=O), 6.47 (1H, br t, J=6 Hz, NHC=O), 7.14 (2H, d, J=10.7 Hz), 8.47 (1H, d, J=8.8 Hz), and 8.48 (1H, d, J=8.8 Hz).

Example 868

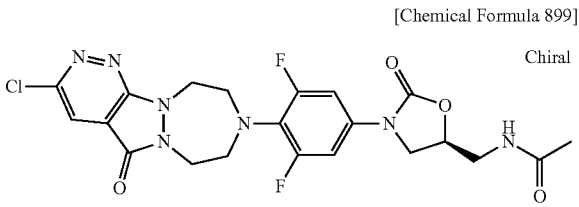 [SMILES: CC(=O)NC[C@H]1CN(c2cc(F)c(N3CCn4c(=O)c5cc(Cl)nnc5n4CC3)c(F)c2)C(=O)O1]

[Chemical Formula 899]

$^1$H NMR (CDCl$_3$) δ=2.03 (3H, s, CH$_3$C=O), 3.44-3.52 (4H, m), 3.62-3.78 (3H, m), 4.00 (1H, t, J=9.1 Hz), 4.40-4.45 (2H, m), 4.61-4.66 (2H, m), 4.74-4.84 (1H, m, NCH$_2$CHCH$_2$NHC=O), 5.93 (1H, br t, J=6 Hz, NHC=O), 7.16 (2H, d, J=10.7 Hz), and 7.92 (1H, s).

Example 869

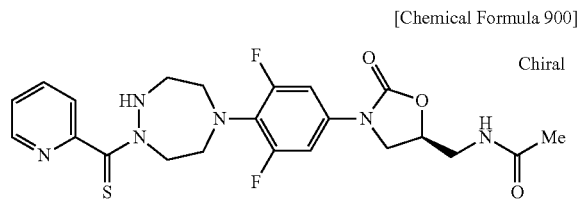 [SMILES: CC(=O)NC[C@H]1CN(c2cc(F)c(N3CCNN(C(=S)c4ccccn4)CC3)c(F)c2)C(=O)O1]

[Chemical Formula 900]

$^1$H NMR (CDCl$_3$) δ=2.02 (3H, s, CH$_3$C=O), 3.30-4.01 (12H, m), 4.72-4.82 (1H, m), 6.10 (1H, t, J=6.0 Hz, NHC=O), 7.08 (2H, d, J=10.7 Hz), 7.49 (1H, br s), 7.60 (1H, br d, J=8 Hz), 7.76 (1H, dt, J=1.7, 7.7 Hz), and 8.53 (1H, br d, J=8 Hz).

Example 870

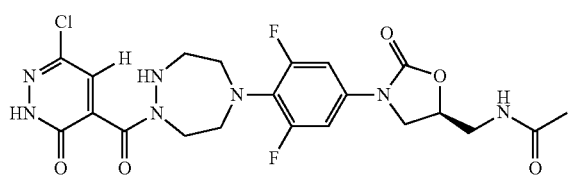

[Chemical Formula 901]

$^1$H NMR (CDCl$_3$) δ=2.03 (3H, s, CH$_3$C=O), 3.05-3.13 (2H, m), 3.25-3.32 (2H, m), 3.40-3.47 (2H, m), 3.64-3.79 (3H, m), 3.93-4.04 (3H, m), 4.75-4.85 (1H, m, NCH$_2$CHCH$_2$NHC=O), 6.36 (1H, br t, J=6 Hz, NHC=O), 7.09 (2H, d, J=10.7 Hz), 7.29 (1H, s), and 11.46 (1H, br s, CO$_2$H).

Example 871

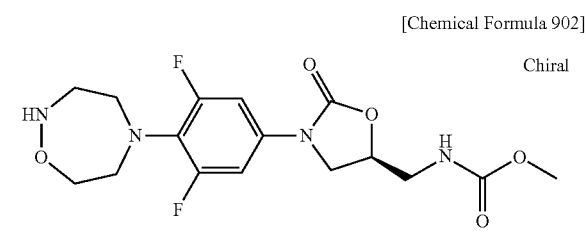 [SMILES: COC(=O)NC[C@H]1CN(c2cc(F)c(N3CCNOCC3)c(F)c2)C(=O)O1]

[Chemical Formula 902]

$^1$H-NMR (300 MHz, CDCl$_3$) δ 3.22 (br t, 5.5, 2H), 3.39 (br t, 5, 2H), 3.48 (br t, 5, 2H), 3.52-3.62 (m, 2H), 3.68 (s, 3H), 3.75 (dd, 9, 7.5, 1H), 3.90 (t, 5.5, 2H), 4.00 (dd, 9, 9, 1H), 4.72-4.82 (m, 1H), 5.65 (br t, 6, NH), 7.01-7.14 (m, 2H)

Example 872

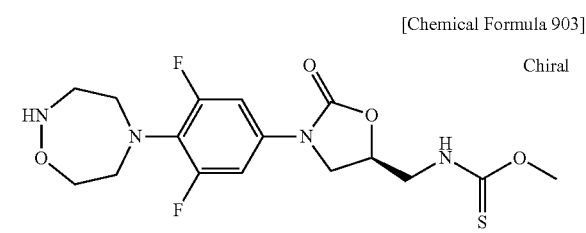

[Chemical Formula 903]

1H-NMR (300 MHz, CDCl$_3$) δ 3.22 (t, 5.5, 2H), 3.40 (br t, 5.5, 2H), 3.49 (t, 5.5, 2H), 3.80 (dd, 9, 7, 1H), 3.90 (t, 5.5, 2H), 3.94-4.12 (m, 3H), 4.00 (s, 3H), 4.88-4.98 (m, 1H), 7.00 (br t, 6, NH), 7.02-7.13 (m, 2H)

Example 873

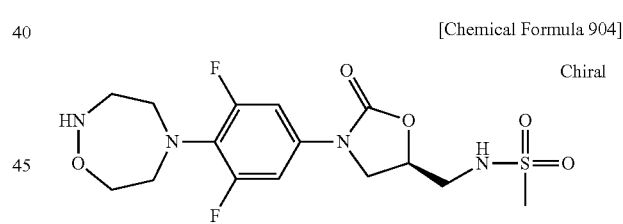

[Chemical Formula 904]

1H-NMR (300 MHz, CDCl$_3$—CD$_3$OD (9:1)) δ 3.00 (s, 3H), 3.19-3.30 (m, 2H), 3.30-3.46 (m, 2H), 3.46-3.56 (m, 3H), 3.92 (t, 5.5, 2H), 3.92 (dd, 9, 6.5, 1H), 4.03 (dd, 9, 9, 1H), 4.75-4.84 (m, 1H), 7.06-7.17 (m, 2H)

Example 874

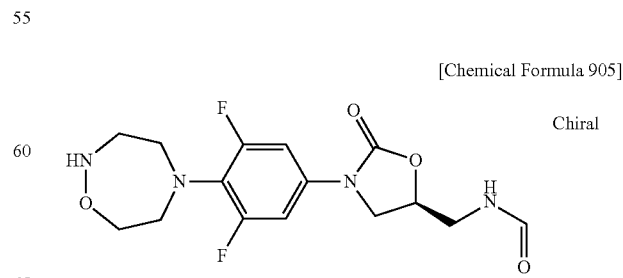

[Chemical Formula 905]

1H-NMR (300 MHz, CDCl$_3$) δ 3.22 (t, 5.5, 2H), 3.40 (t, 5.5, 2H), 3.49 (t, 5.5, 2H), 3.64-3.81 (m, 2H), 3.75 (dd, 9, 7,

1H), 3.90 (t, 5.5, 2H), 4.01 (dd, 9, 9, 1H), 4.77-4.86 (m, 1H), 5.79 (br s, NH), 6.65 (br t, 6, NH), 7.02-7.12 (m, 2H), 8.28 (d, 2, 1H)

Example 875

[Chemical Formula 906]

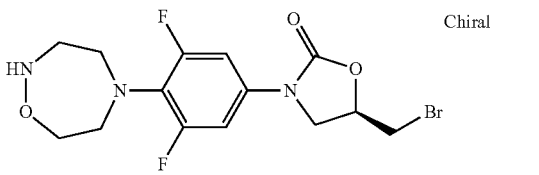

1H-NMR (300 MHz, CDCl₃) δ 2.73 (d, 5, 3H), 3.22 (br t, 5, 2H), 3.39 (br t, 5, 2H), 3.48 (br t, 5.5, 2H), 3.56 (ddd, 15, 6, 3, 1H), 3.70 (ddd, 15, 6, 4.5, 1H), 3.83-3.92 (m, 3H), 3.99 (dd, 9, 9, 1H), 4.75-4.84 (m, 1H), 5.51 (br q, 5, NH), 5.98 (br t, 6, NH), 7.01-7.12 (m, 2H);

Example 876

[Chemical Formula 907]

1H-NMR (300 MHz, CDCl₃) δ 3.22 (t, 5.5, 2H), 3.40 (t, 5.5, 2H), 3.49 (t, 5.5, 2H), 3.58 (dd, 12, 7, 1H), 3.64 (dd, 12, 4, 1H), 3.84 (dd, 9, 6, 1H), 3.90 (t, 5.5, 2H), 4.11 (dd, 9, 9, 1H), 4.88 (dddd, 7, 6, 4, 1H), 5.74 (br s, NH), 7.05-7.16 (m, 2H)

Example 877

[Chemical Formula 908]

1H-NMR (300 MHz, CDCl₃) δ 2.81 (s, 6H), 3.22 (br t, 5.5, 2H), 3.40 (br t, 5, 2H), 3.43-3.54 (m, 4H), 3.88 (dd, 9, 6, 1H), 3.90 (t, 5.5, 2H), 4.01 (dd, 9, 1H), 4.76-4.86 (m, 1H), 5.44 (br s, NH), 7.03-7.14 (m, 2H)

Example 878

[Chemical Formula 909]

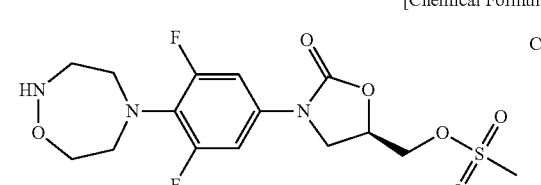

1H-NMR (300 MHz, CDCl₃) δ 3.11 (s, 3H), 3.23 (t, 5, 2H), 3.41 (t, 5, 2H), 3.50 (t, 5, 2H), 3.85-3.93 (m, 3H), 4.10 (dd, 9, 9, 1H), 4.42 (dd, 12, 4, 1H), 4.51 (dd, 12, 3.5, 1H), 4.89-4.98 (m, 1H), 7.04-7.15 (m, 2H);

Example 879

[Chemical Formula 910]

1H-NMR (300 MHz, CDCl₃—CD₃OD (9:1)) δ 3.21 (t, 5, 2H), 3.39 (br t, 5, 2H), 3.47 (br t, 5.5, 2H), 3.90 (t, 5.5, 2H), 3.74-3.88 (m, 3H), 4.07 (dd, 9, 9, 1H), 4.85-4.94 (m, 1H), 6.88 (ddd, 8, 8, 1, 1H), 6.94 (dd, 8, 1, 1H), 7.01-7.12 (m, 2H), 7.39 (ddd, 8, 8, 1.5, 1H), 7.68 (dd, 8, 1.5, 1H);

Example 880

[Chemical Formula 911]

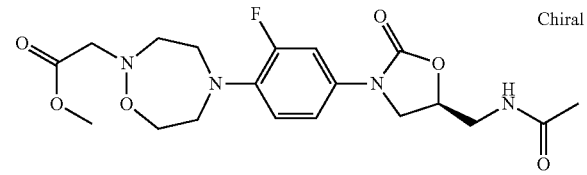

1H-NMR (300 MHz, CDCl₃) δ 2.02 (s, 3H), 3.06 (t, 5.5, 2H), 3.54-3.78 (m, 9H), 3.72 (s, 3H), 3.99 (dd, 9, 9, 1H), 4.00 (t, 6, 2H), 4.70-4.80 (m, 1H), 6.41 (br t, 6, NH), 6.89 (dd, 9, 9, 1H), 7.01 (br dd, 9, 2.5, 1H), 7.34 (dd, 15.5, 2.5, 1H)

Example 881

[Chemical Formula 912]

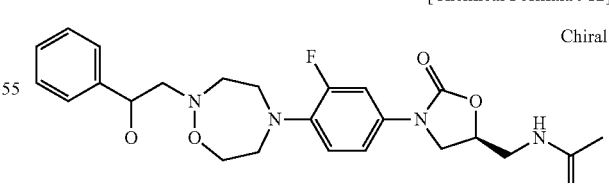

1H-NMR (300 MHz, CDCl₃) δ 2.02 (s, 3H), 3.14 (br t, 5.5, 2H), 3.55-3.71 (m, 6H), 3.73 (dd, 9, 7, 1H), 3.88 (br t, 5.5, 2H), 3.99 (dd, 9, 9, 1H), 4.16 (br s, 2H), 4.71-4.81 (m, 1H), 6.47 (br t, 6, NH), 6.88 (dd, 9, 9, 1H), 7.01 (br dd, 9, 2.5, 1H), 7.33 (dd, 15.5, 2.5, 1H), 7.44 (dd, 7.5, 7.5, 2H), 7.56 (dddd, 7.5, 7.5, 1, 1, 1H), 7.96 (dd, 7.5, 1, 2H);

Example 882

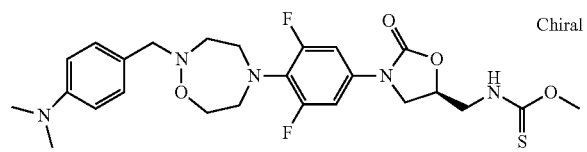

[Chemical Formula 913]

1H-NMR (300 MHz, CDCl$_3$) δ 2.94 (s, 6H), 2.96 (t, 5.5, 2H), 3.37 (br t, 5, 2H), 3.45 (br t, 5.5, 2H), 3.76 (br t, 5.5, 2H), 3.81 (s, 2H), 3.91-4.12 (m, 4H), 4.00 (s, 3H), 4.86-4.95 (m, 1H), 6.70 (A$_2$B$_2$, J=9, 2H), 6.84 (br t, 6, NH), 6.99-7.11 (m, 2H), 7.24 (A$_2$B$_2$, J=9, 2H);

Example 883

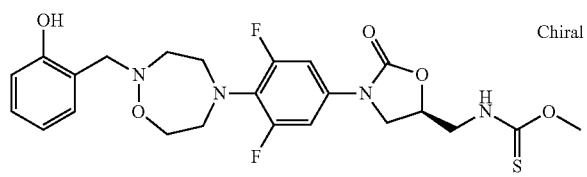

[Chemical Formula 914]

1H-NMR (300 MHz, CDCl$_3$) δ 3.11 (t, 5.5, 2H), 3.40-3.50 (m, 4H), 3.80 (dd, 9, 7, 1H), 3.90 (br t, 5.5, 2H), 3.94-4.14 (m, 4H), 4.00 (s, 3H), 4.10 (s, 2H), 4.86-4.96 (m, 1H), 6.79-6.94 (m, 3H), 7.00-7.15 (m, 2H+NH), 7.20 (ddd, 8.5, 8.5, 1.5, 1H), 9.29 (br s, OH);

Example 884

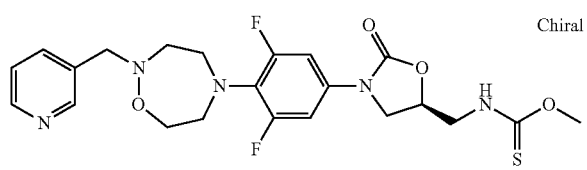

[Chemical Formula 915]

1H-NMR (300 MHz, CDCl$_3$) δ 3.06 (t, 5.5, 2H), 3.38-3.48 (m, 4H), 3.65 (t, 5.5, 2H), 3.80 (dd, 9, 7, 1H), 3.88 (s, 2H), 3.91-4.12 (m, 3H), 4.03 (s, 3H), 4.87-4.97 (m, 1H), 7.00-7.14 (m, 2H+NH), 7.27 (dd, 7.5, 5, 1H), 7.74 (ddd, 7.5, 1.5, 1.5, 1H), 8.52 (dd, 5, 1.5, 1H), 8.62 (d, 1.5, 1H);

Example 885

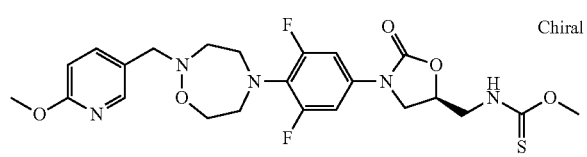

[Chemical Formula 916]

1H-NMR (300 MHz, CDCl$_3$) δ 3.02 (t, 5.5, 2H), 3.36-3.46 (m, 4H), 3.67 (br t, 5.5, 2H), 3.80 (dd, 9, 7, 1H), 3.80 (s, 2H), 3.93 (s, 3H), 3.96-4.11 (m, 3H), 4.00 (s, 3H), 4.87-4.97 (m, 1H), 6.72 (d, 8.5, 1H), 6.99-7.11 (m, 2H+NH), 7.64 (dd, 8.5, 2.5, 1H), 8.12 (d, 2.5, 1H)

Example 886

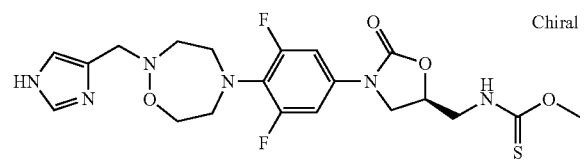

[Chemical Formula 917]

1H-NMR (300 MHz, CDCl$_3$) δ 2.98 (t, 5, 2H), 3.37 (br t, 5, 2H), 3.42 (br t, 5.5, 2H), 3.74-3.86 (m, 3H), 3.92-4.10 (m, 3H), 3.95 (s, 2H), 4.00 (s, 3H), 4.88-4.98 (m, 1H), 6.99 (d, 0.5, 1H), 6.98-7.09 (m, 2H), 7.48 (br t, 6, NH), 7.64 (d, 0.5, 1H);

Example 887

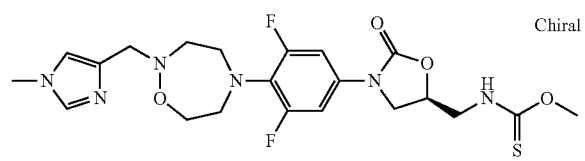

[Chemical Formula 918]

1H-NMR (300 MHz, CDCl$_3$) δ 3.03 (t, 5, 2H), 3.37 (br t, 5, 2H), 3.45 (br t, 5.5, 2H), 3.67 (s, 3H), 3.76-3.87 (m, 3H), 3.92-4.10 (m, 3H), 3.90 (s, 2H), 4.00 (s, 3H), 4.88-4.98 (m, 1H), 6.86 (d, 1, 1H), 6.98-7.10 (m, 2H), 7.39 (d, 1, 1H), 7.50 (br t, 6, NH);

Example 888

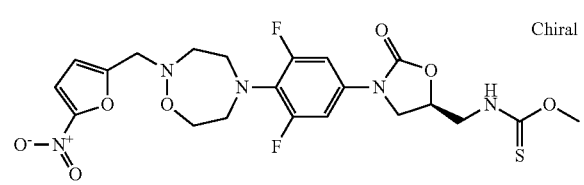

[Chemical Formula 919]

1H-NMR (300 MHz, CDCl$_3$) δ 3.07 (t, 5.5, 2H), 3.40-3.50 (m, 4H), 3.76-3.85 (m, 3H), 3.94-4.12 (m, 3H), 3.98 (s, 2H), 4.00 (s, 3H), 4.88-4.98 (m, 1H), 6.57 (d, 3.5, 1H), 6.95 (br t, 6, NH), 7.01-7.13 (m, 2H), 7.30 (d, 3.5, 1H), 7.50 (br t, 6, NH);

Example 889

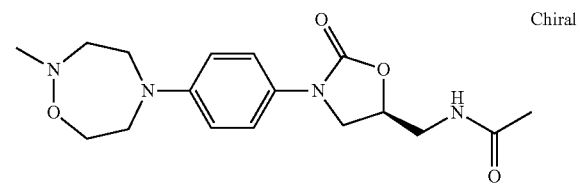

[Chemical Formula 920]

1H-NMR (300 MHz, CDCl₃) δ 2.03 (s, 3H), 2.59 (s, 3H), 2.93 (t, 6, 2H), 3.55-3.69 (m, 3H), 3.73 (t, 6, 4H,), 3.95 (t, 6, 2H), 4.01 (t, 9, 1H), 4.73 (m, 1H), 6.00 (bt, NH), 6.73 (d, 10, 2H), 7.31 (d, 10, 2H);

Example 890

[Chemical Formula 921]

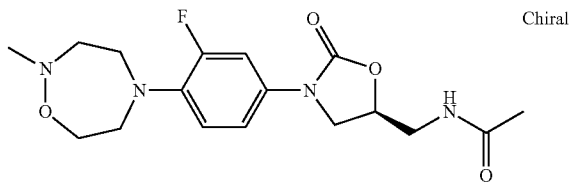

1H-NMR (300 MHz, CDCl₃) δ 2.03 (s, 3H), 2.65 (s, 3H), 2.96 (t, 6, 2H), 3.55 (t, 6, 3H), 3.61 (t, 6, 2H), 3.69-3.75 (m, 3H), 3.94 (t, 6, 2H), 4.00 (t, 9, 1H), 4.74 (m, 1H), 5.93 (bt, NH), 6.89 (t, 10, 1H), 7.02 (dd, 10, 4, 1H), 7.35 (dd, 10, 4, 1H)

Example 891

[Chemical Formula 922]

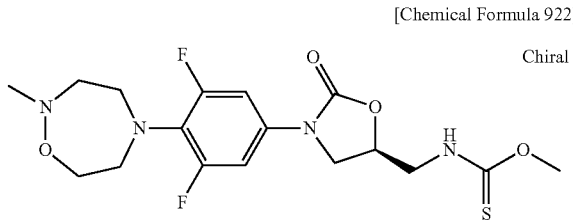

1H-NMR (300 MHz, CDCl₃) δ 2.68 (s, 3H), 2.93 (t, 5.5, 2H), 3.40 (br t, 5, 2H), 3.45 (br t, 5, 2H), 3.80 (dd, 9, 7, 1H), 3.91 (t, 5.5, 2H), 3.95-4.12 (m, 3H), 4.01 (s, 3H), 4.88-4.98 (m, 1H), 6.99 (br s, NH), 7.00-7.12 (m, 2H);

Example 892

[Chemical Formula 923]

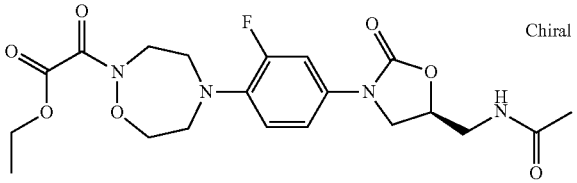

1H-NMR (300 MHz, CDCl₃) δ 1.34 (t, 7, 3H), 2.02 (s, 3H), 3.48-3.57 (m, 4H), 3.57-3.72 (m, 2H), 3.76 (dd, 9, 6.5, 1H), 3.98 (t, 6, 2H), 4.02 (dd, 9, 9, 1H), 4.22 (t, 5, 2H), 4.36 (q, 7, 2H), 4.73-4.82 (m, 1H), 6.47 (br t, 6, NH), 6.91 (dd, 9, 9, 1H), 7.05 (br dd, 9, 3, 1H), 7.42 (dd, 15, 3, 1H);

Example 893

[Chemical Formula 924]

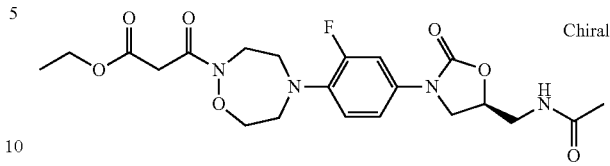

1H-NMR (300 MHz, CDCl₃) δ 1.28 (t, 7, 3H), 2.02 (s, 3H), 3.46-3.55 (m, 4H), 3.55-3.71 (m, 2H), 3.56 (s, 2H), 3.75 (dd, 9, 6.5, 1H), 4.01 (t, 5.5, 2H), 4.01 (dd, 9, 9, 1H), 4.16 (t, 5, 2H), 4.20 (q, 7, 2H), 4.72-4.82 (m, 1H), 6.37 (br t, 6, NH), 6.90 (dd, 9, 9, 1H), 7.04 (br dd, 9, 2.5, 1H), 7.41 (dd, 15, 2.5, 1H);

Example 894

[Chemical Formula 925]

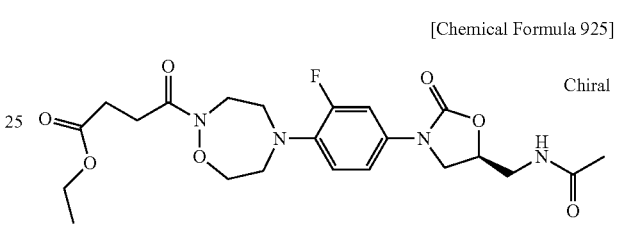

1H-NMR (300 MHz, CDCl₃) δ 1.26 (t, 7, 3H), 2.02 (s, 3H), 2.65 (br t, 7, 2H), 2.79 (br t, 7, 2H), 3.45-3.56 (m, 4H), 3.56-3.71 (m, 2H), 3.75 (dd, 9, 7, 1H), 3.97 (t, 6, 2H) 4.01 (dd, 9, 9, 1H), 4.14 (q, 7, 2H), 4.18 (t, 5.5, 2H), 4.72-4.82 (m, 1H), 6.67 (br t, 6, NH), 6.89 (dd, 9, 9, 1H), 7.03 (br dd, 9, 2.5, 1H), 7.39 (dd, 15, 2.5, 1H);

Example 895

[Chemical Formula 926]

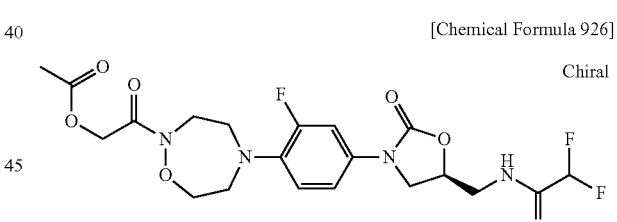

1H-NMR (300 MHz, CDCl₃—CD₃OD (9:1)) δ 2.19 (s, 3H), 3.48-3.58 (m, 4H), 3.62 (dd, 14.5, 6.5, 1H), 3.73 (dd, 14.5, 4, 1H), 3.75 (dd, 9, 6.5, 1H), 3.97 (t, 5.5, 2H), 4.08 (dd, 9, 9, 1H), 4.22 (t, 5, 2H), 4.81 (dddd, 9, 6.5, 6.5, 4, 1H), 4.88 (s, 2H), 5.95 (t, 54, 1H), 6.93 (dd, 9, 9, 1H), 7.05 (br dd, 9, 2.5, 1H), 7.39 (dd, 15, 2.5, 1H);

Example 896

[Chemical Formula 927]

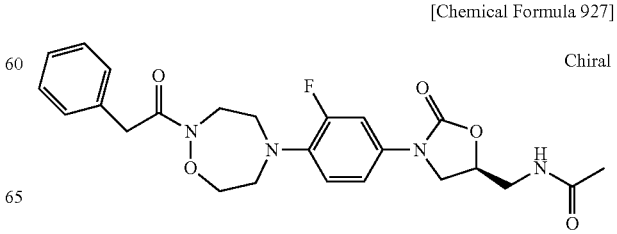

1H-NMR (300 MHz, CDCl₃) δ 2.01 (s, 3H), 3.41-3.50 (m, 4H), 3.73 (dd, 9, 7, 1H), 3.81 (s, 2H), 3.95-4.05 (m, 5H), 4.71-4.80 (m, 1H), 6.38 (br t, 6, NH), 6.85 (dd, 9, 9, 1H), 7.02 (br dd, 9, 2.5, 1H), 7.20-7.34 (m, 5H), 7.39 (dd, 15, 2.5, 1H);

Example 897

[Chemical Formula 928]

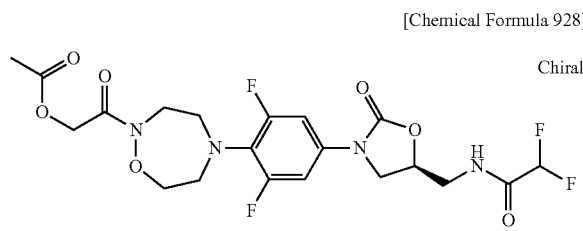 [SMILES: CC(=O)OCC(=O)N1CCN(c2c(F)cc(N3C[C@H](CNC(=O)C(F)F)OC3=O)cc2F)CCO1]

1H-NMR (300 MHz, CDCl₃) δ 2.19 (s, 3H), 3.67 (ddd, 14.5, 6, 6, 1H), 3.72 (dd, 9, 6, 1H), 3.81 (ddd, 14.5, 6, 3.5, 1H), 3.90 (t, 5.5, 2H), 4.05 (dd, 9, 9, 1H), 4.18 (t, 5, 2H), 4.79-4.91 (m, 1H), 4.89 (s, 2H), 5.95 (t, 54, 1H), 7.46 (br t, 6, NH), 7.03-7.14 (m, 2H);

Example 898

[Chemical Formula 929]

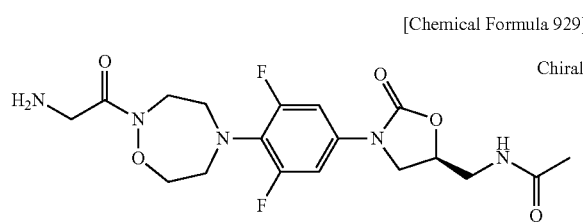 [SMILES: CC(=O)NC[C@H]1CN(c2cc(F)c(N3CCON(C(=O)CN)CC3)c(F)c2)C(=O)O1]

1H-NMR (300 MHz, CDCl₃—CD₃OD (9:1)) δ 2.01 (s, 3H), 3.38-3.48 (m, 4H), 3.54-3.68 (m, 4H), 3.73 (dd, 9, 6.5, 1H), 3.92 (t, 5.5, 2H), 4.01 (dd, 9, 9, 1H), 4.11 (t, 5, 2H), 4.72-4.82 (m, 1H), 7.07-7.17 (m, 2H);

Example 899

[Chemical Formula 930]

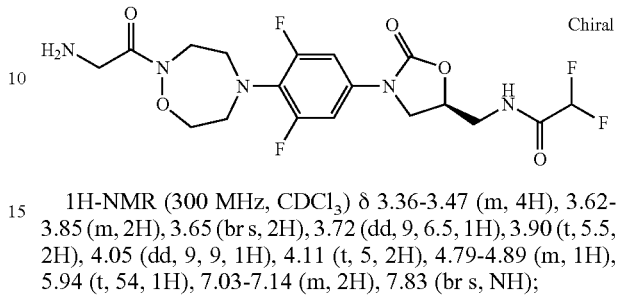

1H-NMR (300 MHz, CDCl₃) δ 3.36-3.47 (m, 4H), 3.62-3.85 (m, 2H), 3.65 (br s, 2H), 3.72 (dd, 9, 6.5, 1H), 3.90 (t, 5.5, 2H), 4.05 (dd, 9, 9, 1H), 4.11 (t, 5, 2H), 4.79-4.89 (m, 1H), 5.94 (t, 54, 1H), 7.03-7.14 (m, 2H), 7.83 (br s, NH);

Example 900

[Chemical Formula 931]

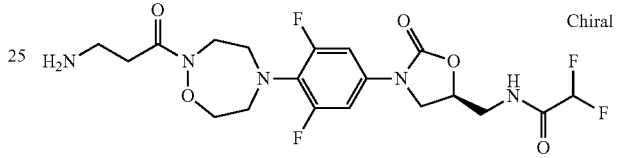

1H-NMR (300 MHz, CDCl₃—CD₃OD (9:1)) δ 2.74 (t, 6, 2H), 3.06 (t, 6, 2H), 3.37-3.47 (m, 4H), 3.64 (dd, 14.5, 6, 1H), 3.69-3.78 (m, 4H), 3.90 (t, 5.5, 2H), 4.05 (dd, 9, 9, 1H), 4.13 (t, 5, 2H), 4.77-4.87 (m, 1H), 5.93 (t, 54, 1H), 7.05-7.16 (m, 2H).

Example 901

[Chemical Formula 932]

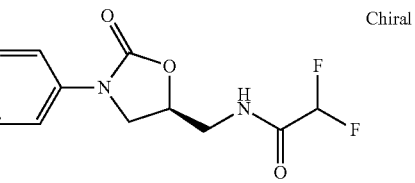

1H-NMR (300 MHz, CDCl₃) δ 1.46 (s, 9H), 3.37-3.47 (m, 4H), 3.67 (ddd, 14.5, 6, 6, 1H), 3.72 (dd, 9, 6.5, 1H), 3.82 (ddd, 14.5, 6, 3.5, 1H), 3.90 (t, 5.5, 2H), 4.06 (dd, 9, 9, 1H), 4.11-4.18 (m 4H), 4.79-4.89 (m, 1H), 5.35 (br s, NH), 5.94 (t, 54, 1H), 7.07-7.17 (m, 2H), 7.34 (br 6, NH);

Example 902

[Chemical Formula 933]

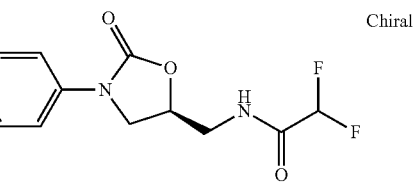

1H-NMR (300 MHz, CDCl₃) δ 1.43 (s, 9H), 2.71 (t, 5.5, 2H), 3.36-3.48 (m, 6H), 3.68 (ddd, 14.5, 6, 6, 1H), 3.74 (dd, 9, 6, 1H), 3.81 (ddd, 14.5, 6, 3.5, 1H), 3.89 (t, 5.5, 2H), 4.06 (dd, 9, 9, 1H), 4.10 (t, 5, 2H), 4.80-4.90 (m, 1H), 5.28 (br s, NH), 5.95 (t, 54, 1H), 7.03-7.14 (m, 2H), 7.60 (br t, 6, NH);

Example 903

[Chemical Formula 934]

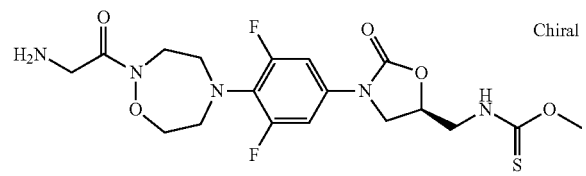

1H-NMR (300 MHz, CDCl₃) δ 3.37-3.48 (m, 4H), 3.66 (br s, 2H), 3.83 (dd, 9, 7, 1H), 3.92 (t, 5.5, 2H), 3.96-4.07 (m, 3H), 4.00 (s, 3H), 4.11 (t, 5, 2H), 4.88-4.98 (m, 1H), 7.05-7.16 (m, 2H), 7.18 (br s, NH);

Example 904

[Chemical Formula 935]

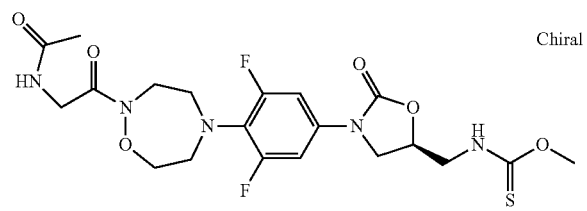

1H-NMR (300 MHz, CDCl₃) δ 2.07 (s, 3H), 3.41 (br t, 5, 2H), 3.45 (br t, 5, 2H), 3.83 (dd, 9, 7, 1H), 3.95-4.12 (m, 3H), 4.00 (s, 3H), 4.14 (t, 5, 2H), 4.17 (br t, 5, 2H), 4.25 (d, 4.5, 2H), 4.89-4.99 (m, 1H), 6.45 (br s, NH), 7.02 (br t, 6, NH), 7.06-7.17 (m, 2H)

Example 905

[Chemical Formula 936]

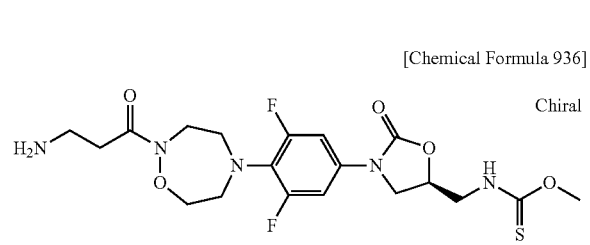 [SMILES: COC(=S)NC[C@H]1CN(c2cc(F)c(N3CCON(C(=O)CCN)CC3)c(F)c2)C(=O)O1]

1H-NMR (300 MHz, CDCl₃) δ 2.69 (t, 6, 2H), 3.06 (t, 6, 2H), 3.37-3.46 (m, 4H), 3.83 (dd, 9, 7, 1H), 3.91 (t, 5.5, 2H), 3.94-4.10 (m, 3H), 4.00 (s, 3H), 4.12 (t, 5, 2H), 4.88-4.98 (m, 1H), 7.03-7.14 (m, 2H);

Example 906

1H-NMR (300 MHz, CDCl₃) δ 3.41-3.53 (m, 4H), 3.82 (dd, 9, 7, 1H), 3.94-4.12 (m, 5H), 4.00 (s, 3H), 4.21 (t, 5, 2H), 4.42 (d, 4, 2H), 4.88-4.97 (m, 1H), 6.85 (br t, 6, NH), 6.87 (ddd, 8, 8, 1, 1H), 6.98 (dd, 8, 1, 1H), 7.06-7.17 (m, 2H), 7.37 (br s, NH), 7.40 (ddd, 8, 8, 1.5, 1H), 7.52 (dd, 8, 1.5, 1H);

Example 907

[Chemical Formula 938]

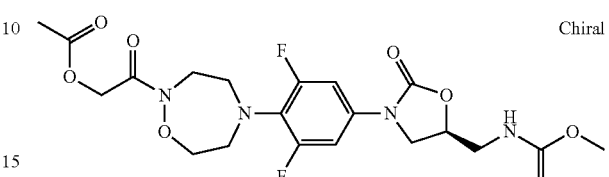

1H-NMR (300 MHz, CDCl₃) δ 2.20 (s, 3H), 3.39-3.48 (m, 4H), 3.54 (ddd, 15, 6.5, 5.5, 1H), 3.63 (ddd, 15, 6.5, 4, 1H), 3.69 (s, 3H), 3.75 (dd, 9, 7, 1H), 3.92 (m, 2H), 3.99 (dd, 9, 9, 1H), 4.18 (t, 5, 2H), 4.78 (dddd, 9, 7, 5.5, 4, 1H), 4.89 (s, 2H), 5.20 (br t, 6.5, NH), 7.07-7.18 (m, 2H);

Example 908

[Chemical Formula 939]

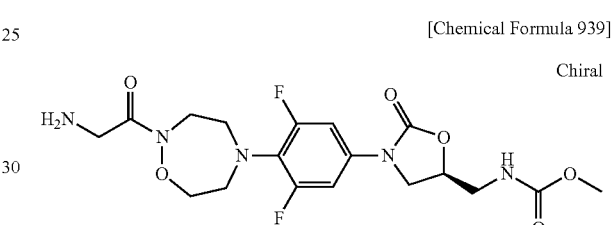

1H-NMR (300 MHz, CDCl₃) δ 3.37-3.47 (m, 4H), 3.49-3.72 (m, 2H), 3.64 (br s, 2H), 3.69 (s, 3H), 3.76 (dd, 9, 7, 1H), 3.99 (dd, 9, 9, 1H), 4.11 (br t, 5, 2H), 4.72-4.82 (m, 1H), 5.49 (br t, 6, NH), 7.06-7.17 (m, 2H);

Example 909

[Chemical Formula 940]

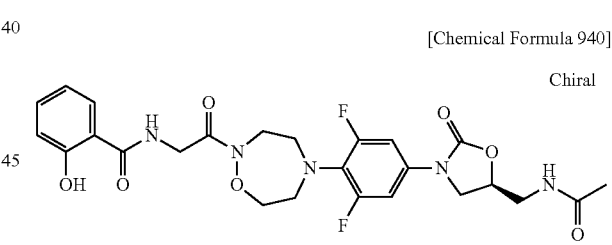

1H-NMR (300 MHz, CDCl₃—CD₃OD (9:1)) δ 201 (s, 3H), 3.40-3.53 (m, 4H), 3.53-3.67 (m, 2H), 3.73 (dd, 9, 6.5, 1H), 3.96 (t, 6, 2H), 4.02 (dd, 9, 9, 1H), 4.24 (t, 5, 2H), 4.43 (s, 2H), 4.72-4.82 (m, 1H), 6.91 (br dd, 8, 8, 1H), 6.97 (br d, 8, 1H), 7.08-7.19 (m, 2H), 7.41 (ddd, 8, 8, 1.5, 1H), 7.65 (dd, 8, 1.5, 1H);

[Chemical Formula 937]

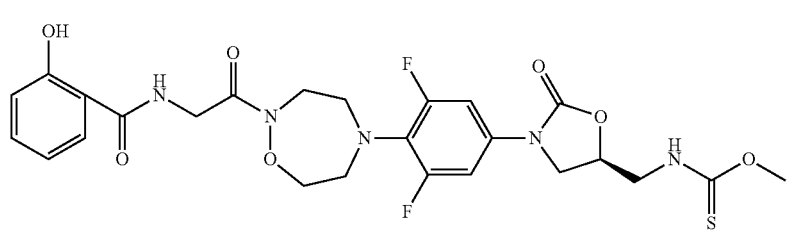

Example 910

[Chemical Formula 941]

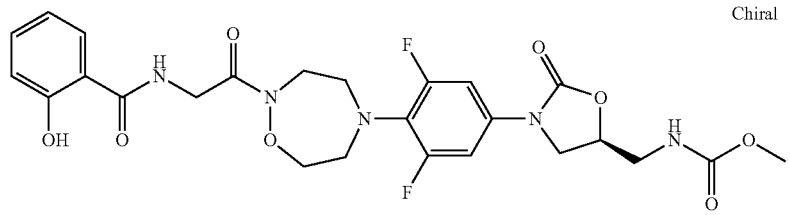

1H-NMR (300 MHz, CDCl₃—CD₃OD (9:1)) δ 3.41-3.63 (m, 6H), 3.68 (s, 3H), 3.77 (dd, 9, 7, 1H), 3.97 (t, 6, 2H), 4.02 (dd, 9, 9, 1H), 4.24 (t, 5, 2H), 4.43 (s, 2H), 4.72-4.82 (m, 1H), 6.91 (ddd, 8.5, 8, 1, 1H), 6.97 (dd, 8.5, 1, 1H), 7.09-7.19 (m, 2H), 7.41 (ddd, 8.5, 8, 1.5, 1H), 7.64 (dd, 8, 1.5, 1H);

Example 911

[Chemical Formula 942]

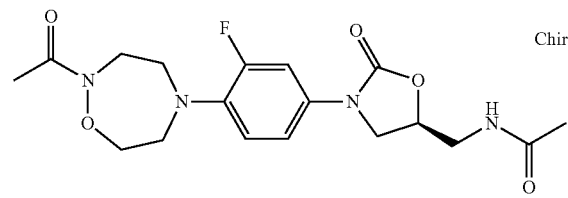

1H-NMR (300 MHz, CDCl₃) δ 2.02 (s, 3H), 2.16 (s, 3H), 3.45-3.56 (m, 4H), 3.58-3.71 (m, 2H), 3.75 (dd, 9, 6, 1H), 3.98 (t, 5, 2H), 4.01 (dd, 9, 9, 1H), 4.14 (t, 5, 2H), 4.72-4.82 (m, 1H), 6.47 (br t, 6, NH), 6.89 (dd, 9, 9, 1H), 7.03 (br dd, 9, 2.5, 1H), 7.40 (dd, 15, 2.5, 1H);

Example 912

[Chemical Formula 943]

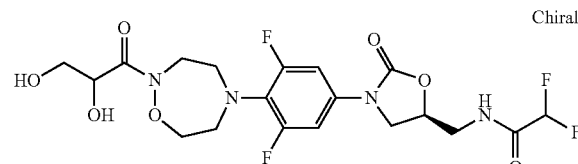

Example 913

[Chemical Formula 944]

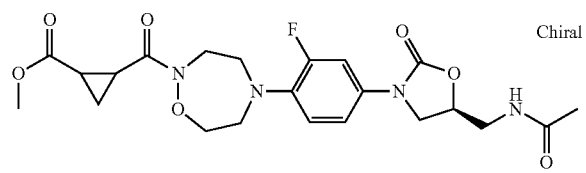

1H-NMR (300 MHz, CDCl₃) δ 1.24 (ddd, 8.5, 8.5, 5, 1H), 1.73 (ddd, 6.5, 6.5, 5, 1H), 2.02 (s, 3H), 2.10 (ddd, 8.5, 8.5, 6.5, 1H), 2.47 (ddd, 8.5, 8.5, 6.5, 1H), 3.38-3.71 (m, 6H), 3.64 (s, 3H), 3.75 (dd, 9, 6.5, 1H), 3.87-4.08 (m, 2H), 4.01 (dd, 9, 9, 1H), 4.19 (t, 5, 2H), 4.72-4.82 (m, 1H), 6.57 (br t, 6, NH), 6.88 (dd, 9, 9, 1H), 7.03 (br dd, 9, 2.5, 1H), 7.40 (dd, 15, 2.5, 1H);

Example 914

[Chemical Formula 945]

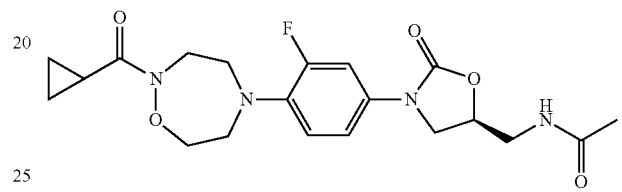

1H-NMR (300 MHz, CDCl₃) δ 0.79-0.88 (m, 2H) 0.96-1.03 (m, 2H), (s, 3H), 2.12-2.23 (m, 1H), 3.49 (t, 6, 2H), 3.56 (t, 5, 2H), 3.58-3.71 (m, 2H), 3.75 (dd, 9, 6.5, 1H), 3.96-4.05 (m, 3H), 4.72-4.82 (m, 1H), 6.52 (br t, 6, NH), 6.90 (dd, 9, 9, 1H), 7.03 (br dd, 9, 2.5, 1H), 7.40 (dd, 15, 2.5, 1H);

Example 915

[Chemical Formula 946]

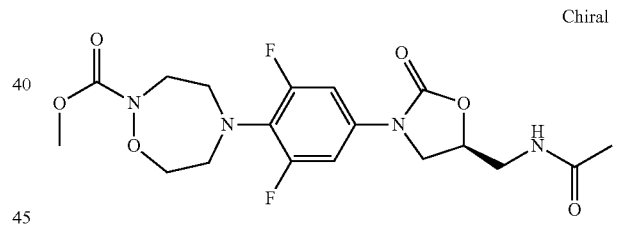

1H-NMR (300 MHz, CDCl₃) δ 2.03 (s, 3H), 3.36-3.47 (m, 4H), 3.60-3.70 (m, 2H), 3.74 (dd, 9, 6, 1H), 3.80 (s, 3H), 3.83 (t, 5.5, 2H), 3.97 (dd, 9, 9, 1H), 4.74-4.83 (m, 1H), 6.36 (br t, 6, NH), 7.04-7.15 (m, 2H);

Example 916

[Chemical Formula 947]

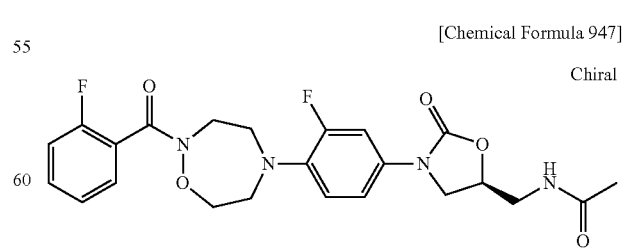

1H-NMR (300 MHz, CDCl₃—CD₃OD (9:1) 50° C.) δ 1.99 (s, 3H), 3.46-3.59 (m, 5H), 3.63 (dd, 14.5, 3.5, 1H), 3.74 (dd, 9, 6.5, 1H), 3.96 (br s, 2H), 4.02 (dd, 9, 9, 1H), 4.11 (br s, 2H), 4.70-4.79 (m, 1H), 6.90-7.23 (m, 4H), 7.25-7.47 (m, 3H);

Example 917

[Chemical Formula 948]

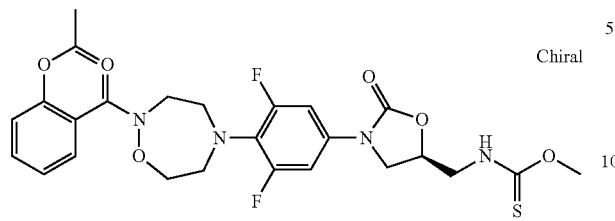

1H-NMR (300 MHz, CDCl₃) δ 2.29 (s, 3H), 3.36 (br s, 2H), 3.47 (br s, 2H), 3.72-3.87 (m, 2H), 3.81 (dd, 9, 7, 1H), 3.90-4.11 (m, 6H), 3.99 (s, 3H), 4.86-4.96 (m, 1H), 7.05 (br t, 6, NH), 7.04-7.16 (m, 2H), 7.19 (br d, 8, 1H), 7.28 (ddd, 7.5, 7.5, 1, 1H), 7.45 (ddd, 8, 7.5, 2, 1H), 7.51 (br d, 7.5, 1H).

Example 918

[Chemical Formula 949]

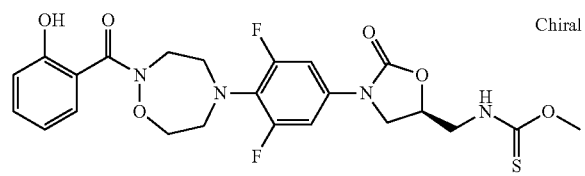

1H-NMR (300 MHz, CDCl₃) δ 3.39 (t, 5.5, 2H), 3.52 (t, 5, 2H), 3.82 (dd, 9, 7, 1H), 3.94-4.17 (m, 7H), 4.00 (s, 3H), 4.88-4.98 (m, 1H), 6.85 (ddd, 8, 8, 1, 1H), 6.88 (br t, 6, NH), 7.00 (dd, 8.5, 1, 1H), 7.06-7.18 (m, 2H), 7.38 (ddd, 8.5, 8, 2, 1H), 8.05 (dd, 8, 2, 1H), 11.24 (br s, OH);

Example 919

[Chemical Formula 950]

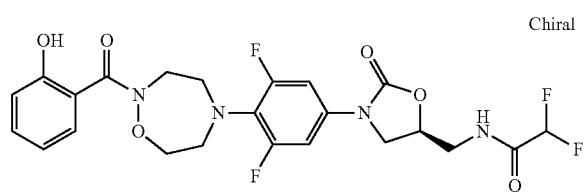

1H-NMR (300 MHz, CDCl₃—CD₃OD (9:1)) δ 3.40 (br t, 5, 2H), 3.53 (br t, 5.5, 2H), 3.63 (dd, 14.5, 6, 1H), 3.73 (dd, 9, 6.5, 1H), 3.75 (dd, 14.5, 3.5, 1H), 4.04 (t, 5, 2H), 4.06 (dd, 9, 9, 1H), 4.13 (br t, 5.5, 2H), 4.77-4.87 (m, 1H), 5.93 (t, 54, 1H), 6.88 (ddd, 8, 8, 1, 1H), 7.00 (dd, 8, 1, 1H), 7.06-7.17 (m, 2H), 7.38 (ddd, 8, 8, 1.5, 1H), 7.99 (dd, 8, 1.5, 1H);

Example 920

[Chemical Formula 951]

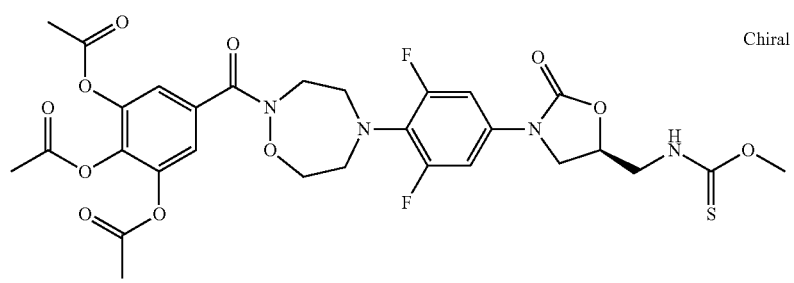

1H-NMR (300 MHz, CDCl₃) δ 2.29 (s, 9H), 3.36 (br t, 4.5, 2H), 3.44-3.51 (m, 4H), 3.80 (dd, 9, 7, 1H), 3.92-4.03 (m, 3H), 3.99 (s, 3H), 4.07 (br t, 5, 2H), 4.85-4.95 (m, 1H), 7.05-7.16 (m, 2H), 7.61 (s, 2H);

Example 921

[Chemical Formula 952]

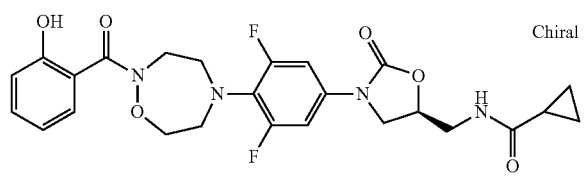

1H-NMR (300 MHz, CDCl₃) δ 0.69-0.83 (m, 2H), 0.85-1.01 (m, 2H), 1.38-1.48 (m, 1H), 3.38 (t, 5, 2H), 3.51 (br t, 5.5, 2H), 3.65-3.72 (m, 2H), 3.76 (dd, 9, 6.5, 1H), 3.98 (dd, 9, 9, 1H), 4.03 (br t, 5, 2H), 4.13 (t, 5.5, 2H), 4.74-4.83 (m, 1H), 6.53 (br t, 6, NH), 6.86 (ddd, 8, 8, 1, 1H), 7.00 (dd, 8, 1, 1H), 7.05-7.16 (m, 2H), 7.38 (ddd, 8.5, 8, 1.5, 1H), 8.04 (dd, 8, 1.5, 1H), 11.25 (br s, OH);

Example 922

[Chemical Formula 953]

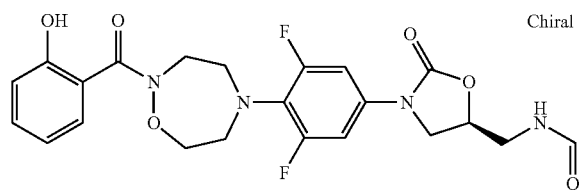

1H-NMR (300 MHz, CDCl₃) δ 3.38 (t, 5.5, 2H), 3.51 (t, 5, 2H), 3.61-3.80 (m, 2H), 3.76 (dd, 9, 6.5, 1H), 4.01 (dd, 9, 9, 1H), 4.03 (br t, 5, 2H), 4.12 (br t, 5.5, 2H), 4.76-4.86 (m, 1H), 6.83 (br t, 6, NH), 6.86 (ddd, 8, 8, 1, 1H), 6.99 (dd, 8, 1, 1H), 7.04-7.14 (m, 2H), 7.37 (ddd, 8, 8, 1.5, 1H), 8.03 (dd, 8, 1.5, 1H), 8.26 (d, 2, 1H), 11.19 (br s, OH);

Example 923

[Chemical Formula 954]

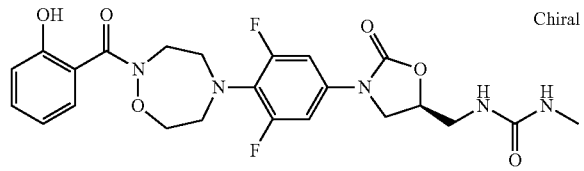

1H-NMR (300 MHz, CDCl₃) δ 2.74 (d, 5, 3H), 3.38 (t, 5, 2H), 3.51 (t, 5.5, 2H), 3.55 (ddd, 15, 6, 3, 1H), 3.69 (ddd, 15, 6, 4.5, 1H), 3.87 (dd, 9, 7, 1H), 3.98 (dd, 9, 9, 1H), 4.03 (br t, 5, 2H), 4.12 (br t, 5.5, 2H), 4.73-4.82 (m, 1H), 5.22 (br q, 5, NH), 5.71 (br t, 6, NH), 6.85 (ddd, 8, 8, 1, 1H), 6.99 (dd, 8, 1, 1H), 7.04-7.15 (m, 2H), 7.37 (ddd, 8, 8, 1.5, 1H), 8.02 (dd, 8, 1.5, 1H), 11.17 (br s, OH);

Example 924

[Chemical Formula 955]

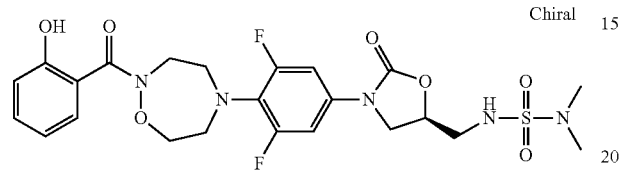

1H-NMR (300 MHz, CDCl₃) δ 2.81 (s, 6H), 3.32-3.60 (m, 6H), 3.88 (dd, 9, 6, 1H), 4.01 (dd, 9, 9, 1H), 4.13 (br t, 5.5, 2H), 4.76-4.85 (m, 1H), 5.33 (br s, NH), 6.86 (ddd, 8, 8, 1, 1H), 6.99 (dd, 8, 1, 1H), 7.07-7.17 (m, 2H), 7.38 (ddd, 8, 8, 1.5, 1H), 8.04 (dd, 8, 1.5, 1H), 11.24 (br s, OH);

Example 925

[Chemical Formula 956]

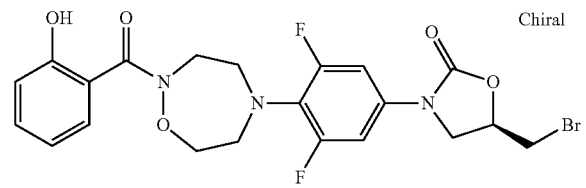

1H-NMR (300 MHz, CDCl₃) δ 3.40 (br t, 5, 2H), 3.51 (br t, 5.5, 2H), 3.57 (dd, 11, 6.5, 1H), 3.64 (dd, 11, 4, 1H), 3.84 (dd, 9, 6, 1H), 4.04 (t, 5, 2H), 4.10 (dd, 9, 9, 1H), 4.14 (t, 5.5, 2H), 4.83-4.93 (m, 1H), 6.86 (ddd, 8, 8, 1, 1H), 7.00 (dd, 8, 1, 1H), 7.10-7.21 (m, 2H), 7.36 (ddd, 8, 8, 2, 1H), 8.06 (dd, 8, 2, 1H), 11.29 (br s, OH);

Example 926

[Chemical Formula 957]

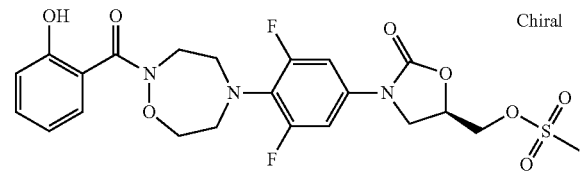

1H-NMR (300 MHz, CDCl₃) δ 3.10 (s, 3H), 3.40 (br t, 5, 2H), 3.53 (br t, 5.5, 2H), 3.89 (dd, 9, 6, 1H), 4.04 (t, 5, 2H), 4.09 (dd, 9, 9, 1H), 4.14 (t, 5.5, 2H), 4.88-4.97 (m, 1H), 4.42 (dd, 12, 3.5, 1H), 4.50 (dd, 12, 3.5, 1H), 6.86 (ddd, 8, 8, 1, 1H), 7.00 (br d, 8, 1H), 7.08-7.19 (m, 2H), 7.38 (ddd, 8, 8, 1.5, 1H), 8.01 (dd, 8, 1.5, 1H), 11.29 (br s, OH);

Example 927

[Chemical Formula 958]

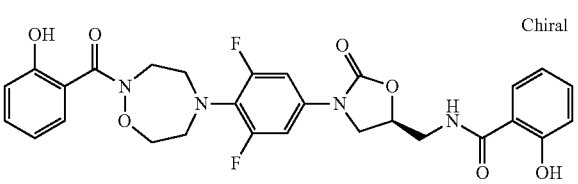

1H-NMR (300 MHz, CDCl₃) δ 3.67 (br t, 4.5, 2H), 3.50 (br t, 5.5, 2H), 3.74-3.84 (m, 2H), 3.91 (ddd, 15, 6, 3.5, 1H), 4.02 (t, 5.5, 2H), 4.05 (dd, 9, 9, 1H), 4.09-4.15 (m, 2H), 4.84-4.94 (m, 1H), 6.82 (ddd, 8, 8, 1, 1H), 6.85 (ddd, 8, 8, 1, 1H), 6.96 (dd, 8, 1, 1H), 6.98 (dd, 8, 1, 1H), 7.02-7.14 (m, 2H), 7.29-7.42 (m, 2H), 7.48 (dd, 8, 1.5, 1H), 8.04 (dd, 8, 1.5, 1H), 11.23 (br, OH);

Example 928

[Chemical Formula 959]

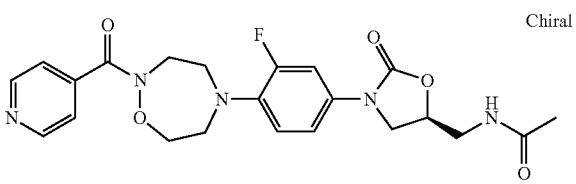

1H-NMR (300 MHz, CDCl₃) δ 2.02 (s, 3H), 3.47 (t, 5, 2H), 3.57 (t, 6, 2H), 3.61-3.73 (m, 2H), 3.76 (dd, 9, 7, 1H), 3.93 (br s, 2H), 4.02 (dd, 9, 9, 1H), 4.16 (br s, 2H), 4.73-4.82 (m, 1H), 6.55 (br t, 6, NH), 6.92 (dd, 9, 9, 1H), 7.06 (br dd, 9, 2.5, 1H), 7.42 (dd, 15.5, 2.5, 1H);

Example 929

[Chemical Formula 960]

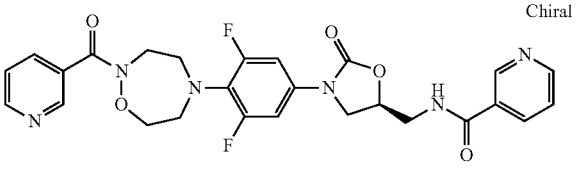

1H-NMR (300 MHz, CDCl₃) δ 3.37 (br t, 4.5, 2H), 3.51 (br t, 5.5, 2H), 3.80-3.98 (m, 5H), 4.08 (dd, 9, 9, 1H), 4.11 (br 7, 5.5, 2H), 4.88-4.98 (m, 1H), 7.05-7.16 (m, 2H), 7.56 (br t, 6, NH), 7.38 (dd, 8, 5, 1H), 7.40 (dd, 8, 5, 1H), 8.07 (ddd, 8, 2, 1.5, 1H), 8.14 (ddd, 8, 2, 1.5, 1H), 8.69 (dd, 5, 1.5, 1H), 8.72 (dd, 5, 1.5, 1H), 9.00 (d, 2, 1H), 9.06 (d, 2, 1H);

Example 930

[Chemical Formula 961]

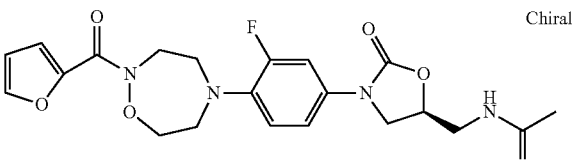

1H-NMR (300 MHz, CDCl₃) δ 2.02 (s, 3H), 3.52-3.71 (m, 6H), 3.75 (dd, 9, 7, 1H), 4.00 (dd, 9, 9, 1H), 4.14 (br t, 5.5, 2H), 4.23 (t, 5, 2H), 4.72-4.82 (m, 1H), 6.47 (br t, 6, NH), 6.52 (dd, 3.5, 2, 1H), 6.91 (dd, 9, 9, 1H), 7.03 (dd, 9, 3, 1H), 7.19 (d, 3.5, 1H), 7.40 (dd, 15, 3, 1H), 7.60 (d, 2, 1H);

Example 931

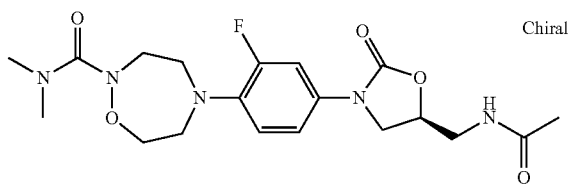
[Chemical Formula 962]

1H-NMR (300 MHz, CDCl₃) δ 2.02 (s, 3H), 2.95 (s, 6H), 3.47-3.59 (m, 4H), 3.59-3.69 (m, 2H), 3.69-3.80 (m, 3H), 4.00 (dd, 9, 9, 1H), 4.10 (t, 5, 2H), 4.71-4.81 (m, 1H), 6.52 (br t, 6, NH), 6.90 (dd, 9, 9, 1H), 7.01 (br dd, 9, 2.5, 1H), 7.38 (dd, 14.5, 2.5, 1H);

Example 932

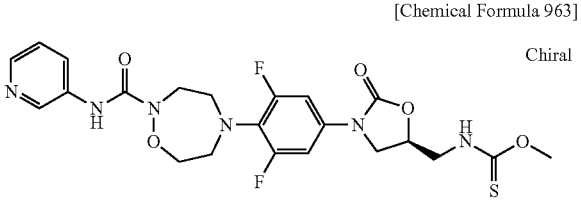 [SMILES: COC(=S)NC[C@H]1CN(c2cc(F)c(N3CCON(C(=O)Nc4cccnc4)CC3)c(F)c2)C(=O)O1]
[Chemical Formula 963]

1H-NMR (300 MHz, CDCl₃) δ 3.45-3.76 (m, 4H), 3.82 (dd, 9, 6.5, 1H), 3.93 (br t, 5.5, 2H), 3.96-4.15 (m, 3H), 4.01 (s, 3H), 4.21 (t, 5, 2H), 4.88-4.98 (m, 1H), 6.71 (br, NH), 7.07-7.19 (m, 2H), 7.27 (dd, 8, 5, 1H), 8.11 (ddd, 8, 3, 1.5, 1H), 8.32 (dd, 5, 1.5, 1H), 8.54 (d, 3, 1H);

Example 933

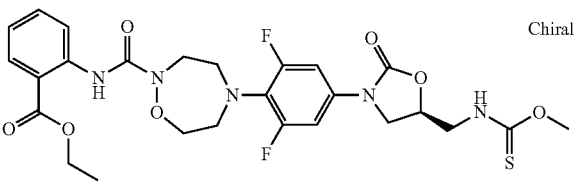
[Chemical Formula 964]

1H-NMR (300 MHz, CDCl₃) δ 1.43 (t, 7, 3H), 3.46-3.55 (m, 4H), 3.81 (br t, 5.5, 2H), 3.95-4.15 (m, 3H), 4.01 (s, 3H), 4.28 (t, 5, 2H), 4.38 (q, 7, 2H), 4.88-4.97 (m, 1H), 6.64 (br t, 6, NH), 7.02 (ddd, 8, 8, 1, 1H), 7.06-7.17 (m, 2H), 7.52 (ddd, 8, 8, 2, 1H), 8.05 (dd, 8, 2, 1H), 8.62 (br d, 8, 1H);

Example 934

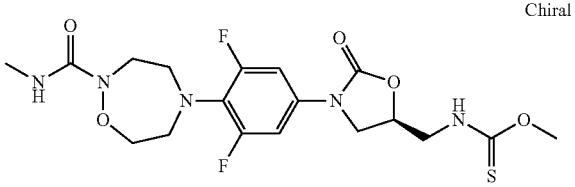
[Chemical Formula 965]

1H-NMR (300 MHz, CDCl₃) δ 2.85 (d, 5, 3H), 3.40 (br t, 5, 2H), 3.47 (br t, 5.5, 2H), 3.79 (br t, 5.5, 2H), 3.82 (dd, 9, 7, 1H), 3.93-4.15 (m, 5H), 4.00 (s, 3H), 4.88-4.98 (m, 1H), 5.84 (br q, 5, NH), 7.00 (br t, 6, NH), 7.03-7.14 (m, 2H);

Example 935

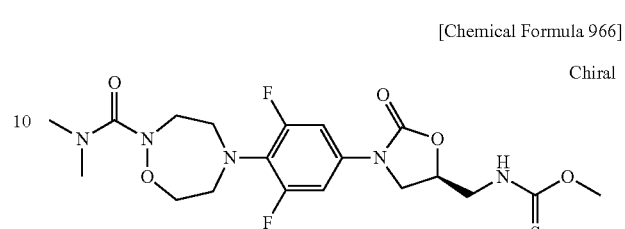
[Chemical Formula 966]

1H-NMR (300 MHz, CDCl₃) δ 2.98 (s, 6H), 3.38-3.50 (m, 4H), 3.73 (br t, 5.5, 2H), 3.82 (dd, 9, 7, 1H), 3.95-4.12 (m, 5H), 4.00 (s, 3H), 4.88-4.98 (m, 1H), 7.02-7.14 (m, 2H+NH);

Example 936

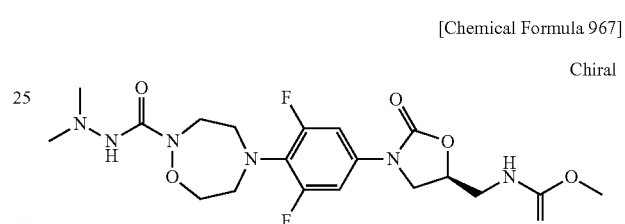
[Chemical Formula 967]

1H-NMR (300 MHz, CDCl₃) δ 2.63 (s, 6H), 3.38 (br t, 5.5, 2H), 3.46 (br t, 5, 2H), 3.78 (br t, 5.5, 2H), 3.85 (dd, 9, 6.5, 1H), 3.96-4.10 (m, 5H), 4.00 (s, 3H), 4.90-5.00 (m, 1H), 6.62 (br s, NH), 7.04-7.16 (m, 2H), 7.21 (br t, 6, NH);

Example 937

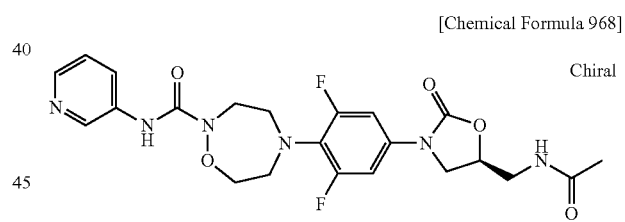
[Chemical Formula 968]

1H-NMR (300 MHz, CDCl₃) δ 2.03 (s, 3H), 3.44-3.54 (m, 4H), 3.57-3.70 (m, 2H), 3.74 (dd, 9, 6.5, 1H), 4.00 (dd, 9, 9, 1H), 4.02 (t, 5, 2H), 4.74-4.84 (m, 1H), 6.63 (br t, 6, NH), 7.05-7.17 (m, 2H), 7.27 (dd, 8, 5, 1H), 7.90 (br s, NH), 8.11 (ddd, 8, 3, 1.5, 1H), 8.30 (dd, 5, 1.5, 1H), 8.56 (d, 3, 1H);

Example 938

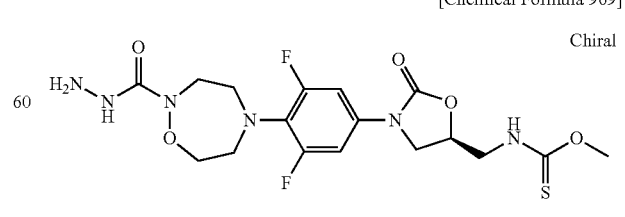
[Chemical Formula 969]

1H-NMR (300 MHz, CDCl₃—CD₃OD (9:1)) δ 3.34-3.50 (m, 4H), 3.74-3.90 (m, 3H), 3.94-4.12 (m, 5H), 4.00 (s, 3H), 4.89-4.99 (m, 1H), 7.05-7.17 (m, 2H);

Example 939

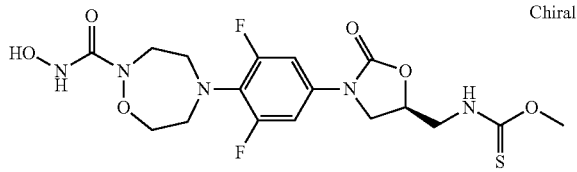
[Chemical Formula 970]

1H-NMR (300 MHz, CDCl₃—CD₃OD (9:1)) δ 3.38-3.48 (m, 4H), 3.79 (br t, 5.5, 2H), 3.84 (dd, 9, 7, 1H), 3.92-4.11 (m, 5H), 4.00 (s, 3H), 4.88-4.99 (m, 1H), 7.04-7.15 (m, 2H)

Example 940

[Chemical Formula 971]

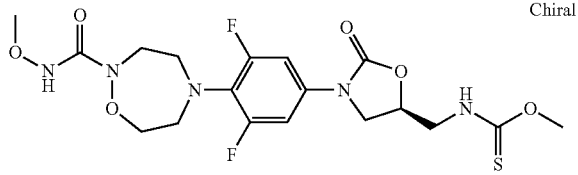

1H-NMR (300 MHz, CDCl₃) δ 3.38-3.47 (m, 4H), 3.76-3.84 (m, 2H), 3.79 (s, 3H), 3.82 (dd, 9, 7, 1H), 3.94-4.11 (m, 5H), 4.00 (s, 3H), 4.89-4.98 (m, 1H), 7.03-7.16 (m, 2H+NH), 8.39 (br s, NH);

Example 941

[Chemical Formula 972]

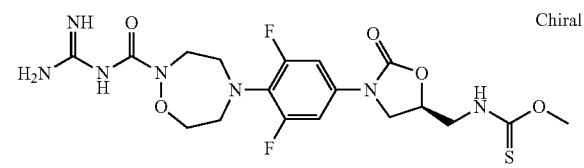

1H-NMR (300 MHz, CDCl₃—CD₃OD (9:1)) δ 3.38-3.48 (m, 4H), 3.81 (dd, 9, 7, 1H), 3.92 (br t, 5.5, 2H), 3.97-4.12 (m, 3H), 4.01 (s, 3H), 4.19 (br t, 5, 2H), 4.88-4.98 (m, 1H), 7.04-7.15 (m, 2H);

Example 942

[Chemical Formula 973]

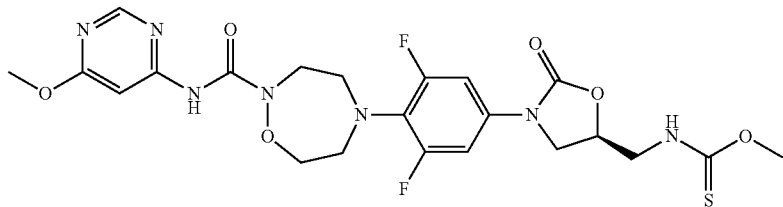

1H-NMR (300 MHz, CDCl₃) δ 3.44-3.52 (m, 4H), 3.82 (dd, 9, 7, 1H), 3.92 (br t, 5.5, 2H), 3.95-4.11 (m, 3H), 3.97 (s, 3H), 4.00 (s, 3H), 4.19 (t, 5, 2H), 4.89-4.98 (m, 1H), 7.03 (br t, 6, NH), 7.05-7.16 (m, 2H), 7.47 (d, 1, 1H), 8.33 (br s, NH), 8.44 (d, 1, 1H);

Example 943

[Chemical Formula 974]

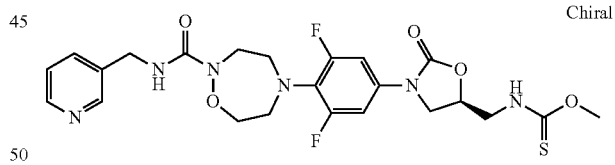

1H-NMR (300 MHz, CDCl₃) δ 3.38-3.49 (m, 4H), 3.78-3.86 (m, 3H), 3.96-4.16 (m, 5H), 4.00 (s, 3H), 4.47 (s, 2H), 4.88-3.98 (m, 1H), 6.33 (t, 6, NH), 7.03-7.14 (m, 2H), 7.27 (dd, 8, 4.5, 1H), 7.47 (br t, 6, NH), 7.69 (ddd, 8, 2, 1, 1H), 8.52 (dd, 4.5, 1, 1H), 8.57 (d, 2, 1H);

Example 944

[Chemical Formula 975]

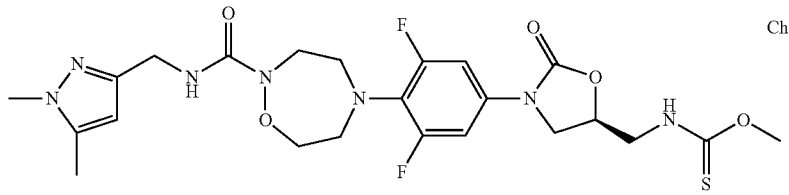

1H-NMR (300 MHz, CDCl₃) δ 2.24 (s, 3H), 3.40 (br t, 5.5, 2H), 3.45 (br t, 5.5, 2H), 3.67-3.86 (m, 3H), 3.73 (s, 3H), 3.95-4.10 (m, 3H), 4.00 (s, 3H), 4.37 (d, 6, 2H), 4.88-3.98 (m, 1H), 5.97 (s, 1H), 6.25 (t, 6, NH), 7.02-7.14 (m, 2H), 7.24 (br t, 6, NH);

Example 945

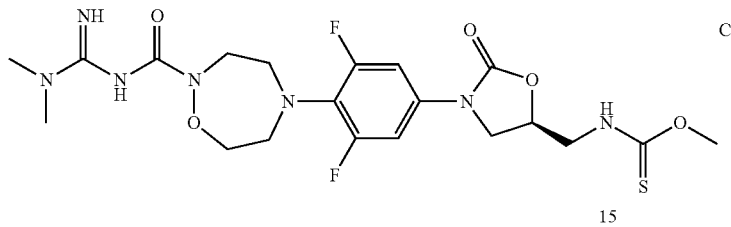

1H-NMR (300 MHz, CDCl₃) δ 2.01 (s, 6H), 3.36-3.44 (m, 4H), 3.81 (dd, 9, 7, 1H), 3.93-4.09 (m, 5H), 4.00 (s, 3H), 4.14 (br t, 5, 2H), 4.88-4.98 (m, 1H), 7.02-7.13 (m, 2H), 7.29 (br t, 6, NH);

Example 946

[Chemical Formula 977]

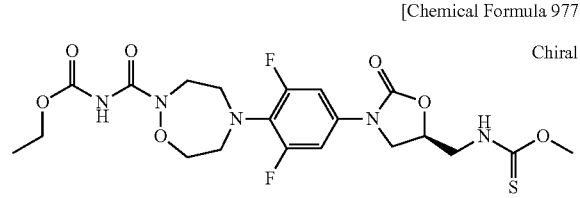

1H-NMR (300 MHz, CDCl₃) δ 1.33 (t, 7, 3H), 3.38-3.48 (m, 4H), 3.79-3.91 (m, 3H), 4.00 (s, 3H), 4.07-4.11 (m, 3H), 4.15 (t, 5, 2H), 4.26 (q, 7, 2H), 4.90-5.00 (m, 1H), 7.14 (br t, 6, NH), 7.06-7.17 (m, 2H), 8.00 (br s, NH);

Example 947

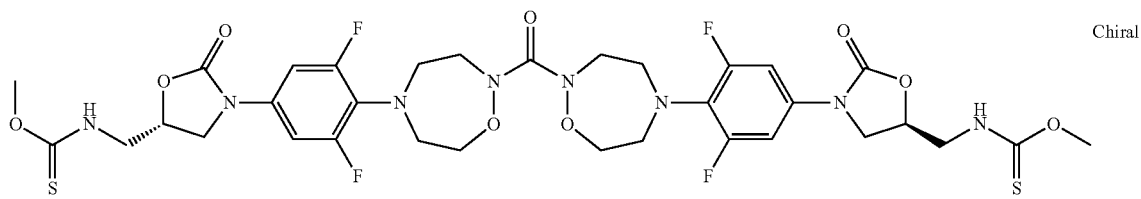

1H-NMR (300 MHz, CDCl₃) δ 3.40-3.49 (m, 8H), 3.78-3.88 (m, 6H), 3.96-4.10 (m, 6H), 4.00 (s, 6H), 4.13 (t, 5, 4H), 4.89-4.99 (m, 2H), 7.01-7.14 (m, 4H+NH);

Example 948

[Chemical Formula 979]

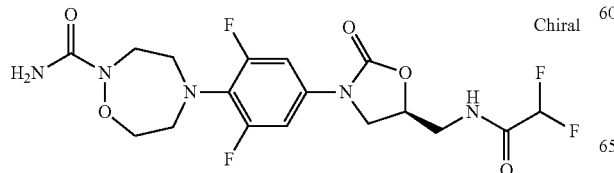

1H-NMR (300 MHz, CDCl₃) δ 3.36-3.48 (m, 4H), 3.64 (dd, 14.5, 6, 1H), 3.70-3.83 (m, 4H), 3.90 (br t, 5, 2H), 4.07 (dd, 9, 9, 1H), 4.78-4.88 (m, 1H), 5.95 (t, 54, 1H), 7.04-7.16 (m, 2H);

[Chemical Formula 976]

Example 949

[Chemical Formula 980]

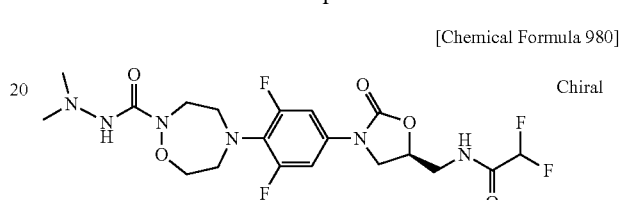

1H-NMR (300 MHz, CDCl₃) δ 2.62 (s, 6H), 3.37 (br t, 5, 2H), 3.45 (br t, 5, 2H), 3.64-3.83 (m, 5H), 4.04-4.16 (m, 3H), 4.84-4.94 (m, 1H), 5.36 (br s, NH₂), 7.08-7.19 (m, 2H);

Example 950

[Chemical Formula 981]

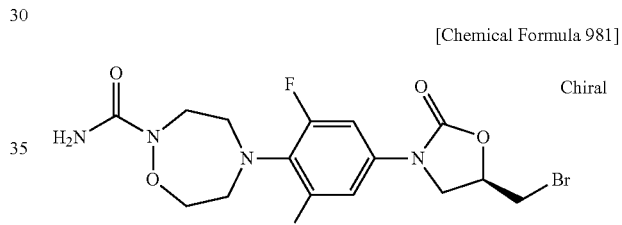

1H-NMR (300 MHz, CDCl₃) δ 3.39-3.52 (m, 4H), 3.58 (dd, 12, 7, 1H), 3.65 (dd, 12, 4, 1H), 3.80-3.92 (m, 3H), 3.90 (br t, 5, 2H), 4.07 (dd, 9, 9, 1H), 4.78-4.88 (m, 1H), 5.95 (t, 54, 1H), 7.04-7.16 (m, 2H);

Example 951

[Chemical Formula 982]

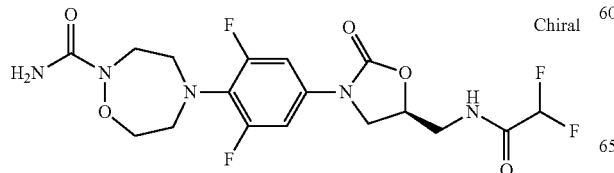

1H-NMR (300 MHz, CDCl₃—CD₃OD (9:1)) δ 3.40-3.50 (m, 4H), 3.82 (br t, 2H), 3.91 (dd, 9, 6, 1H), 4.11 (t, 5, 2H), 4.13 (dd, 9, 9, 1H), 4.44 (dd, 12, 4, 1H), 4.53 (dd, 12, 3.5, 1H), 4.96 (dddd, 9, 6, 4, 3.5, 1H), 5.65 (br s, NH), 7.09-7.20 (m, 2H);

Example 952

[Chemical Formula 983]

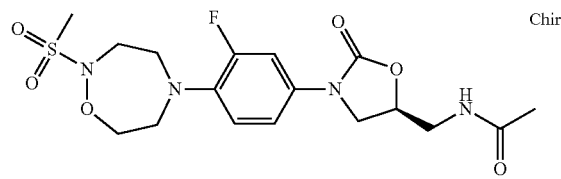

1H-NMR (300 MHz, CDCl₃) δ 2.03 (s, 3H), 2.94 (s, 3H), 3.55-3.78 (m, 9H), 4.01 (dd, 9, 9, 1H), 4.13 (t, 5.5, 2H), 4.72-4.82 (m, 1H), 6.21 (br t, 6, NH), 6.90 (dd, 9, 9, 1H), 7.05 (dd, 9, 2.5, 1H), 7.38 (dd, 15, 2.5, 1H);

Example 953

[Chemical Formula 984]

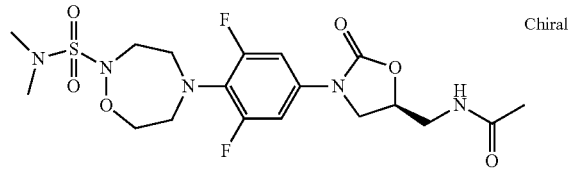

1H-NMR (300 MHz, CDCl₃) δ 2.03 (s, 3H), 3.04 (s, 6H), 3.44-3.54 (m, 4H), 3.59 (t, 5.5, 2H), 3.61-3.69 (m, 2H), 3.73 (dd, 9, 6.5, 1H), 3.99 (dd, 9, 9, 1H), 4.04 (t, 5.5, 2H), 4.73-4.83 (m, 1H), 6.18 (br t, 6, NH), 7.04-7.15 (m, 2H);

Example 954

[Chemical Formula 985]

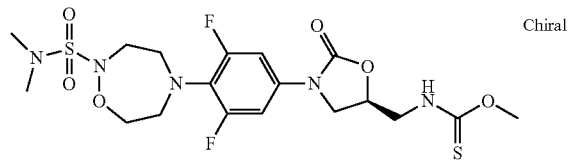

1H-NMR (300 MHz, CDCl₃) δ 3.04 (s, 6H), 3.44-3.54 (m, 4H), 3.59 (t, 5.5, 2H), 3.81 (dd, 9, 7, 1H), 3.97-4.12 (m, 5H), 4.01 (s, 3H), 4.88-4.98 (m, 1H), 7.04-7.15 (m, 2H);

Example 955

[Chemical Formula 986]

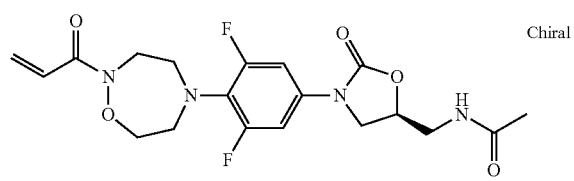

1H-NMR (300 MHz, CDCl₃) δ 2.03 (s, 3H), 3.40 (br t, 6, NH), 3.37-3.49 (m, 4H), 3.58-3.70 (m, 2H), 3.74 (dd, 9, 6.5, 1H), 3.94-4.03 (m, 3H), 4.13 (t, 5, 2H), 4.74-4.83 (m, 1H), 5.78 (dd, 10.5, 2, 1H), 6.46 (dd, 17, 2, 1H), 6.80 (dd, 17, 10.5, 1H), 7.04-7.15 (m, 2H)

Example 956

[Chemical Formula 987]

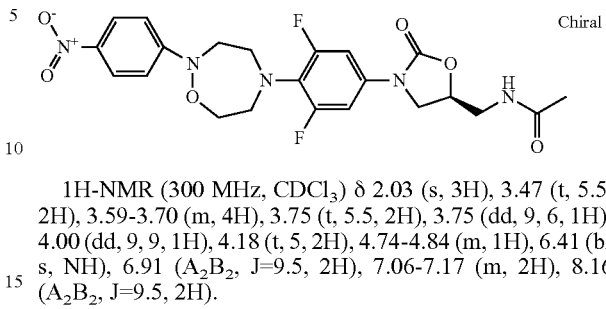

1H-NMR (300 MHz, CDCl₃) δ 2.03 (s, 3H), 3.47 (t, 5.5, 2H), 3.59-3.70 (m, 4H), 3.75 (t, 5.5, 2H), 3.75 (dd, 9, 6, 1H), 4.00 (dd, 9, 9, 1H), 4.18 (t, 5, 2H), 4.74-4.84 (m, 1H), 6.41 (br s, NH), 6.91 (A₂B₂, J=9.5, 2H), 7.06-7.17 (m, 2H), 8.16 (A₂B₂, J=9.5, 2H).

Test Example 1

The compounds of the above Examples were tested for antimicrobial activity.
(Test Method)
Minimal inhibitory concentration (MIC: μg/ml) against different strains of bacteria was assayed according to the standard method recommended by CLSI (clinical and laboratory standards institute). Samples were prepared from test compound solution in DMSO (1280 μg/mL) by two fold (serial) dilution with DMSO. The sample was added to bacteria suspension at the concentration of 5%, and MIC was determined. Mueller Hinton Broth, which has been adjusted for cation concentration, was used for culture media in this test. The inoculation concentration was about 5×10⁵ CFU/mL.
(Result)
The compound of the invention showed strong antimicrobial activity, which was comparable to or more (e.g., four times or more) than linezolid and vancomycin, against various strains of bacteria, such as VRE (vancomycin resistance enterococcus), VISA (vancomycin-intermediate Staphylococcus aureus). For example, the MIC value (μg/mL) of the compound of the working examples (e.g., Examples 81, 82, 83, 84, 85, 86 and 91) was equal to or less than 1, against bacteria such as S. aureus FDA 209P, S. aureus smith, S. aureus ATCC 700787, E. faecalis ATCC 29212, E. faecalis SR7914, E. faecium SR7917.

Example 957

Synthesis of Quinolone Compound

The compound of the invention, wherein Ring B is quinolone in formula I, was prepared according to the following procedure.

7-bis(hydroxyethyl)amino compound (62)

[Chemical Formula 988]

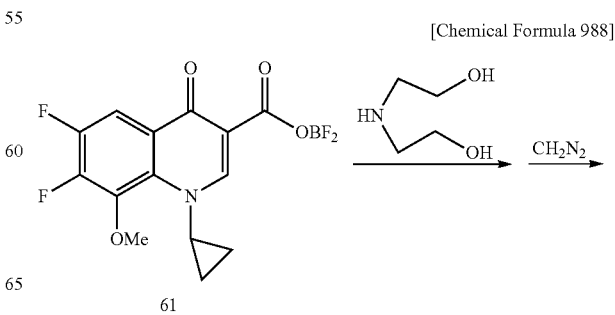

61

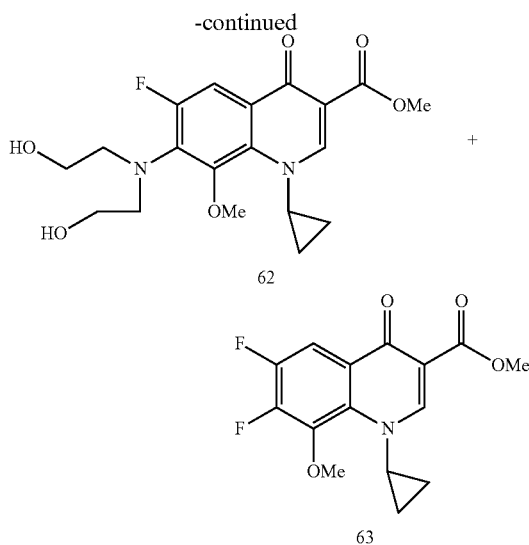

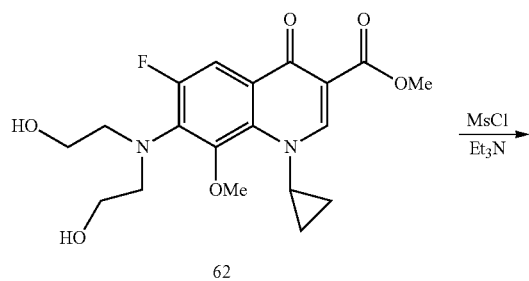

The difluoro complex (61) (686 mg, 2.0 mmol) is added with diethanolamine (4.20 g, 40 mmol) and heated to 60° C. with stirring. After determining the disappearance of the compound 61 by TLC, water was added to dissolve, and the solution was neutralized to pH 6-7 with diluted hydrochloric acid. The solution was extracted with chloroform, washed with water and dried. Solvent was removed to obtain a yellow solid (820 mg). The yellow solid was dissolved in chloroform, and a solution of diazo methane in ether as preliminarily prepared was added.

After determining the disappearance of the carboxylic acid by TLC, solvent was removed. The residue was purified by silica gel column chromatography (WAKO gel B0, 40 ml, chloroform to 2-5 methanol/chloroform) to afford desired 282 mg (36%) of 7-bis(hydroxyethyl)amino compound (62), and 269 mg (43%) of difluoro compound (63).

62: $^1$H-NMR (300 MHz, CDCl$_3$): δ 0.93 (m, 2H), 1.18 (m, 2H), 3.43 (br t, 5.1, 4H), 3.74 (br t, 5.1, 4H), 3.89 (s, 3H), 3.92 (m, 1H), 3.92 (s, 3H), 7.95 (d, 12.3, 1H), 8.64 (s, 1H).

63: $^1$H-NMR (300 MHz, CDCl$_3$): δ 1.05 (m, 2H), 1.22 (m, 2H), 3.93 (s, 3H), 3.99 (m, 1H), 4.09 (d, 1.8, 3H), 8.05 (dd, 10.2, 8.4, 1H), 8.63 (s, 1H).

Example 958

7-bis(methanesulfonyloxyethyl)amino compound (64)

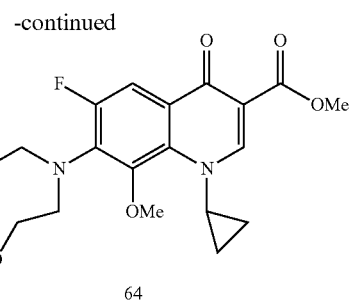

To a solution of the amino compound (62, 282 mg, 0.7 mmol), triethylamine (0.5 ml) in acetonitrile (15 ml), and methanesulfonyl chloride (0.5 ml) were added dropwise under ice-cooling with stirring. After determining the disappearance of the starting material, the solution was poured into diluted hydrochloric acid, extracted with chloroform. After washing with water and dryness, solvent was removed. The residue was purified by silica gel column chromatography (WAKO GEL B0, 30 ml, chloroform to 2% methanol/chloroform) to afford 397 mg (quant.) of 7-bis (methanesulfonyloxyethyl)amino compound (64) as yellow oil. 64: $^1$H-NMR (300 MHz, CDCl$_3$): δ 0.87 (m, 2H), 1.18 (m, 2H), 2.96 (s, 6H), 3.79 (br t, 5.1, 4H), 3.87 (s, 3H), 3.92 (m, 1H), 3.93 (s, 3H), 4.34 (br t, 5.2, 4H), 7.95 (d, 12.3, 1H), 8.65 (s, 1H).

Example 959

7-bisBOC triazacycloheptyl compound (65)

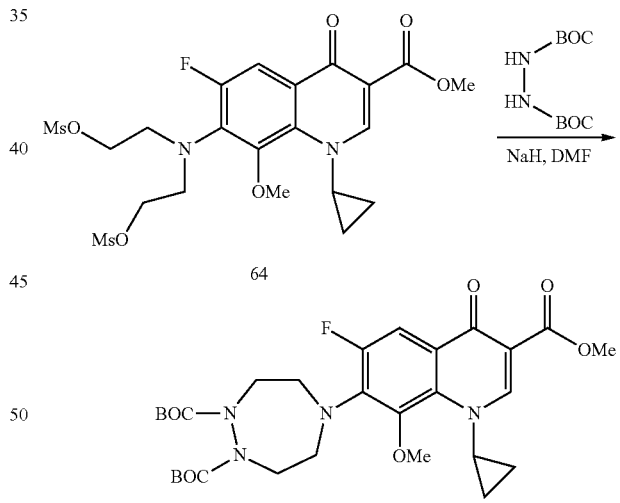

60% NaH (92 mg, 2.3 mmol) was washed with n-hexane and suspended in DMF (5 ml) under argon atmosphere. Under ice-cooling, bis-Boc-hydrazine (243 mg, 1.04 mmol) in DMF (5 ml) was added dropwise and stirred for 5 minute at this temperature and additional 10 minutes at room temperature. To the resultant pale-yellow solution, the mesyl compound (64, 480 mg, 0.87 mmol) in DMF (10 ml) was added dropwise under ice-cooling, stirred at room temperature for 30 minute, and followed by heating to 80-90° C. with stirring. After determining the disappearance of the starting material, solvent was removed under reduced pressure. Diluted hydrochloric acid water was added and the solution was extracted with chloroform. After washing with water and dryness, solvent was removed. The residue was purified by silica gel column chromatography (WAKO GEL B0, 40 ml, chloroform to 2% methanol/chloroform) to afford 195 mg (38%) of triazacycloheptyl compound (65) as yellow oil.

65: $^1$H-NMR (300 MHz, CDCl$_3$): δ 0.94 (m, 2H), 1.15 (m, 2H), 1.48-1.49 (br s, 18H), 3.27-3.38 (m, 4H), 3.60-3.70 (m, 3H), 3.74 (s, 3H), 3.92 (s, 3H), 3.92 (m, 1H), 4.16 (m, 1H), 7.95 (d, 12.3, 1H), 8.60 (s, 1H).

Example 960

7-bistriazacycloheptyl compound (66)

[Chemical Formula 991]

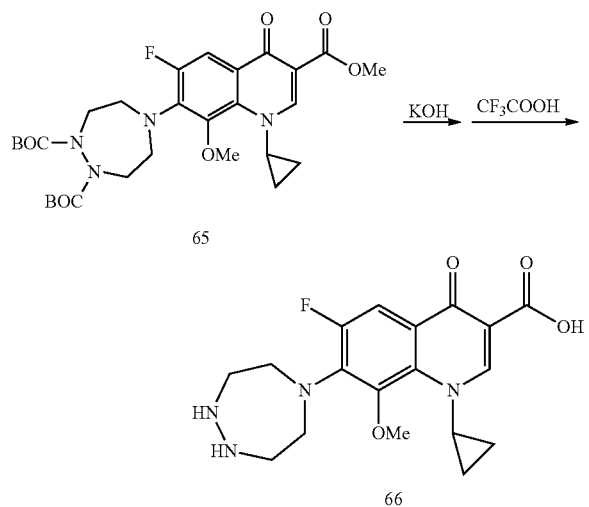

To a solution of the bis-Boc-triazacycloheptyl compound (65, 114 mg) in methanol (10 ml), 10% aqueous potassium hydroxide solution (5 ml) was added under ice-cooling, and the solution was stirred at room temperature for 4 hours. After the reaction, pH was adjusted with diluted hydrochloric acid to 4, and the solution was extracted with chloroform. After washing with water and dryness, solvent was removed. The residue was dissolved in dichloromethane (1 ml), and TFA (1 ml) was added. The mixture was left stand overnight. Removing solvent and recrystallization from methanol-ether afforded 83 mg of the titled compound (46) as yellow needle-like crystal.

66: yellow needle-like crystal mp: 169-172° C. (MeOH-Et$_2$O); 1H-NMR (300 MHz, DMSO): δ 1.02-1.11 (m, 4H), 3.63 (m, 4H), 3.72 (s, 3H), 4.16 (m, 1H), 7.77 (d, 12, 1H), 8.71 (s, 1H).

Example 961

Monoacetyl Derivative of 7-bis-triaza-cycloheptyl Compound (67)

[Chemical Formula 992]

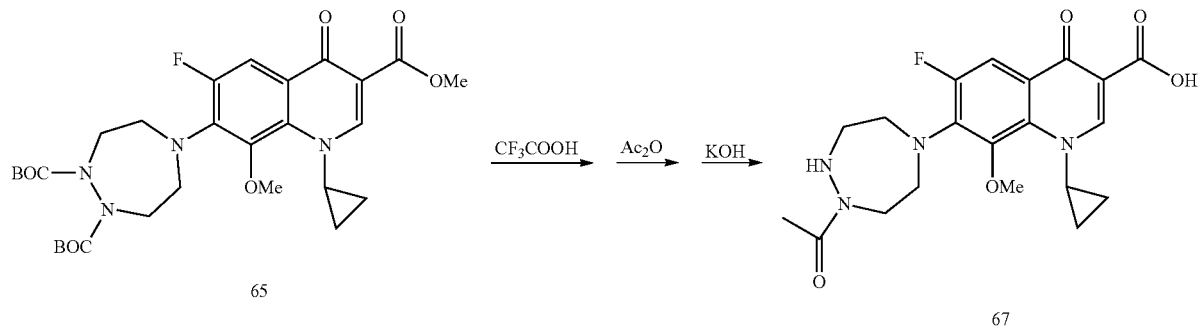

To a solution of the bis-Boc-triaza-cycloheptyl compound (65, 72 mg, 0.12 mmol) in dichloromethane (2 ml), TFA (2 ml) was added, and the mixture was left stand overnight. Sodium hydrogen carbonate solvent was added, extracted with chloroform, washed with water and dried, and solvent was removed. The residue (52 mg) was dissolved in chloroform (5 ml), added with acetic anhydride (15 μmL, 1.5 eq.) and stirred at room temperature for 10 min. Sodium hydrogen carbonate solvent was added, extracted with chloroform, washed with water, dried, and solvent was removed. The residue was purified by silica gel column chromatography (WAKO GEL B0, 30 ml, chloroform to 1-4% methanol/chloroform) to afford 34 mg (64%) of monoacyl methyl ester compound.

To a solution of the monoacyl methyl ester compound (34 mg) in methanol (2 ml), 10% aqueous potassium hydroxide solution (2 ml) was added under ice-cooling and stirred at room temperature for 30 min. After the reaction, pH was adjusted with diluted hydrochloric acid to 5-6, the solution was extracted with chloroform. After washing with water and dryness, solvent was removed. The residue was dissolved in dichloromethane (1 ml) and added with TFA (1 ml). The mixture was left stand overnight. Solvent was removed, and the residue was purified by silica gel column chromatography (WAKO GEL B0, 20 ml, chloroform to 5% methanol/chloroform) and recrystallized from methanol-hexane to afford 25 mg (76%) of the titled compound (67) as a pale-orange needle-like crystal.

67: pale-orange needle-like crystal mp: 193-196° C. (MeOH-Hexane); 1H-NMR (300 MHz, CDCl$_3$): δ 0.94 (m, 2H), 1.15 (m, 2H), 2.13 & 2.25 (s, 3H), 3.09-3.72 (m, 7.5H), 3.73 & 3.74 (s, 3H), 3.92 (m, 1H), 4.56 (m, 0.5H), 7.92 (d, 12, 1H), 8.60 (s, 1H).

Example 962

Monohydroxy Acetyl Derivative of 7-bis-triaza-cycloheptyl Compound (69)

69: pale-orange needle-like crystal mp: 15 7-159° C. (EtOH-Hexane); 1H-NMR (300 MHz, CDCl$_3$): δ 1.00 (m, 2H), 1.22 (m, 2H), 3.23-3.90 (m, 8H), 3.77 (s, 3H), 4.03 (m, 1H), 7.93 (d, 12, 1H), 8.84 (s, 1H).

[Chemical Formula 993]

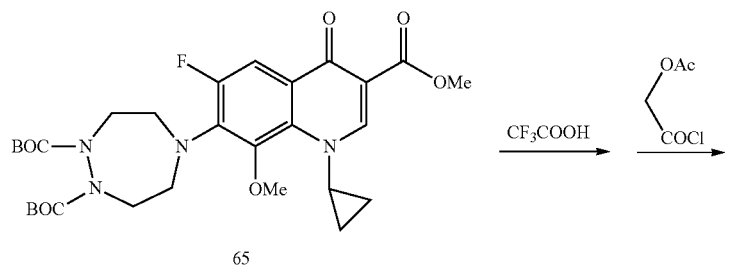

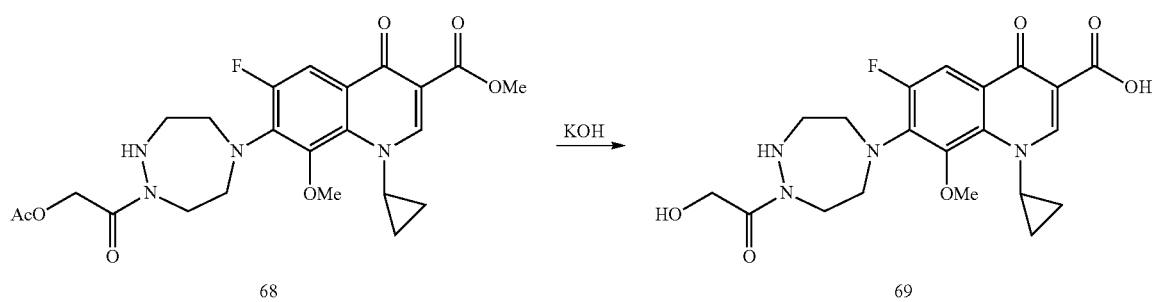

To a solution of the bis-Boc-triaza-cycloheptyl compound (65, 100 mg, 0.18 mmol) in dichloromethane (2 ml), TFA (2 ml) was added and stirred for 30 min. sodium hydrogen carbonate solvent was added, extracted with chloroform, washed with water, and dried, and solvent was removed. The residue (70 mg) was dissolved in chloroform (5 ml), and added with acetoxyacetyl chloride (18 μmL, 1.5 eq.) at room temperature and stirred for 5 min. Sodium hydrogen carbonate solvent was added, extracted with chloroform, washed with water, and dried, and solvent was removed. The residue was purified by silica gel column chromatography (WAKO GEL B0, 20 ml, chloroform to 1% methanol/chloroform) to afford 19 mg (19%) of monoacetoxy acetyl methyl ester compound (68). 68: $^1$H-NMR (300 MHz, CDCl$_3$): δ 0.94 (m, 2H), 1.15 (m, 2H), 2.14 (s, 3H), 3.09-3.90 (m, 8H), 3.73 & 3.76 (s, 3H), 3.92 (s, 3H), 3.92 (m, 1H), 5.00 (s, 2H), 7.93 (d, 12, 1H), 8.61 (s, 1H).

To a solution of the monoacetoxy acetyl methyl ester compound (48, 27 mg) in methanol (2 ml), 10% aqueous potassium hydroxide solution (2 ml) was added under ice-cooling, and the solution was stirred at room temperature for 10 min. After the reaction, pH was adjusted with diluted hydrochloric acid to 5-6, and the solution was extracted with chloroform. After washing with water and dryness, solvent was removed. The residue was recrystallized from ethanol-hexane to afford 10 mg (42%) of the titled compound (69) as pale-orange needle-like crystal.

Example 963

7-BOC-diazaoxy cycloheptyl Compound (70)

[Chemical Formula 994]

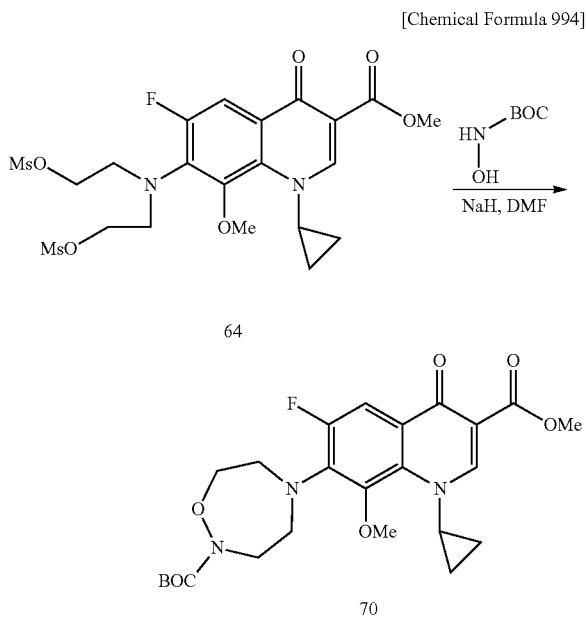

60% NaH (96 mg, 2.4 mmol) was washed with n-hexane, and suspended in DMF (3 ml) under argon atmosphere. N-BOC hydroxylamine (106 mg, 0.8 mmol) in DMF (5 ml) was added dropwise and stirred at the temperature for 10 min. To the resultant pale-yellow solution, mesyl compound (64, 430 mg, 0.78 mmol) in DMF (3 ml) was added dropwise under ice-cooling, and heated to 70-80° C. with stirring for 2 hours. After determining the disappearance of the starting material, the mixture was diluted with ethyl acetate, washed with water, and dried, and solvent was removed. The residue was purified by silica gel column chromatography (WAKO GEL B0, 40 ml, chloroform to 1% methanol/chloroform) to afford 88 mg (23%) of the titled compound (70) as orange oil.

70: $^1$H-NMR (300 MHz, CDCl$_3$): δ 0.94 (m, 2H), 1.15 (m, 2H), 1.48-1.49 (br s, 18H), 3.27-3.38 (m, 4H), 3.60-3.70 (m, 3H), 3.74 (s, 3H), 3.92 (s, 3H), 3.92 (m, 1H), 4.16 (m, 1H), 7.95 (d, 12.3, 1H), 8.60 (s, 1H).

Example 964

7-diazaoxy cycloheptyl Compound (71)

[Chemical Formula 995]

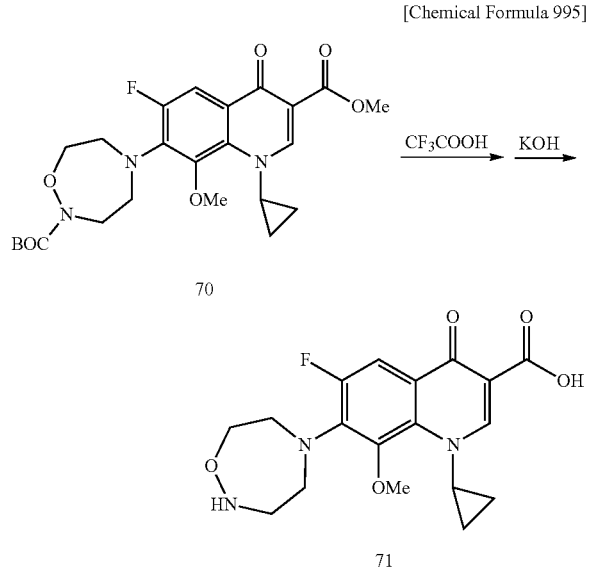

To a solution of the N-BOC-diazaoxy cycloheptyl compound (50, 88 mg) in dichloromethane (1 ml), TFA (1 ml) was added and stirred at room temperature for 10 min. Toluene was added, and solvent was removed. To a solution of the residue in methanol (2 ml), 10% aqueous potassium hydroxide solution (2 ml) was added under ice-cooling, the solution was stirred at room temperature for 10 min. After the reaction, pH was adjusted with diluted hydrochloric acid to 5-6, and the solution was extracted with chloroform. After washing with water and dryness, solvent was removed. The residue (80 mg) was recrystallized from methanol-ether to afford the titled compound (71) as orange needle-like crystal.

71: pale-orange needle-like crystal mp: 222-224° C. (MeOH-Hexane); 1H-NMR (300 MHz, CDCl$_3$): δ=1.01 (m, 2H), 1.22 (m, 2H), 3.66 (t, J=6 Hz, 4H), 3.83 (t, J=6 Hz, 4H), 3.88 (s, 3H), 4.06 (m, 1H), 7.94 (d, J=12 Hz, 1H), 8.86 (s, 1H).

Test Example 2

Antimicrobial Activity of the Quinolone Compounds of the Invention

The quinolone compounds of the invention were tested for antimicrobial activity according to the procedure in Test Example 1

Result

The compound of the invention showed strong antimicrobial activity, which was comparable to or more (e.g., four times or more) than commercially available newquinolone antimicrobial agents (e.g., ciprofloxacin, gatifloxacin moxifloxacin), against various strains of bacteria, such as VRE (vancomycin resistance *enterococcus*), MRSA (methicillin-resistant *Staphylococcus aureus*). For example, the MIC values (μg/mL) of Compound (66) of Examples 960, Compound (71) of Examples 964 were equal to or less than 1, against bacteria such as *S. aureus* FDA 209P, *S. aureus* SR3637, *E. faecalis* ATCC 29212, *E. faecalis* SR7914.

Example 965

Synthesis of Compound 88

[Chemical Formula 996]

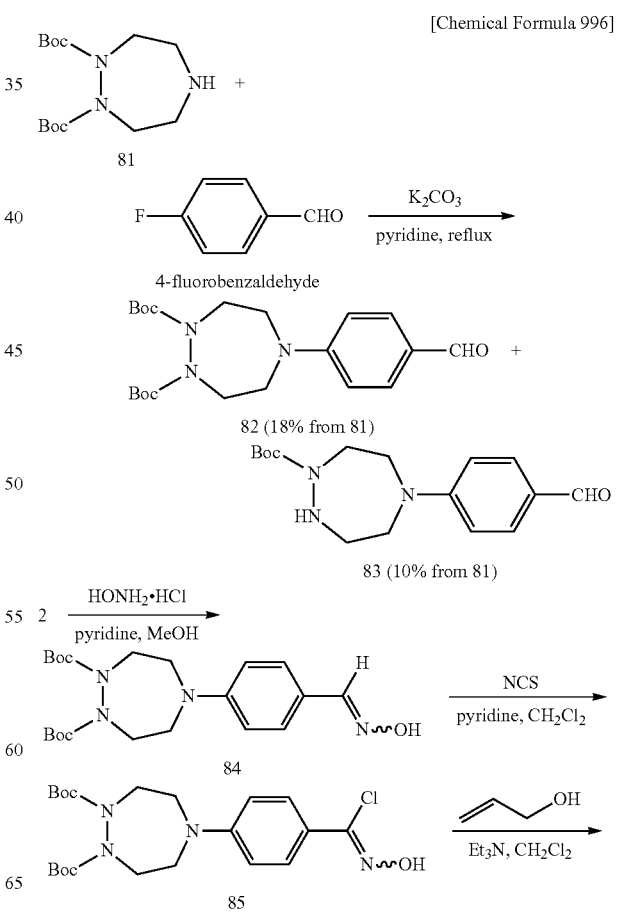

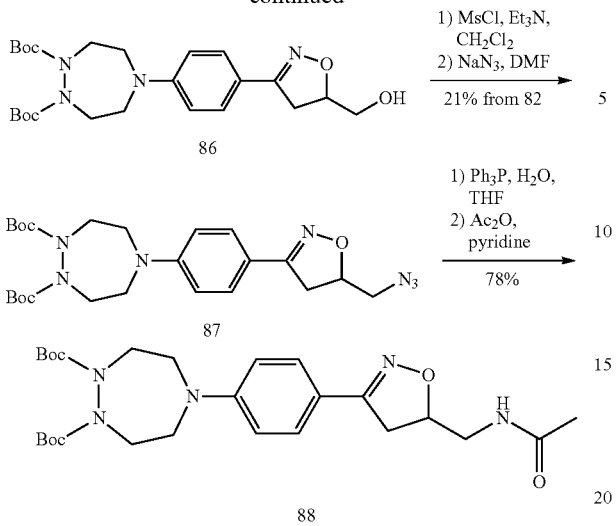

Compounds 82 and 83

To 50 cm³ egg-plant flask, charged with Compound 81 (3.1291 g, 10.38 mmol), 4-fluorobenzaldehyde (1.9321 g, 15.57 mmol) and K₂CO₃ (2.9080 g, 21.04 mmol), pyridine (10 cm³) was added to obtain a suspension. The suspension was heated with stirring for 88 hours. Pyridine was removed to obtain the residue, which was then added with H₂O (100 cm³), extracted three times with AcOEt, washed with saturated aqueous NaCl, dried over Na₂SO₄, filtrated and concentrated. The resultant residue was purified by silica gel column chromatography (BW-200, 30 g, eluent; 5%→10%→50% AcOEt/n-hexane→10% MeOH/CH₂Cl₂) to afford Compound 82 (0.7581 g, 1.87 mmol) and compound 83 (0.3143 g, 1.03 mmol). The respective carboxyl compounds of Compounds 82 and 83, wherein the formyl group is oxidized, were also obtained.

Yield: 18% (compound 82), 10% (compound 83), unreacted Compound 81 (65%) was recovered.

Compound 82: ¹H NMR (CDCl₃) δ=1.33 & 1.36 & 1.41 (18H, three singlet peaks of the conformers, t-Bu×2), 3.14-3.91 (6H, m), 4.10-4.32 (2H, m), 6.77 (2H, d, J=9.1 Hz), 7.74 (2H, d, J=9.1 Hz), and 9.75 (1H, s, CHO).

Compound 83: ¹H NMR (CDCl₃) δ=1.20 (9H, s, t-Bu), 3.09 (2H, t, J=5.2 Hz), 3.70 (2H, t, J=5.2 Hz), 3.70-3.86 (4H, m), 4.82 (1H, br s, NH), 6.76 (2H, d, J=8.5 Hz), 7.73 (2H, d, J=8.5 Hz), and 9.73 (1H, s, CHO).

Example 966

Compound 84

To 100 cm³ egg-plant flask, charged with Compound 82 (1.2082 g, 2.98 mmol), pyridine (1 cm³) and MeOH (10 cm³) were added to prepare a solution. To this solution, HONH₂·HCl (0.3584 g, 5.16 mmol) was added, and the mixture was stirred at room temperature for 21 hours. After removing pyridine and MeOH, H₂O (50 cm³) and AcOEt (100 cm³) was added to separate the phase, and the aqueous layer was extracted once with AcOEt. The combined organic layer was washed once with H₂O and once with saturated aqueous NaCl, dried over Na₂SO₄, filtrated, and concentrated to afford the residue (1.1838 g) containing Compound 84 as main product.

Example 967

Compound 85

To 100 cm³ egg-plant flask, charged with the residue containing Compound 84 as main product (1.1838 g), pyridine (3 cm³) and CH₂Cl₂ (15 cm³) were added to dissolve. To this solution, NCS (0.5020 g, 3.76 mmol) was added at 0° C., and the mixture was stirred at this temperature for 3 hours and for additional 15 hours at room temperature. The residue was added with H₂O (50 cm³) and AcOEt (100 cm³) to separate the phase, and the aqueous layer was extracted once with ≚ AcOEt. The combined organic layer was washed once with H₂O and once with saturated aqueous NaCl, dried over Na₂SO₄, filtrated, and concentrated to afford the residue containing Compound 85 as main product.

Example 968

Compound 86

To 100 cm³ egg-plant flask, charged with the residue containing Compound 85 as main product (1.1838 g), Et₃N (0.80 cm³, 5.69 mmol) and CH₂Cl₂ (20 cm³) was added to dissolve. To this solution, allyl alcohol (0.40 cm³, 5.85 mmol) was added at room temperature and stirred for 24 hours at this temperature. The residue obtained by removing the solvent was subjected to purification by silica gel column chromatography (BW-200, 30 g, eluent; AcOEt→5% MeOH/CH₂Cl₂), but there were fractions containing substantial by-product. Therefore, the fraction containing Compound 86 was only collected.

¹H NMR (CDCl₃) δ=1.34-1.42 (18H, t-Bu), 2.19 (1H, br s, OH), 3.13-3.86 (10H), 4.09-4.28 (2H), 4.74-4.86 (1H, m), 6.71 (2H, d, J=8.8 Hz), and 7.53 (2H, d, J=8.8 Hz).

Example 969

Compound 87

The above fraction containing Compound 86 was concentrated to the residue (1.0953 g), which was then dissolved in CH₂Cl₂ (20 cm³) and added with Et₃N (0.80 cm³, 5.69 mmol). MsCl (0.40 cm³, 5.17 mmol) in CH₂Cl₂ (5 cm³) was added dropwise at 0° C., and warmed to room temperature and stirred for 2.5 hours.

The reaction was quenched with saturated aqueous NaHCO₃ (30 cm³), extracted four times with CH₂Cl₂, washed once with saturated aqueous NaCl, dried over Na₂SO₄, filtered, and concentrated to obtain the residue (1.2848 g). The residue was dissolved in DMF (20 cm³), added with NaN₃ (0.6000 g, 9.23 mmol) and stirred at 60° C. for 3 hours and at room temperature for additional 40 hours. The solution was added with H₂O (50 cm³) and AcOEt (40 cm³) to separate the phase, the aqueous layer was extracted once with AcOEt. The combined organic layer was washed once with H₂O and once with saturated aqueous NaCl, dried over Na₂SO₄, filtrated, and concentrated. The residue was purified by silica gel column chromatography (BW-200, 30 g, eluent; 50%→80% AcOEt/n-hexane) to afford 0.3171 g (0.632 mmol) of Compound 87.

Yield (from 82): 21%

¹H NMR (CDCl₃) δ=1.34-1.48 (18H, t-Bu), 3.06-3.86 (10H), 4.07-4.28 (2H), 4.78-4.91 (1H, m), 6.65-6.73 (2H, m), and 7.44-7.56 (2H, m).

Example 970

Synthesis of Compound 88

To 50 cm³ egg-plant flask, charged with Compound 87 (0.3171 g, 0.632 mmol), THF (3 cm³) was added to dissolve. To this solution, Ph₃P (0.2525 g, 0.963 mmol) and H₂O (0.20 cm³, 11.1 mmol) were added at room temperature, and stirred at room temperature for 52 hours. The residue obtained by removing the solvent was purified by silica gel column chromatography (BW-200, 30 g, eluent; 50%→100% AcOEt/n-hexane→10% MeOH/CHCl₃) to afford 0.2413 g (0.507 mmol, 80%) of amine.

The amine (0.2413 g, 0.507 mmol) was charged in 50 cm³ egg-plant flask, and pyridine (5 cm³) was added to dissolve. Ac₂O (2.0 cm³) was added at room temperature and stirred at this temperature for 15 hours. Solvent was removed to obtain the residue (0.2556 g) as Compound 88.

Yield: 78%

¹H NMR (CDCl₃) δ=1.27-1.41 (18H, t-Bu), 1.90 (3H, s, Ac), 2.80-3.68 (10H), 4.02-4.20 (2H), 4.66-4.78 (1H, m), 6.10 (1H, t, J=6.0 Hz), 6.63 (2H, d, J=8.8 Hz), and 7.42 (2H, d, J=8.8 Hz).

Example 971

Synthesis of Compound 94

[Chemical Formula 997]

Compound 91

NaH (60% in mineral oil; 3.4311 g, 85.8 mmol), charged in 200 cm³ egg-plant flask, was washed three times with n-hexane. Residual n-hexane was removed under reduced pressure, and DMF (150 cm³) was added. Compound 90 (10.26 g, 34.2 mmol) was added at room temperature, and the mixture was stirred at this temperature for 10 min. Compound 89 (9.8497 g, 40.7 mmol) in DMF (50 cm³) was then added dropwise to this mixture, and the mixture was stirred at this temperature for 18 hours. The mixture was poured into H₂O (500 cm³), extracted three times with AcOEt, washed once with water and with saturated aqueous NaCl, dried over anhydrous Na₂SO₄, filtered, and concentrated.

The resultant residue was purified by silica gel column chromatography (BW-200, 150 g, eluent; 10%→20%→30%→50% AcOEt/n-hexane) to afford 3.9235 g (8.36 mmol) of Compound 91.

Yield: 25%

¹H NMR (CDCl₃) δ=1.31-1.43 (9H, t-Bu), 3.08-3.74 (6H), 4.00-4.28 (2H), 4.98-5.24 (4H, m, CH₂Ph), and 7.20-7.38 (10H, m).

Example 972

Compounds 93 and 94

To 500 cm³ egg-plant flask, charged with Compound 91 (3.9235 g, 8.36 mmol) and 10% Pd/C (0.7777 g), MeOH (60 cm³) and CH₂Cl₂ (20 cm³) were added to obtain a suspension. The suspension was subjected to H₂ substitution and stirred for 7 days. The reaction was filtered through celite Pad, the filtrate was concentrated to the crude product (92). The crude product (2.2861 g) was dissolved in MeCN (50 cm³), and K₂CO₃ (3.3520 g, 24.25 mmol) and 3,4-difluoro nitro benzene (3.6271 g, 22.80 mmol) were added, and the mixture was heated with stirring for 14 hours. H₂O (50 cm³) was added, and the mixture was extracted five times with AcOEt, washed with saturated aqueous NaCl, dried over anhydrous Na₂SO₄, filtrated and concentrated. The resultant residue was purified by silica gel column chromatography (BW-200, 60 g, eluent; 10%→20%→30%→40% AcOEt/n-hexane) to afford Compound 93 (0.5019 g, 1.47 mmol) and Compound 94 (0.4347 g, 0.91 mmol).

Yield: 18% (compound 93), 11% (compound 94).

Compound 93: ¹H NMR (CDCl₃) δ=1.45 (9H, s, t-Bu), 3.00-3.14 (2H), 3.36-3.74 (7H), 7.48 (1H, t=9.1 Hz), and 7.84-8.01 (2H, m).

Compound 94: ¹H NMR (CDCl₃) δ=1.53-1.57 (9H, t-Bu), 3.38-5.76 (8H), 6.61 (2H, t, J=8.6 Hz), and 7.84-8.01 (4H, m).

Example 973

Synthesis of Compound 103

[Chemical Formula 998]

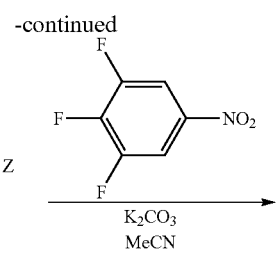

102
74%

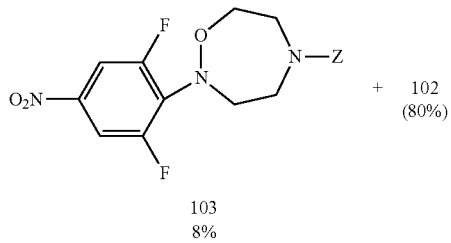

103
8%

Z = C b z (benzyloxycarbonyl)

Compound 102

To a solution of BOC compound (101, 1.01 g) in chloroform (25 ml), trifluoroacetic acid (2 ml) was added and stirred at room temperature for 19 hours.

After the reaction, saturated aqueous NaHCO$_3$ was added, and the mixture was extracted with chloroform-methanol (9:1). After dryness (Na$_2$SO$_4$), solvent was removed. The residue was purified by silica gel chromatography (hexane-ethyl acetate (1:1)) to afford 526 mg (74%) of Compound (102) as colorless syrup.

102: colorless syrup; 1H-NMR (300 MHz, CDCl$_3$) δ 3.09 (t, 5.5, 1H), 3.14 (t, 5.5, 1H), 3.54-3.70 (m, 4H), 3.82 (t, 5.5, 1H), 3.91 (t, 5.5, 1H), 5.16 (s, 2H), 5.84 (br, NH), 7.29-7.40 (m, 5H)

Example 974

Compound 103

To a solution of the amino compound (102, 321 mg) and 3,4,5-trifluoro nitrobenzene (487 mg) in acetonitrile (12 ml), K$_2$CO$_3$ (561 mg) was added, and the mixture was heated with stirring for 21 hours. After the reaction, aqueous NH$_4$Cl was added, and the mixture was extracted with chloroform-methanol (9:1). After dryness (Na$_2$SO$_4$), solvent was removed. The residue was purified by silica gel chromatography (hexane-ethyl acetate (2:1)) to afford 45 mg (8%) of pale-yellow candy-like compound (103) in the first fraction, and 258 mg (80%) of the starting material was recovered in the eluted fraction with hexane-ethyl acetate (1:1).

103: pale-yellow candy-like material; $^1$H-NMR (300 MHz, CDCl$_3$) δ 3.55 (br t, 5.5, 1H), 3.62 (br t, 5.5, 1H), 3.70-3.81 (m, 4H), 4.01 (t, 5.5, 1H), 4.09 (t, 5.5, 1H), 5.19 (s, 2H), 7.31-7.39 (m, 5H), 7.75-7.84 (m, 2H)

INDUSTRIAL APPLICABILITY

The compound of the invention is useful as a pharmaceutical active ingredient or an intermediate in the synthesis thereof. Particularly, the compound of the invention is useful as an antimicrobial agent based on its antimicrobial activity.

What is claimed is:

1. A compound of the formula:

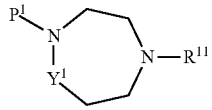

[Chemical Formula 6]

or a pharmaceutically acceptable salt thereof,
wherein
Y$^1$ is O;
P$^1$ is hydrogen, acyl group or an amino protecting group;
R$^{11}$ is hydrogen, acyl group or an amino protecting group, provided that —CO(CH$_2$)$_3$—CO$_2$H, -Ph and —CH$_2$Ph (Ph: phenyl) are excluded.

2. A compound of the formula:

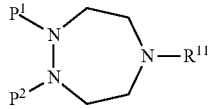

[Chemical Formula 7]

or a pharmaceutically acceptable salt thereof,
wherein
P$^1$ and P$^2$ are independently hydrogen or a lower alkoxycarbonyl;
R$^{11}$ is hydrogen, acyl group or a lower alkoxycarbonyl, provided that —CO(CH$_2$)$_3$—CO$_2$H is excluded.

3. The compound according to claim 2 wherein P$^1$ and P$^2$ are independently a lower alkoxycarbonyl and R$^{11}$ is hydrogen.

* * * * *